(12) United States Patent
Newell et al.

(10) Patent No.: US 7,976,554 B2
(45) Date of Patent: Jul. 12, 2011

(54) DEVICES, TOOLS AND METHODS FOR PERFORMING MINIMALLY INVASIVE ABDOMINAL SURGICAL PROCEDURES

(75) Inventors: Matthew B. Newell, Portola Valley, CA (US); Pankaj Rathi, Mountain View, CA (US); Robert M. George, San Jose, CA (US); Marlo Dreissigacker, Redwood City, CA (US); Narvel M. Brooks, III, Palo Alto, CA (US); Shuji Uemura, San Francisco, CA (US); Theodore M. Bender, Oakland, CA (US); Joshua Makower, Los Altos, CA (US); Dane A. Johnson, San Francisco, CA (US); Brian K. Shiu, Sunnyvale, CA (US); Pablo G. Acosta, Newark, CA (US); Timothy A. Limon, Cupertino, CA (US); Beverly Huss, Menlo Park, CA (US); Crystine M. Lee, San Rafael, CA (US)

(73) Assignee: Vibrynt, Inc., Redwood City, CA (US)

( * ) Notice: Subject to any disclaimer, the term of this patent is extended or adjusted under 35 U.S.C. 154(b) by 209 days.

(21) Appl. No.: 12/474,251

(22) Filed: May 28, 2009

(65) Prior Publication Data

US 2009/0281556 A1 Nov. 12, 2009

Related U.S. Application Data

(63) Continuation-in-part of application No. 11/716,985, filed on Mar. 10, 2007, and a continuation-in-part of application No. 11/716,986, filed on Mar. 10, 2007, and a continuation-in-part of application No. 11/407,701, filed on Apr. 19, 2006.

(60) Provisional application No. 61/130,244, filed on May 28, 2008.

(51) Int. Cl.
*A61B 17/04* (2006.01)
(52) U.S. Cl. ......................................... 606/144; 606/139
(58) Field of Classification Search .................. 606/139, 606/144–148, 232; 112/452, 169
See application file for complete search history.

(56) References Cited

U.S. PATENT DOCUMENTS 233,457 A 10/1880 Cook et al.
(Continued)

FOREIGN PATENT DOCUMENTS

EP 1 016 377 A2 7/2000
(Continued)

OTHER PUBLICATIONS

About the Vertical Sleeve Gastrectomy. Mar. 24, 2006, pp. 1-1. http://obesityhelp.com/forums/VSG/about.html.
(Continued)

*Primary Examiner* — Gary Jackson
*Assistant Examiner* — Michael G Mendoza
(74) *Attorney, Agent, or Firm* — Alan W. Cannon; Law Office of Alan W. Cannon

(57) ABSTRACT

Methods, systems, devices and assemblies are provided for treating a patient by: making an incision or puncture though the patient's skin over the abdominal cavity; establishing an initial tract through an opening formed by the incision or puncture; advancing an instrument through the tract; contacting a distal end portion of the instrument against an inner surface of the abdominal cavity; driving at least one stitching needle through the inner surface of the abdominal cavity, continuing the driving until the at least one stitching needle exits the inner surface of the abdominal cavity, anchoring a suture carried by each of the at least one stitching needle to a suture anchor at an exit location, respectively; and applying tension to each of the sutures.

21 Claims, 92 Drawing Sheets

U.S. PATENT DOCUMENTS

| | | | |
|---|---|---|---|
| 659,422 A | 10/1900 | Shidler |
| 780,392 A | 1/1905 | Wanamaker et al. |
| 789,467 A | 5/1905 | West |
| 1,461,524 A | 7/1923 | Goddard |
| 2,579,192 A | 12/1951 | Kohl et al. |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Semple |
| 3,326,586 A | 6/1967 | Frost et al. |
| 3,470,834 A | 10/1969 | Bone |
| 3,521,918 A | 7/1970 | Hammond |
| 3,571,864 A | 3/1971 | Oger |
| 3,664,435 A | 5/1972 | Klessig |
| 3,675,639 A | 7/1972 | Climber |
| 3,713,680 A | 1/1973 | Pagano |
| 3,756,638 A | 9/1973 | Stockberger |
| 3,873,140 A | 3/1975 | Bloch |
| 3,931,667 A | 1/1976 | Merser et al. |
| 3,976,079 A | 8/1976 | Samuels et al. |
| 4,006,747 A | 2/1977 | Kronenthal et al. |
| 4,060,089 A | 11/1977 | Noiles |
| 4,133,315 A | 1/1979 | Berman et al. |
| 4,210,148 A | 7/1980 | Stivala |
| 4,246,893 A | 1/1981 | Berson |
| 4,291,698 A | 9/1981 | Fuchs et al. |
| 4,328,805 A | 5/1982 | Akopov et al. |
| 4,416,267 A | 11/1983 | Garren et al. |
| 4,458,681 A | 7/1984 | Hopkins |
| 4,472,226 A | 9/1984 | Redinger et al. |
| 4,485,805 A | 12/1984 | Foster, Jr. et al. |
| 4,493,323 A | 1/1985 | Albright et al. |
| 4,558,699 A | 12/1985 | Bashour |
| 4,592,339 A | 6/1986 | Kuzmak et al. |
| 4,592,342 A | 6/1986 | Salmasian |
| 4,621,640 A | 11/1986 | Mulhollan et al. |
| 4,669,473 A | 6/1987 | Richards et al. |
| 4,694,827 A | 9/1987 | Weiner et al. |
| 4,696,288 A | 9/1987 | Kuzmak et al. |
| 4,705,040 A | 11/1987 | Mueller et al. |
| 4,714,281 A | 12/1987 | Peck |
| 4,723,547 A | 2/1988 | Kullas et al. |
| 4,738,255 A | 4/1988 | Goble et al. |
| 4,739,758 A | 4/1988 | Lai et al. |
| 4,744,364 A | 5/1988 | Kensey |
| 4,750,492 A | 6/1988 | Jacobs |
| 4,803,985 A | 2/1989 | Hill |
| 4,823,794 A | 4/1989 | Pierce |
| 4,899,747 A | 2/1990 | Garren et al. |
| 4,955,913 A | 9/1990 | Robinson |
| 5,002,550 A | 3/1991 | Li |
| 5,041,129 A | 8/1991 | Hayhurst et al. |
| 5,084,061 A | 1/1992 | Gau et al. |
| 5,100,421 A | 3/1992 | Christoudias |
| 5,112,310 A | 5/1992 | Grobe |
| 5,123,914 A | 6/1992 | Cope |
| 5,129,912 A | 7/1992 | Noda et al. |
| RE034,021 E | 8/1992 | Mueller et al. |
| 5,151,086 A | 9/1992 | Duh et al. |
| 5,188,104 A | 2/1993 | Wernicke et al. |
| 5,217,470 A | 6/1993 | Weston |
| 5,220,928 A | 6/1993 | Oddses et al. |
| 5,234,454 A | 8/1993 | Bangs |
| 5,246,456 A | 9/1993 | Wilkinson |
| 5,257,713 A | 11/1993 | Green et al. |
| 5,258,000 A | 11/1993 | Gianturco et al. |
| 5,258,015 A | 11/1993 | Li et al. |
| 5,259,399 A | 11/1993 | Brown |
| 5,269,809 A | 12/1993 | Hayhurst et al. |
| 5,282,832 A | 2/1994 | Toso et al. |
| 5,290,217 A | 3/1994 | Campos |
| 5,292,344 A | 3/1994 | Douglas |
| 5,334,200 A | 8/1994 | Johnson |
| 5,354,271 A | 10/1994 | Voda |
| 5,364,408 A | 11/1994 | Gordon |
| 5,391,182 A | 2/1995 | Chin |
| 5,405,352 A | 4/1995 | Weston |
| 5,423,872 A | 6/1995 | Cigaina |
| 5,428,123 A | 6/1995 | Ward et al. |
| 5,433,723 A | 7/1995 | Lindenberg |
| 5,445,608 A | 8/1995 | Chen et al. |
| 5,470,337 A | 11/1995 | Moss |
| 5,472,446 A | 12/1995 | de la Torre |
| 5,480,406 A | 1/1996 | Nolan et al. |
| 5,496,311 A | 3/1996 | Abele et al. |
| 5,507,754 A | 4/1996 | Green et al. |
| 5,527,321 A * | 6/1996 | Hinchliffe ..................... 606/144 |
| 5,545,171 A | 8/1996 | Sharkey et al. |
| 5,545,178 A | 8/1996 | Kensey et al. |
| 5,549,621 A | 8/1996 | Bessler et al. |
| 5,554,162 A | 9/1996 | DeLange |
| 5,573,540 A | 11/1996 | Yoon |
| 5,591,177 A | 1/1997 | Lehrer |
| 5,601,604 A | 2/1997 | Vincent |
| 5,626,614 A | 5/1997 | Hart |
| 5,634,936 A | 6/1997 | Linden et al. |
| 5,647,836 A | 7/1997 | Blake, III et al. |
| 5,669,935 A | 9/1997 | Rosenman et al. |
| 5,690,691 A | 11/1997 | Chen et al. |
| 5,716,368 A | 2/1998 | de la Torre et al. |
| 5,725,557 A | 3/1998 | Gatturna et al. |
| 5,741,277 A * | 4/1998 | Gordon et al. ................. 606/144 |
| 5,846,254 A | 12/1998 | Schulze et al. |
| 5,888,196 A | 3/1999 | Bonutti |
| 5,931,788 A | 8/1999 | Keen et al. |
| 5,938,669 A | 8/1999 | Klaiber et al. |
| 5,951,590 A | 9/1999 | Goldfarb |
| 5,957,939 A | 9/1999 | Heaven et al. |
| 5,961,440 A | 10/1999 | Schweich, Jr. et al. |
| 5,971,447 A | 10/1999 | Steck, III |
| 5,993,473 A | 11/1999 | Chan et al. |
| 6,006,002 A | 12/1999 | Motoki et al. |
| 6,013,053 A | 1/2000 | Bower et al. |
| 6,067,991 A | 5/2000 | Forsell |
| 6,080,160 A | 6/2000 | Chen et al. |
| 6,097,984 A | 8/2000 | Douglas |
| 6,102,922 A | 8/2000 | Jakobsson et al. |
| 6,113,609 A | 9/2000 | Adams |
| 6,143,006 A | 11/2000 | Chan |
| 6,162,234 A | 12/2000 | Freedland et al. |
| 6,174,280 B1 | 1/2001 | Oneda et al. |
| 6,186,149 B1 | 2/2001 | Pacella et al. |
| 6,270,530 B1 | 8/2001 | Eldridge et al. |
| 6,420,452 B1 | 7/2002 | Gunatillake et al. |
| 6,425,900 B1 | 7/2002 | Knodel et al. |
| 6,437,073 B1 | 8/2002 | Gunatillake et al. |
| 6,447,533 B1 | 9/2002 | Adams |
| 6,475,136 B1 | 11/2002 | Forsell |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,148 B1 | 12/2002 | Pinchuk et al. |
| 6,506,196 B1 | 1/2003 | Laufer |
| 6,511,490 B2 | 1/2003 | Robert et al. |
| 6,535,764 B2 | 3/2003 | Imran et al. |
| 6,551,241 B1 | 4/2003 | Schultz |
| 6,558,400 B2 | 5/2003 | Deem et al. |
| 6,656,182 B1 | 12/2003 | Hayhurst |
| 6,663,639 B1 | 12/2003 | Laufer et al. |
| 6,669,713 B2 | 12/2003 | Adams |
| 6,675,809 B2 | 1/2004 | Stack et al. |
| 6,736,793 B2 | 5/2004 | Meyer et al. |
| 6,746,458 B1 | 6/2004 | Cloud |
| 6,746,460 B2 | 6/2004 | Gannoe et al. |
| 6,755,869 B2 | 6/2004 | Geitz |
| 6,773,441 B1 | 8/2004 | Laufer et al. |
| 6,790,213 B2 | 9/2004 | Cherok et al. |
| 6,821,285 B2 | 11/2004 | Laufer et al. |
| 6,835,200 B2 | 12/2004 | Laufer et al. |
| 6,869,395 B2 | 3/2005 | Page et al. |
| 6,900,055 B1 | 5/2005 | Fuller |
| 6,908,487 B2 | 6/2005 | Cigaina |
| 6,981,978 B2 | 1/2006 | Gannoe |
| 6,994,715 B2 | 2/2006 | Gannoe et al. |
| 7,033,373 B2 | 4/2006 | de la Torre et al. |
| 7,037,315 B2 | 5/2006 | Sancoff et al. |
| 7,037,344 B2 | 5/2006 | Kagan et al. |

| | | | | | | |
|---|---|---|---|---|---|---|
| 7,131,980 B1 | 11/2006 | Field et al. | | 2005/0267596 A1 | 12/2005 | Chen et al. |
| 7,153,314 B2 | 12/2006 | Laufer et al. | | 2005/0273138 A1 | 12/2005 | To et al. |
| 7,167,750 B2 | 1/2007 | Knudson et al. | | 2005/0277960 A1 | 12/2005 | Hassler, Jr. et al. |
| 7,223,277 B2 | 5/2007 | DeLegge | | 2005/0277974 A1 | 12/2005 | Hassler, Jr. et al. |
| 7,255,675 B2 | 8/2007 | Gertner et al. | | 2006/0009789 A1 | 1/2006 | Gambale et al. |
| 7,310,557 B2 | 12/2007 | Maschino et al. | | 2006/0025783 A1 | 2/2006 | Smith et al. |
| 7,334,822 B1 | 2/2008 | Hines, Jr. | | 2006/0025789 A1 | 2/2006 | Laufer et al. |
| 7,338,433 B2 | 3/2008 | Coe | | 2006/0025819 A1 | 2/2006 | Nobis et al. |
| 7,354,454 B2 | 4/2008 | Stack et al. | | 2006/0030867 A1 | 2/2006 | Zadno |
| 7,374,565 B2 | 5/2008 | Hassler et al. | | 2006/0030884 A1 | 2/2006 | Yeung et al. |
| 7,402,166 B2 | 7/2008 | Feigl | | 2006/0058829 A1 | 3/2006 | Sampson |
| 7,416,554 B2 | 8/2008 | Lam et al. | | 2006/0069396 A1 | 3/2006 | Meade et al. |
| 7,490,602 B2 | 2/2009 | Sabri | | 2006/0089571 A1 | 4/2006 | Gertner |
| 7,534,248 B2 | 5/2009 | Mikkaichi et al. | | 2006/0089646 A1 | 4/2006 | Bonutti |
| 7,618,426 B2 | 11/2009 | Ewers et al. | | 2006/0106288 A1 | 5/2006 | Roth et al. |
| 7,666,195 B2 | 2/2010 | Kelleher et al. | | 2006/0161186 A1 | 7/2006 | Hassler, Jr. et al. |
| 7,775,967 B2 | 8/2010 | Gertner | | 2006/0161256 A1 | 7/2006 | Ziegler et al. |
| 2001/0010005 A1 | 7/2001 | Kammerer et al. | | 2006/0195139 A1 | 8/2006 | Gertner |
| 2001/0011543 A1 | 8/2001 | Forsell | | 2006/0212053 A1 | 9/2006 | Gertner |
| 2001/0044639 A1 | 11/2001 | Levinson | | 2006/0229623 A1 | 10/2006 | Bonutti et al. |
| 2002/0055757 A1 | 5/2002 | Torre et al. | | 2006/0247206 A1 | 11/2006 | Feins |
| 2002/0077660 A1 | 6/2002 | Kayan et al. | | 2006/0253131 A1 | 11/2006 | Wolniewicz |
| 2002/0128684 A1 | 9/2002 | Foerster | | 2006/0264699 A1 | 11/2006 | Gertner |
| 2002/0161382 A1 | 10/2002 | Neisz et al. | | 2006/0265042 A1 | 11/2006 | Catanese, III et al. |
| 2002/0161414 A1 | 10/2002 | Flesler et al. | | 2006/0276871 A1 | 12/2006 | Lamson et al. |
| 2002/0188354 A1 | 12/2002 | Peghini et al. | | 2006/0282081 A1 | 12/2006 | Fanton et al. |
| 2003/0021822 A1 | 1/2003 | Lloyd | | 2006/0282088 A1 | 12/2006 | Ryan |
| 2003/0055463 A1 | 3/2003 | Gordon et al. | | 2007/0027358 A1 | 2/2007 | Gertner et al. |
| 2003/0055465 A1 | 3/2003 | Ben-Haim et al. | | 2007/0049970 A1 | 3/2007 | Belef et al. |
| 2003/0093117 A1 | 5/2003 | Saadat | | 2007/0055095 A1 | 3/2007 | Chu et al. |
| 2003/0114863 A1 | 6/2003 | Field et al. | | 2007/0060940 A1 | 3/2007 | Brazzini et al. |
| 2003/0208208 A1 | 11/2003 | Chu | | 2007/0068538 A1 | 3/2007 | Anderson et al. |
| 2003/0208212 A1 | 11/2003 | Cigaina | | 2007/0073318 A1 | 3/2007 | Carter et al. |
| 2003/0216613 A1 | 11/2003 | Suzuki | | 2007/0073323 A1 | 3/2007 | Carter et al. |
| 2004/0006351 A1 | 1/2004 | Gannoe et al. | | 2007/0088362 A1 | 4/2007 | Bonutti et al. |
| 2004/0024386 A1 | 2/2004 | Deem et al. | | 2007/0088373 A1 | 4/2007 | Baker |
| 2004/0030347 A1 | 2/2004 | Gannoe et al. | | 2007/0112363 A1 | 5/2007 | Adams |
| 2004/0044353 A1 | 3/2004 | Gannoe | | 2007/0112385 A1 | 5/2007 | Conlon |
| 2004/0044357 A1 | 3/2004 | Gannoe et al. | | 2007/0129738 A1 | 6/2007 | Kraemer et al. |
| 2004/0054352 A1 | 3/2004 | Adams et al. | | 2007/0167982 A1 | 7/2007 | Gertner et al. |
| 2004/0059289 A1 | 3/2004 | Garza Alvarez | | 2007/0173869 A1 | 7/2007 | Gannoe et al. |
| 2004/0068224 A1 | 4/2004 | Couvillon et al. | | 2007/0173888 A1 | 7/2007 | Gertner et al. |
| 2004/0092892 A1 | 5/2004 | Kagan et al. | | 2007/0179335 A1 | 8/2007 | Gertner et al. |
| 2004/0092967 A1 | 5/2004 | Sancoff et al. | | 2007/0197896 A1 | 8/2007 | Moll et al. |
| 2004/0097986 A1 | 5/2004 | Adams | | 2007/0198038 A1 | 8/2007 | Cohen et al. |
| 2004/0098060 A1 | 5/2004 | Ternes | | 2007/0203517 A1 | 8/2007 | Williams et al. |
| 2004/0116949 A1 | 6/2004 | Ewers et al. | | 2007/0233170 A1 | 10/2007 | Gertner et al. |
| 2004/0122456 A1 | 6/2004 | Saadat et al. | | 2007/0235083 A1 | 10/2007 | Dlugos |
| 2004/0122473 A1 | 6/2004 | Ewers et al. | | 2007/0239284 A1 | 10/2007 | Skerven et al. |
| 2004/0138525 A1 | 7/2004 | Saadat et al. | | 2007/0250103 A1 | 10/2007 | Makower |
| 2004/0148034 A1 | 7/2004 | Kagan et al. | | 2007/0250112 A1 | 10/2007 | Ravikumar et al. |
| 2004/0176785 A1 | 9/2004 | Hermann et al. | | 2007/0255308 A1 | 11/2007 | Williams et al. |
| 2004/0186503 A1 | 9/2004 | DeLegge | | 2007/0260259 A1 | 11/2007 | Fanton et al. |
| 2004/0193194 A1 | 9/2004 | Laufer et al. | | 2007/0270892 A1 | 11/2007 | Makower |
| 2004/0194790 A1 | 10/2004 | Laufer et al. | | 2007/0276293 A1 | 11/2007 | Gertner |
| 2004/0243178 A1 | 12/2004 | Haut et al. | | 2007/0276432 A1 | 11/2007 | Stack |
| 2004/0243179 A1 | 12/2004 | Foerster | | 2008/0009888 A1 | 1/2008 | Ewers et al. |
| 2004/0243180 A1 | 12/2004 | Donnelly et al. | | 2008/0015501 A1 | 1/2008 | Gertner |
| 2004/0260345 A1 | 12/2004 | Foerster | | 2008/0033488 A1 | 2/2008 | Catanese, III et al. |
| 2004/0267378 A1 | 12/2004 | Gazi et al. | | 2008/0039894 A1 | 2/2008 | Catanese, III et al. |
| 2005/0022827 A1 | 2/2005 | Woo et al. | | 2008/0051823 A1 | 2/2008 | Makower et al. |
| 2005/0049718 A1 | 3/2005 | Dann et al. | | 2008/0051824 A1 | 2/2008 | Gertner |
| 2005/0055038 A1 | 3/2005 | Kelleher | | 2008/0051850 A1 | 2/2008 | Sparks et al. |
| 2005/0085832 A1 | 4/2005 | Sancoff et al. | | 2008/0058710 A1 | 3/2008 | Wilk |
| 2005/0096638 A1 | 5/2005 | Starkebaum et al. | | 2008/0071306 A1 | 3/2008 | Gertner |
| 2005/0159769 A1 | 7/2005 | Alverdy | | 2008/0082113 A1 | 4/2008 | Bishop et al. |
| 2005/0197687 A1 | 9/2005 | Molaei et al. | | 2008/0086082 A1 | 4/2008 | Brooks |
| 2005/0203344 A1 | 9/2005 | Orban, III et al. | | 2008/0086172 A1 | 4/2008 | Martin et al. |
| 2005/0216040 A1 | 9/2005 | Gertner et al. | | 2008/0091220 A1 | 4/2008 | Chu |
| 2005/0216042 A1 | 9/2005 | Gertner et al. | | 2008/0091237 A1 | 4/2008 | Schwartz et al. |
| 2005/0222638 A1 | 10/2005 | Foley et al. | | 2008/0109027 A1 | 5/2008 | Chen et al. |
| 2005/0228415 A1 | 10/2005 | Gertner | | 2008/0147002 A1 | 6/2008 | Gertner |
| 2005/0240222 A1 | 10/2005 | Shipp | | 2008/0161717 A1 | 7/2008 | Gertner |
| 2005/0261712 A1 | 11/2005 | Balbierz | | 2008/0167519 A1 | 7/2008 | St-Germain |
| 2005/0267405 A1 | 12/2005 | Shah | | 2008/0167647 A1 | 7/2008 | Gertner |
| 2005/0267406 A1 | 12/2005 | Hassler, Jr. | | 2008/0167648 A1 | 7/2008 | Gertner |
| 2005/0267529 A1 | 12/2005 | Grockett et al. | | 2008/0172074 A1 | 7/2008 | Baker et al. |
| 2005/0267533 A1 | 12/2005 | Gertner | | 2008/0172079 A1 | 7/2008 | Birk |
| 2005/0267595 A1 | 12/2005 | Chen et al. | | 2008/0208240 A1 | 8/2008 | Paz |

| | | | |
|---|---|---|---|
| 2009/0005633 | A9 | 1/2009 | Montpetit et al. |
| 2009/0012538 | A1 | 1/2009 | Saliman et al. |
| 2009/0072006 | A1 | 3/2009 | Clauson et al. |
| 2009/0082792 | A1 | 3/2009 | Koyfman et al. |
| 2009/0093850 | A1 | 4/2009 | Richard |
| 2010/0145324 | A1 | 6/2010 | Nihalani |
| 2010/0145370 | A1 | 6/2010 | Nihalani |

FOREIGN PATENT DOCUMENTS

| | | |
|---|---|---|
| EP | 1 602 392 A1 | 7/2005 |
| EP | 1 591 140 A1 | 11/2005 |
| EP | 1 520 563 A1 | 4/2006 |
| EP | 1 547 642 B1 | 8/2007 |
| EP | 1 607 071 B1 | 8/2007 |
| EP | 1 884 198 A2 | 2/2008 |
| EP | 1 884 199 A1 | 2/2008 |
| EP | 1 670 361 B1 | 4/2008 |
| FR | 2 907 665 | 5/2008 |
| WO | WO 87/00034 | 1/1987 |
| WO | WO 99/25418 | 5/1999 |
| WO | WO 9925418 | 5/1999 |
| WO | WO 00/09049 | 2/2000 |
| WO | WO 00/18330 | 4/2000 |
| WO | WO 00/74573 A1 | 12/2000 |
| WO | WO 01/47435 | 7/2001 |
| WO | WO 02/24078 | 3/2002 |
| WO | WO 02/35980 A2 | 5/2002 |
| WO | WO 02071951 | 9/2002 |
| WO | WO 03/055420 | 7/2003 |
| WO | WO 03095015 | 11/2003 |
| WO | WO 2004004542 | 1/2004 |
| WO | WO 2004014237 | 2/2004 |
| WO | WO 2004019765 | 3/2004 |
| WO | WO 2004021894 | 3/2004 |
| WO | WO 2004/037064 A2 | 5/2004 |
| WO | WO 2005007232 | 1/2005 |
| WO | WO 2005/009288 | 2/2005 |
| WO | WO 2005/018417 A2 | 3/2005 |
| WO | WO 2005/018417 A3 | 3/2005 |
| WO | WO 2005018417 | 3/2005 |
| WO | WO 2005020802 | 3/2005 |
| WO | WO 2005/094447 A2 | 10/2005 |
| WO | WO 2006/020370 A2 | 2/2006 |
| WO | WO 2006/049725 A2 | 5/2006 |
| WO | WO 2006/063593 A2 | 6/2006 |
| WO | WO 2006/108203 | 10/2006 |
| WO | WO 2006127431 | 11/2006 |
| WO | WO 2006134106 A1 | 12/2006 |
| WO | WO 2007/017880 A2 | 2/2007 |
| WO | WO 2007/067206 A2 | 6/2007 |
| WO | WO 2007064906 A2 | 6/2007 |
| WO | WO 2007/110866 A2 | 10/2007 |
| WO | WO 2008/006084 A2 | 1/2008 |
| WO | WO 2008/013814 | 1/2008 |
| WO | WO 2008006084 A2 | 1/2008 |
| WO | WO 2008043044 A2 | 4/2008 |

OTHER PUBLICATIONS

Akira., JP63277063, Japanese and English Abstract, Nov. 15, 1988, pp. 1-4.

Abhyankar et al, Use of a tissue expander and a polyglactic acid (Vicryl) mesh to reduce radiation enteritis: case report and literature view, 21: pp. 755-757, Aug. 2005.

Buchwald, Overview of Bariatric Surgery, vol. 194, No. 3, Mar. 2002, pp, 367-375.

Burnett, et al., The Use of a Pelvic Displacement Prosthesis to Exclude the Small Intestine from the Radiation Field Following Radical Hysterectomy, 79, pp. 438-443, 2000. http://www.idealibrary.com.

Brolin, Robert E., Gastric Bypass. vol. 81, No. 5, Oct. 2001, pp. 1077-1095.

Cheng, Splenic Epidermoid Cyst, pp. 1-3, 1997.

Conroy, et al. Lubricious Coatings for Medical Devices. vol. 3, No. 4, Jan. 2004, pp. 89-92.

DeMaria, Eric J., Laparoscopic Adjustable Silicone Gastric Banding vol. 81, No. 5, Oct. 2001, pp. 1129-1143.

Deitel,Mervyn., Overview of Operations for Morbid Obesity. vol. 22, No. 9, Sep. 1998, pp. 913-918.

Doherty, Cornelius., Technique of Verticle Banded Gastroplasty. vol. 81, No. 5, Oct. 2001, pp. 1097-1111.

Fried et al., Physical Principles of Available Adjustable Gastric Bands: How they Work. Obesity Surgery, 14, 2004, pp. 1118-1121.

Foglia et al., Management of giant omphalocele with rapid creation of abdominal domain, 41, pp. 704-709, 2006.

Geliebter et al; Extra-abdominal pressure alters food intake, intragastric pressure, and gastric emptying rate. 1986, pp. R549-R552.

Gertner MD, Stomach Restriction with an Extragastric Balloon, pp. 1, Abstract for 2007.

Hainaux et al., Laparoscopic adustable silicone gastric banding: radiological appearances of a new surgical treatment for morbid obesity. 1999, Abdom Imaging 24: 533-537.

Hoffman et al., Morbidity after Intraperitoneal Insertion of Saline-Filled Tissue Expanders for Small Bowel Exclusion from Radiotherapy Treatment Fields: A Prospective Four Year Experience with 34 Patients, pp. 473-483, No. 7, vol. 60, Jul. 1994.

Konturek et al., Neuro-Hormaonal Control of Food Intake; Basic Mechanisms and Clinical Implications, 2005, 56, Supp 6, 5-25, www.jpp.krakow.pl.

Lam et al., Huge Splenic Epidemoid Cyst: A Case Report, 1997; 60:113-6.

Laparoscopic Duodenal Switch, Mar. 24, 2006, http://wo-pub2.med.cornell.edu/chi.bin/WebObjects/PublicA.woa/5/w... p. 1.1.

Lee et al., Laparoscopic Vertical Sleeve Gastrectomy: A Novel Bariatric Procedure—superior to Established Operations? pp 1- 27. 90$^{th}$ Annual Clinical Congress, New Orleans, LA, Oct. 10, 2004.

Med-4840, Product Profile, Mar. 30, 2007, pp. 1-2.

Malassagne, et al., Intra-abdominal Sengstaken-Blakemore tube Placement for acute venous outflow obstruction in reduced-size Liver, Nov. 1996, 83, pp. 1086.

Marceau, et al., Malabsorptive Obesity Surgery. vol. 81, Oct. 2001, No. 5, pp. 1113-1127.

Mera, et al., Use of the Breast Implant for Liver Graft Malposition. vol. 5, No. 6, Nov. 1999, pp. 534-535.

Obesity Surgery Including Laparoscopy and Allied Care. vol. 16, No. 1, Jan. 2006, pp. 1-2. www.obesitysurgey.com.

Pomerri et al., Adjustable Silicone Gastric Banding of Obesity. , 1992, Gastrointest Radiol 17: pp. 207-210.

Schauer, et al., New applications for endoscopy: the emerging field of endoluminal and transgastric bariatric surgery, DOI:10.1007/s00464-006-9008-8, 2006.

The Sleeve Gastrectomy (or 2-Stage Procedure). 2006, pp. 1-2. http://surgicallyslim.com/sleeve.htm.

Tucker, Diana, Medical Device Daily. vol. 10, No. 102, pp. 1-10, May 26, 2006.

Walker, et al. Bladder Augmentation in Dogs Using the Tissue Capsule Formed Around a Perivesical tissue Expander, vol. 168, pp. 1534-1536, 2002.

Zwart et al., Gastric Motility: Comparison of Assessement with Real-Time MR Imagaing or Barostat Experience1., 224: pp. 592-597, Aug. 2002.

McMillan, et al., Arthroscopic Knot-tying techniques. pp. 81-95, 2003.

Buchwald—Overview of Bariatric Surgery. Journal of the American College of Surgeons. pp. 367-375, Mar. 2002.

Sharp, et al., The 4-S Modification of the Roeder Knot: How to Tie It. pp. 1004-1006, vol. 90, No. 6, Dec. 1997.

Schauer, et al., New application for Endoscopy: the emerging field of endoluminal and transgastric bariatric surgery. 10 pgs., Apr. 24, 2006.

Shoulderdoc.co.uk. pp. 1-2, Feb. 28, 2008. http://www.shoulderdoc.co.uk/article=518§ion.

Buchwald et al., "Bariatric Surgery: A Systematic Review and Meta-analysis", JAMA 2004, vol. 292, No. 14, pp. 1724-1737.

Buchwald et al., "Evolution of Operative Procedures for the Management of Morbid Obesity 1950-2000", Obesity Surgery 2002, 12:705-717.

Camerini et al., "Thirteen Years of Follow-up in Patients with Adjustable Silicone Gastric Banding for Obesity: Weight Loss and Constant Rate of Late Specific Complications" Obesity Surgery 2004, 14:1343-1348.

Cope et al., "Percutaneous Transgastric Technique for Creating Gastroenteric Anastomoses in Swine", Journal of Vascular and Interventional Radiology, 2004, 15:177-181.

Cummings et al., "Genetics and Pathophysiology of Human Obesity", An Annual Review of Medicine, 2003, 54:453-471/.

Johnston et al., "The Magenstrasse and Mill Operation for Morbid Obeisty", Obesity Surgery 2003, 13:10-16.

Monno et al., "Laparoscopic Adjustable Silicone Gastric Banding Versus Vertical Banded Gastroplasty in Morbidly Obese Patients" Analysis Obesity Surgery vol. 238, No. 6, 2003, pp. 835-842.

Roman et al., "Intragastric Balloon of Non-Morbid Obesity: A Restrospective Evaluation of Tolerance and Efficacy", Obesity Surgery, 2004, 14:539-544.

Sallet et al., Brazillian Multicenter Study of the Intragastric Ballon; Obesity Surgery, 2004, 14, pp. 991-998.

Sjostrom et al., LIfestyle Diabeters, and Cardiovascular Risk Factors 10 years after Bariaric Surgery, New England Journal of Medicine, 2004, 351, (6) 2683-2693.

Smith et al., "Modification of the Gastric Partitioning Operation for Morbid Obesity", Am J Surgery 142, Dec. 1981 pp. 725-730.

Smith et al., "Results and Complications of Gastric Partitioning. Four Years Follow-Up of 300 Morbidly Obese Patients", The American Journal of Surgery, 1983, (146) pp. 815-819.

Trumble et al., "Method for measuring long-term function of muscle-powered implants via radiotelemetry" J. Appl. Physiol. 2001,90: pp. 1977-1985.

\* cited by examiner

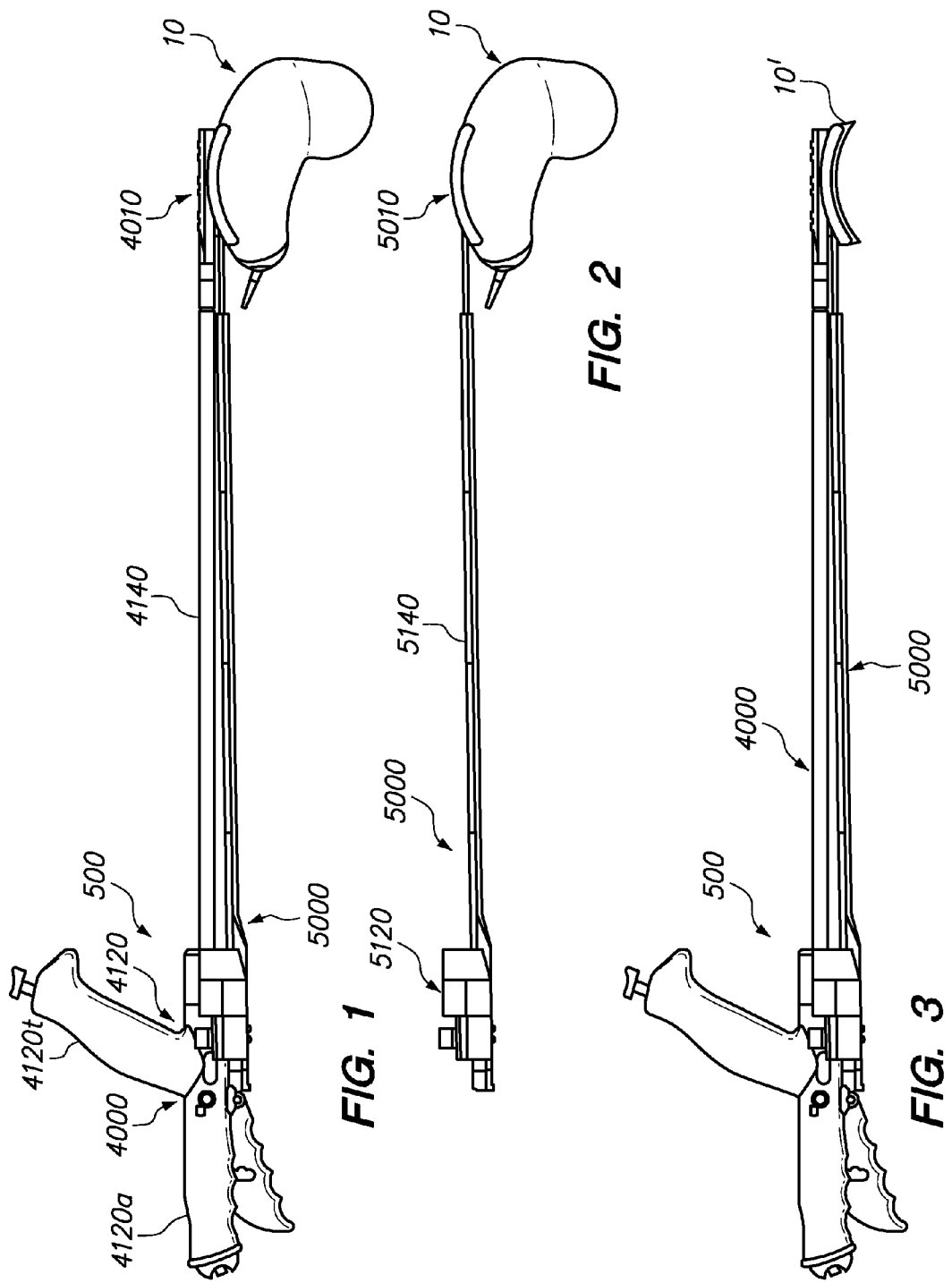

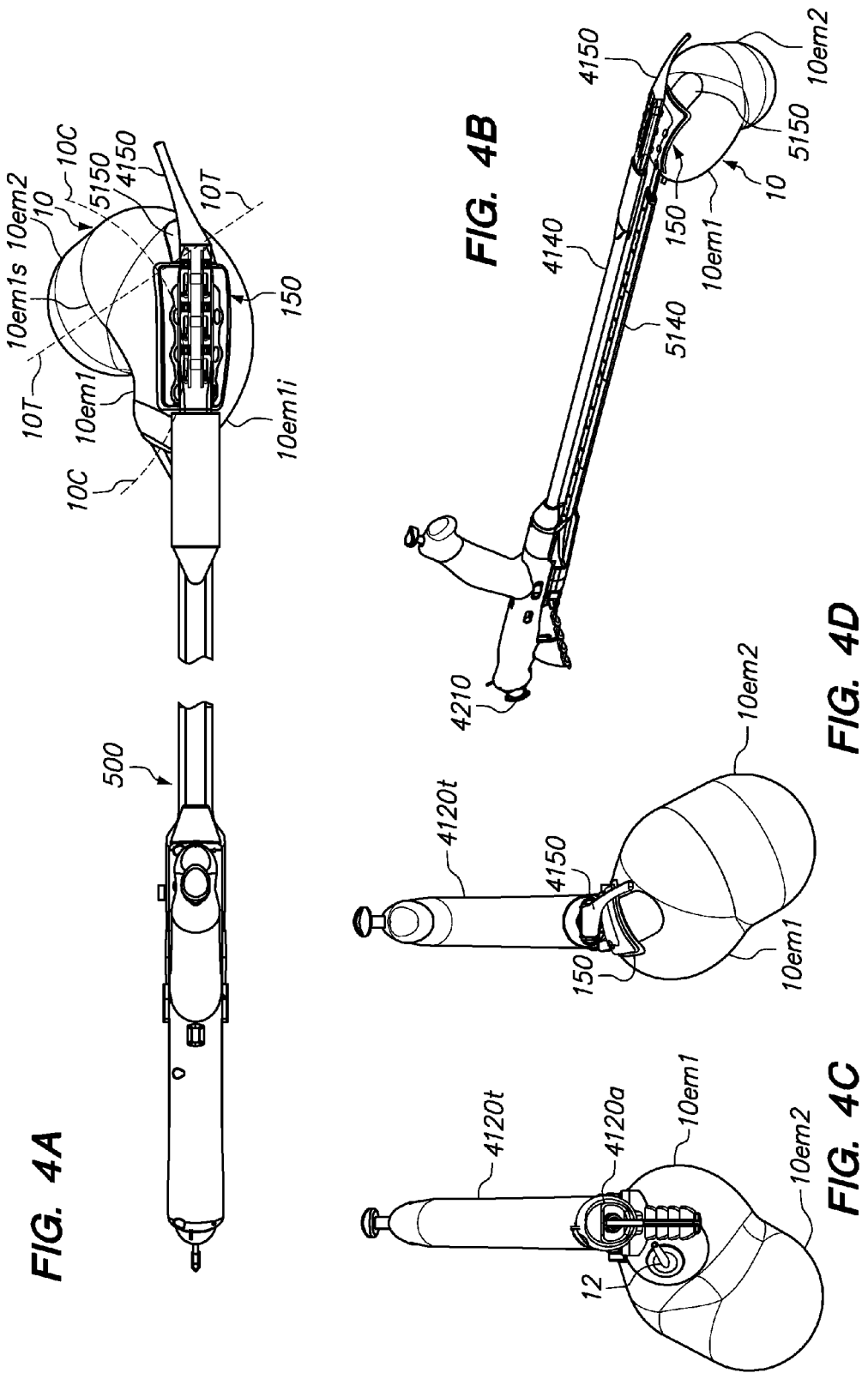

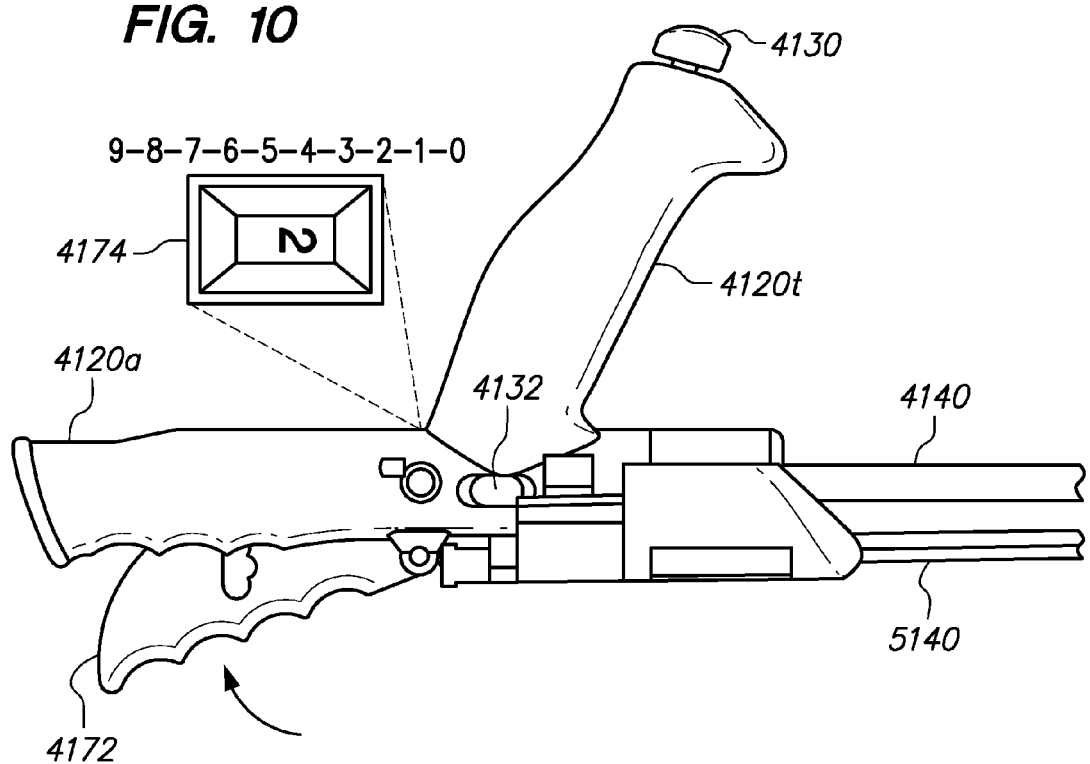

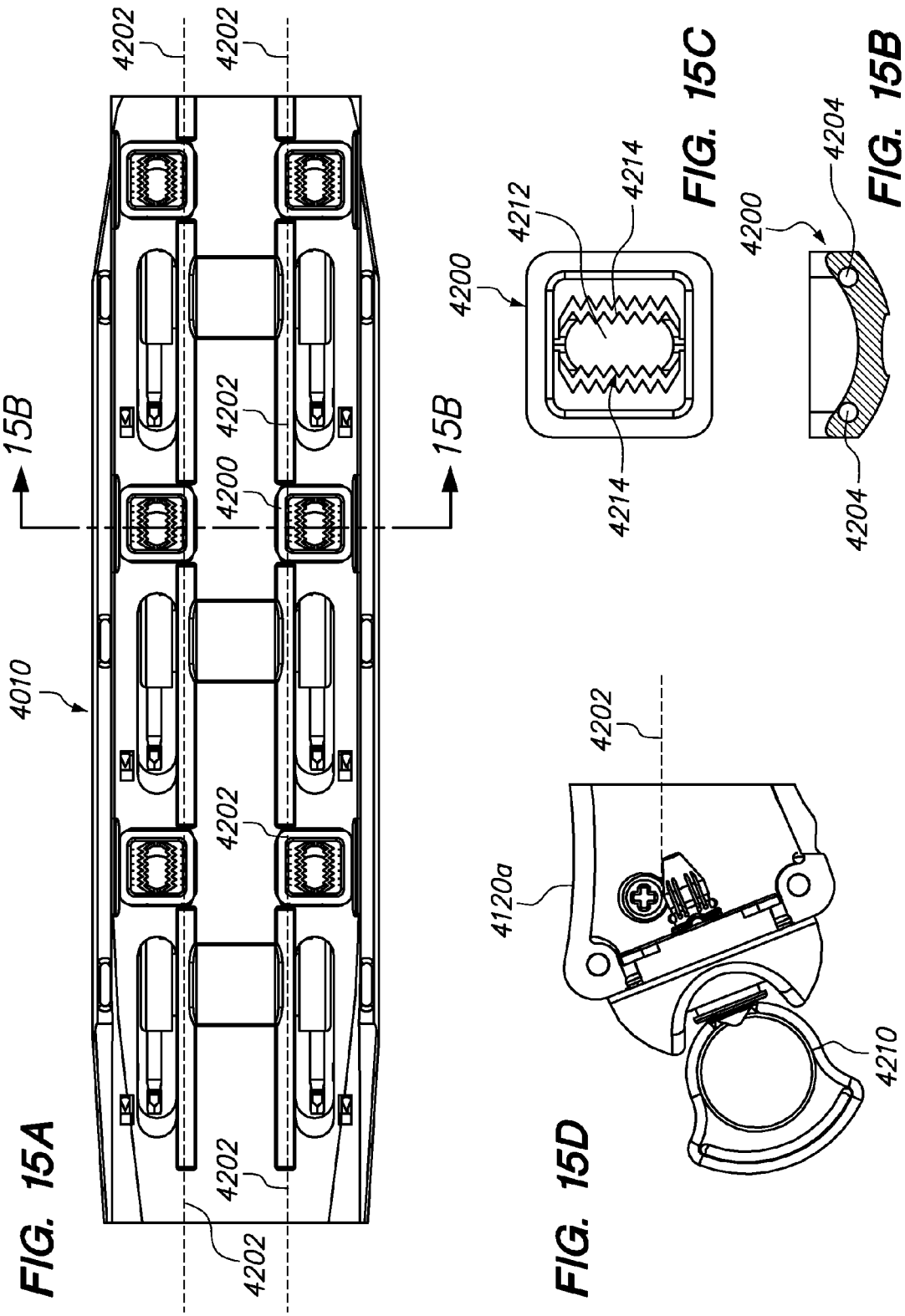

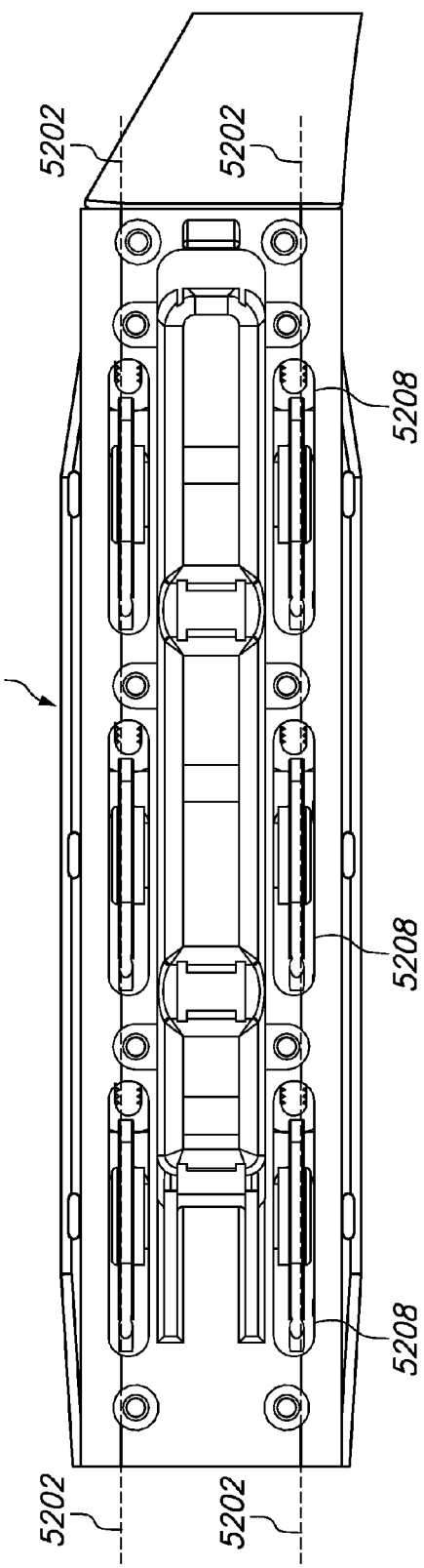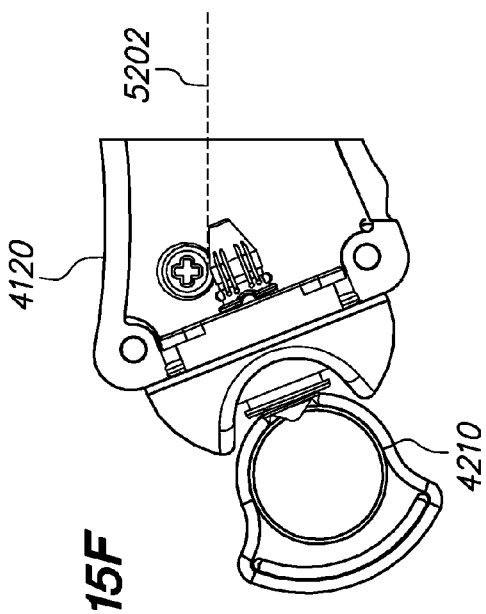

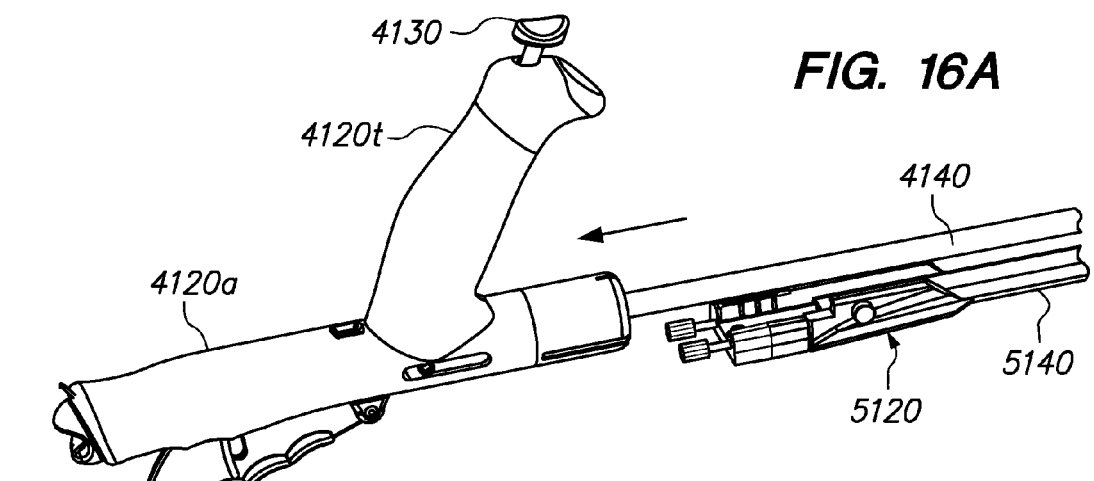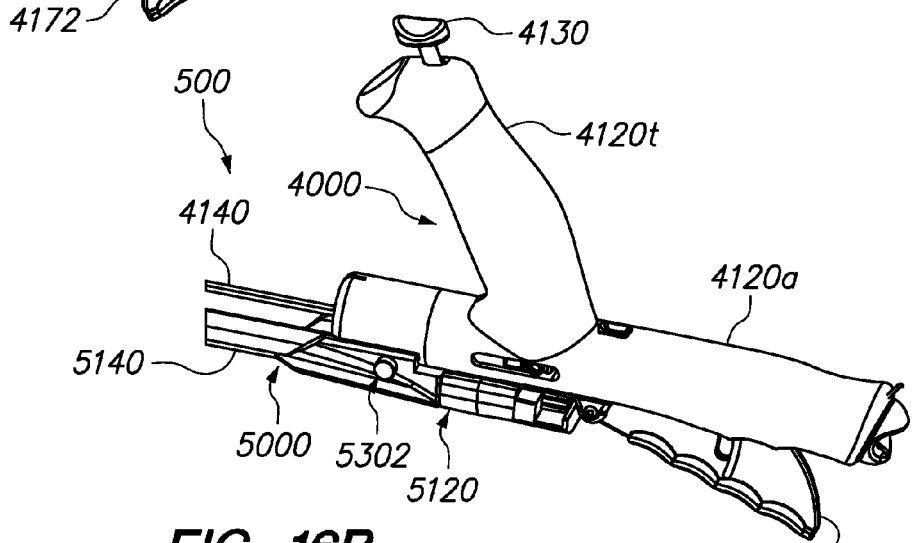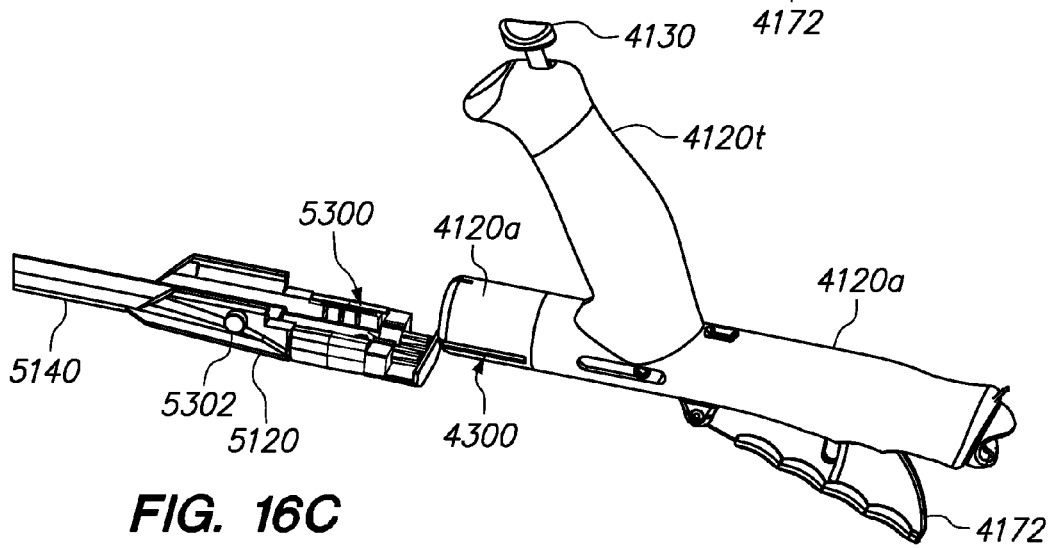

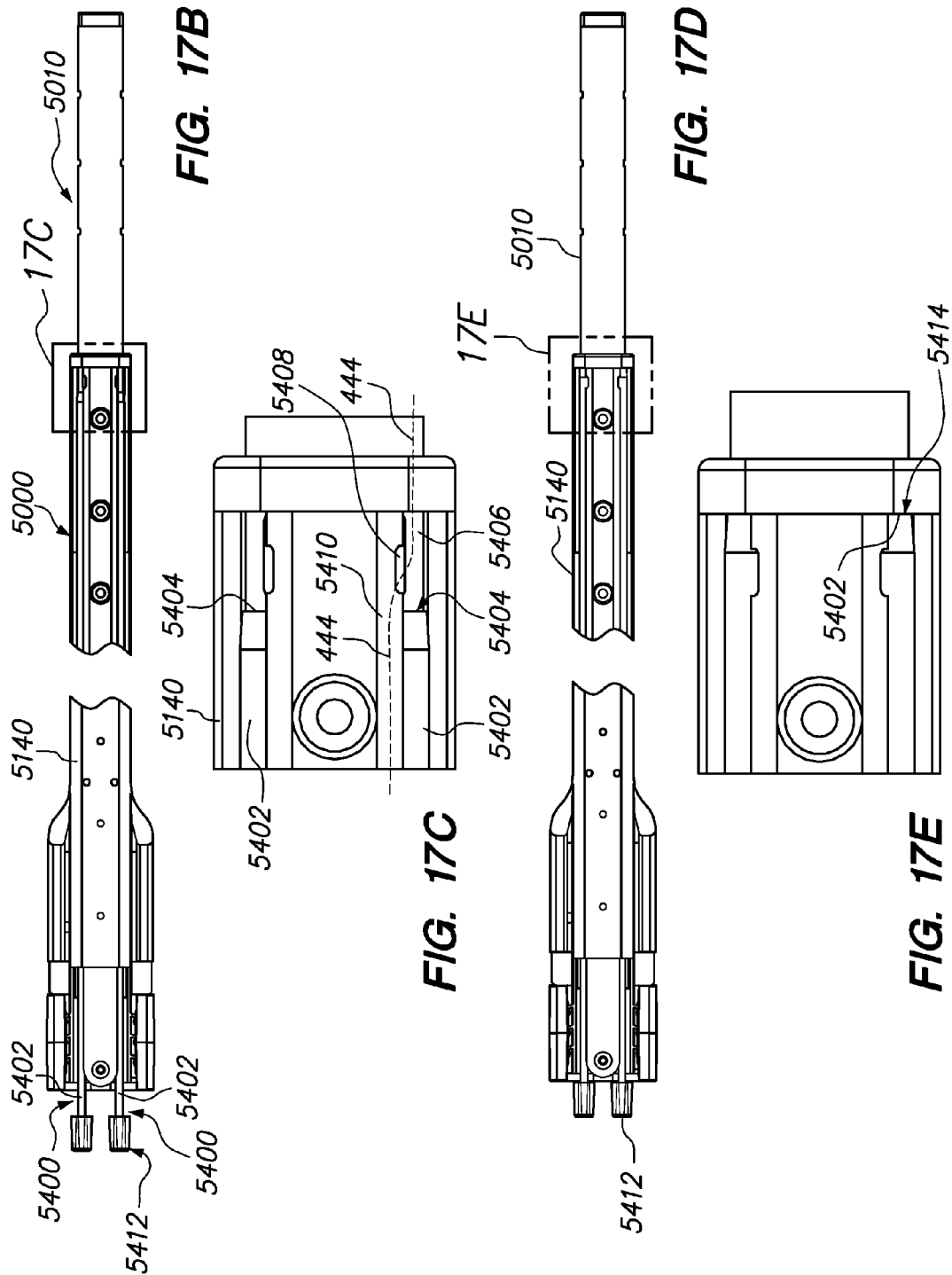

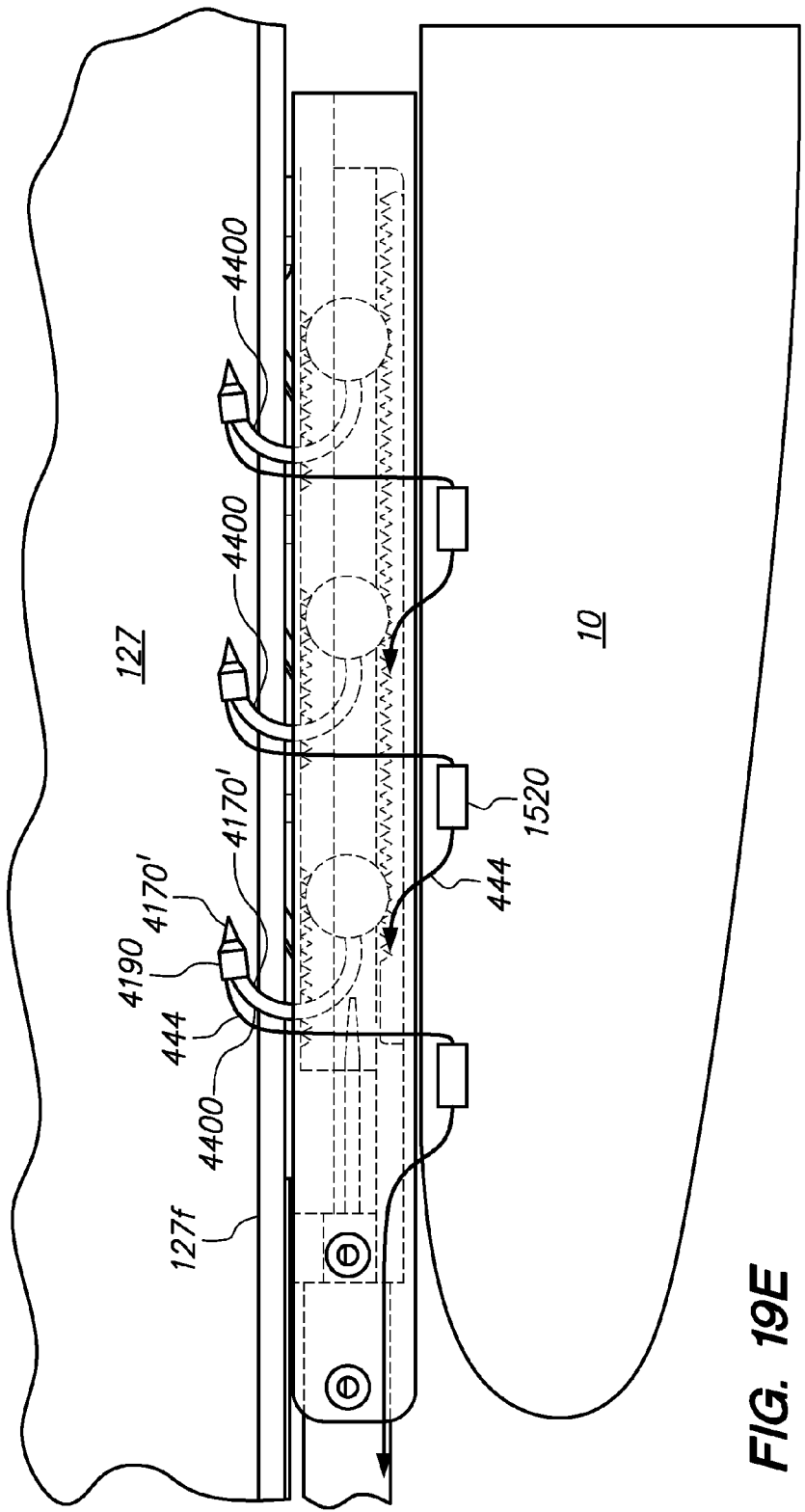

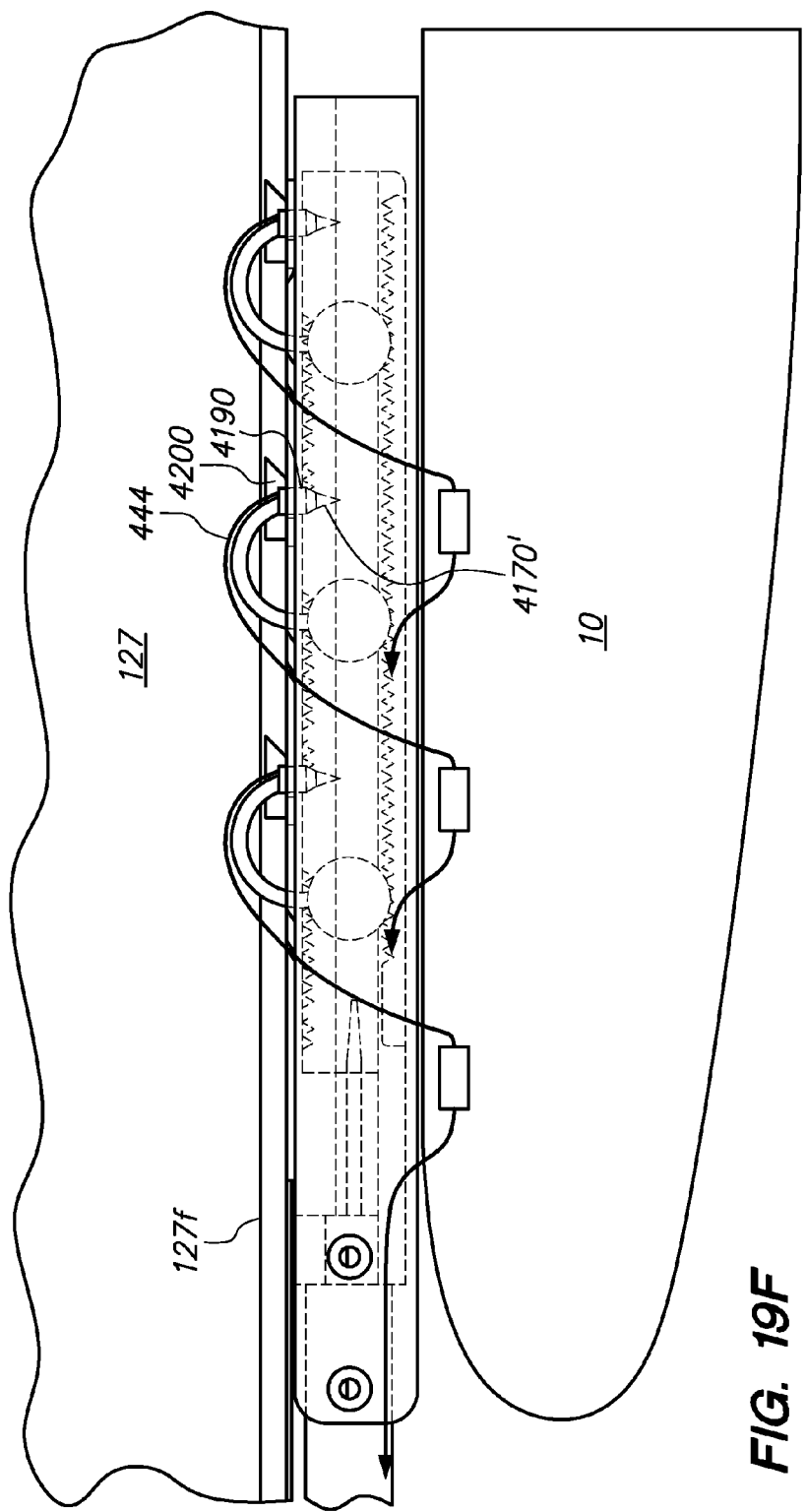

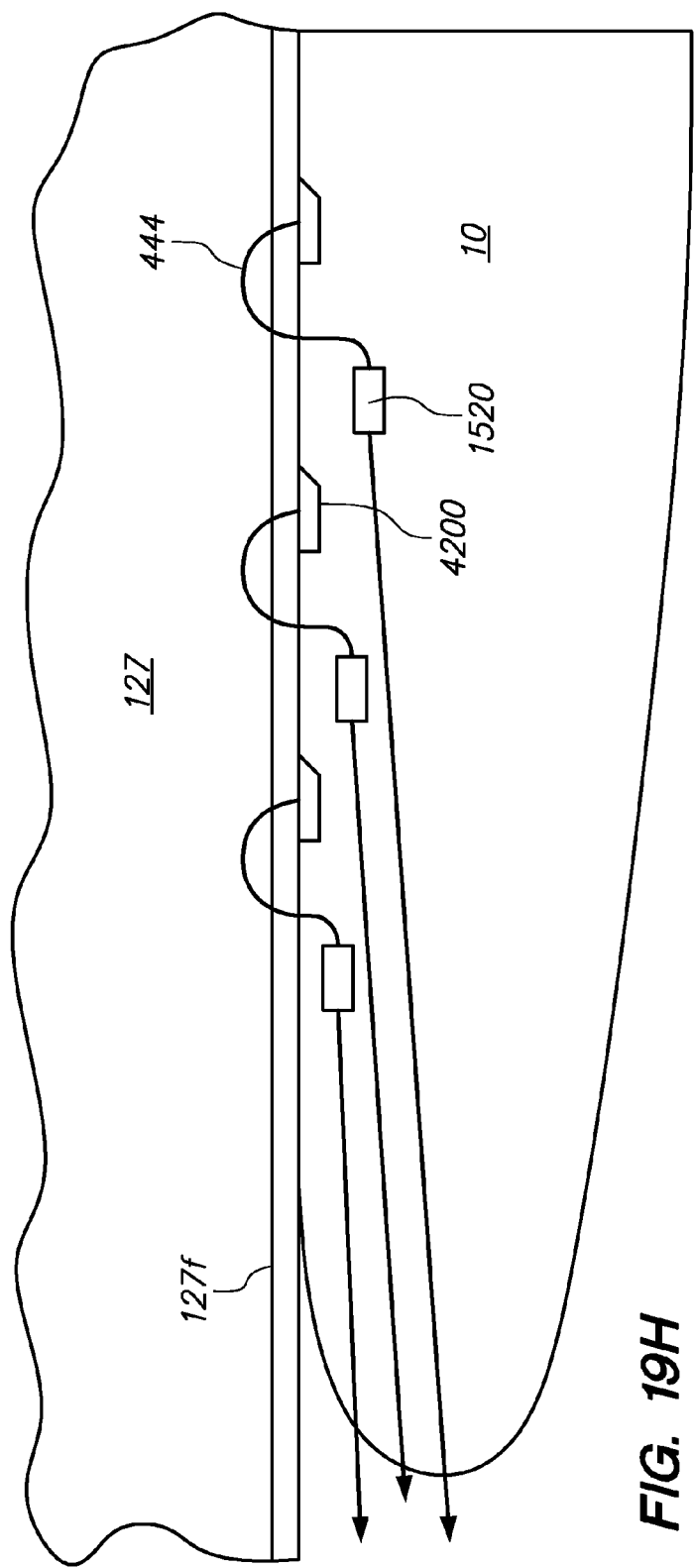

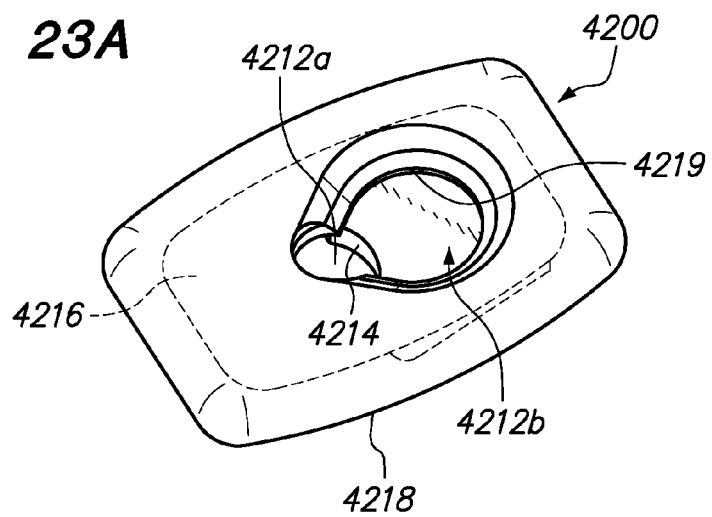
FIG. 23A
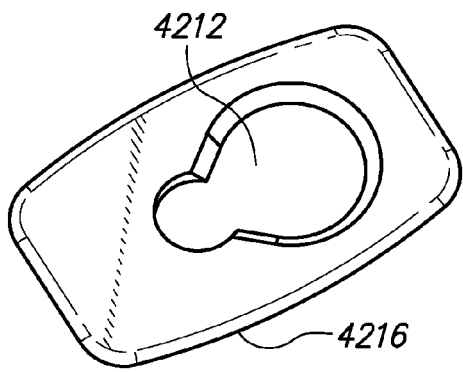
FIG. 23B
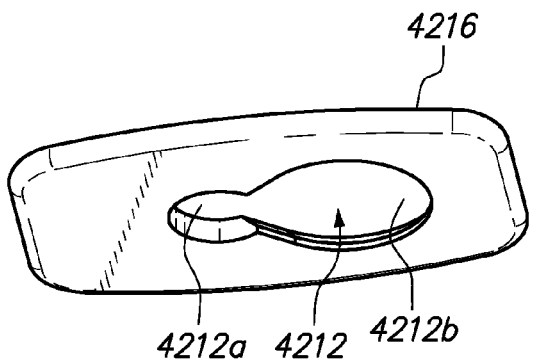
FIG. 23C
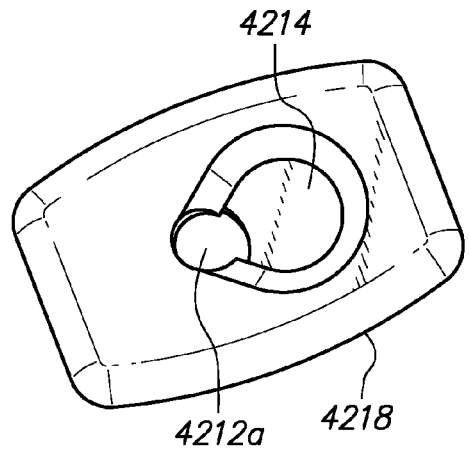
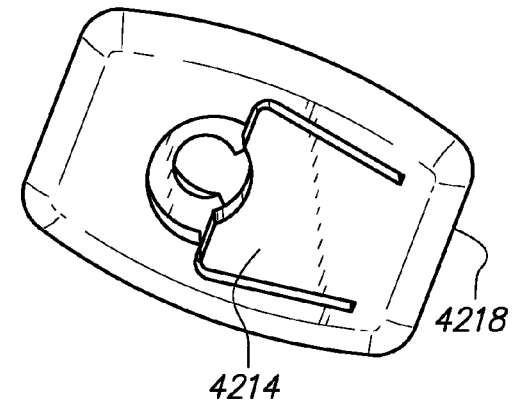
FIG. 23D  FIG. 23E

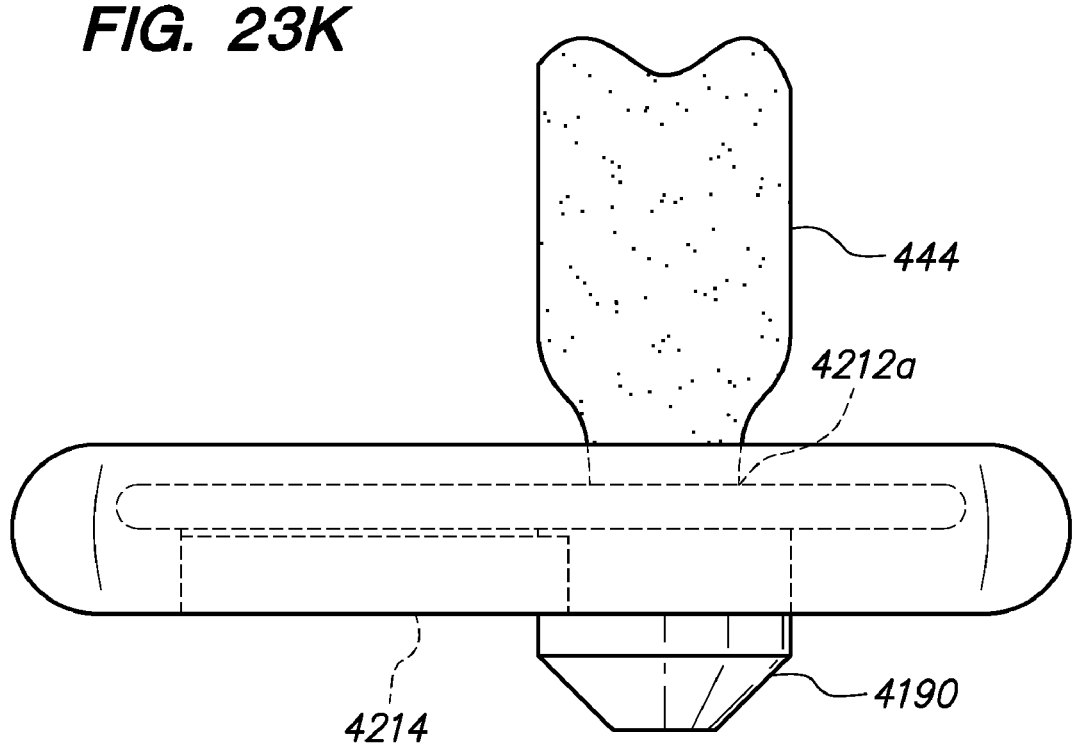

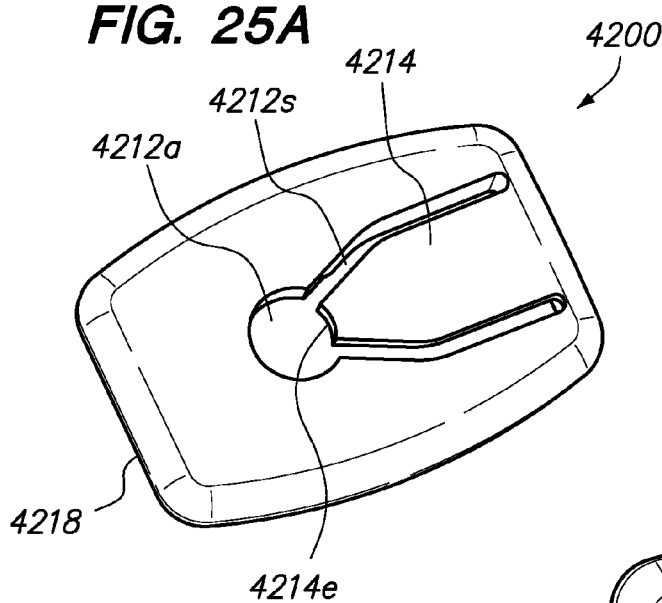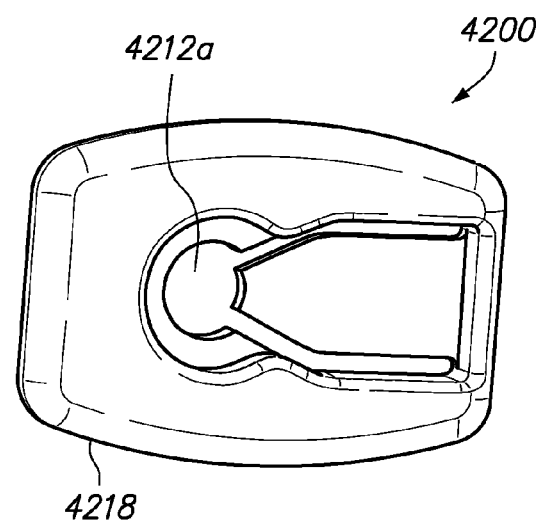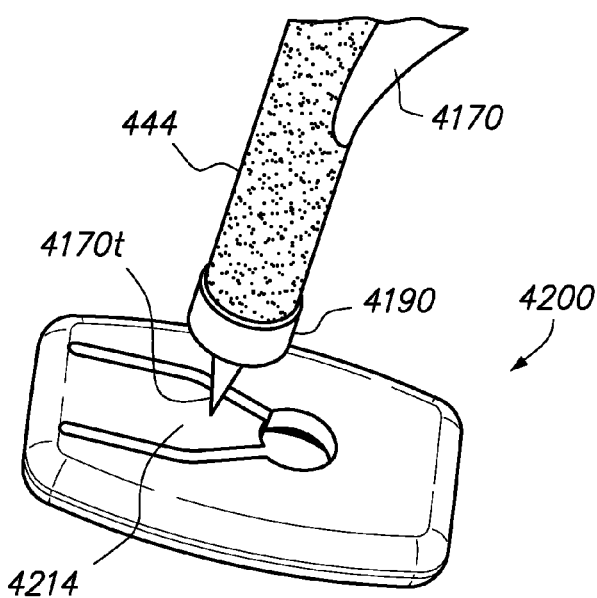

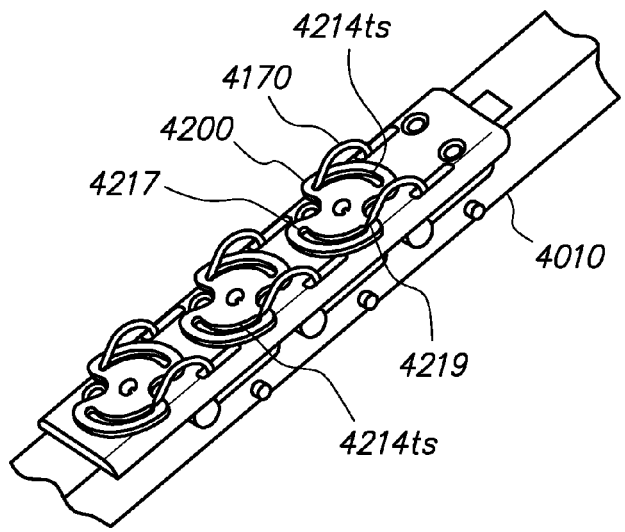
FIG. 32
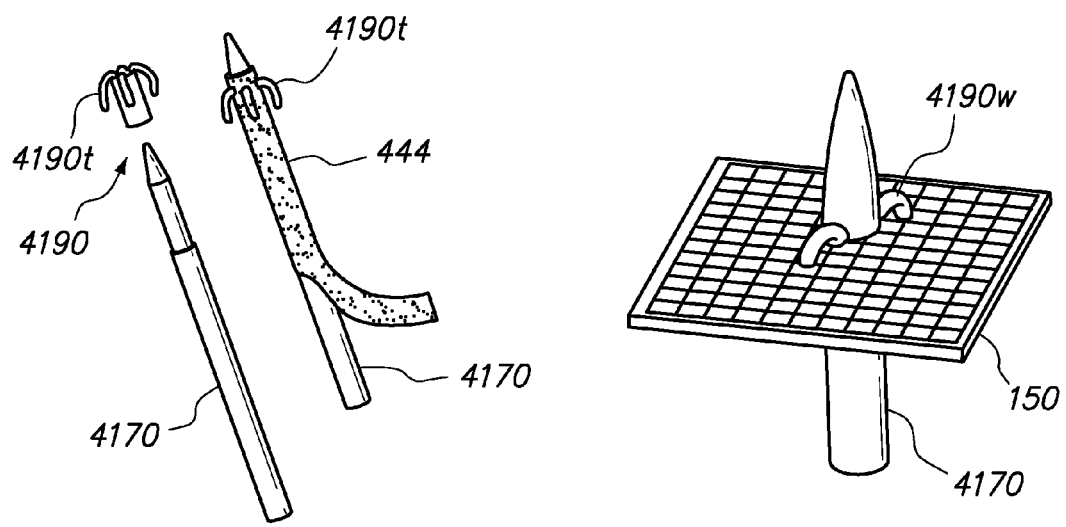
FIG. 33
FIG. 34

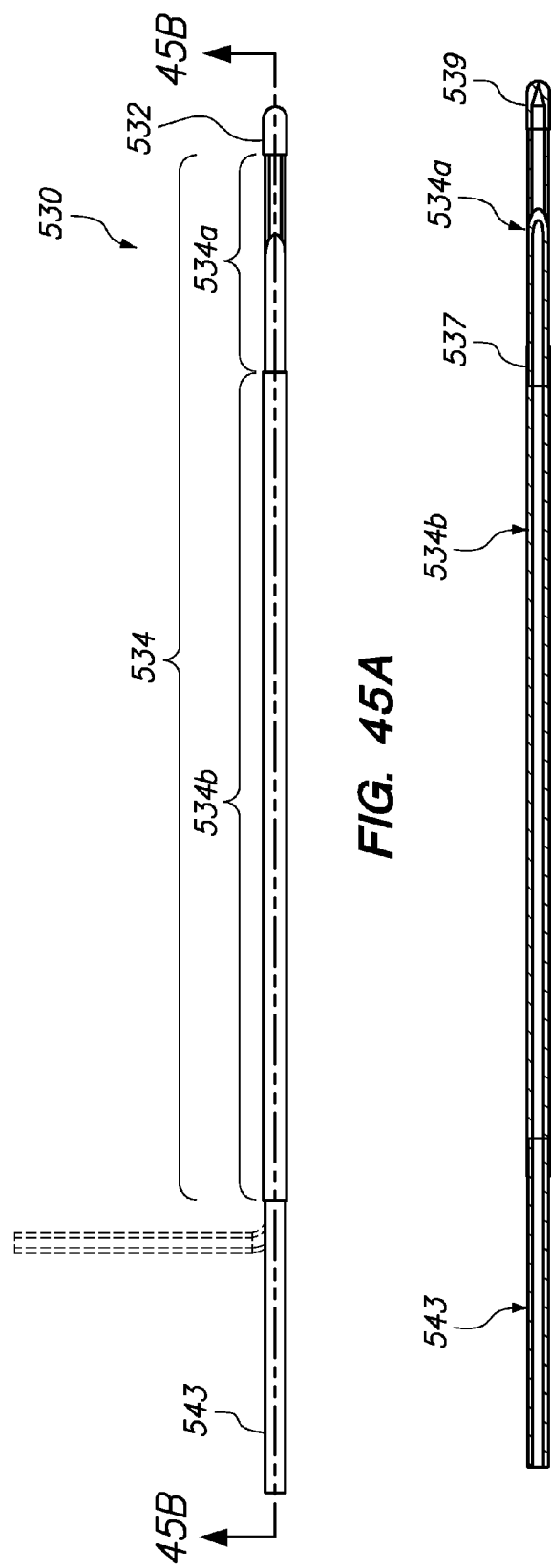
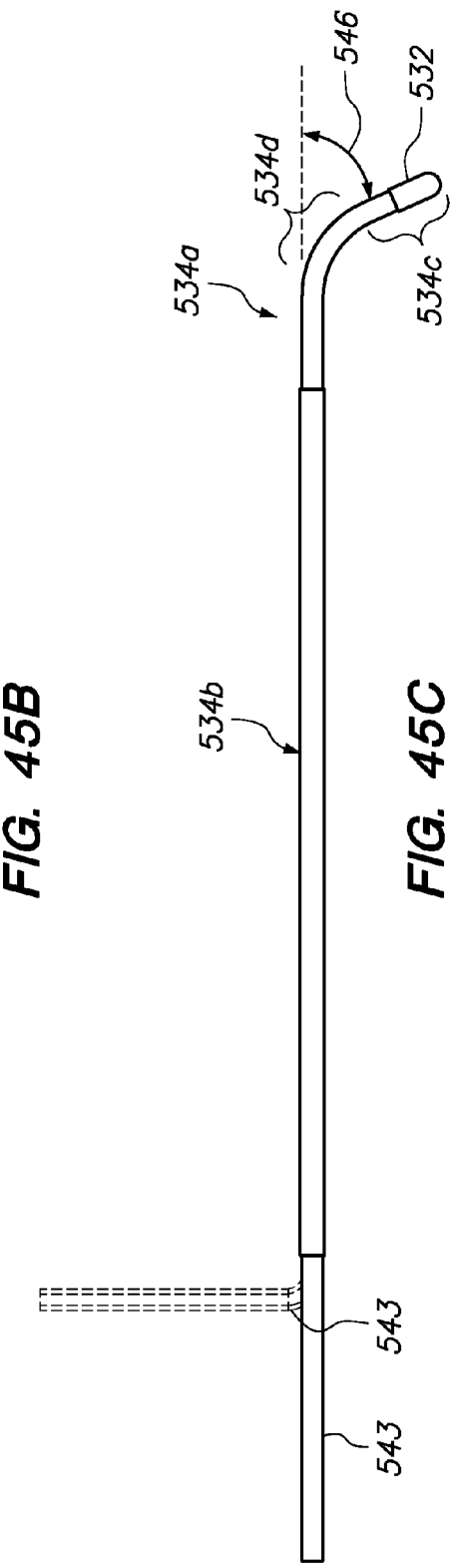
FIG. 45A
FIG. 45B
FIG. 45C

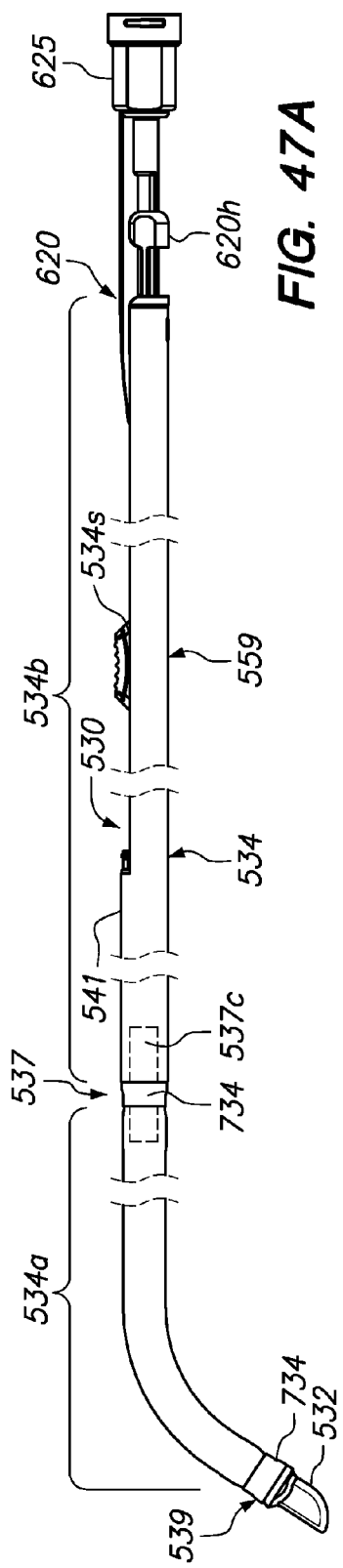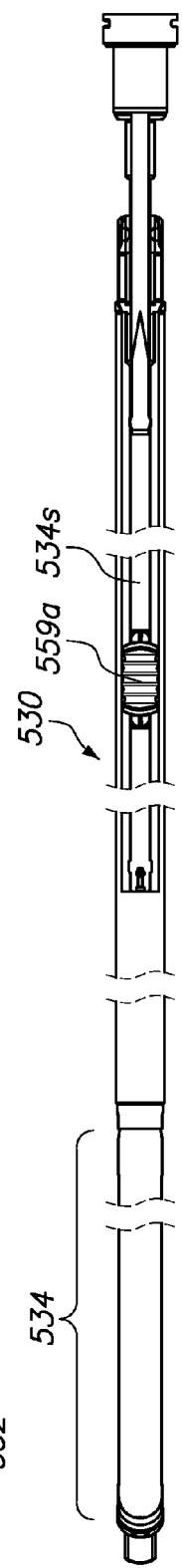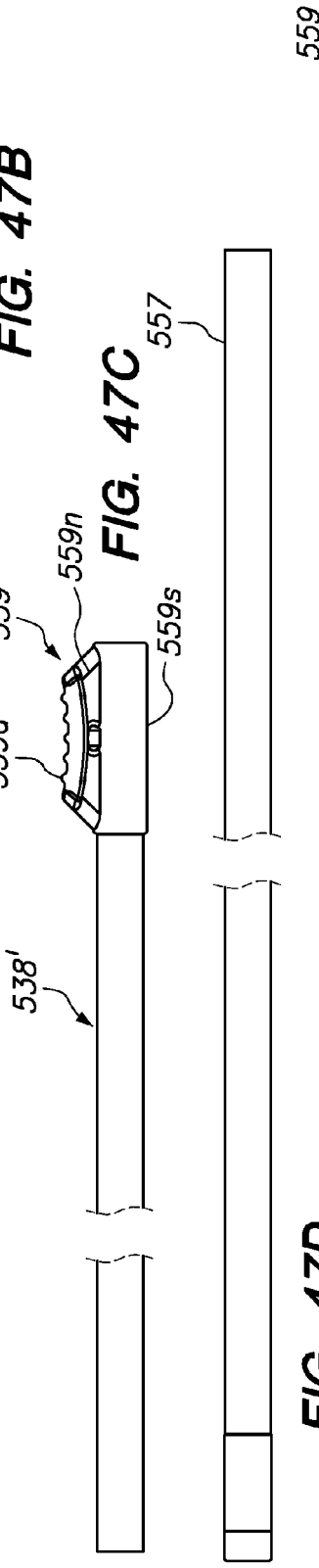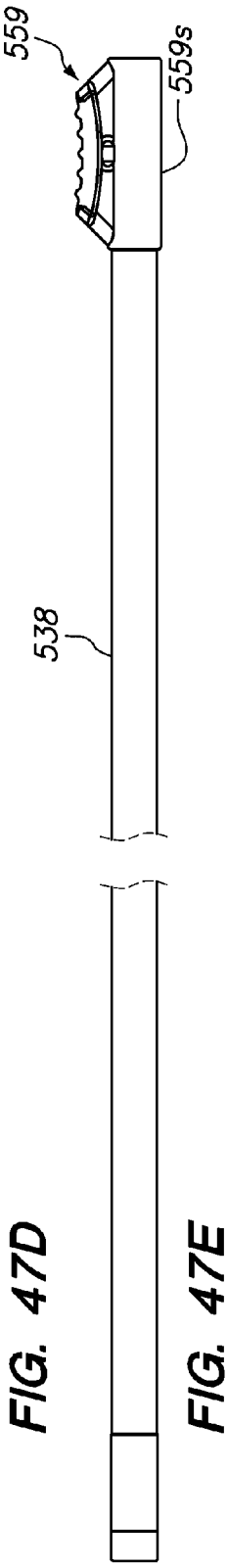
FIG. 47A  FIG. 47B  FIG. 47C  FIG. 47D  FIG. 47E

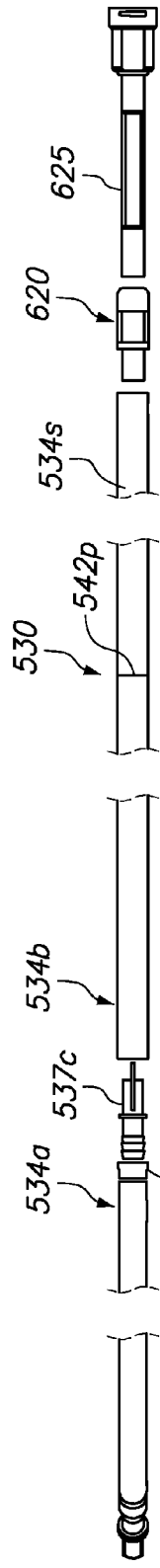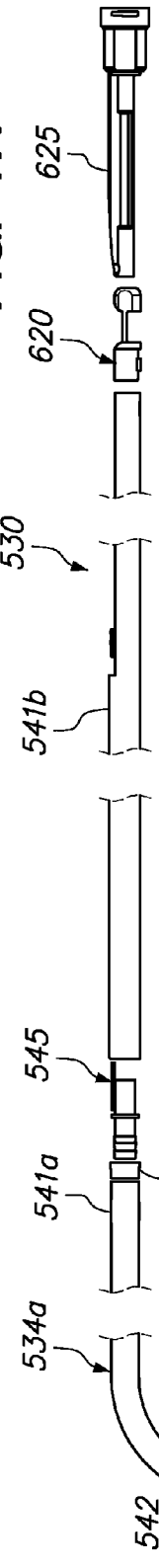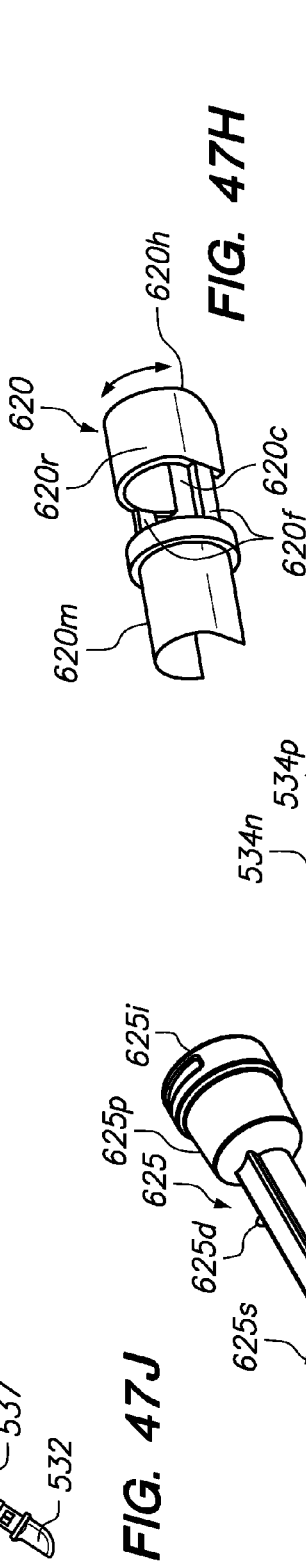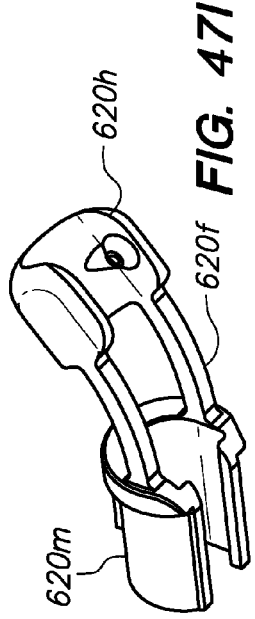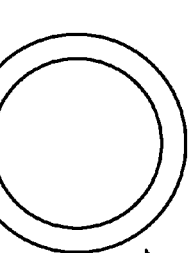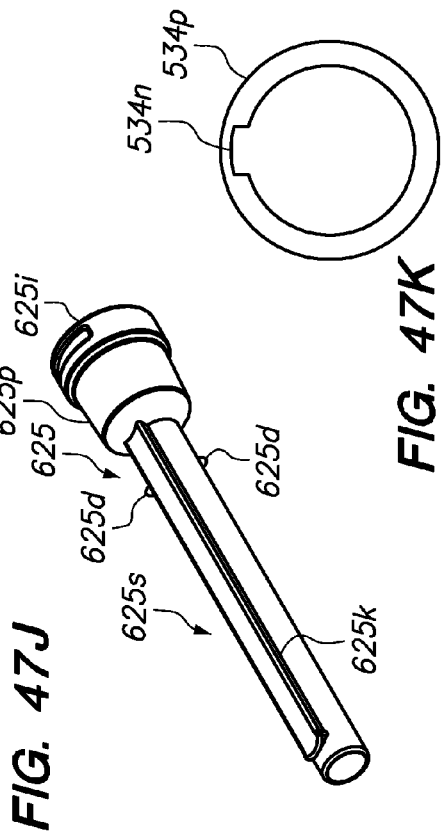

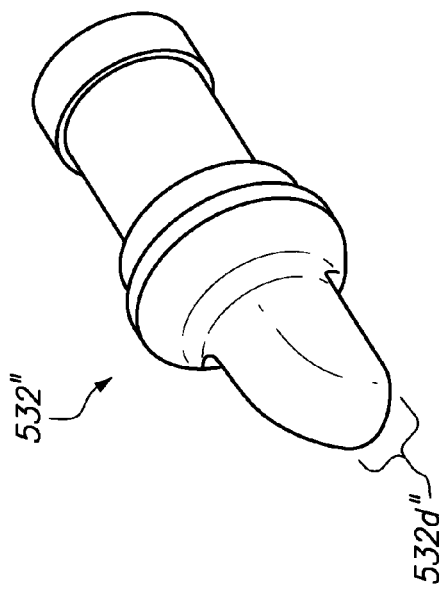
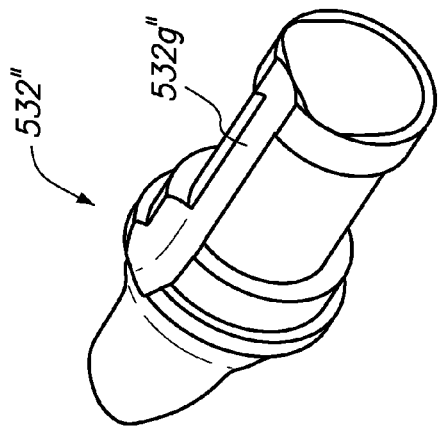
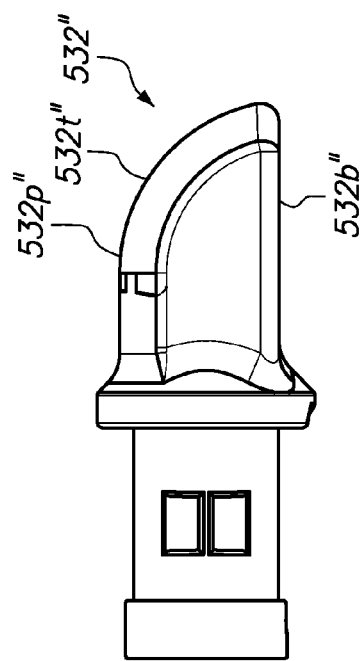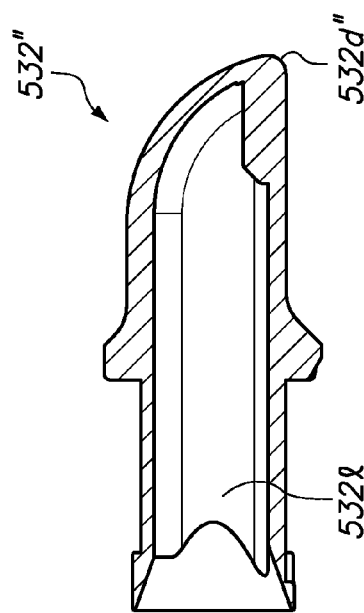

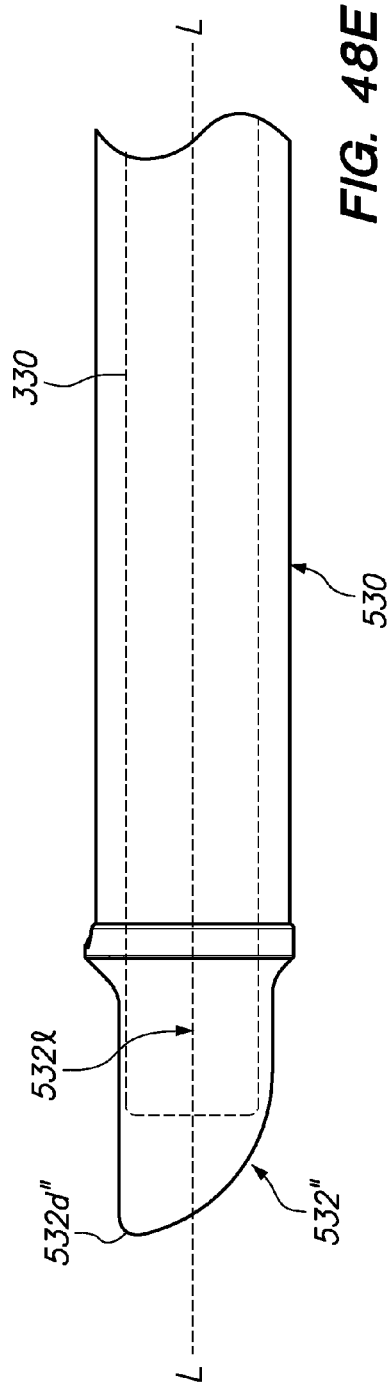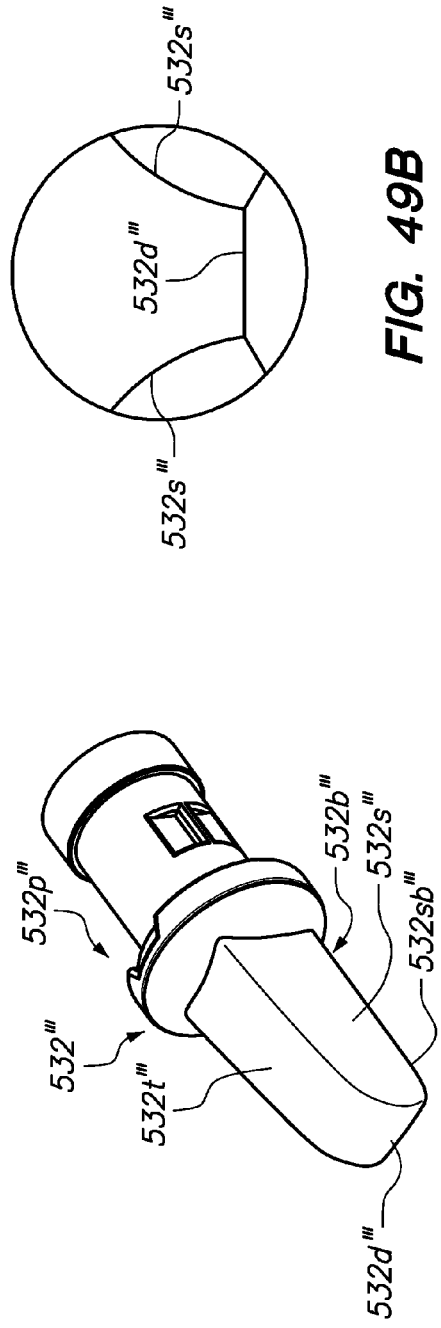

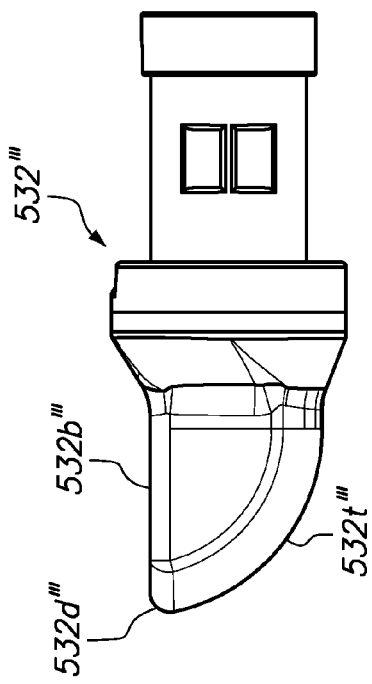
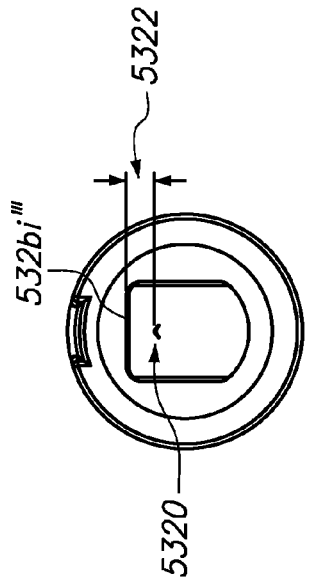
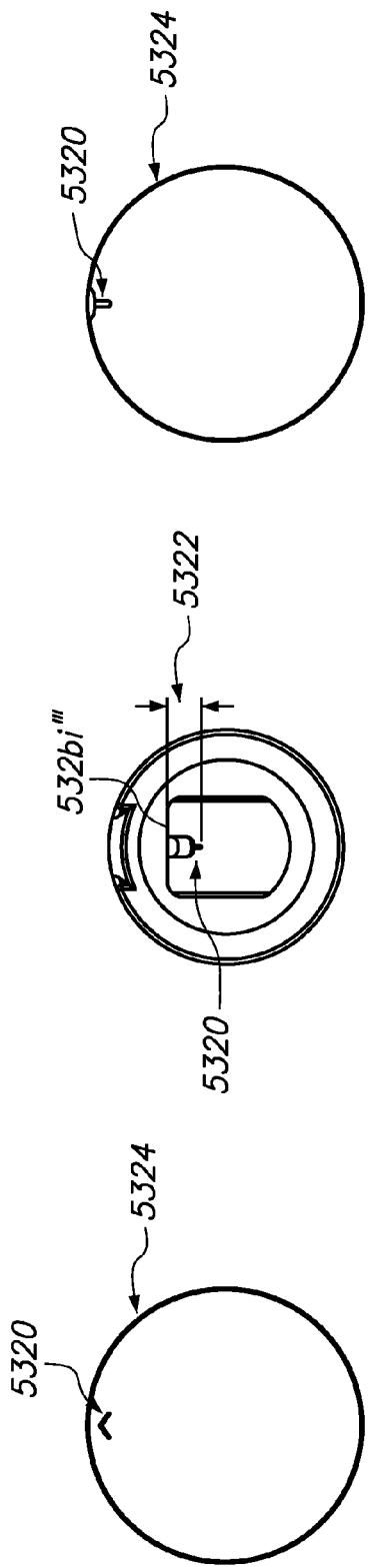
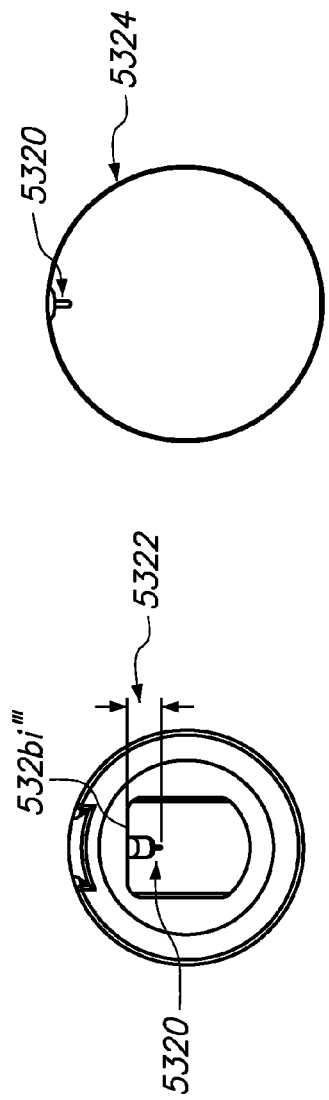
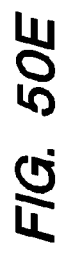

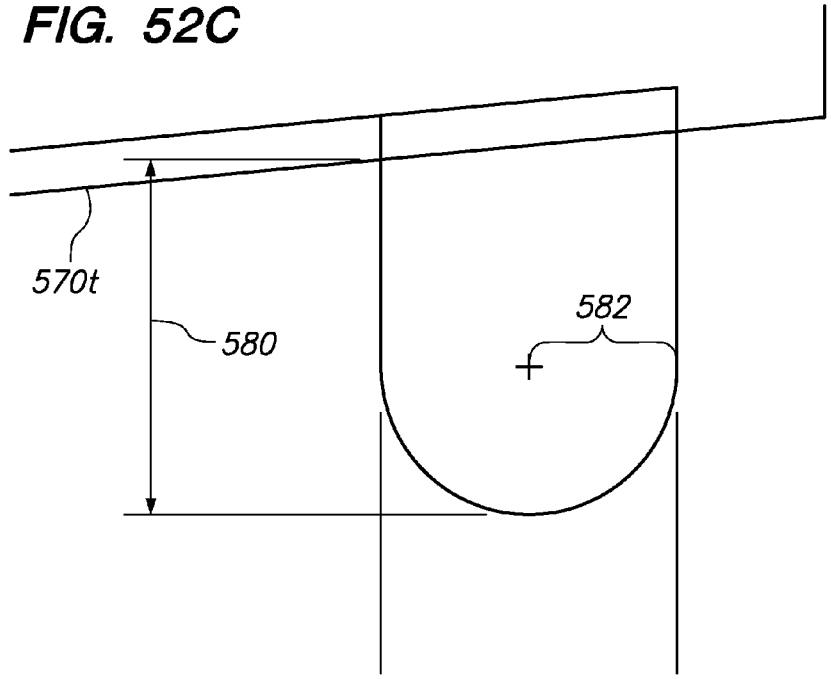
FIG. 52C
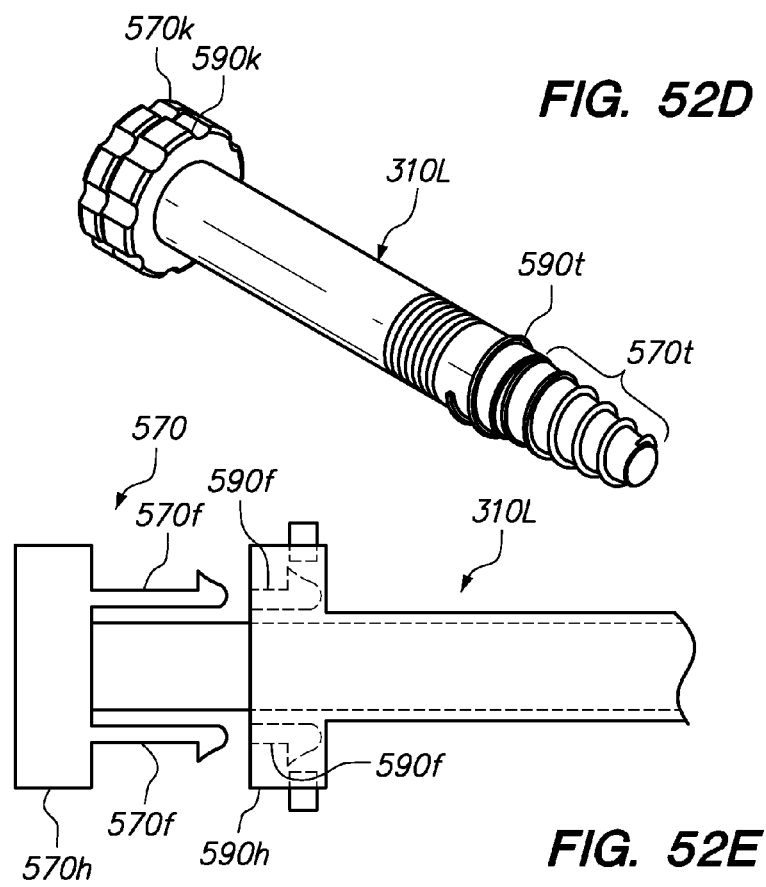
FIG. 52D
FIG. 52E

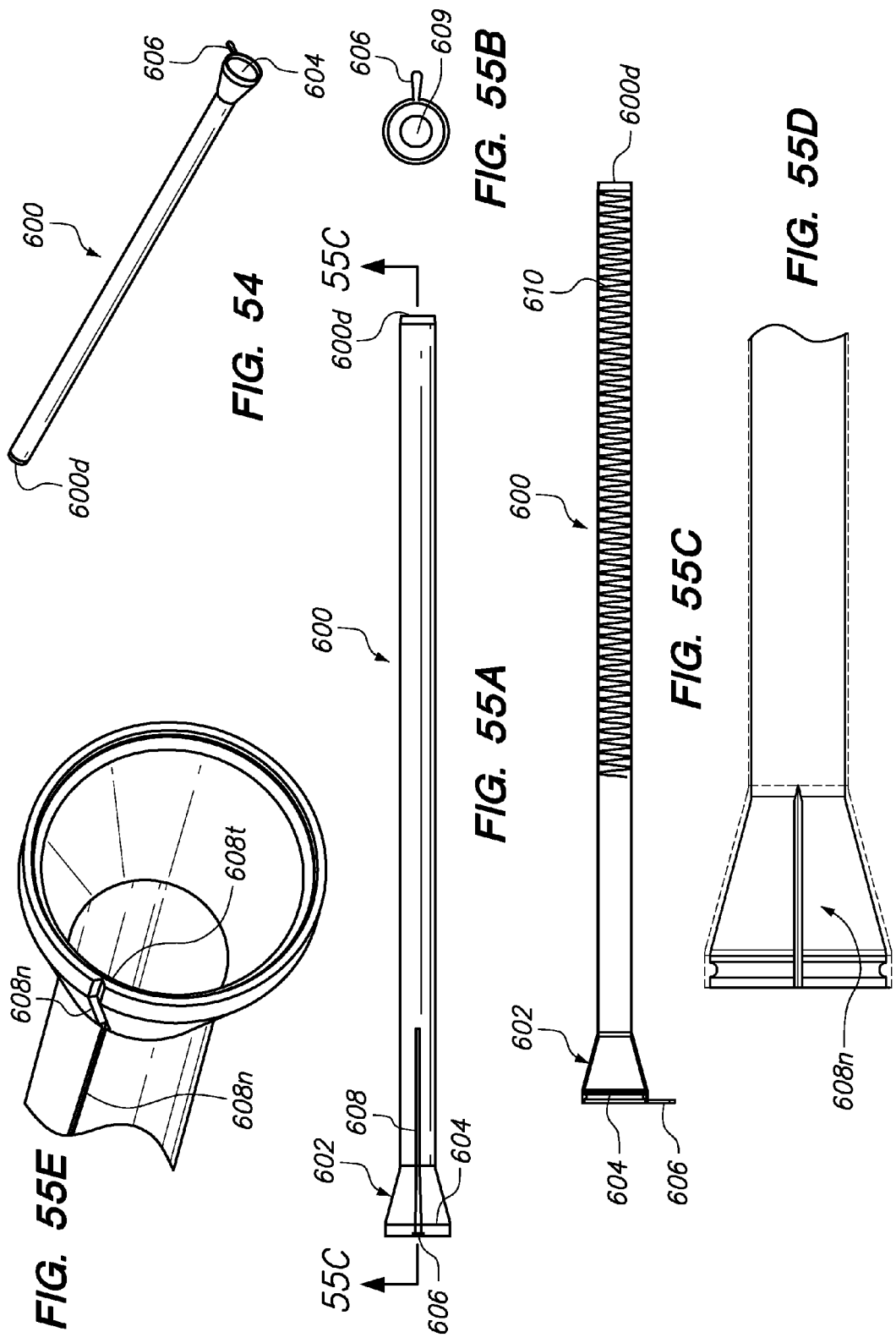

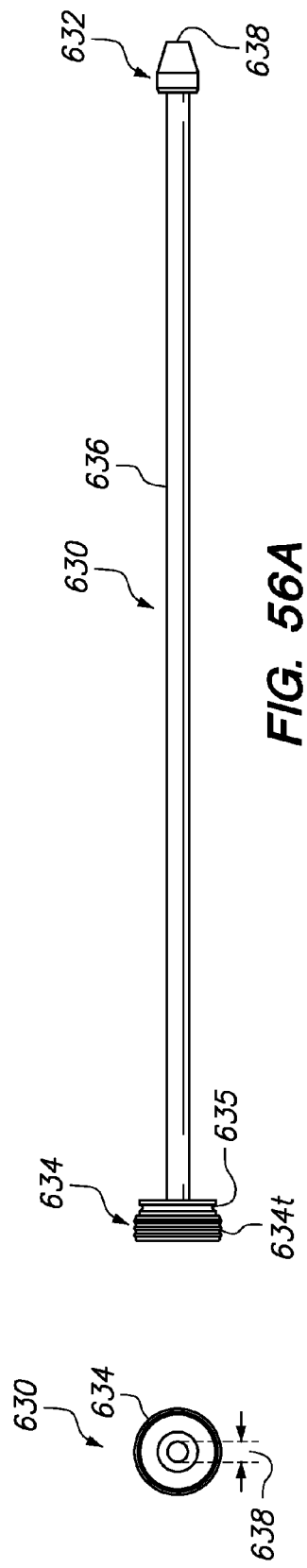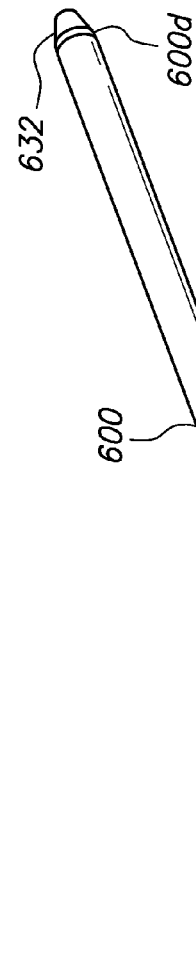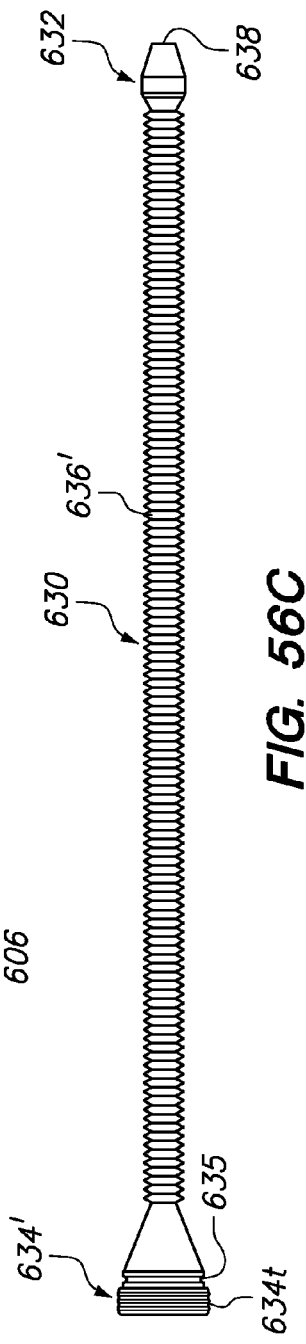
FIG. 56A
FIG. 56B
FIG. 56C
FIG. 57

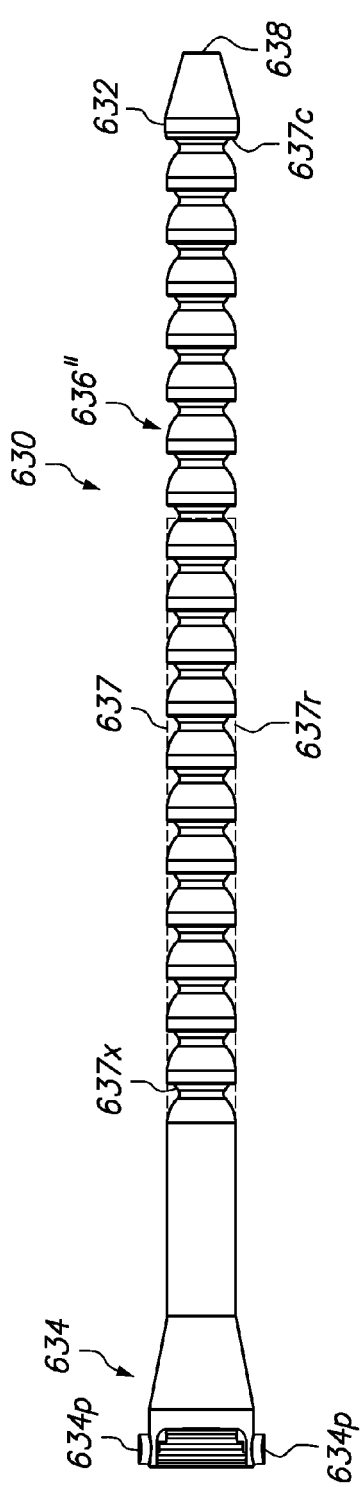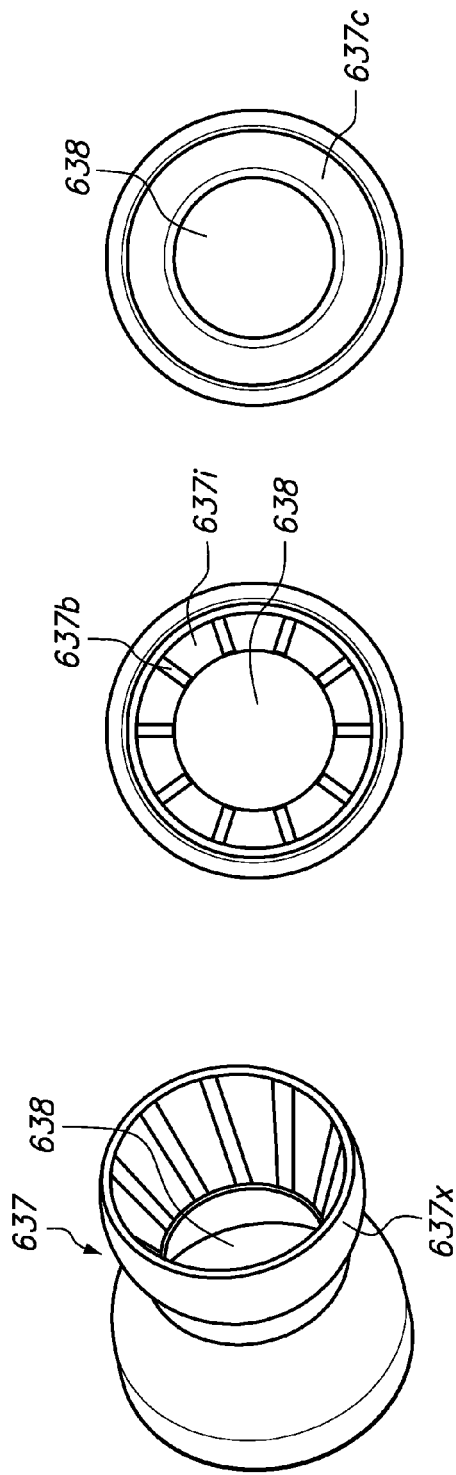

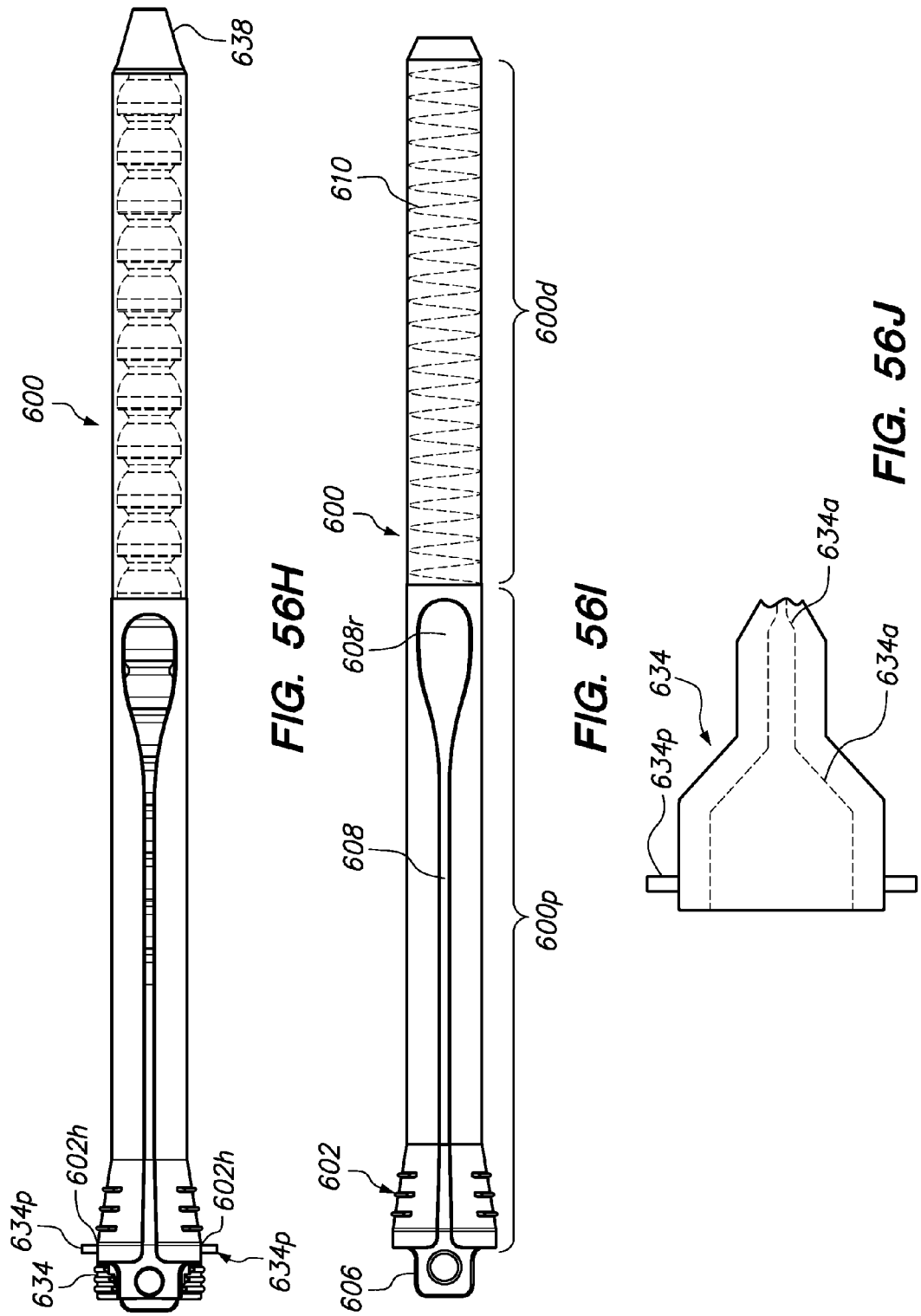

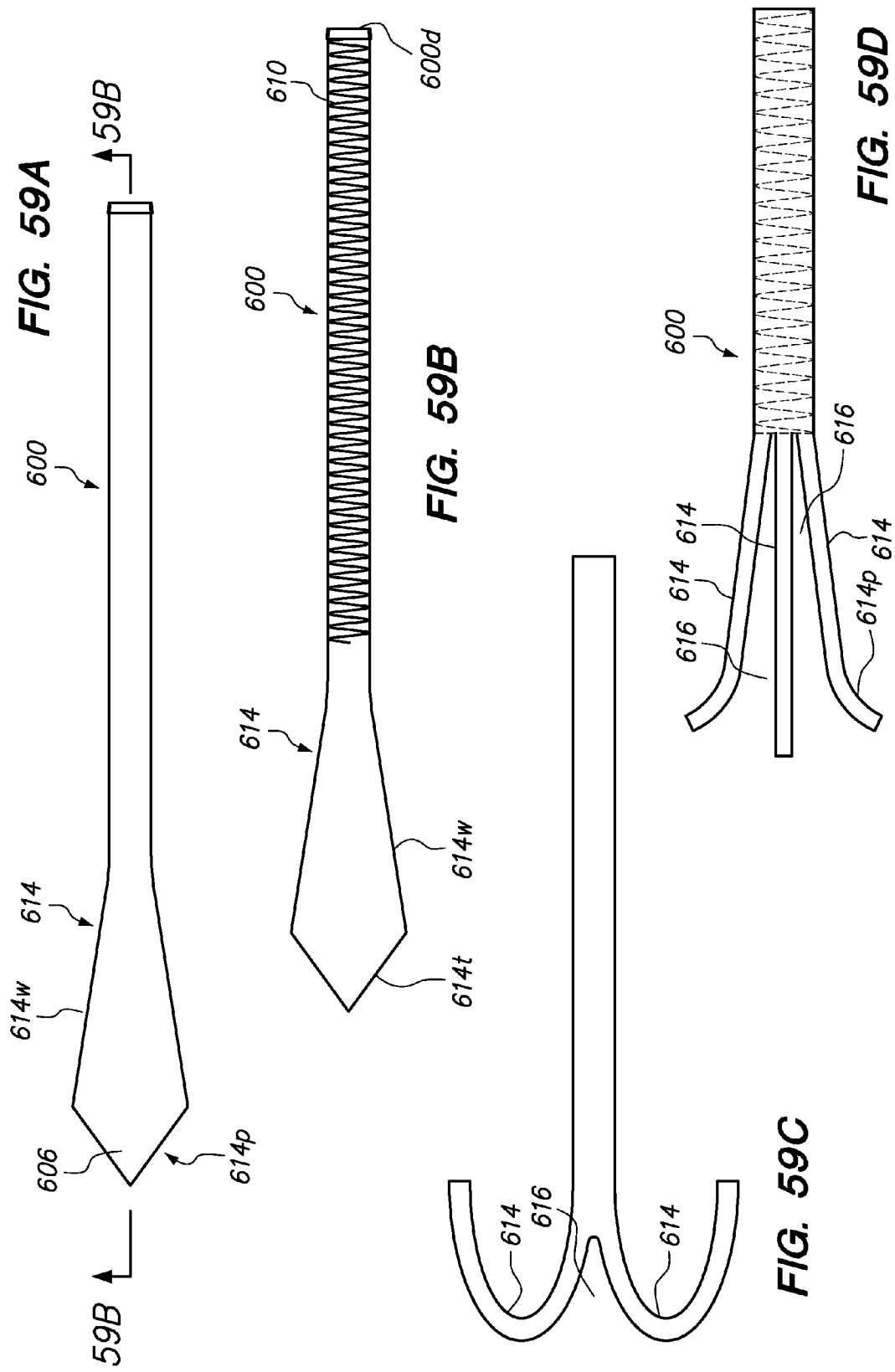

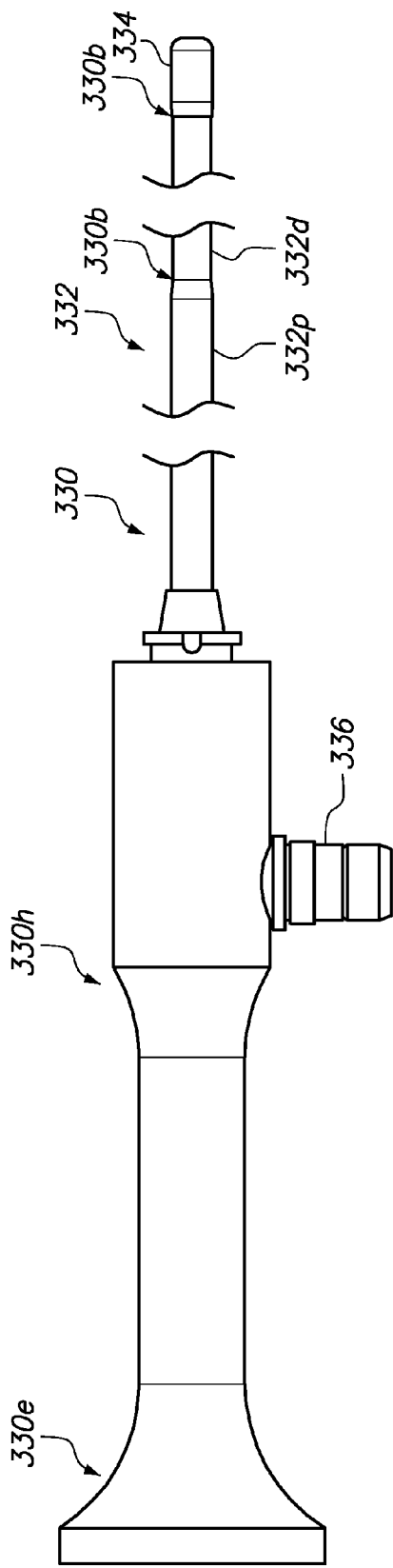
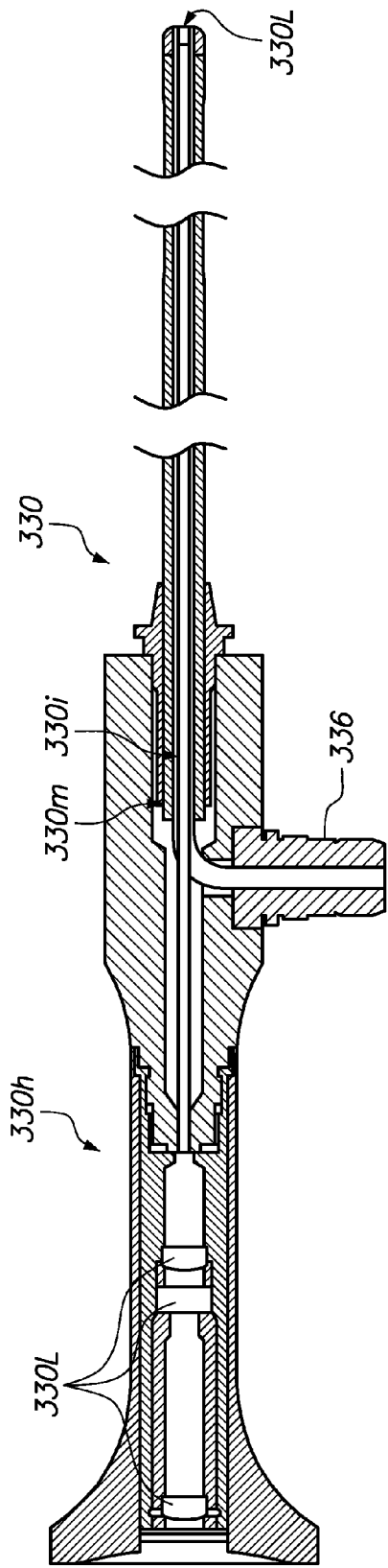
FIG. 62A
FIG. 62B

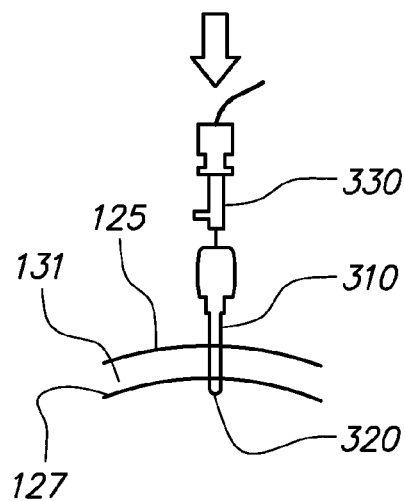
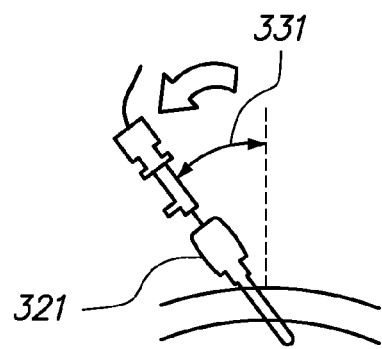
FIG. 63B   FIG. 63C
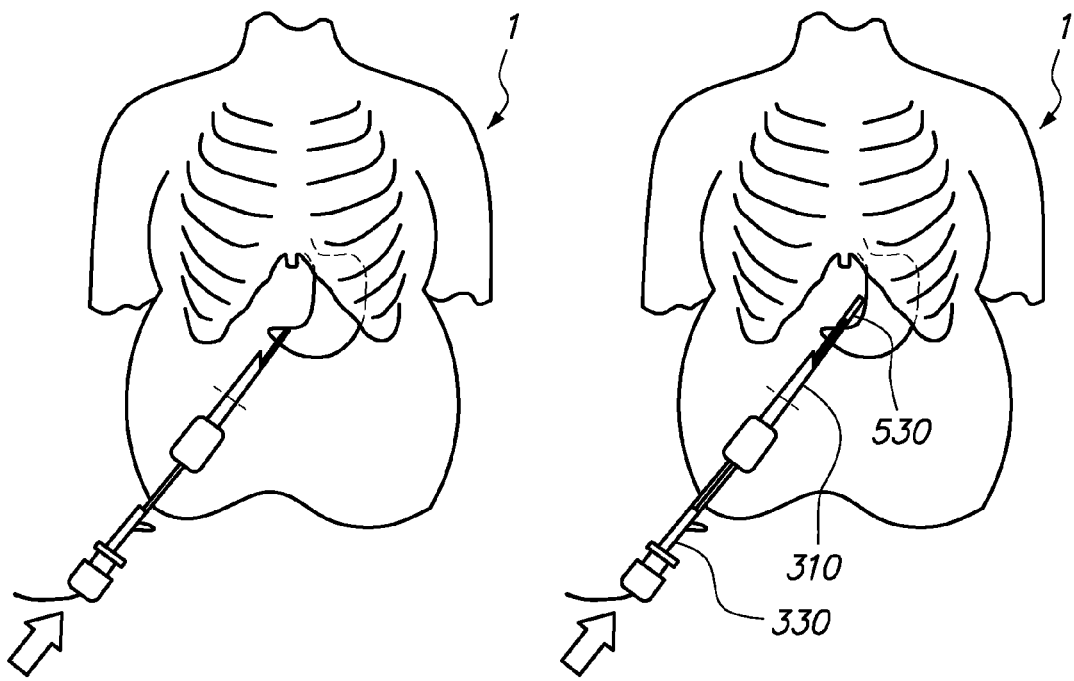
FIG. 63F   FIG. 63G

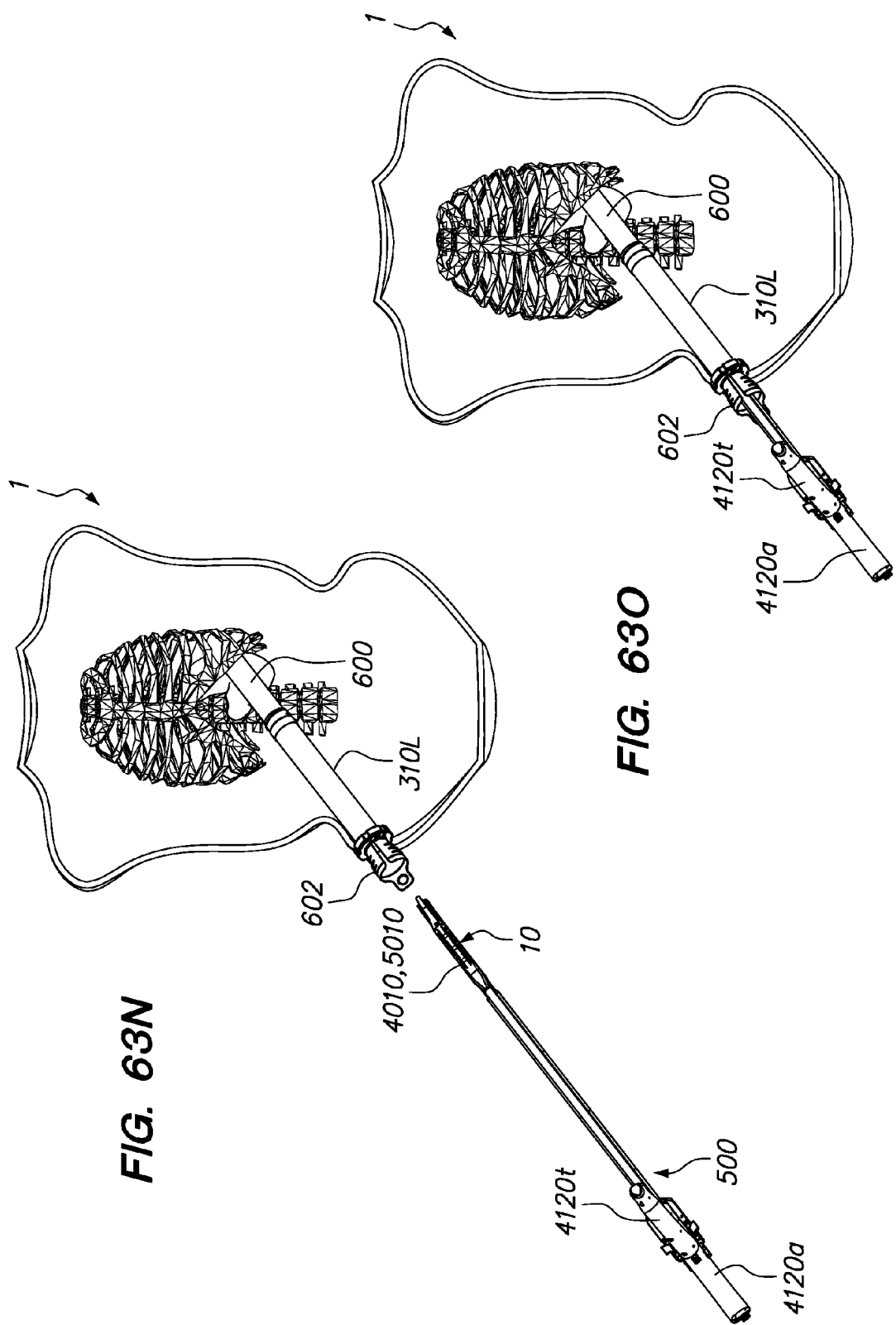

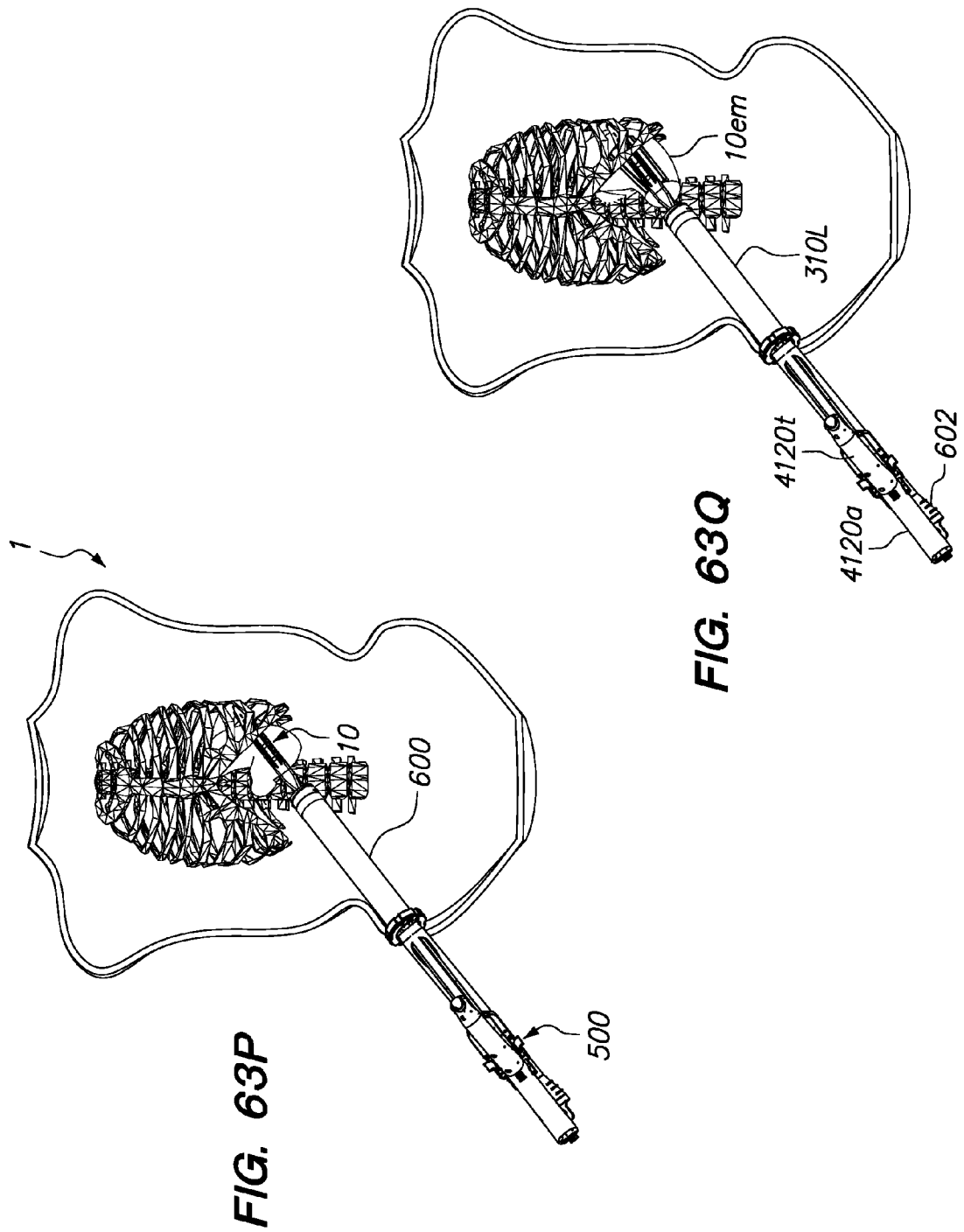

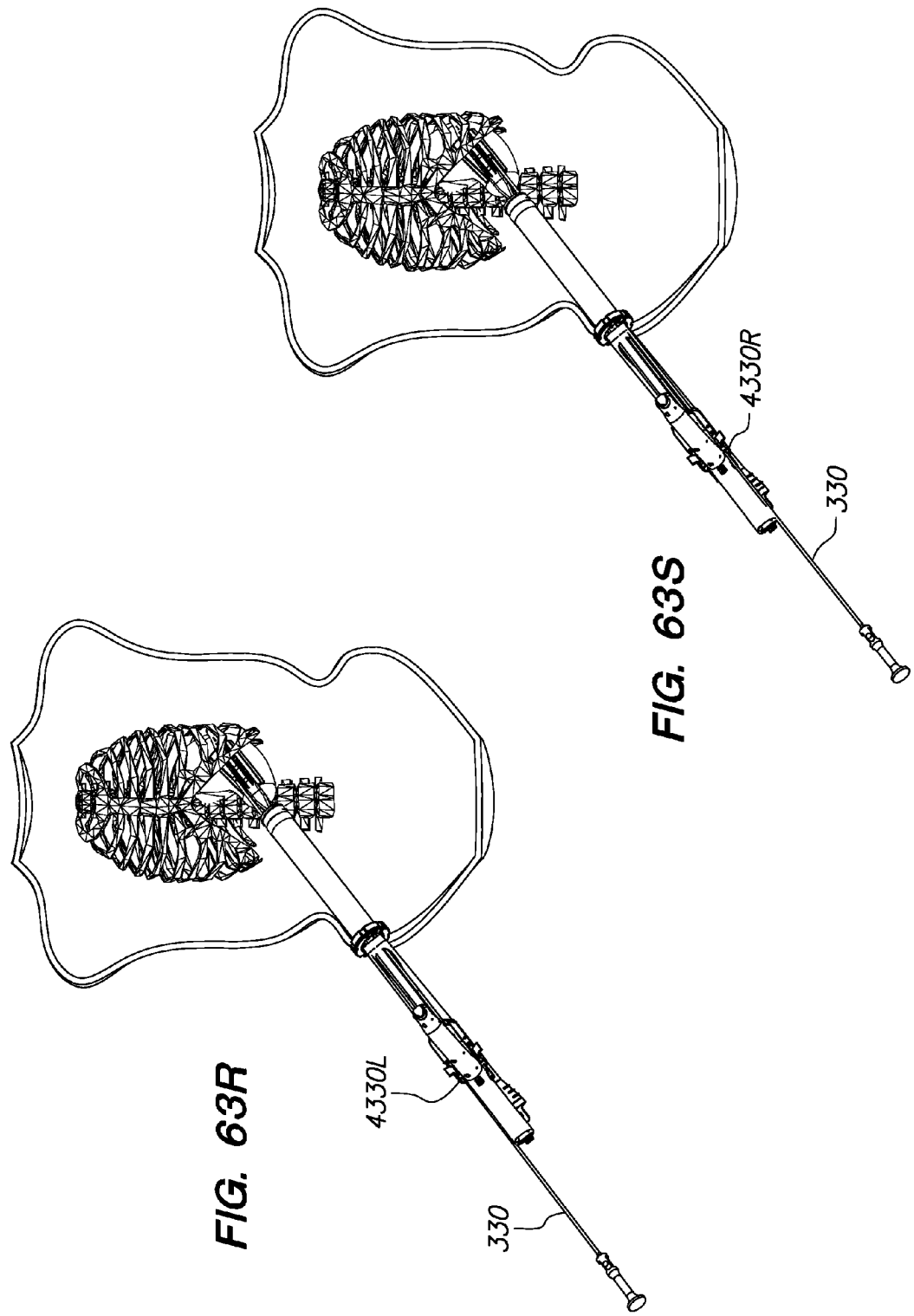

DEVICES, TOOLS AND METHODS FOR PERFORMING MINIMALLY INVASIVE ABDOMINAL SURGICAL PROCEDURES

CROSS-REFERENCE

This application is a continuation-in-part application of co-pending application Ser. No. 11/716,985, filed Mar. 10, 2007 to which application we claim priority and which application is incorporated herein, in its entirety, by reference thereto.

This application is a continuation-in-part application of co-pending application Ser. No. 11/716,986, filed Mar. 10, 2007, to which application we claim priority and which application is incorporated herein, in its entirety, by reference thereto.

This application is a continuation-in-part application of co-pending application Ser. No. 11/407,701, filed Apr. 19, 2006 to which application we claim priority and which application is incorporated herein, in its entirety, by reference thereto.

This application claims the benefit of U.S. Provisional Application No. 61/130,244, filed May 28, 2008, which application is hereby incorporated herein, in its entirety, by reference thereto.

This application also hereby incorporates herein by reference thereto, in their entireties, co-pending application Ser. No. 12/473,818 filed on even date herewith, and titled "Minimally-Invasive Methods for Implanting Obesity Treatment Devices" and co-pending application Ser. No. 12/474,118 filed on even date herewith, and titled "Devices, Systems and Methods for Minimally-Invasive Abdominal Surgical Procedures".

FIELD OF THE INVENTION

The present invention relates to the field of minimally invasive surgery, and more particularly to methods, devices, tools and systems employing an endoscope for at least part of a procedure.

BACKGROUND OF THE INVENTION

There is a current ongoing trend toward the advancement of minimally invasive surgical techniques. Such techniques not only reduce the amount of trauma to the patient but consequently reduce the amount of recovery time needed for healing, thereby reducing the lengths of hospital stays and, in some cases, even making it possible to perform procedures on an outpatient basis, such as in a physician's office.

Examples of existing procedures include laparoscopic procedures, wherein a procedure is conducted transdermally to reach an internal surgical target location. Typically this involves the formation of several (typically three or more) ports or openings through the skin and into the patient for placement of an endoscope through one opening and tools, instruments, devices through the other openings.

Other examples of existing procedures include those where an endoscope and or other instrumentation is inserted through a natural orifice, such as the mouth, anus, vagina, etc. The endoscope/instrument may be advanced along a natural pathway and then used to access the surgical site by piercing through a natural conduit forming the natural pathway. Alternatively, a procedure may be performed within the natural pathway, or on the natural conduit forming the natural pathway.

In any of these cases, the use of an endoscope may be limited when obstacles are present in a pathway leading to the surgical target location. Such obstacles may be fat or other soft tissue obstruction, tumors, or even the fact that the route from the insertion location of the endoscope/instrument to the surgical target location is very tortuous, making it difficult to establish a pathway to the surgical target location.

Traditionally, suturing has been performed to attach devices to tissues, to attach tissues to one another and/or to close wounds and incisions. However, successful suturing requires significant skill to perform, is time consuming, and is often difficult, if not impossible to perform in a minimally invasive procedure through a port, or even through multiple ports in a laparoscopic procedure.

Alternatives to suturing are known, but may result in less desirable outcomes. For example, gastric reduction techniques have been attempted, such as by inserting instruments trans-orally and reducing the volume of the stomach by stapling portions of it together. However, this technique is prone to failure due to the staples pulling through the tissues that they are meant to bind.

In an example of laparoscopic hernia repair, multiple instruments are used through multiple ports to conduct the repair, but suturing is often replaced by stapling due to the reduced access space that is not sufficient to successfully carry out the suturing operations.

It would be desirable to provide instruments and techniques useable in less invasive surgical methods, such as minimally invasive surgical procedures using only one small opening into a patient, or laparascopic surgical procedures using two to five small openings into the patient, that provide the capability of fastening by sutures to fasten a device to an anatomical structure, to repair an opening or tear, or to otherwise fasten two or more tissues together.

SUMMARY OF THE INVENTION

Methods, systems, devices, tools and assemblies are provided for treating a patient by minimally invasive procedures.

In at least one embodiment, the instrument comprises an attachment tool and a suturing tool that are releasably connected and wherein a suture anchor for each suture anchored is releasably connected to the attachment tool, wherein the method comprises: disconnecting the attachment tool from each suture anchor after anchoring a suture; disconnecting the attachment tool from the suturing tool; and removing the attachment tool from the tract and from the patient, prior to applying tension to each suture, wherein the application of tension is carried out using the suturing tool.

In at least one embodiment, the instrument comprises an attachment tool and a suturing tool that are releasably connected and wherein a suture anchor for each suture anchored is releasably connected to the attachment tool, wherein the method comprises: disconnecting the attachment tool from the implant and each suture anchor after anchoring the suture; disconnecting the attachment tool from the suturing tool; and removing the attachment tool from the tract and from the patient prior to applying tension to each suture, wherein the application of tension is carried out using the suturing tool.

In at least one embodiment, the instrument comprises an attachment tool and a suturing tool that are releasably connected and wherein a suture anchor for each suture anchored is releasably connected to the attachment tool, wherein the method comprises: retracting the stabilizing pins from the surgical target; retracting the at least one needle from the abdominal wall; and disconnecting the attachment tool from each suture anchor after anchoring a suture; disconnecting the attachment tool from the suturing tool; and removing the attachment tool from the tract and from the patient, prior to applying tension to each suture, wherein the application of tension is carried out using the suturing tool.

A surgical instrument is provided that includes: an elongate shaft; a working end platform formed on a distal end portion of the elongate shaft; a handle mounted on a proximal end portion of the elongate shaft; a needle rotatably mounted relative to the platform and rotatable from a concealed position in which a tip of the needle is concealed within the platform to an exit position where the tip is inserted into a suture anchor releasably attached to the platform, and counter-rotatable from the position where the tip is inserted into the suture anchor to the position in which the tip is concealed within the platform; and a stabilizing pin movably mounted to the platform, the stabilizing pin being actuatable from a recessed position in which a tip of the stabilizing pin is concealed within the platform to a stabilizing position where the tip extends out of the platform, and vice versa.

In at least one embodiment, the stabilizing pin, in the stabilizing position angles away from a direction of movement of the needle as the needle moves from the concealed position to the exit position.

In at least one embodiment the instrument includes a stabilizing pin actuator, operable by a user from a location proximal of the elongate shaft, the stabilizing pin actuator configured to actuate the stabilizing pin to move from the recessed position to the stabilizing position and vice versa; and a stabilizing pin mechanism extending from the actuator to the stabilizing pin, along the elongate shaft, the stabilizing pin mechanism configured to extend as well as retract the stabilizing pin.

In at least one embodiment the instrument includes a stitching needle actuator, operable by a user from a location proximal of the elongate shaft, the stitching needle actuator configured to actuate the stitching needle to move from the concealed position to the exit position; and a stitching needle mechanism extending from the actuator to the stabilizing pin, along the elongate shaft, the stitching needle mechanism configured to extend the stitching needle from the concealed position to the exit position.

In at least one embodiment the instrument includes a stitching needle retraction mechanism configured to automatically counter-rotate the stitching needle from the exit position to the concealed position, after the stitching needle has reached the exit position.

A surgical instrument is provided that includes: an elongate shaft; a stitching needle rotatably mounted relative to the elongate shaft and rotatable from a concealed position in which a tip of the stitching needle is concealed within the platform to an exit position where the tip is inserted into a suture anchor releasably attached to the platform, and counter-rotatable from the position where the tip is inserted into the suture anchor to the position in which the tip is concealed within the platform; and a suture releasably mounted on the stitching needle, the suture including a catch member fixed to a distal end portion of the suture, wherein the stitching needle delivers the suture to the suture trap or anchor when advanced from the concealed position to the exit position, and wherein the catch member is retained by the suture trap or anchor, preventing the suture from returning to the concealed position when the stitching needle counter-rotates to the concealed position.

In at least one embodiment, the instrument includes a sleeve extending distally from the catch member over a portion of the suture.

In at least one embodiment, the sleeve is fixed at a distal end to the catch member and a proximal end of the sleeve is free.

An assembly for surgical treatment of a patient is provided that includes: a stitching instrument comprising: a first elongate shaft; a stitching needle rotatably mounted relative to the elongate shaft and rotatable from a concealed position in which a tip of the stitching needle is concealed within the platform to an exit position where the tip is inserted into a suture trap or anchor releasably attached to the platform, and counter-rotatable from the position where the tip is inserted into the suture trap or anchor to the position in which the tip is concealed within the platform; a suture releasably mounted on the stitching needle, the suture including a catch member fixed to a distal end portion of the suture, wherein the stitching needle delivers the suture to the suture trap or anchor when driven from the concealed position to the exit position, and wherein the catch member is retained by the suture trap or anchor, preventing the suture from returning to the concealed position when the stitching needle counter-rotates to the concealed position; and a suturing instrument connected to the stitching instrument the suturing instrument comprising: a second elongate shaft; each suture extending proximally from each suturing needle, respectively, thorough the second elongated shaft and proximally of the second elongated shaft; and a cutting mechanism configured to cut each suture at a location of a distal end portion of the second elongate shaft, proximal of the suturing needle, respectively.

In at least one embodiment the stitching instrument is releasably connected to the suturing instrument.

In at least one embodiment the assembly includes a suture retainer on each suture located proximal of each stitching needle respectively, each suture retainer being configured to slide along the suture in a distal direction, while preventing sliding of the suture retainer along the suture in a proximal direction.

In at least one embodiment, the assembly includes an implantable device releasably mounted to at least one of the stitching instrument and the suturing instrument.

In at least one embodiment at least one of the at least one suture retainer is fixed to the implantable device.

In at least one embodiment, the implantable device comprises a hernia repair patch.

In at least one embodiment the implantable device is an expandable implant configured for paragastric, extragastric implantation.

In at least one embodiment, the stitching instrument comprises a first handle mounted at a proximal end of the first elongated shaft and the suturing instrument comprises a second first handle mounted at a proximal end of the second elongated shaft, wherein the first and second handles are releasably connected to one another, and, upon releasing the first handle from the second handle, the stitching instrument and the suturing instrument are separable from one another.

In at least one embodiment, the stitching instrument further comprises a decoupling mechanism operable from a proximal end of the stitching instrument to decouple the implantable device from a distal end portion of the stitching instrument.

In at least one embodiment, the implant comprises: an expandable member having a main body portion which, when in an expanded configuration, extends along a central axis of curvature that extends substantially in a single plane, the main body having a superior portion and an inferior portion, wherein the superior portion has a substantially larger cross-sectional area than a cross-sectional area of the inferior portion when the expandable member is in an expanded configuration; the expandable member further comprising a superior lobe portion extending along a transverse axis that is transverse to the central axis of curvature at a location from which the superior lobe extends.

These and other features of the invention will become apparent to those persons skilled in the art upon reading the details of the methods, systems, devices, and apparatus as more fully described below.

BRIEF DESCRIPTION OF THE DRAWINGS

FIG. 1 illustrates an embodiment of an implantable device (shown in an expanded configuration) assembled on a surgical apparatus that is configured to deliver the device from outside of a patient, through a percutaneous opening and into the patient, according to the present invention.

FIG. 2 illustrates the suturing instrument of FIG. 1, after removal of the stitching instrument therefrom.

FIG. 3 illustrates an embodiment of a hernia patch assembled on assembled on a surgical apparatus that is configured to deliver the device from outside of a patient through a percutaneous opening and into the patient, according to the present invention.

FIGS. 4A-4D illustrate different views of an extragastric, paragastric device in an expanded, working configuration, mounted on an apparatus according to the present invention.

FIG. 10 shows a proximal end portion of an assembly according to an embodiment of the present invention, demonstration actuation of a needle actuator.

FIG. 15A shows a secured configuration of suture anchors or traps according to an embodiment of the present invention.

FIG. 15B shows a schematic, cross-sectional representation of a suture anchor or trap taken along line 15B-15B in FIG. 15A.

FIG. 15C is a top view of an embodiment of a suture anchor or trap that is shown in FIG. 15A.

FIG. 15D is a partial view of a stitching apparatus according to an embodiment of the present invention, showing an actuator used to release the suture anchors or traps.

FIG. 15E shows the bottom surface of the working end portion of a stitching instrument according to an embodiment of the present invention.

FIG. 15F is a partial view of a stitching apparatus according to an embodiment of the present invention, showing an actuator used to release the implant.

FIG. 16A illustrates removing the stitching instrument from the suturing instrument according to an embodiment of the present invention.

FIG. 16B illustrates tongues that slide into mating grooves to join instruments according to an embodiment of the present invention.

FIG. 16C illustrates the handle of the stitching instrument separated from the handle of the suturing instrument according to an embodiment of the present invention.

FIG. 17B is a partial view of a suturing instrument according to an embodiment of the present invention.

FIG. 17C is an enlarged, detail view of a portion of FIG. 17B.

FIG. 17D is a partial view of a suturing instrument according to an embodiment of the present invention.

FIG. 17E is an enlarged, detail view of a portion of FIG. 17D.

FIGS. 19A-19I schematically illustrate implantation of an expandable, paragastric, extra-gastric implantable device to the fascia/peritoneum and abdominal wall according to an embodiment of the present invention.

FIG. 23A shows a top perspective view of another embodiment of a suture anchor or trap according to the present invention.

FIGS. 23B-23C shows top and bottom views, respectively, of an inner keyhole component of the anchor or trap of FIG. 23A.

FIGS. 23D-23E show a main body of the suture anchor or trap of FIG. 23A.

FIG. 23F-23K show an embodiment of a suture and locking tip being anchored in a suture anchor or trap.

FIGS. 25A-25B show top and bottom perspective view of another embodiment of a suture anchor or trap according to the present invention.

FIGS. 25C-25H show an embodiment of a suture and locking tip being anchored in a suture anchor or trap according to an embodiment of the present invention.

FIG. 32 illustrates another embodiment of suture anchor or trap according to an embodiment of the present invention.

FIG. 33 illustrates another embodiment of a locking tip according to an embodiment of the present invention.

FIG. 34 illustrates another embodiment of a locking tip according to an embodiment of the present invention.

FIGS. 45A-45C illustrate an embodiment of a guide according to the present invention in which a distal end portion of a tube is flexible, while the proximal end portion of the tube is rigid.

FIGS. 47A-47K and 47Q-47R show another embodiment (and portions thereof) of a guide 530 according to the present invention.

FIGS. 48A-48E show embodiments of a tip arrangement useable with any of the embodiments of guide described herein.

FIGS. 49A-49B show another embodiment of tip arrangement useable with any of the embodiments of guide described herein.

FIG. 50A is a side view of the tip shown in FIG. 49A, which is shown in the upright orientation in FIG. 50A.

FIG. 50B shows an end view of a tip having an orientation marker according to an embodiment of the present invention.

FIG. 50C illustrates how the orientation marker of FIG. 50B appears to a user in the field of view.

FIG. 50D shows an end view of a tip having an orientation marker according to another embodiment of the present invention.

FIG. 50E illustrates how the orientation marker of FIG. 50D appears to a user in the field of view.

FIGS. 52A-52E show another embodiment of a dilator and large cannula or introducer that can be used in any of the same manners described with regard to the dilator and large cannula described with regard to FIGS. 51A-51F.

FIG. 54 illustrates an embodiment of a conduit that can be inserted through a large cannula described herein, to extend distally far past the distal end of the large cannula.

FIGS. 55A-55C illustrate another embodiment of a conduit in which at least a distal end portion thereof is flexible.

FIGS. 55D and 55E are enlarged, partial views of a proximal end portion of the conduit of FIGS. 55A-55C.

FIGS. 56A-56B illustrate a plan view and a proximal end view of an obturator that is configured to be placed in a conduit and used to deliver the conduit through a large cannula and over a guide to deliver a distal end portion of the conduit far distally of the large cannula, according to the present invention.

FIG. 56C illustrates an alternative embodiment of an obturator in which the shaft thereof is made of corrugated tubing.

FIG. 56D illustrates an alternative embodiment of obturator according to the present invention, in which the shaft is made of rigid links.

FIG. 56E is a perspective view of one of the links of the obturator shown in FIG. 56D.

FIG. 56F is a distal end view of the link shown in FIG. 56E.

FIG. 56G is a proximal end view of the link shown in FIG. 56E.

FIG. 56H shows the obturator of FIG. 56D installed in a conduit.

FIG. 56I shows the conduit of FIG. 56H, absent the obturator.

FIG. 56J is a partial, proximal end view of the obturator shown in FIG. 56H.

FIG. 57 illustrates an embodiment of an obturator having been inserted into a conduit according to the present invention.

FIGS. 59A-59D illustrate further alternative embodiments of conduit according to the present invention.

FIG. 62A is a partial view of an endoscope that may be inserted into a guide according to the present invention.

FIG. 62B shows a longitudinal sectional view of the endoscope in FIG. 62A.

FIGS. 63A-63Y illustrate an example of a procedure and variations thereof for percutaneously implanting an extragastric device according to an embodiment of the present invention.

FIG. 64A is a side view of a cap that may be used with large cannula according to an embodiment of the present invention.

FIG. 64B is a longitudinal sectional view of FIG. 64A taken along line 64B-64B.

FIGS. 65A-65B are side and top views of another embodiment of a cap that may be used with a large cannula according to an embodiment of the present invention.

DETAILED DESCRIPTION OF THE INVENTION

Figure 5:
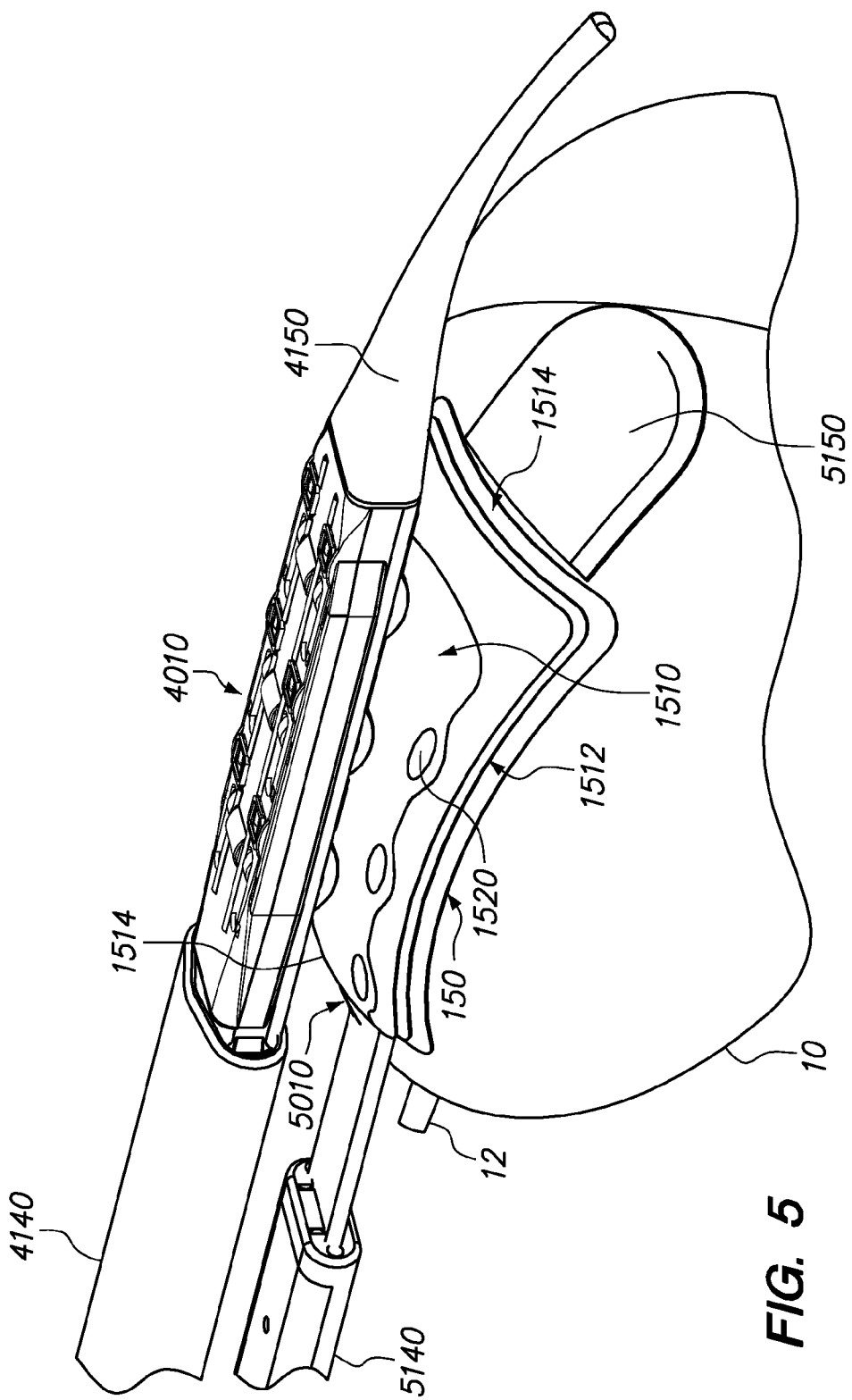
FIG. 5 is an enlarged partial view of FIG. 1 showing more details of the working ends of the stitching instrument and suturing instrument according to an embodiment of the present invention.

Before the present apparatus, devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and or materials in connection with which the publications are cited.

It must be noted that as used herein and in the appended claims, the singular forms "a", "an", and "the" include plural referents unless the context clearly dictates otherwise. Thus, for example, reference to "a tool" includes a plurality of tools and reference to "the handle" includes reference to one or more handles and equivalents thereof known to those of ordinary skill in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A "proximal" end of an instrument is the end that is nearer the surgeon when the surgeon is using the instrument for its intended surgical application.

A "distal" end of an instrument is the end that is further from the surgeon when the surgeon is using the instrument for its intended surgical application.

An "internal body structure" refers to a structure internal to the skin of a patient and which can be within the abdominal cavity or other cavity of the patient or just outside of it such as including the outer surface of a wall that partially defines the cavity. Further, an internal body structure may be located anywhere in the body internal to the skin.

A "surgical target location" or "surgical target area" as used herein refers to a location internal of a patient where a surgical procedure is to be performed. Such surgical procedures include, but are not limited to, treatment of existing tissues with one or more tools and or implantation of one or more devices at the surgical target location.

Tools, Devices, Systems and Methods

The preferred embodiments of the present invention facilitate minimally-invasive procedures for implanting one or more devices within a patient, and/or minimally invasive features for joining tissues or repairing tissue defects such as a hernia, for example.

Thus, although the majority of the specific embodiments focus on implantation of a device to treat obesity, the present tools and methods are not limited to such procedures, as tools described herein may be used in other minimally invasive procedures, including, but not limited to hernia repair.

Preferred embodiments include use of an attachment tool that is useable from a location outside of a patient to attach a device internally to a patient or to perform repairs of tissue defects, etc. Advantageously, apparatus provided are configured to and capable of applying sutures to a target arranged substantially in a flat plane or having a slightly curved surface. Thus tissue does not have to be sucked in, folded, bunched up, or otherwise gathered in order to apply sutures as is required for prior art tools.

In at least one procedural embodiment, a tract is established from an opening in a patient that opens to the outside of the patient to a surgical target location located internally of the patient. Direct visualization through a preferred device is possible during the establishment of such tract.

Further provided are tools/devices that are advanceable over a tool device used to establish the tract to temporarily place a device through which an implant and/or other tools can be inserted and delivered to the surgical target location.

In preferred embodiments, a minimally-invasive procedure does not require putting the patient under general anesthesia and insufflation is not required. Preferably, only a single small opening is required for insertion of the tools/devices and optionally, an implantable device. The small opening will generally be less than about 2.5" in diameter, or less than about 2.2" in diameter, or less than about 2" in diameter, or less than about 1.5", less than about 1.25" or less. For use with general anesthesia, the opening may be up to about 3 inches in diameter or up to about 3.5 inches in diameter. Alternatively, more than one opening may be used for viewing through and/or inserting additional instruments. Further alternatively, minimal amounts of insufflation may be used. Also, the surgeon always has the option of using general anesthesia, regardless of the size of the opening, though it may not required by methods described herein.

For weight loss applications, weight loss is achieved by restriction of the stomach and filling of the space into which the stomach normally expands into in the abdominal cavity when filled with food. An implantable device expands outwardly when filled to occupy space within the abdominal cavity such that when food is ingested the stomach is restricted from being able to hold any more than a small volume of food. The implantable, outwardly expandable device is implanted outside of the stomach in the left upper quadrant of the abdominal cavity to achieve these functions. The expandable portion of the implantable device does not pierce or encircle nerve tissue or other tissue. The implantable, expandable device may be positioned with direct visualization (i.e., using an endoscope) and/or fluoroscopic visualization. No dissection, suturing, attachment or other invasive manipulation or trauma into or on the stomach is required in order to implant the implantable, expandable device. By appropriate placement of the implantable, expandable device, the device can achieve restriction of the stomach. Further, the volume of the implantable, expandable device is adjustable so that the amount of restriction of the stomach can be adjusted. This can be advantageous over time, as the patient may be able to accept, or require, additional restriction of the stomach as weight loss progresses. Likewise, the loss of fat in the abdominal cavity may require the implantable, expandable device to be increased in volume to occupy additional space that is freed up by the weight loss. Both the shape of the implantable, expandable device and its fill volume, in combination, cause the desired stomach compression. Implant materials are chosen that are compatible with magnetic resonance imaging (MRI), computed tomography (CT) imaging, fluoroscopy, and X-ray imaging.

Implantation of the implantable, outwardly expandable device is carried out so as not to encircle any muscle or nerve tissue with the expandable member. Various implantable, outwardly expandable device sizes are provided, so that the present invention can treat a wide range of patients, with BMI's ranging from about 35 to about 50 and above, and including different rib cage dimensions. The present invention minimizes stress to the stomach.

FIG. 1 illustrates an embodiment of an implantable device 10 (shown in an expanded configuration) assembled on a surgical apparatus 500 that is configured to deliver the device 10 from outside of a patient, through a percutaneous opening and into the patient (e.g., into the abdominal cavity of the patient), and to implant the device 10 by suturing it to a surgical target location within the patient, e.g., the internal wall surface of the abdominal cavity, internal fascia, and/or some other internal body structure. Implant device 10 is inserted into the patient in a compact, non-expanded configuration. Apparatus 500 includes a stitching instrument 4000 releasably coupled with a suturing instrument 5000. Stitching instrument 4000 includes a working end portion 4010 that is preferably radiolucent so that the needles and suture anchors are easier to visualize when using fluoroscopy, with the working end portion 4010 having been inserted into the patient. Working end portion 4010 is provided at a distal end portion of the instrument from which and into which end effectors (e.g., tissue pins, stitching needles) move, as described below. An elongate shaft 4140 extends between working end portion 4010 and handle 4120. In one embodiment, shaft 4140 has a length from the distal end of handle 4120 to the proximal end of working end portion 4010 of about 20.25"±about 0.25", where the overall length of the instrument 400 is about 37.2" (excluding the length of guide 4150) With the implant guide 4150, the overall length is about 40". All of the foregoing length measurements may vary depending on multiple factors including, but not limited to: the size of the implant 10 to be delivered, the size of the patient, etc. Shaft 4140 has a length sufficient to allow a user to operate the controls on handle 4120 from a location outside of an obese or overweight patient when the working end portion 4010 is contacted to a surgical target area where stitching and suturing are to be performed. Handle 4120 includes an axial portion 4120a and a transverse portion 4120t. These portions are configured so that the user can apply both hands to the handle 4120 if desired and, by pulling on handle portion 4120t and pushing down on handle portion 4120a can apply a force to the working end portion 4010 to press it up against a surgical target where stitching and suturing is to be performed.

FIG. 2 illustrates the suturing instrument 5000 of FIG. 1, after removal of the stitching instrument 4000 therefrom. Suturing instrument 500 includes a working end portion 5010 that releasably mounts an implantable device (such as the expandable, paragastric, extragastric implantable device shown in FIG. 2, a hernia patch 10' shown in FIG. 3, or some other implantable device that can be implanted by suturing it to a surgical target) thereon. An elongate shaft 5140 extends between working end portion 5010 and handle 5120. In one embodiment, the length of shaft 5140 was about 24.3" and the overall length of the instrument 5000 was about 29.6". However, described with regard to instrument 4000, these lengths may vary. Shaft 5140 has a length sufficient to allow a user to operate the controls on handle 5120 from a location outside of an obese or overweight patient when the working end portion 5010 is contacted to a surgical target area where suturing is to be performed.

FIGS. 4A-4D illustrate different views of an extragastric, paragastric device 10 in an expanded, working configuration, mounted on apparatus 500. A flexible implant guide 4150 is mounted distally of the working portion 4010 so that, during advancement of the assembly 500 and 10 into the patient implant guide 4150 provides an atraumatic guiding function that helps guide the delivery of the implant along the delivery tract. Implant guide 4150 is particularly useful in embodiments where the assembly 500 and 10 is tracked around the curvature of the diaphragm of a patient (described in more detail below). As the implant guide atraumatically contacts the curved wall that tracks along the diaphragm, it bends (taking on a further smooth curvature, but does not kink), facilitating a smooth tracking of the implantable device 10 along the curvature of the diaphragm. Implant guide 4150 is inserted into pocket 5150 that extends distally of the attachment tab 150 of device 10. By inserting implant guide 4150 into pocket 5150, this prevents the implant 10, when in a non-expanded configuration, from folding backward as it emerges from the distal end of conduit 600 (as described in more detail below). The curved shape of the implant guide 4150 helps direct the distal end portion of the implant 10 along the intended delivery tract.

The device 10, in an expanded configuration as shown in FIGS. 4A-4D, includes a main expandable body portion $10em1$ that, when in an expanded configuration as shown, extends along a central axis of curvature 10C that extends generally in a single plane. The main body $10em1$ has a superior portion $10em1s$ and an inferior portion $10em1i$, wherein said superior portion $10em1s$ has a substantially larger cross-sectional area transverse to the axis $10c$ than a cross-sectional area transverse to the axis $10c$ of the inferior portion $10em1i$ when the expandable member $10em1$ is in an expanded configuration. The expandable portion of device 10 further includes a superior lobe portion $10em2$ in fluid communication with main body $10em1$ and extending along a transverse axis 10T that is generally transverse to the central axis of curvature 10C at a location from which the superior lobe $10em2$ extends. Thus, the majority of superior lobe portion $10em2$ extends out of the plane of central axis 10C and therefore extends out of the general plane along which the main body portion $10em1$ generally extends. This can be seen in FIG. 4B where main body $10em1$ extends generally parallel to the direction in which the shafts 4140 and 5140 extend, while superior lobe $10em2$ extends substantially transverse to that direction (in a downward direction as shown in FIG. 4B). FIG. 4A shows that the curvature of the main body $10em1$ curves to the left, relative to apparatus 500, in a direction from the proximal end (end where inferior portion $10em1i$ is located) to the distal end (end where superior portion $10em1s$ is located). Likewise, in addition to extending downward, superior lobe $10em2$ also extends in a direction further leftwardly. This is further evident in the rear and front views of FIGS. 4C and 4D, respectively.

With this embodiment device 10 is configured to be implanted so that the main body $10em1$ extends substantially in a superior-inferior direction in a patient while the superior lobe $10em2$ extends substantially posteriorly from the superior portion $10em1s$ of main body $10em1$. With this configuration, the superior lobe $10em2$ extends deeper into the abdominal cavity and displaces more volume in the abdominal cavity where the stomach (particularly the fundus, but also the main body) would normally be able to expand into.

FIG. 5 is an enlarged partial view of FIG. 1 showing more details of the working ends of the stitching instrument 4000 and suturing instrument 5000. Device 10 includes an attachment tab 150 fixed thereto. Multiple layers of material (three are shown in FIG. 5, but more or fewer can be used) are provided to both reinforce the attachment tab 150 and to provided additional surfaces into which tissue can ingrow. At least one layer of the attachment tab 150 is fixed only at the sides 1512 (only one side is visible in FIG. 5) while both ends 1514 of that at least one layer are not fixed, so that a passageway extends between the at least one layer and one or more underlying layers of attachment tab 150. This allows the working end portion 5010 of suturing instrument 5000 to be slid between the layers of the attachment tab 150, where it can be temporarily attached to the attachment tab 150 in a manner that is described in greater detail below. The distal end of the suturing instrument ends underneath the mesh layer 1510.

At least the outer layer of attachment tab 150 is formed of a mesh material that is configured to encourage tissue to grow into it, and may be made of polyester-reinforced silicone sheeting, polypropylene-reinforced silicone sheeting or polyethylene-reinforced polyurethane sheeting for example, or any of the same materials described in earlier applications that are incorporated herein. Additionally, at least one suture retainer 1520 (six suture retainers 1520 are provided in the attachment tab of FIG. 5, but more or fewer can be used) is embedded in, molded in, welded to, or otherwise fixed to the attachment tab 150. Each suture retainer 1520 receives a suture therethrough and is used to cinch the suture and retain the suture under tension, respectively, as described in greater detail below. The working end 4010 of stitching instrument 4000 passes above the attachment tab 150 and overlies it in a position configured for driving sutures through a surgical target above the attachment tab 150.

Figure 6:
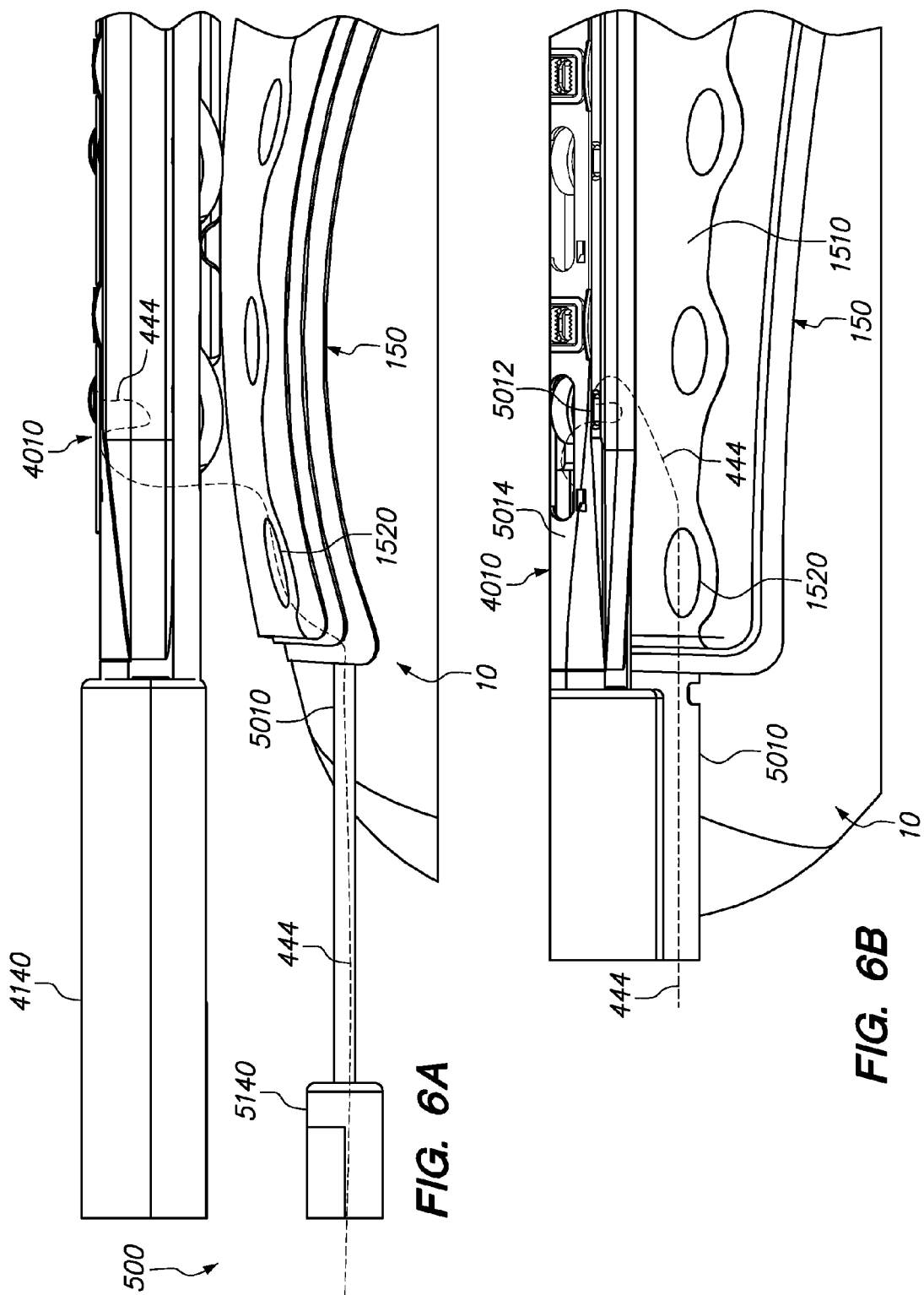
FIGS. 6A-6B illustrate the routing of a suture through the apparatus and device as exists in the configuration of FIG. 1.

FIGS. 6A-6B illustrate the routing of a suture 444 through the apparatus 500 and device 10 as exists in the configuration of FIG. 1, for example. Only one suture 44 is shown for clarity. However, as noted previously additional sutures would routed in a similar manner, one for each suture retainer 1520. Suture 444 extends proximally out of the proximal end (not shown in FIGS. 6A-6B) of instrument 5000. From the proximal end portion, suture 444 extends through handle 5120, elongated shaft 5140, and working portion 5010. It exits working portion 5010 underneath the top layer 1510 of ingrowth mesh and is routed through suture retainer 1520. From there it extends up the side of working portion 4010, loops through a hole 5012 (see FIG. 6B) towards the top of the side of working portion 4010, comes back out of hole 5012 and enters the roof 5014 of the working portion 4010 where it is releasably connected to a stitching needle (not shown in FIGS. 6A-6B, but shown and described in detail below).

Figure 7:
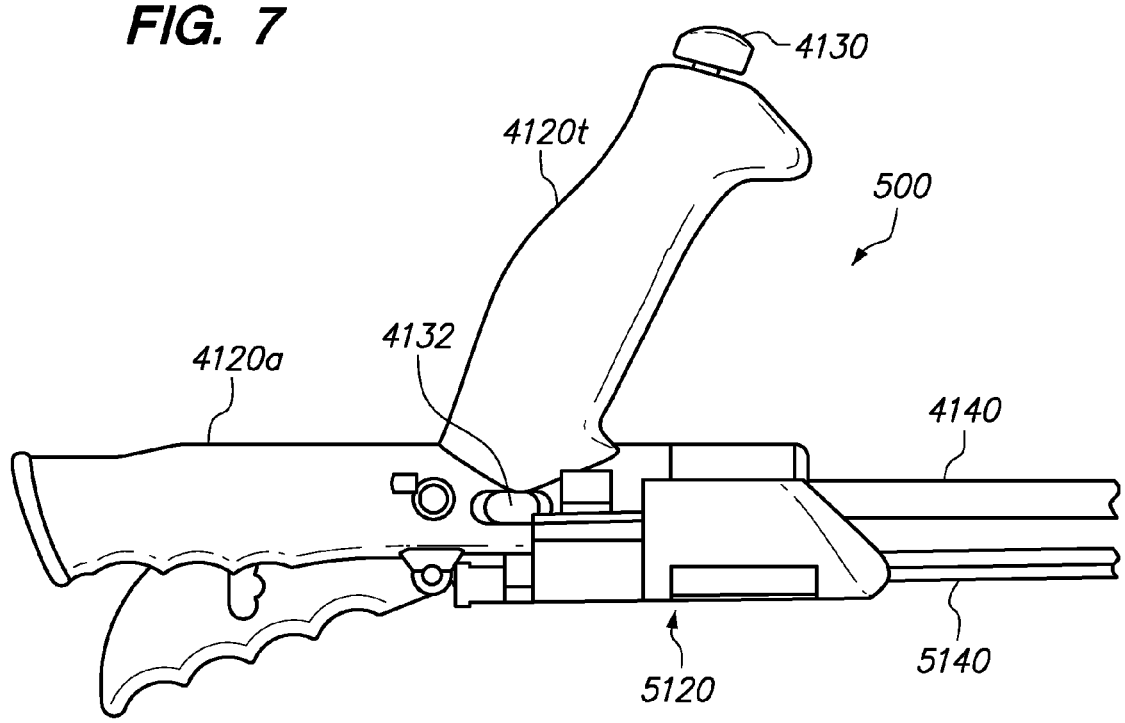
FIG. 7 illustrates a proximal end portion of an assembly according to an embodiment of the present invention.
Figure 9A:
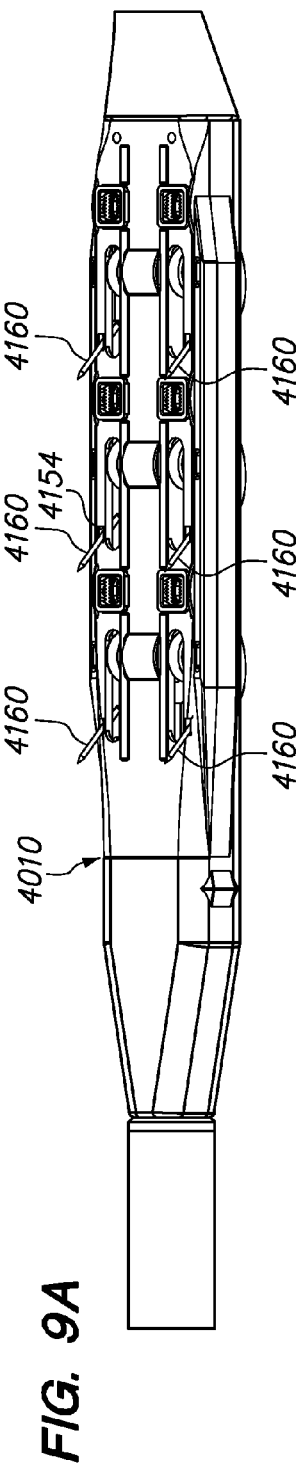
FIG. 9A illustrates the counter-traction or stabilizing pins having been deployed from the working portion of an instrument according to an embodiment of the present invention.
Figure 9B:
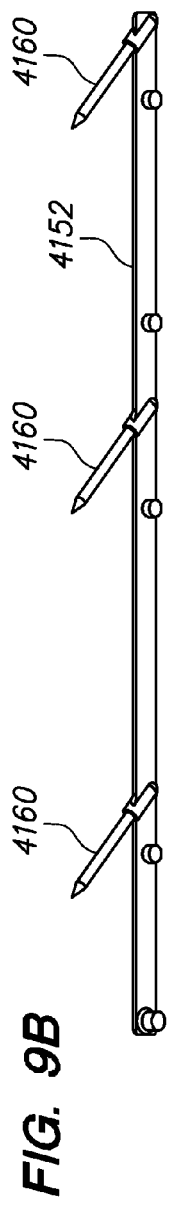
FIG. 9B shows the stabilizing pins of FIG. 9A mounted on strips.

FIG. 7 illustrates a proximal end portion of assembly 500 and actuation of a stabilizing pin actuator 4130 to deploy stabilizing pins 4170 (see FIGS. 9A-9B). A safety mechanism is provided to prevent accidental deployment of the stabilizing pins 4160 as well as to prevent accidental deployment of the stitching needles. When safety switch 4132 is slid to the "on" position, this prevents actuator 4130 from being depressed. When safety switch 4132 is slid to the "off" position as shown in FIG. 7, stabilizing pin actuator can then be operated to actuate the deployment of the stabilizer pins 4160. This operation is performed by depressing the actuator 4130 in the embodiment of FIG. 7, as illustrated in FIG. 7.

Figure 8:
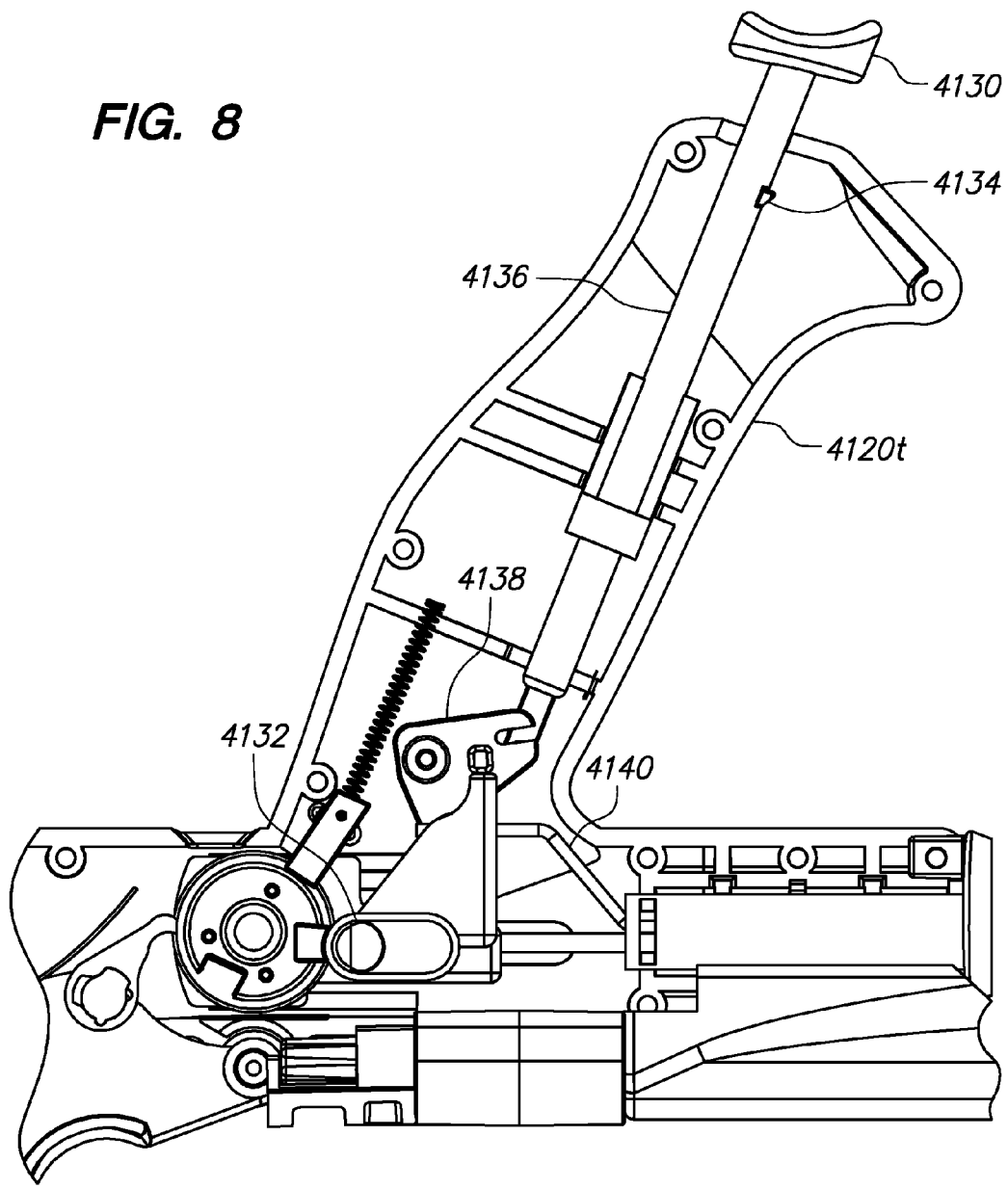
FIG. 8 is a cutaway view showing the mechanism by which the stabilizing pins actuator actuates the deployment of stabilizing pins for the embodiment of FIG. 7.

FIG. 8 is a cutaway view showing the mechanism by which stabilizing pins actuator 4130 actuates the deployment of stabilizing pins 4160 for the embodiment of FIG. 7. Upon depressing actuator 4130, a spring (not shown) that normally holds the actuator 4130 up on the non-actuating position shown in FIG. 8, is compressed. When the actuator 4130 is fully depressed, catch 4134 catches on a rib in the portion of handle 4120*t* that is not shown in FIG. 8, thereby maintaining the actuator 4130 in the depressed, actuated position shown in FIG. 7. As the actuator 4130 is depressed, the shaft 4136 of the actuator 4130 rotates cam 4138 which in turn pulls wire or rod 4140 (i.e., retracts proximally, to the left as shown in FIG. 8) in a proximal direction. Wire 4140 extends through shaft 5140 and into working end 5010 where it connects to strips 4152 on which stabilizing pins 4160 are mounted. FIG. 8 illustrates the safety switch 4132 in the "on" position, where the top portion of the safety switch 4132 abuts the cam 4138 and prevents it from rotating. Upon sliding the safety switch to the right cam 4138 is then allowed to rotate.

Figure 9C:
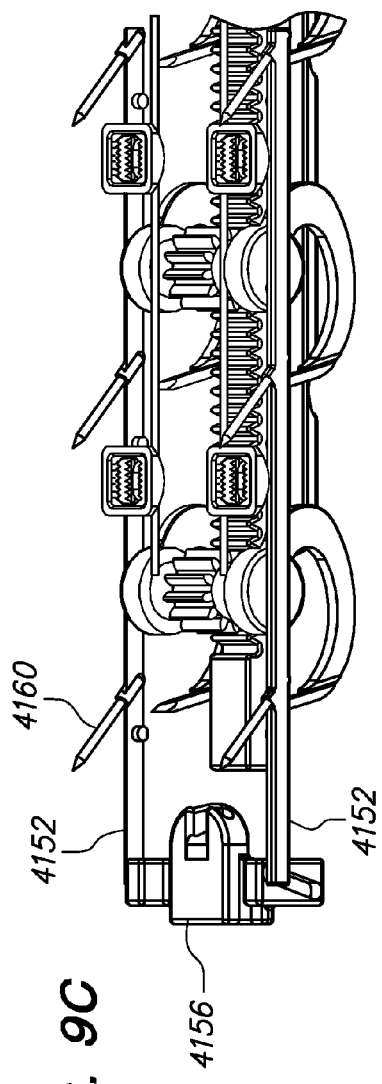
FIG. 9C shows a yoke connecting the strips shown in FIG. 9B.

FIG. 9A illustrates the counter-traction or stabilizing pins 4160 having been deployed from the working portion 4010 of instrument 4000. The stabilizing pins 4160 are mounted on strips 4152, an example of which is shown in FIG. 9B. Pins 4160 may be welded, glued or otherwise fixed to strips 4152. In one embodiment, pins 4160 are co-molded into plastic strips 4152. Pins 4160 may be made of stainless steel or other biocompatible metal, alloy, composite or polymer with similar characteristics, for example. When strips 4152 are retracted (pulled proximally, which is to the left in FIGS. 9A-9B), pins 4160 slide out of their diagonally oriented tracks 4154 in the working portion 4010. FIG. 9C illustrates a yoke 4156 that connects the strips 4152. Wire or rod 4140 connects to the yoke 4156 and pulls (retracts) the yoke 4156 to deploy the stabilizing pins 4160. Rod 4140 drives the yoke 4156 distally to retract the stabilizing pins 4160 back into the working portion 4010 as described in more detail below.

With the counter-traction or stabilizing pins 4160 having been deployed, the instrument 4000 can next be actuated to rotate the needles 4170 into a surgical target and back out of a surgical target. The needles 4170 are curved needles that are rotationally mounted relative to the working portion 4010 and are rotationally driven into and back out of the surgical target to perform a stitch. This rotational driving is performed by stitching needle actuator 4172 and the associated mechanism interconnecting actuator 4172 to the needles 4170. In one embodiment, the rotation is performed in incremental steps by iteratively moving the actuator 4172 toward handle 4120*a*, see FIG. 10. An indicator 4174 may be provided (such as on handle 4120*a* in the embodiment of FIG. 10) to keep track of how many iterations the actuator 4172 has been moved through. Upon moving the actuator 4172 for the last iteration (number 9 in the embodiment of FIG. 10), the stitching needles will have been successfully retracted back out of the surgical target, and the sutures 444 are joined to suture anchors or traps (described and shown below), into working portion 4010. In an alternative embodiment, the needles 4170 can be rotated out and retracted back with two squeezes, or even one squeeze of the actuator.

Figure 11:
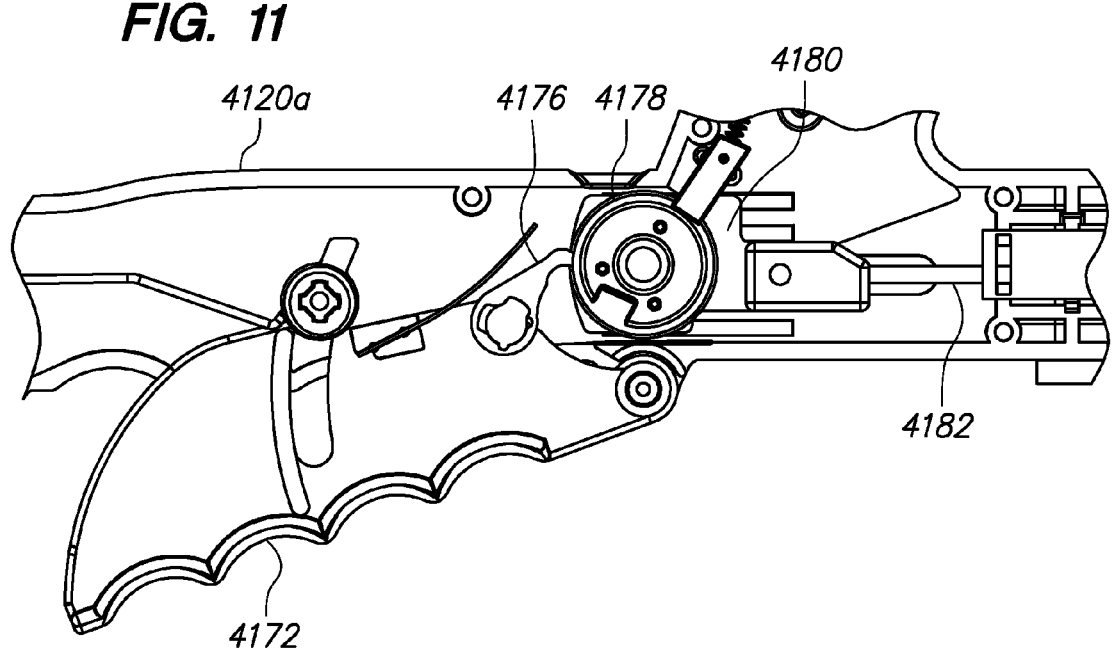
FIG. 11 is an enlarged cutaway view of the proximal portion of the mechanism for actuating the needles according to an embodiment of the present invention.

FIG. 11 is an enlarged cutaway view of the proximal portion of the mechanism for actuating the stitching needles 4170. As actuator 4172 is pulled toward handle 4120*a*, it drives a pawl 4176 against ratchet teeth of wheel 4178, thereby driving it clockwise n FIG. 11. Wheel 4178 has a pin (not shown) on the backside that engages a slot (not shown) in traveler block 4180. Over a full turn of the wheel 4178, the pin drives the traveler block 4180 proximally for one-half of the rotation of the turn of the wheel 4178 (which deploys the stitching needles forward into the suture anchors or traps) and during the second half of the wheel's rotation, it drives the traveler block 4180 distally for the other half of the turn of the wheel 4178 (which retracts the stitching needles). Thus, initially, as the operator is iteratively pulling the actuator 4172 toward handle 4120*a*, each of the indicated pulls at 4174 indicates show further advancement of the rotation of the stitching needles clockwise. The first half of the total number of lever actuations indicated rotate the wheel half way and deploy the stitching needles, while the second half of the total number of lever actuations rotates the wheel through its second half of rotation and retracts the stitching needles. At the end of the first half of the turn of wheel 4178, when sutures 444 have been attached to suture anchors, the rotation of the wheel 4178 through the second half of the rotation pushes the travelling block 4180 distally, thereby driving the stitching needles back to their concealed starting positions within the working portion 4010.

Figure 12:
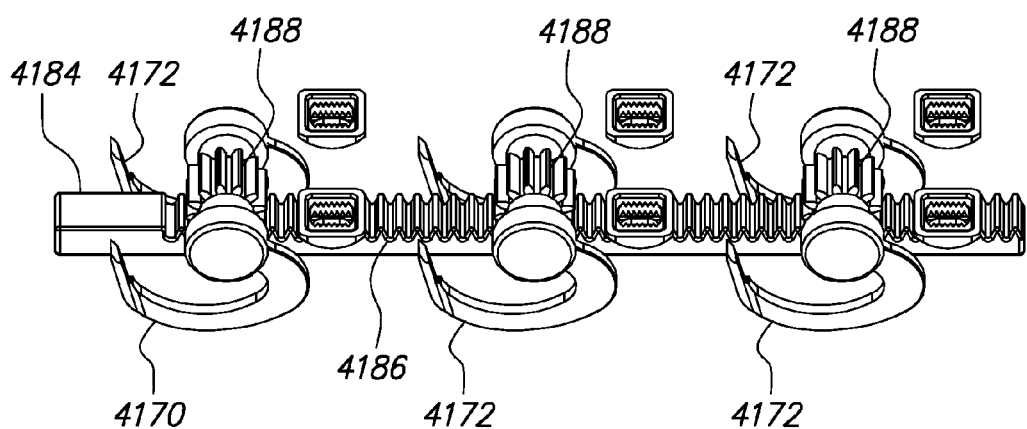
FIG. 12 is an isolated view of a distal portion of a mechanism for driving the needles for deployment and retraction thereof, according to an embodiment of the present invention.

FIG. 12 is an isolated view of the distal portion of the mechanism for driving the stitching needles 4170 for deployment and retraction thereof. As the traveling block 4180 is retracted by the stitching needle actuating mechanism described above, a wire or rod 4182 that interconnects the traveling block and a rack 4184 of gears, pulls the rack 4184, causing it to slide proximally relative to the needles 4170 which are translationally fixed relative to the working portion 4010. This causes the gear teeth 4186 in rack 4184 to interact with gears 4188 to which needles 4170 are mounted, causing the gears 4188 and, with them, the needles 4170 to rotate clockwise. Reverse motion of the traveling block 4180 pushes the wire or rod 4182 distally, thereby sliding the rack 4184 to the right in FIG. 12. This drives the gears 4188 and needles 4170 in counterclockwise rotation, thereby returning the needles 4170 to the concealed orientations shown in FIG. 12.

Figure 13A:
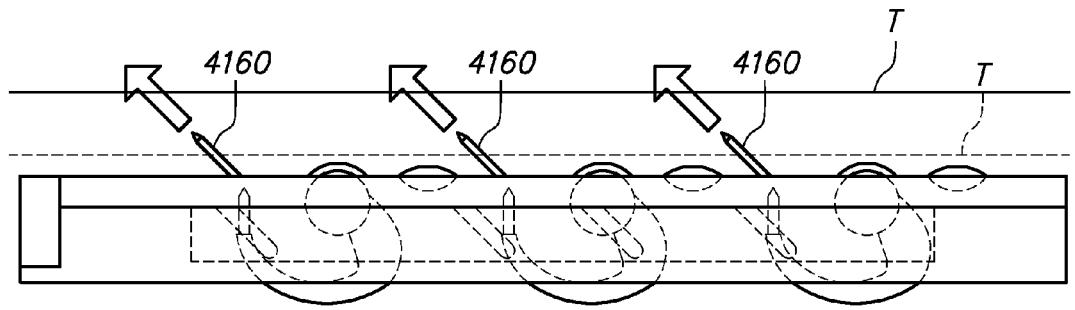
FIGS. 13A-13E illustrate movements of the counter-traction or stabilizing pins and stitching needles when actuated by the actuators of the stitching instrument according to an embodiment of the present invention.

FIGS. 13A-13E illustrate movements of the counter-traction or stabilizing pins 4160 and stitching needles 4170 when actuated by the actuators of the stitching instrument 4000 as described above. FIG. 13A shows the stabilizing pins 4160 having been deployed through operation of actuator 4130 and its associated mechanism, as described above. Note that depending upon the surgical target (e.g., internal abdominal wall) to be sutured, stabilizing pins 4160 may pierce entirely through the target T (shown in phantom lines) or may simply pierce into the target T (shown by solid line).

Figure 13B:
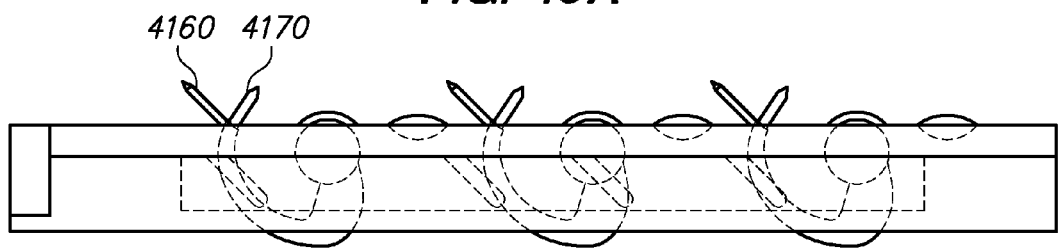
Figure 13C:
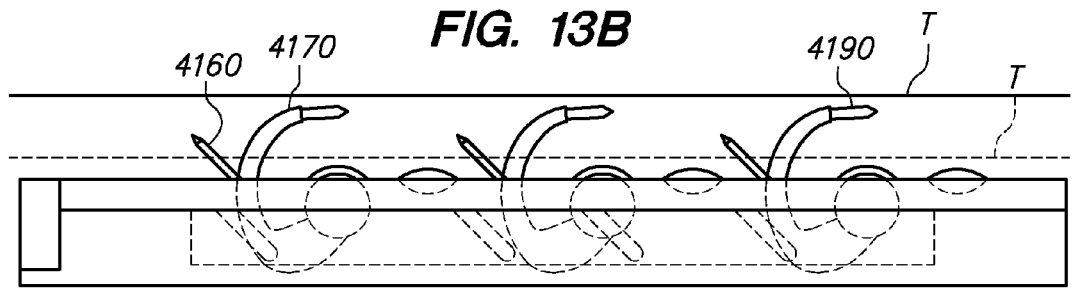
Figure 13D:
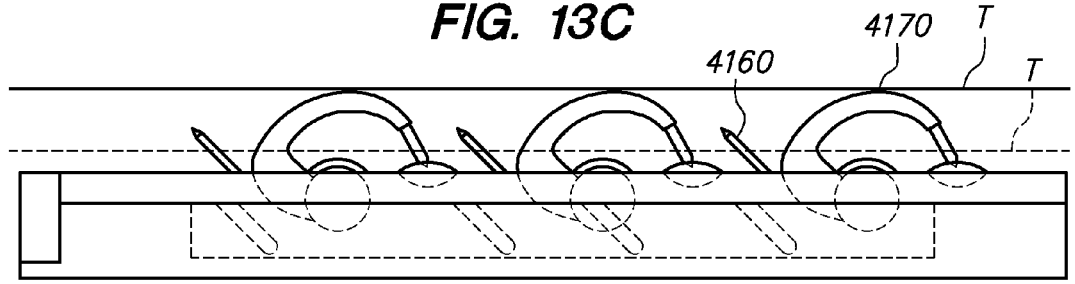
Figure 13E:
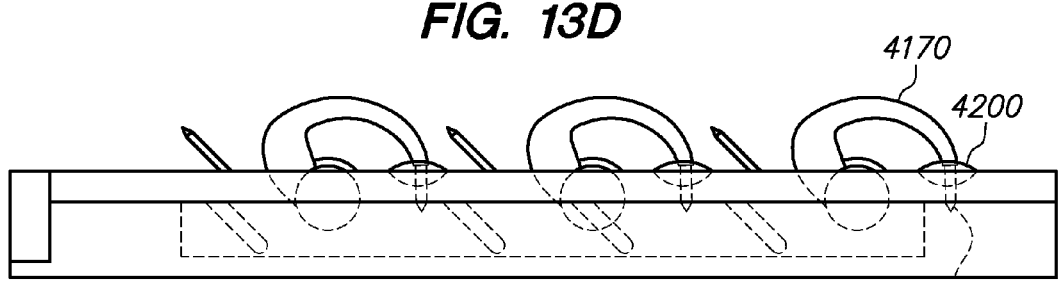

FIG. 13B illustrates deployment of stitching needles at an early stage of the process, e.g., after only one or two pulls of the actuator 4172. Note that the locations where the stitching needles 4170 pierce into the target T are substantially aligned with the locations where the corresponding stabilizing pins 4160 pierce into the target. In the embodiment shown, the tip of the needle 4170 is aligned axially (i.e., at the same length along the proximal-distal axis of the stitching instrument, i.e., the left-right direction in FIG. 13B) with the tip of the stabilizing pin 4160, when both are in their starting positions, ready to pierce into tissue. Laterally (i.e., the direction into the page, with regard to FIG. 13B), the tip of the stabilizing pin is about 0.094" further from the central axis of the working portion 4010 than the tip of the needle. It is preferred to have the lateral spacing as close as practically possible, but the pins and needles can still be effective in their functions at a lateral spacing up to about 0.5". Also, pins 4160 are angled in a direction opposite to a direction toward which the stitching needles are angled, relative to the surface of the target T, as they enter the target T. In this way, the stabilizing pins 4160 provide counter-traction and prevent the target tissue T from being dragged or bunched up or pushed away by the stitching needles as they sweep through the target tissue, being rotated into and then out of the target tissue T. Pins 4160 may have an angle to the top surface of the working portion 4010 at a location proximal of the pin 4160 in the range of about thirty degrees to about sixty degrees. FIG. 13C illustrates the stitching needles having been rotated about halfway through the target T. Note that the stabilizing pins 4160 remain in position as originally deployed. FIG. 13D illustrates the stitching needles 4170 having been rotated to the extent where the tips of the needles have emerged back out of the target T. Like the stabilizing pins, the needles 4170 may pass all the way through a target T (phantom lines) or may rather be inserted into the target, rotated through the target T without ever passing through a back side of the target, and pass back out of the target at another location (exit location) different from the entry location, but located on the same surface of the target. FIG. 13E illustrates the needles 4170 having been rotated to the extent where the tips of the needles 4170 and the locking tips 4190 have been driven through the respective suture anchors or traps 4200. Upon counter-rotation of the needles 4170, the tips of the needles slide out of contact with the locking tips 4190 and pass back out of the suture anchors or traps 4200, while the suture anchors or traps 4200 retain the locking tips 4190 and prevent them from passing back through, thereby securing the sutures 444 to the suture anchors or traps 4200.

Figure 14:
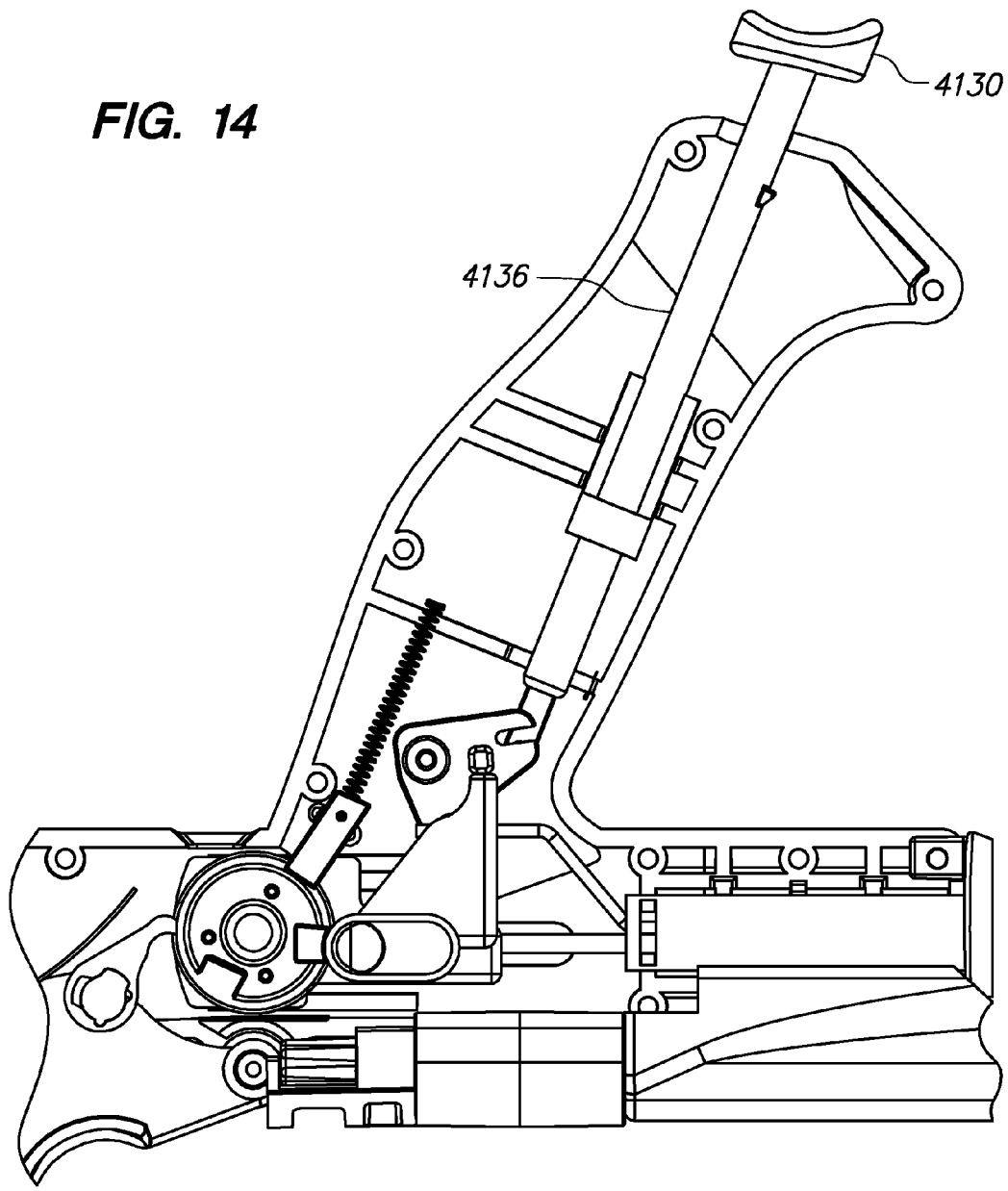
FIG. 14 is a cutaway view illustrating returning the stabilizing pins actuator to the non-actuated position according to an embodiment of the present invention.

Upon anchoring the sutures 444 to the suture anchors or traps 4200 as described above and when the stitching needles have been fully returned to their concealed positions in the working portion 4010, the stabilizing pins 4160 can be retracted by pulling on actuator 4130. This releases the latch 4134 from the rib in the handle 4120*t* and the compressed spring (not shown) returns the actuator 4130 to the non-actuated position shown in FIG. 14. The upward movement of shaft 4136 counter-rotates cam 4138 which pushes the wire or rod 4140 distally, thereby causing distal sliding of the strips 4152 which causes pins 4160 to retract into their concealed positions within the working portion 4010. FIG. 14 also shows that the safety mechanism, when in the "on" configuration, has a proximal portion that fits in a notch in wheel 4178 thereby also preventing actuation of the stitching needles 4170.

When the sutures 444 have been locked into suture anchors or traps 4200 and stitching needles have been retracted into their concealed positions, the suture anchors or traps 4200 can be released from the working portion 4010 and from stitching instrument 4000 by withdrawing wires 4202 from their pathways through working portion 4010. FIG. 15A shows the secured configuration, where wires 4202 pass through the pathways in the working portion 4010, including bores 4204 through suture anchors that wires 4202 pass through, thereby skewering them to lock them into cradles 4206 that the suture retainers 4200 are received in the working portion. FIG. 15B shows a schematic, cross-sectional representation of suture anchor 4000 taken along line 15B-15B in FIG. 15A, to show the bores 4204 that pass through the suture anchors or traps 4200 so that wires 4202 can be passed therethrough to removably secure the suture anchors or traps 4200 to the working portion 4010 To release the suture anchors, an actuator 4210, such as a ring or other feature than can be readily grasped and pulled by the user is pulled proximally from the proximal end of the handle 4120*a* (see the partial view of FIG. 15D). Suture anchor release actuator 4210 is connected to wires 4204. By pulling the actuator 4210 proximally relative to handle 4120, this pulls the wires out of the working portion 4010 and out from the suture anchors or traps 4200, thereby freeing the suture anchors from the working portion 4010.

FIG. 15C is a top view of an embodiment of a suture anchor 4200 that is shown in FIG. 15A. Suture anchor includes an opening 4212 through which the needle 4170 tip, suture locking tip 4190 and a distal end portion of suture 444 are passed during the anchoring or locking procedure. One or more flexures 4214 are provided on each side of the opening 4212 and are deflected by locking tip 4190 when the locking tip 4190 passes through opening 4212. After the locking tip 4190 passes the flexures, the flexures 4214 spring back to prevent the locking tip from passing back through the opening 4212. Although the details of the flexures are not shown in FIG. 15B, the flexures are angled downwardly in directions from the outsides of the suture retainer 5200 toward opening 4212. This prevents the flexures from flexing upwardly as much as they flex downwardly, and insures that the locking tip cannot escape, once captured. Optionally, the flexures 4214 can have lengths that extend sufficiently far into the opening, when flexed in an upward direction, to physically prevent the locking tip 4190 from passing through the reduced size opening 4212. Additionally, the flexure may be provided with teeth 4214*t* as shown in FIG. 15C. In this case, any flexing upwardly of the flexures 4214 causes the teeth 4214*t* to bite into the suture 444 or a braid surrounding the suture 444 if present, thereby further securing the suture 444 to the suture lock 4200. The flexures and/or teeth also help to strip off any tissue that may be caught on the locking tip 4190 as it enters the anchor or trap.

The implant 10, 10' can be released from the stitching instrument 5000 in preparation for removing the stitching instrument from the surgical target and from the patient. FIG. 15E shows the bottom surface of the working end portion 4010. The implant 10, 10' is releasably coupled to the working end 4010 in a similar manner to the way that the suture anchors or traps 4200 are releasably coupled to the working end 4010. Wires 5202 extend from actuator 4210, such as a ring or key, other feature than can be readily grasped and pulled by the user, through elongate shaft 4140 and into working end 4010. Thus, one actuator 4210 pulls two wires 4202 to release the suture anchors/traps and, at the same time pulls two wires 5202 to release the implant 10. FIG. 15E is an illustration of a bottom view of working end portion 4010, showing the undersides of the needles 4170. Slots in the base of the working portion 5208 and gaps in the mesh attachment tab layer 1510 (not shown) are woven into and out of by the wires 5202 used to temporarily fix the implant 10 to the assembly 500.] Wires 5202 are threaded into and out of the top layer 1510 of the attachment member 150 (not shown in FIG. 15E) as it abuts the bottom surface of the working portion 4010, thereby skewering the layer 1510 and attaching it, and the implant 10, 10' to the working end portion 4010.

To release the implant 10, 10', the actuator 5210 is pulled proximally from the proximal end of the handle 4120*a* (see the partial view of FIG. 15F). Implant release actuator 5210 is connected to wires 5202. By pulling the actuator 5210 proximally relative to handle 4120*a*, this pulls the wires 5202 out of the working portion 4010 and out from the mesh layer 1510, thereby freeing the implant 10, 10' from the working portion 4010. Accordingly, the working portion 4010 can be removed from the surgical target area by withdrawing instrument 4000 from the patient, for example.

Once the suture anchors or traps 4200 have been released, and the implant 10, 10' has been released the stitching instrument 4000 can be removed from the suturing instrument 5000, as illustrated by FIG. 16A. Instruments 4000 and 5000 couple together at their handle portions such as with a tongue-and groove sliding connection, as shown by "tongues" or ribs 5300 and grooves 4300 (another groove exists on opposite side of handle 4120a, not shown) shown in FIG. 16C. Tongues 5300 slide into the mating grooves 4300 to join the instruments 4000, 5000 as shown in FIG. 16B. A locking member 5302 is provided to secure the connection between the two instruments, see FIG. 16B. In the embodiment of FIG. 16B, the locking member 5302 is a thumbscrew that threads into handle 5120 and tightens down against handle 4120a when the handles 4120a and 5120 are joined as in FIG. 16B. Of course, other locking arrangements could be substituted. By releasing the locking mechanism 5302 (unscrewing the thumbscrew in the embodiment of FIG. 16B), the handle 4120a can be slid off of handle 5120 as illustrated in FIGS. 16A and 16C, thereby effectively separating instrument 4000 from instrument 5000. As instrument 5000 is held in position, instrument 4000 can be removed from the surgical target and from this patient at this stage.

The suturing tool 5000 can next be operated to secure the implant 10 or 10' to the surgical target. Handle 5120 includes suture stays 5310 that keep the free, proximal end portions of the sutures 444 organized during the performance of the procedure described up until this stage. In order to cinch the sutures 444 and fix the device 10, 10' to the surgical target, the user takes each suture 444 out of its stay 5310 and pulls on it to apply tension to the suture. This draws the suture 444 through the suture retainer 1520, thereby drawing the implant 10, 10' up against the surgical target. As noted previously, the suture retainer 1520 allows the suture 444 to be drawn proximally therethrough, but prevents the suture from backsliding distally therethrough. Thus, the suture retainer maintains the suture 444 under tension once the user has performed the cinching operation. The suture remains under tension between the suture retainer 1520 and the suture anchor 4200.

Figure 17A:
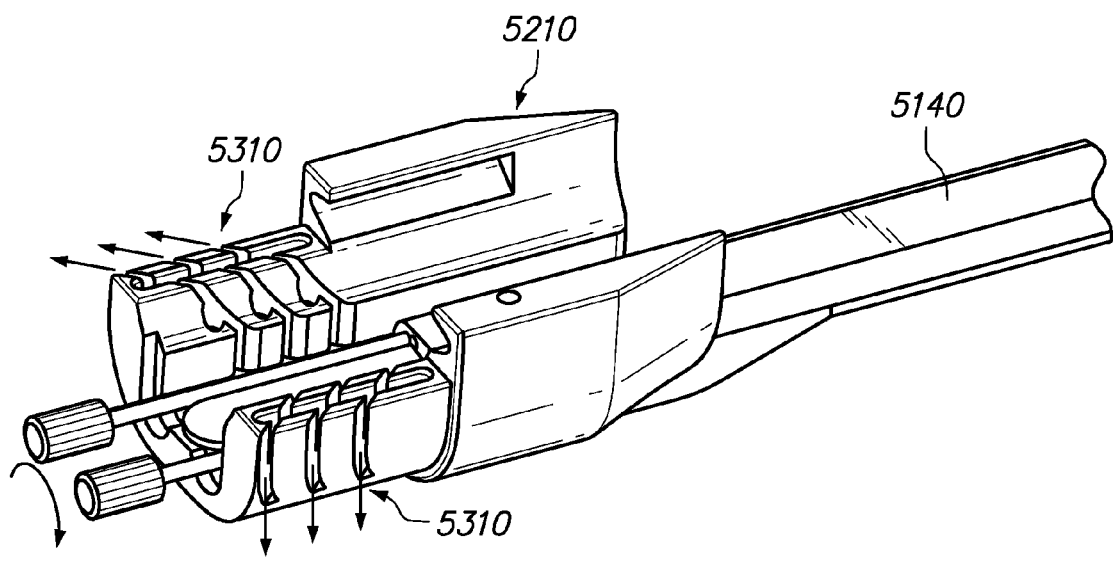
FIG. 17A illustrates a handle portion of a suturing instrument according to an embodiment of the present invention.

When the sutures 444 have been cinched and are satisfactorily held by the suture retainers 1520 to maintain the implant 10,10' in position against the surgical target portions of the sutures 444 proximal of the suture retainers 1520 can be cut off and removed from the patient. Cutters 5400 are provided that include tubes that pass proximally out of the proximal end of device 5000 (see FIG. 17B) and distally through shaft 5140, where they end just proximally of the working portion 5010. The distal end of each tube 5402 comprises a cutting tip or sharpened distal end 5404 configured to slice through sutures 444, see the enlarged partial view of FIG. 17C. FIG. 17C also illustrates only one suture 444 for clarity, although three sutures 444 would be cut by each cutter 5400 from the embodiment shown in FIG. 17A. Suture 444 routes through a lumen 5406 in a portion of shaft 5140 that is distal of cutter 5400, as suture 444 is routed from working portion 5010. Lumen 5406 may be substantially aligned with tube 5402, as shown in FIG. 17C. Suture 444 passes through a window 5408 and into adjacent lumen 5410 as it extends further proximally therethrough. Once the suture 444 has been cinched as described, the cutter 540 is advanced distally relative to instrument 5000 as illustrated in FIG. 17C, such as by pushing on actuator 5412 by a user. This action causes the cutter tip 5404 to collide with the suture path and thus the suture 444. The cutter can push the suture up against a cutting board wall feature 5414 as shown in the detail view of FIG. 17E (suture 444 not shown) to perform a chopping action on the suture 444 and or the actuator (e.g., cutter knob) 5412 can be twisted to perform a slicing cut against the cutting board face. By pushing and twisting, the chopping slicing actions can be continuously actuated until all sutures are cut (three sutures per cutter in this embodiment).

Once the suture cinching and cutting operations have been completed, suture instrument 5000 can be removed from the surgical target and the patient.

Figure 18A:
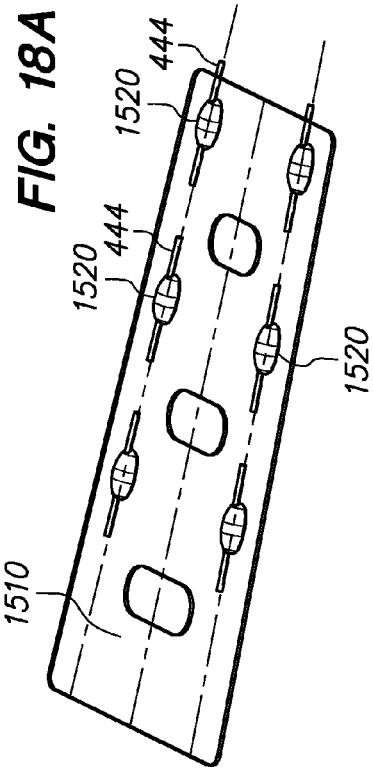
FIG. 18A is a schematic illustration of a preferred embodiment of suture retainers according to the present invention.
Figure 18B:
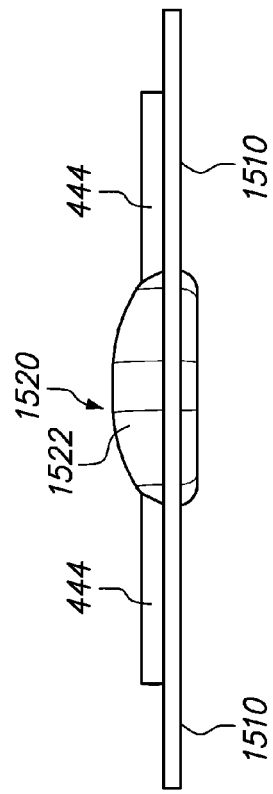
FIG. 18B is an enlarged schematic representation of one suture retainer of FIG. 18A.
Figure 18D:
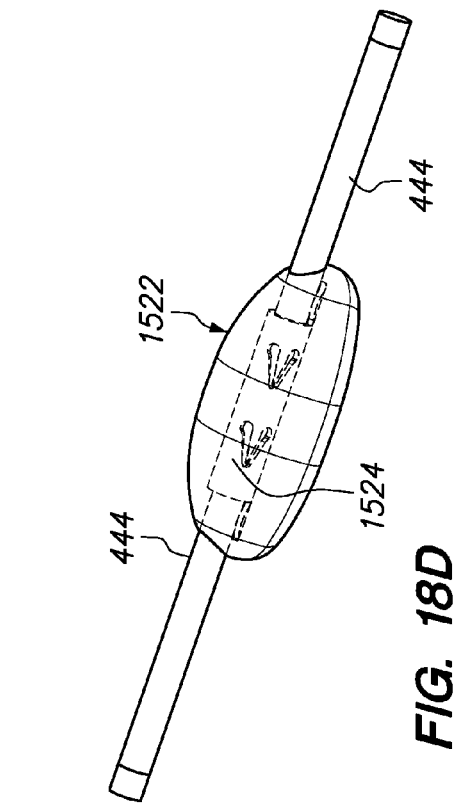
FIG. 18D illustrates the inner body embedded within the outer body of the suture retainer of FIG. 18B.
Figure 18C:
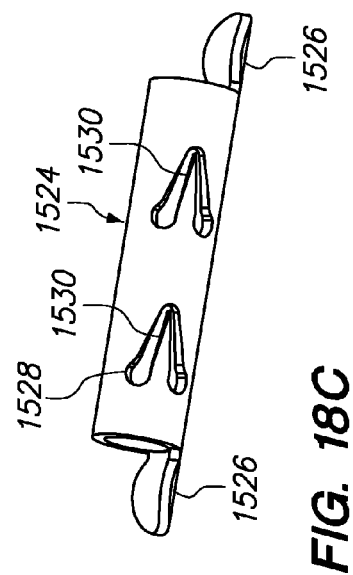
FIG. 18C illustrates the inner body of the suture retainer of FIG. 18B.

FIG. 18A is a schematic illustration of a preferred embodiment of suture retainers 1520 encapsulated on top mesh layer 1510 of attachment tab 150. FIG. 18B is an enlarged schematic representation of one suture retainer, illustrating that it is embedded into the mesh layer as an outer body 1522 (preferably made of silicone) of suture retainer 1520 encapsulates fibers of the mesh layer 1510. FIG. 18C illustrates the inner body 1524 of the suture retainer 1520. Tabs 1526 that extend proximally and distally of the inner body 1522 are inserted through holes in the mesh layer 1510 in preparation for embedding the suture retainers 1520 in the mesh layer 1510. The outer body 1522 is then molded around the inner body 1524, tabs 1526 and mesh layer 1510, so that there is molded polymer (preferably silicone) above and below the mesh layer 1510 and through the holes in the mesh layer 1510. FIG. 18D illustrates the inner body 1524 embedded within the outer body 1522. Sharp, chevron shaped cuts 1528 are made through the wall of the inner body 1524. The portions of the wall inside the cuts are then bent inwardly such that the points 1530 of these inner portions point toward the proximal end of the inner body. In this way, suture 444 can be pulled proximally through the inner body, but attempts to pull the suture 444 distally through the inner body result in pints 1530 piercing into the suture 444 and preventing it from sliding distally through the inner body 1524.

Figure 19A:
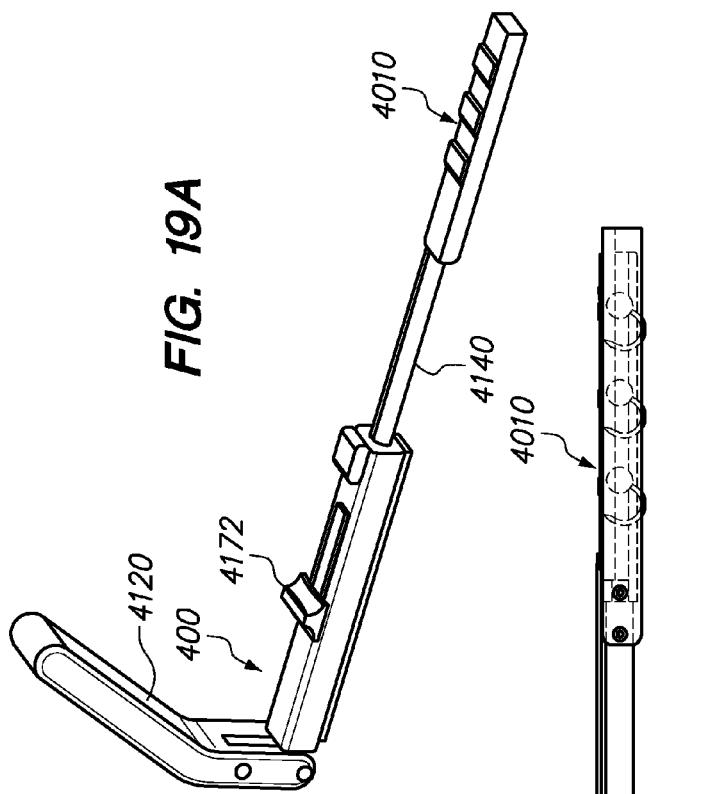
Figure 19B:
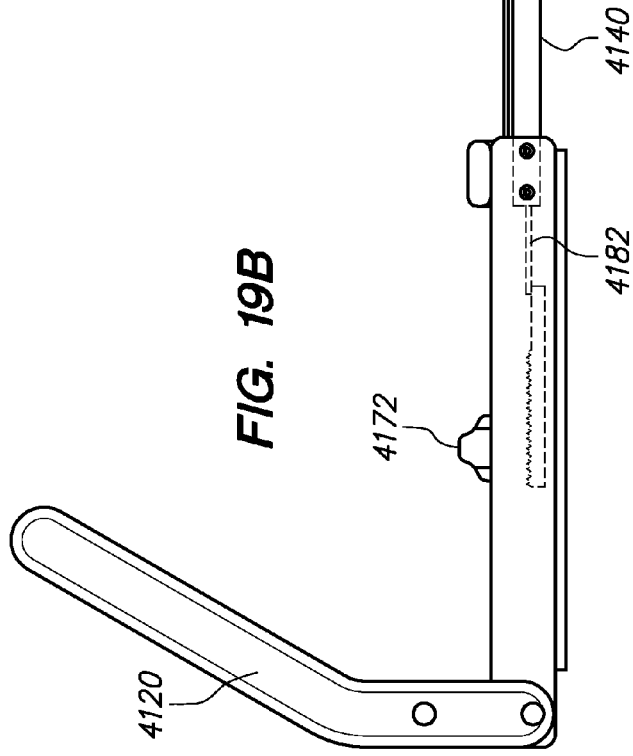
Figure 19C:
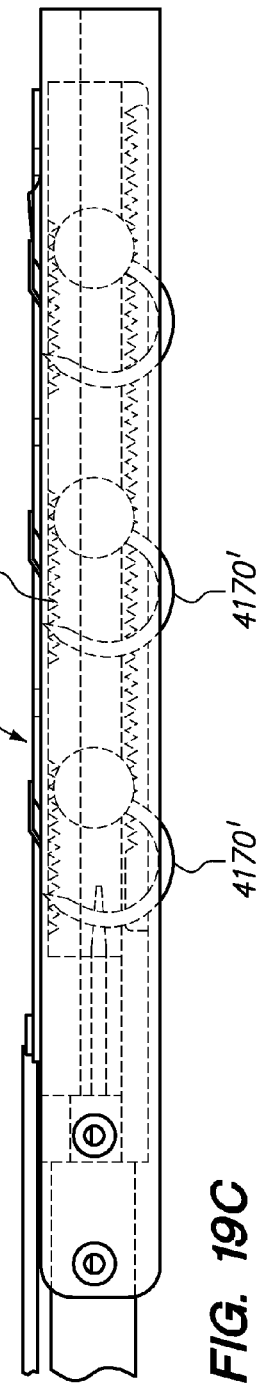

FIGS. 19A-19I schematically illustrate implantation of an expandable, paragastric, extra-gastric implantable device 10 to the fascia/peritoneum 127f and abdominal wall 127 using another embodiment of a stitching instrument 400 according to the present invention. Note in FIGS. 19A-19B, that the stitching needle actuator 4172 differs from that of the earlier embodiment described, in that it is slidable distally and proximally relative to the instrument to drive and retract the stitching needles 4170'. Also, the stitching needles 4170' have a more continuous radius of curvature than that of needles 4170. Needles 4170 have a relatively more flattened shaped and tend less toward accumulating tissues as they are passed through the surgical target. Needles 4170' are similarly advanced and retracted using a rack and pinion type driving mechanism, as illustrated in FIG. 19C.

Figure 19D:
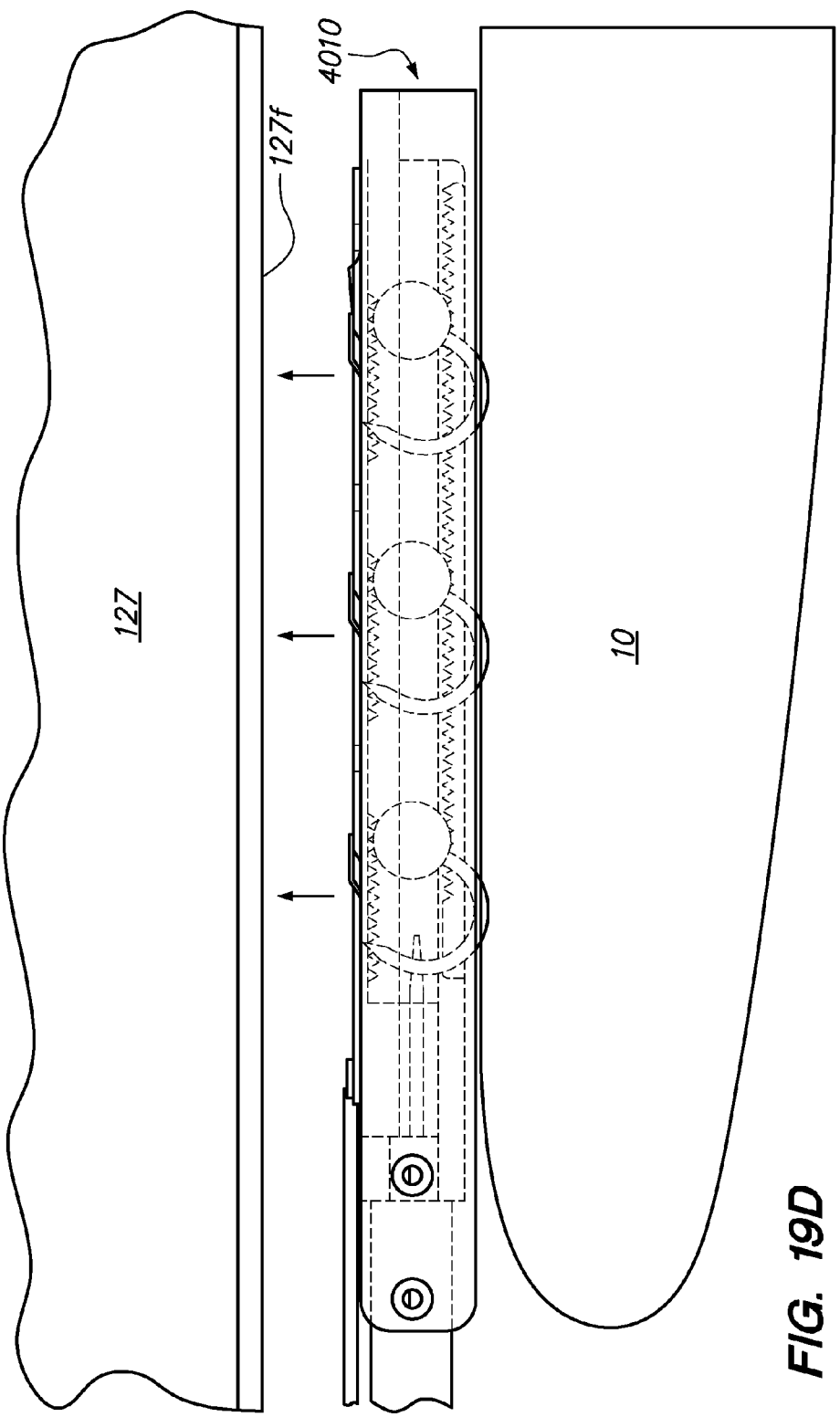

At FIG. 19D, after having attached the implant to the working portion 4010 and inserted the working portion and implant into the patient the working end portion is positioned adjacent the surgical target, in this case, the peritoneum and fascia 127f and abdominal wall 127. The working end portion 4010 is positioned up into contact with the peritoneum and fascia 127f and abdominal wall 127, and while being held in contact diving of the stitching needles is begun as illustrated in FIG. 19E, by advancing the actuator 4172 relative to the instrument 400, thereby driving the stitching needles into the surgical target at entry locations 4400. Note that this embodiment also does not employ stabilization pins, but if an embodiment employing stabilization pins were used, the stabilization pins would be inserted adjacent the entry locations 4400 prior to beginning the driving of the stitching needles 4170, 4170'.

Figure 19G:
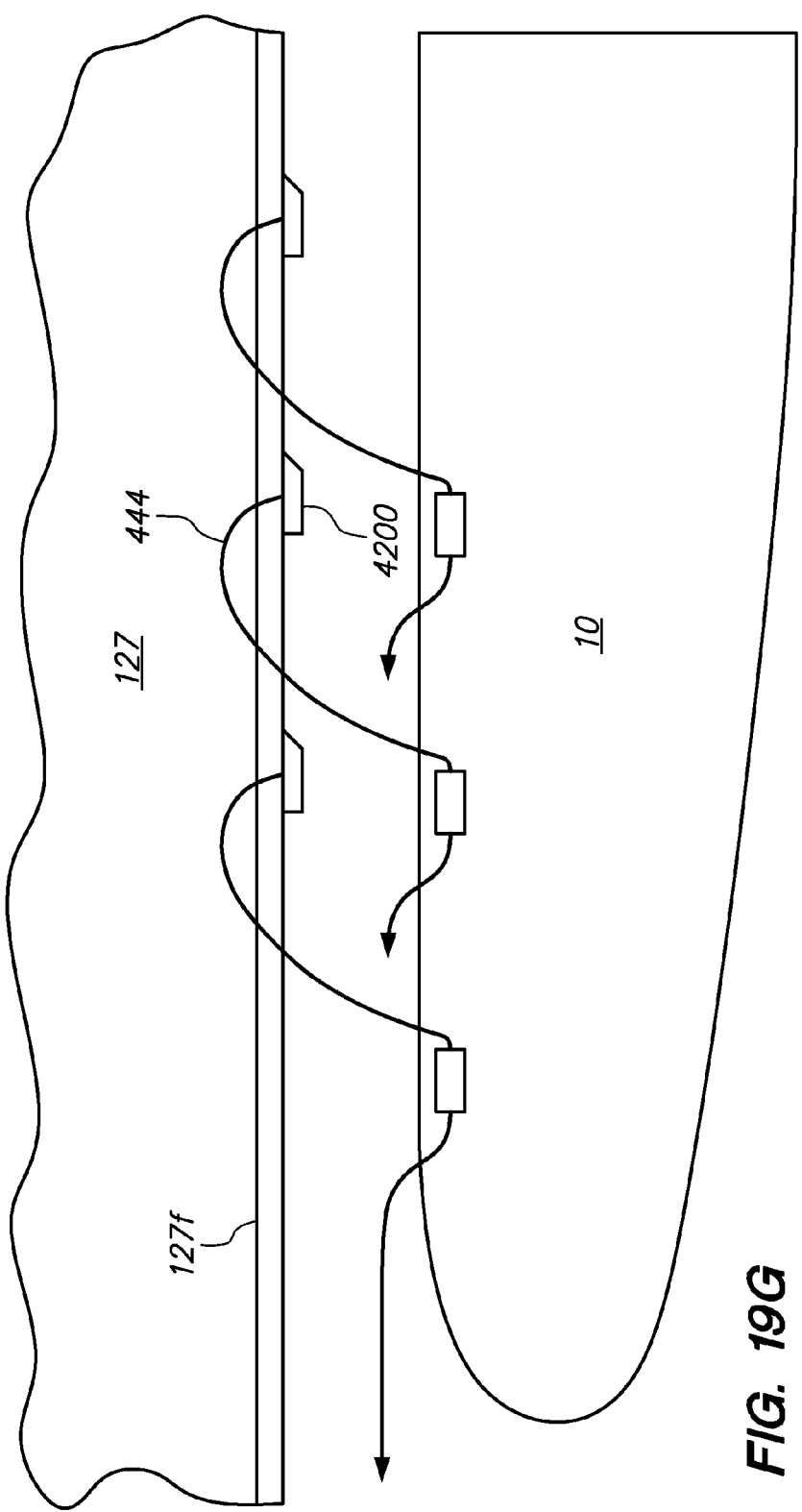
Figure 19I:
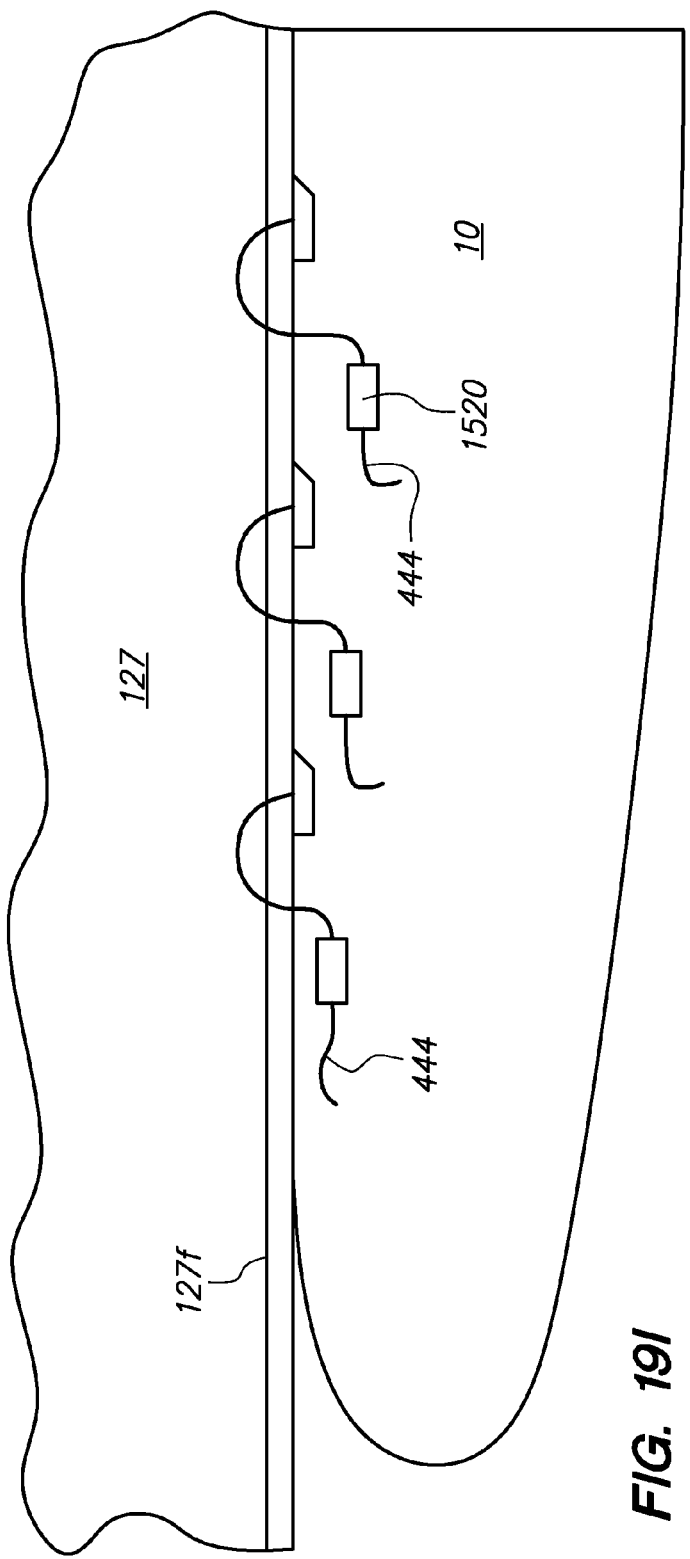

FIG. 19F illustrates completion of the stitches by continuing to advance the actuator 4172 to dive the tips of the needles 4170' and the locking tips 4190 through the respective suture anchors or traps 4200. After retracting the stitching needles 4170' and releasing the suture anchors or traps 4200 in the manners described previously, instrument 400 is removed from the patient, leaving the implant 10 tethered to the abdominal wall 127 via sutures 444 as illustrated in FIG. 19G.

Next, the implant 10 is cinched against the abdominal wall 127 using techniques described previously. Note that although this embodiment does not use a suturing instrument 5000, that cinching can still be performed by pulling on the sutures 444, causing them to slide proximally through the suture retainers 1520 to generate tension in the sutures between the suture retainers 1520 and suture anchors or traps 4200, thereby drawing the implant 10 against the abdominal wall. This position is maintained, as the suture retainers do not allow the sutures to backtrack therethrough. Next the excess suture material proximal of the suture retainers is cut off and removed, see FIG. 19I. Since a suturing instrument 5000 is not used in this embodiment cutting can be performed with scissors configured for endoscopic procedures, for example.

Figure 20:
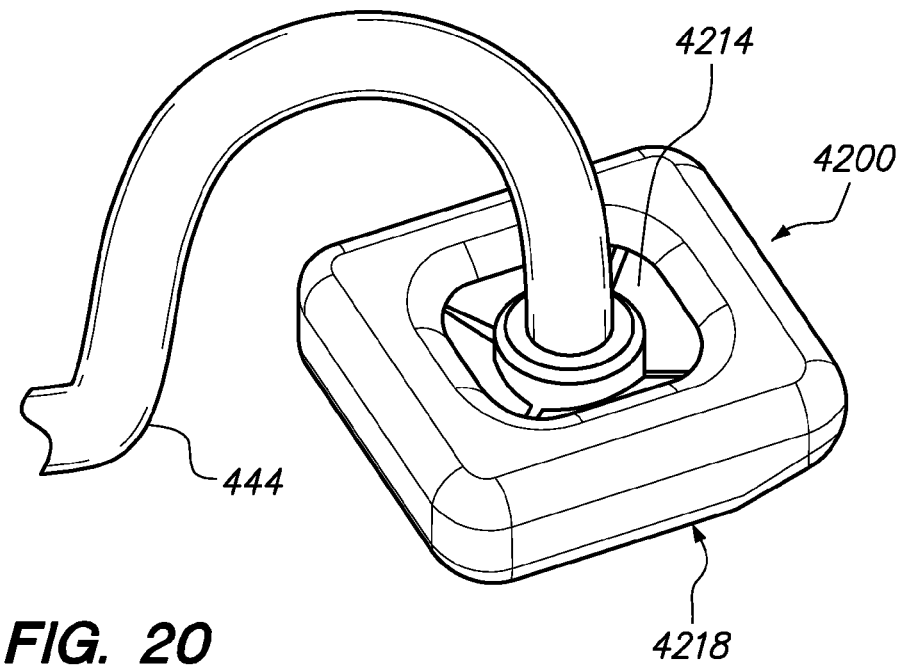
FIG. 20 shows an alternative embodiment of a suture and suture anchor or trap according to the present invention.

FIG. 20 shows an alternative embodiment of a suture 444 and suture anchor or trap 4200 that can be used. Although shown being used together, it is noted that the suture 444 and locking tip 4190 shown can be used with other embodiments of suture anchor shown and described herein. Likewise, the suture anchor 4200 shown can be used with other embodiments of suture 444 and locking tip 4190 shown and described herein. The previous two sentences apply likewise to the other embodiments of sutures 444, locking tips 4190 and suture anchors or traps 4200 described and shown herein. In FIG. 20, suture 444 is formed of a polyester braid. The main body 4218 of suture anchor 4200 is molded from polyester. The locking tip 4190 may also be molded from polyester. In this embodiment the flexures or "trap doors" 4214 provided are made of stainless steel. Also, rather than having just two flexures 4214, this embodiment has four flexures 4214 that extend from each of four sides of the main body 4218 toward the opening.

Figure 21:
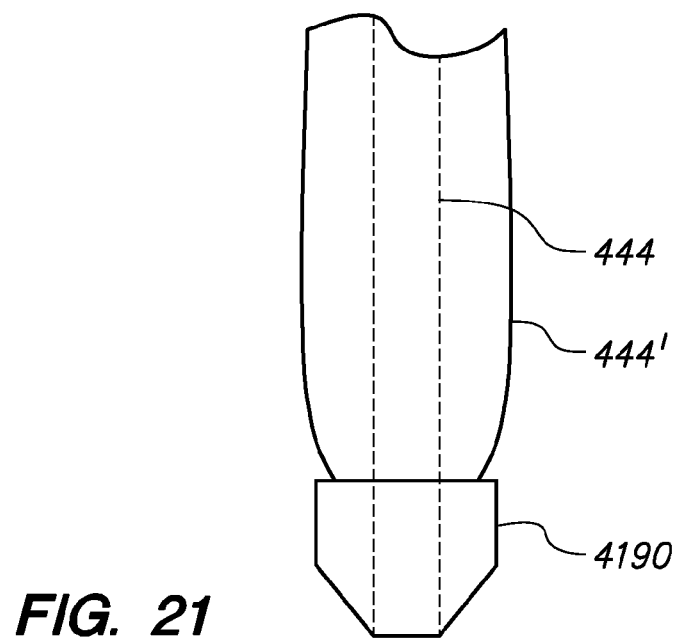
FIG. 21 shows a suture provided together with an overbraid, according to an embodiment of the present invention.

Alternatively to forming suture 444 as a braided structure as in FIG. 20, a suture 444 may be provided together with an overbraid 444' as illustrated in FIG. 21. The braided structure 444 of FIG. 20 may be the same as that of 444' in FIG. 21. Suture 444 in FIG. 21 may be a monofilament strand suture, although a braid is preferred. One embodiment of braided structure that may be used is a polyester braided suture with a braid pattern of 1×1., 32±2 picks per inch (post heat set) 85 Denier, 24 filament (85/24) yarn size, high tenacity white polyester. The suture flat width (measured with a snap gauge with no tension applied) is about 0.0170 inches ±about 0.0010 inches. Another embodiment of a braided structure that may be used is a polyester braided suture with a braid pattern of 1×1., 32±2 picks per inch (post heat set) 40 Denier, 27 filament (40/27) yarn size, black polyester. The suture flat width (measured with a snap gauge with no tension applied) is about 0.0170 inches ±about 0.0010 inches. Another embodiment of a braided structure that may be used is a polyester braided suture with a braid pattern of 1×1, 32±2 picks per inch (post heat set) 85 Denier, 24 filament (85/24) yarn size high tenacity white polyester and 40 Denier, 27 filament (40/27) yarn size, black polyester formed in a patter of white with black candy stripe. The suture flat width (measured with a snap gauge with no tension applied) is about 0.0170 inches ±about 0.0010 inches.

Figure 22A:
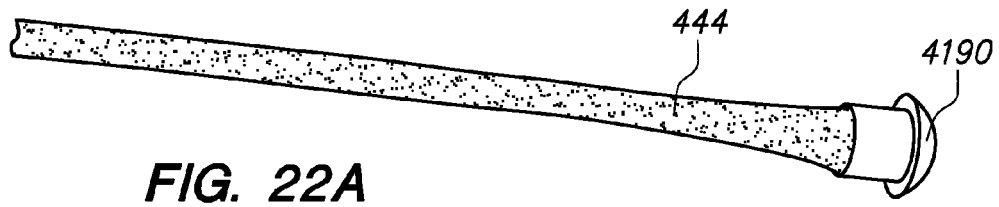
FIG. 22A illustrates a braided suture like that in FIG. 20 wherein the suture comprises braided polyester.
Figure 22B:
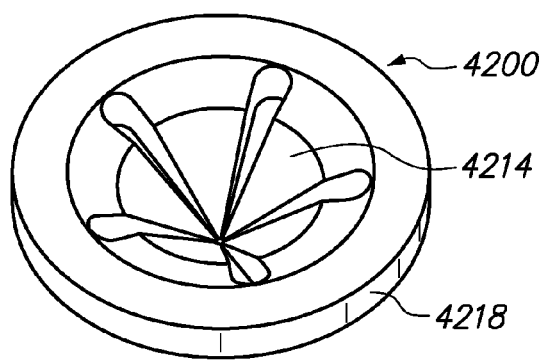
FIGS. 22B-22C show another embodiment of a suture anchor or trap according to an embodiment of the present invention.
Figure 22C:
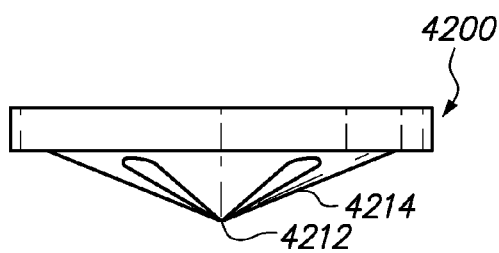
Figure 22D:
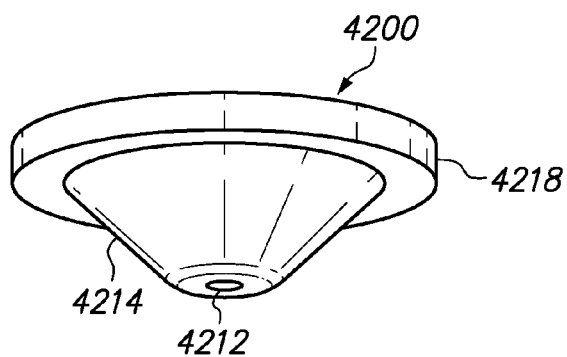
FIG. 22D shows a variation of the embodiment of FIGS. 22B-22C.

FIG. 22A illustrates a braided suture 444 like that in FIG. 20 wherein the suture comprised braided polyester. Likewise, locking tip 4190 is made of polyester. FIGS. 22B-22C show another embodiment of a suture anchor 4200 that is made of silicone and can function as described in previous embodiments above. Alternatively, this embodiment be co-molded into a layer 1510 of attachment tab, where it still performs the function of a suture anchor 4200, but is integrated into the attachment tab 150. Like the embodiment of FIG. 20, flexures 4214 are separated by slots. However, the main body 4218 is substantially circular. The embodiment of FIG. 33D is similar to that of FIG. 22B, but the flexures 4214 are integrated and not separated by slots. Thus, opening 4212 is continuously surrounded by flexure 4214.

Figure 22E:
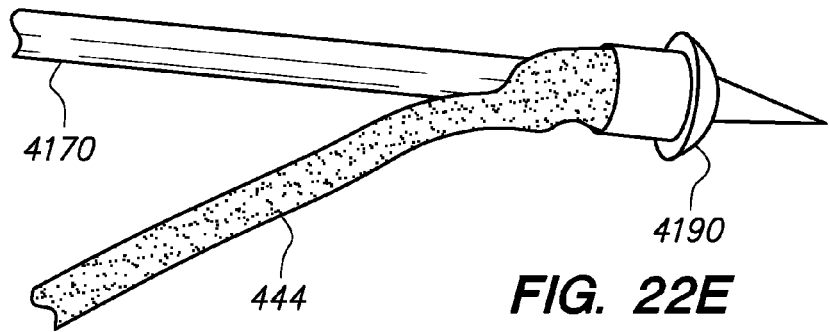
FIG. 22E illustrates assembly of the suture and locking tip of FIG. 22A on a stitching needle according to an embodiment of the present invention.
Figure 22F:
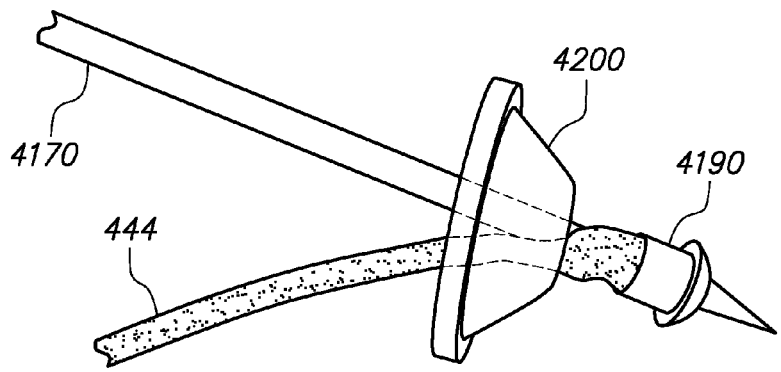
FIG. 22F illustrates the needle and locking tip of FIG. 22E, along with the distal end of the suture having been inserted through a suture anchor or trap.
Figure 22G:
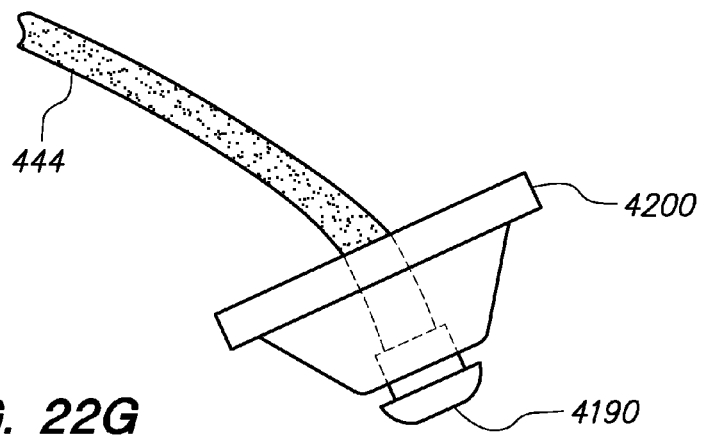
FIG. 22G shows that the suture anchor or trap prevents the locking tip from passing back through the suture anchor or trap.
Figure 22H:
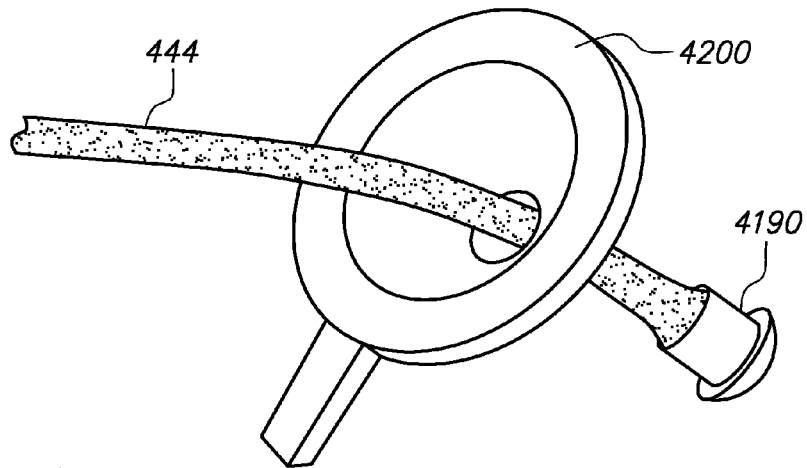
FIG. 22H shows an alternative embodiment in which the suture anchor or trap is molded from implantable polyester.

FIG. 22E illustrates assembly of the suture 444 and locking tip 4190 of FIG. 22A on stitching needle 4170. Needle 4170 in inserted through the wall of the suture and thus inserted inside the tube of the braid and is inserted through the locking tip 4190 as shown. FIG. 22F illustrates the needle 4170 and locking tip 4190, along with the distal end of suture 444 having been inserted through the suture anchor 4200. This illustrates the relationship between the components at the end of the deployment stroke of needle 4170. When the needle 4170 is retracted, the suture anchor 4200 prevents the locking tip 4190 from passing back through the suture anchor 4200, as illustrated in FIG. 22G. FIG. 22H shows an alternative embodiment in which the suture anchor 4200 is molded from implantable polyester.

FIG. 23A shows top perspective view of another embodiment of a suture anchor 4200 according to the present invention. In this embodiment, an inner keyhole component 4216 (see top and bottom views of FIGS. 23B-23C is provided to be relatively rigid. In one embodiment keyhole component is made of rigid plastic, such as polyester, but has atraumatic, relatively soft edges. Opening 4212 has a "keyhole" appearance resulting from the joining of a relatively large diameter opening 4212b with a relatively smaller diameter opening 4212a. Main body 4218 has a flexure 4214 formed integrally therewith, see FIGS. 23D-23E. The keyhole component 4216 can be co-molded inside the main body 4218 to provide the finished product shown in FIG. 23A. In at least one embodiment main body 4218 is molded of silicone. The trap door or flexure 4212b underlies the majority of the large diameter portion 4212b of the opening 4212 as shown in FIG. 23A. Keyhole component 4216 includes a beveled edge 4219 around at least the large portion 4212b of opening 4212 that helps direct the needle 4170 into the opening 4212.

Figure 23F:
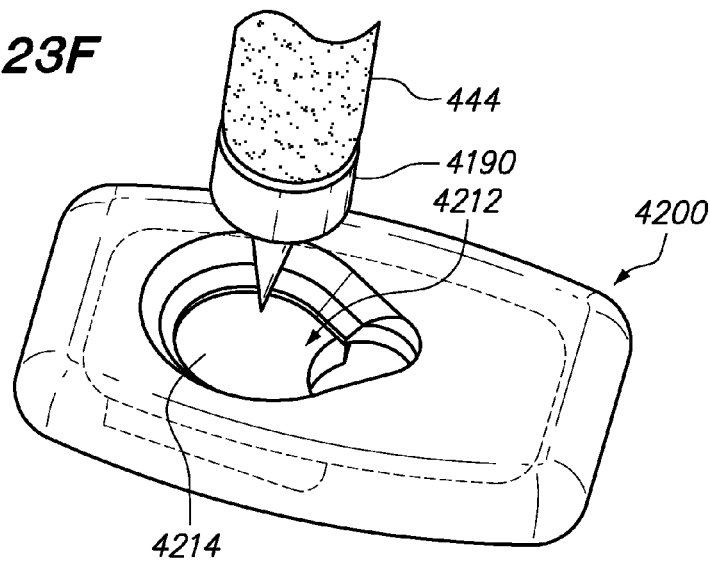
Figure 23G:
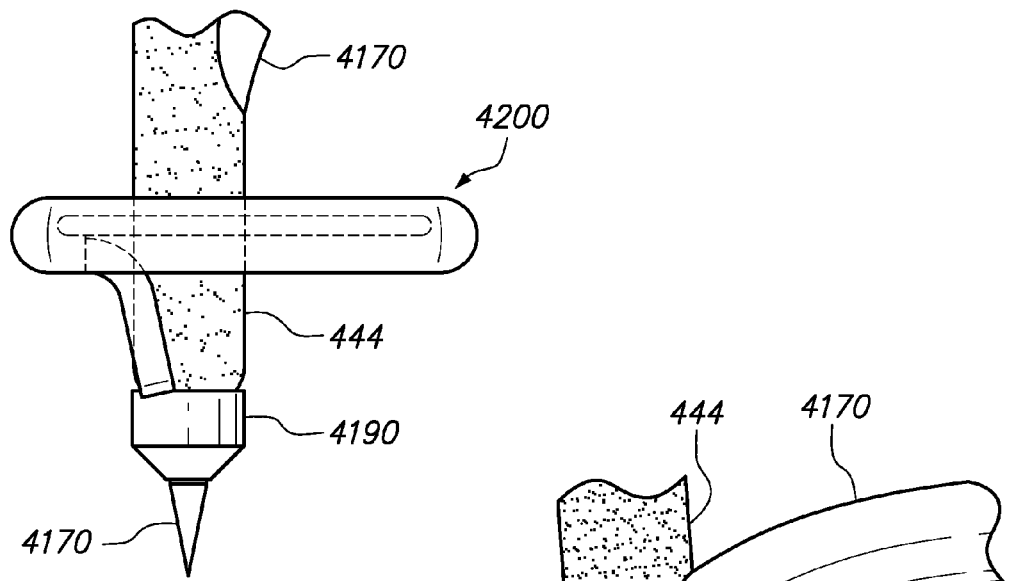
Figure 23H:
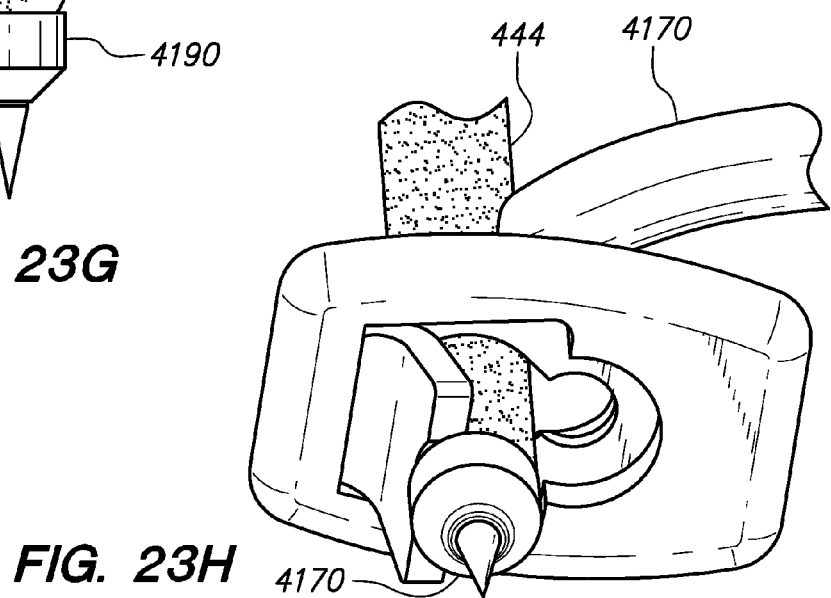
Figure 23I:
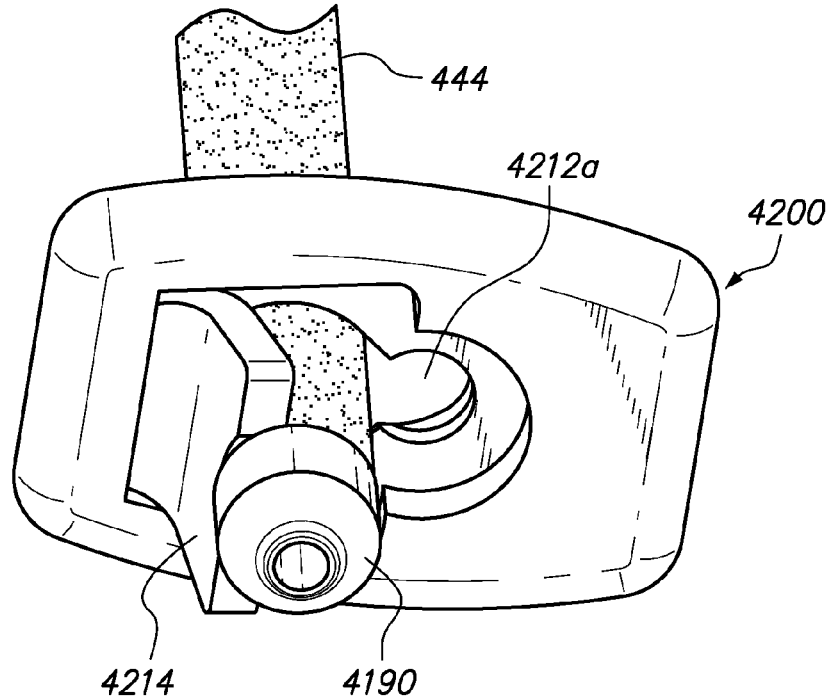
Figure 23J:
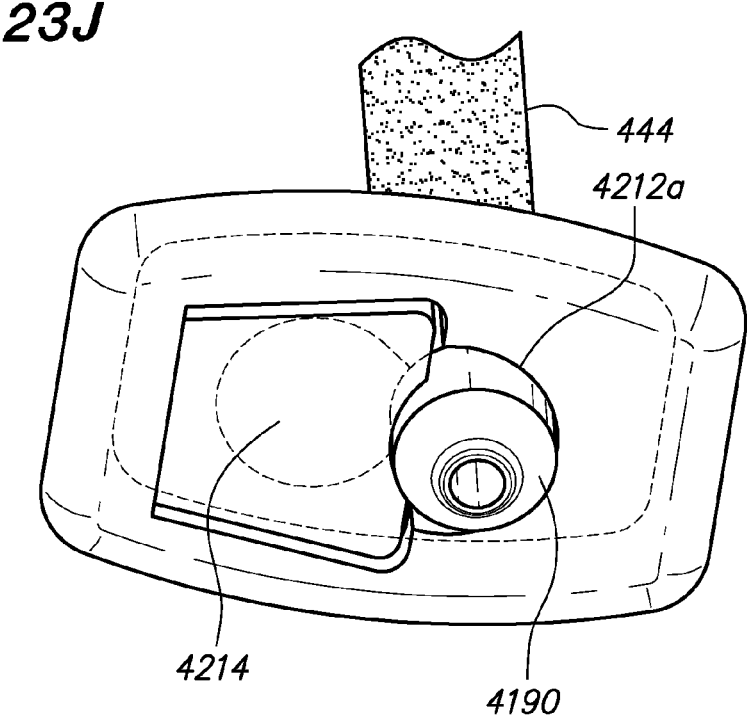

FIGS. 23F-23K show an embodiment of a suture 444 and locking tip 4190 being anchored in suture anchor 4200. As the needle tip 4170, locking tip 4190 and suture 444 (locking tip 4190 is co-molded with suture braid 444 in this embodiment) enter the opening 4212, the needle 4170 tip strikes the trap door (flexure) 4214. As the needle 4170 passes through the opening 4212, it deflects the trap door flexure 4214 as illustrated in the side and bottom views of FIGS. 23G-23H, respectively. The opening 4212 is large enough to allow the needle 4170 and locking tip 4190 to pass therethrough When the needle 4170 beings to retract the edge of the trap door 4214 catches on the proximal end of the locking tip 4190 as shown in FIG. 23I. The trap door 4214 straightens, driven by the retraction force of the needle 4170 and elastic recoil of the flexed trap door 4214. This pushes the suture braid 444 into the smaller portion 4212a of the opening 4212, as shown in FIG. 23J. The diameter of the smaller portion 4212a is smaller than the outside diameter of locking tip 4190. Accordingly, the locking tip cannot retract past the keyhole component as it is locked in place by trap door flexure 4214 and the smaller opening portion 4212*a*, as shown in FIG. 23J. FIG. 23K is a side view illustration showing the locking of the locking tip by trap door 4214 and the smaller portion of the opening 4212*a*.

Figure 24A:
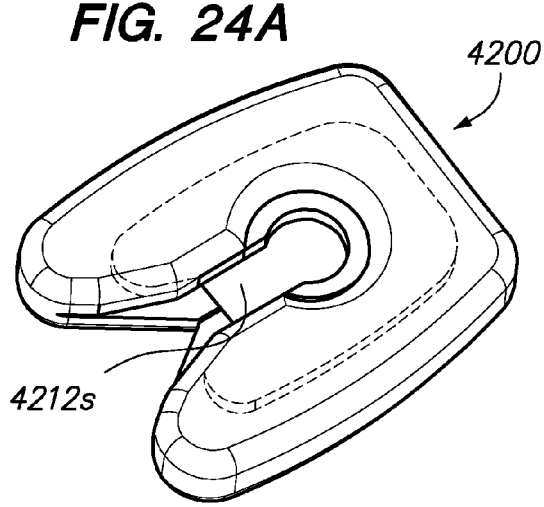
FIGS. 24A and 24B show top and bottom perspective views, respectively, of another embodiment of a suture anchor or trap according to the present invention.
Figure 24B:
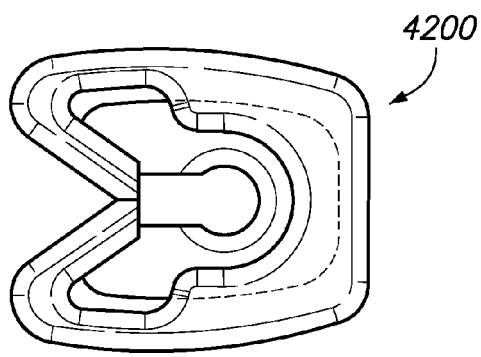
Figure 24C:
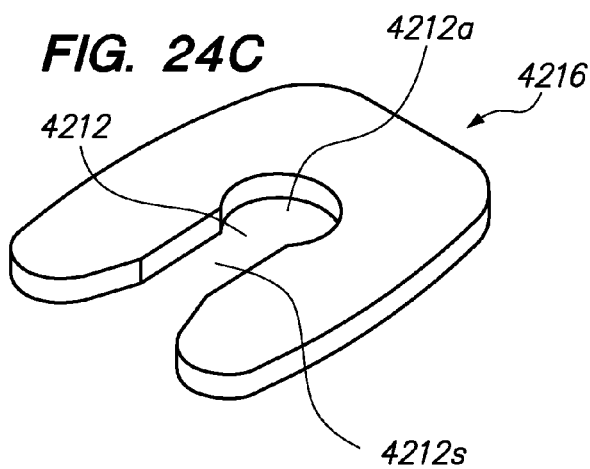
FIGS. 24C-24D show top and bottom views of an inner keyhole component of the embodiment of FIGS. 24A-24B.
Figure 24D:
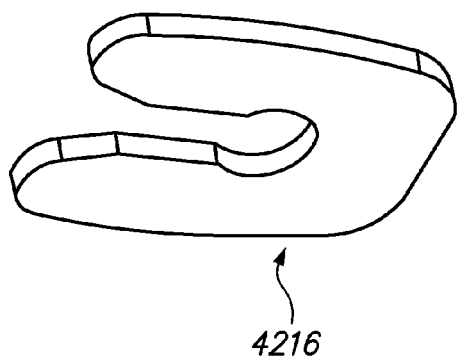
Figure 24E:
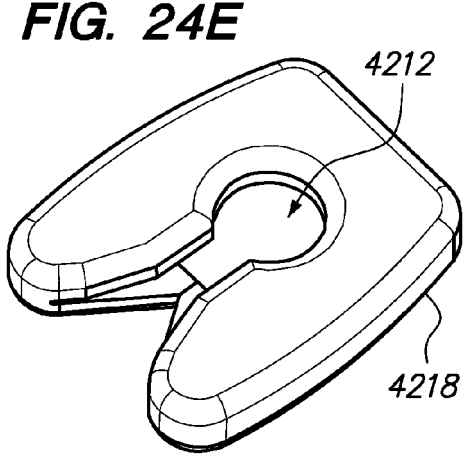
FIGS. 24E-24F show a main body of the embodiment of FIGS. 24A-24B.
Figure 24F:
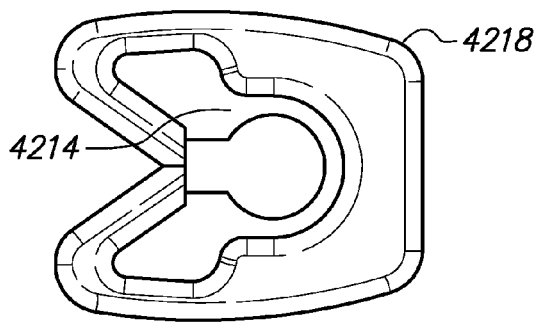

FIGS. 24A and 24B show top and bottom perspective views, respectively, of another embodiment of a suture anchor 4200 according to the present invention. In this embodiment, an inner keyhole component 4216 (see top and bottom views of FIGS. 24C-24D, respectively is provided to be relatively rigid. In one embodiment keyhole component is made of rigid plastic, such as polyester, but has atraumatic, relatively soft edges. Opening 4212 has a "keyhole" appearance resulting from the joining of a slot 4212*s* with a substantially circular opening 4212*a*. Main body 4218 has a flexure 4214 formed integrally therewith, see FIGS. 24E-24F. The keyhole component 4216 can be co-molded inside the main body 4218 to provide the finished product shown in FIGS. 24A-24B. In at least one embodiment main body 4218 is molded of silicone.

Figure 24G:
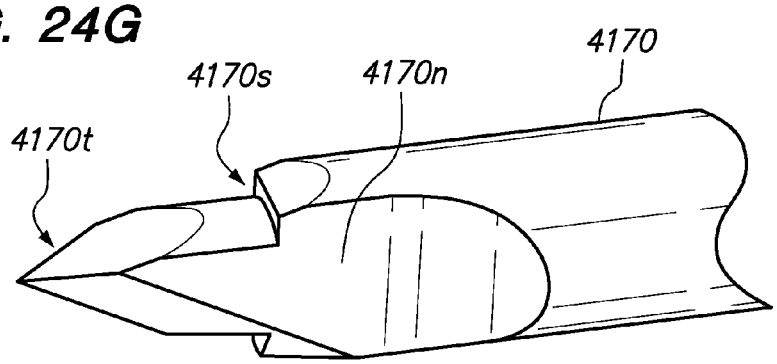
FIG. 24G illustrates a distal end portion of a needle that can be used to lock a suture and locking tip to a suture anchor or trap such as shown in FIGS. 24A-24F.
Figure 24H:
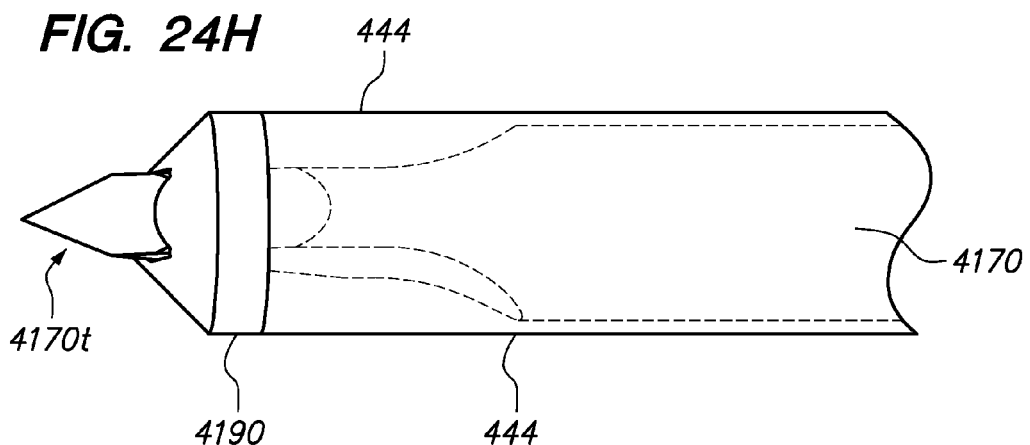
FIG. 24H shows a locking tip and suture mounted over the tip of the needle shown in FIG. 24G.
Figure 24I:
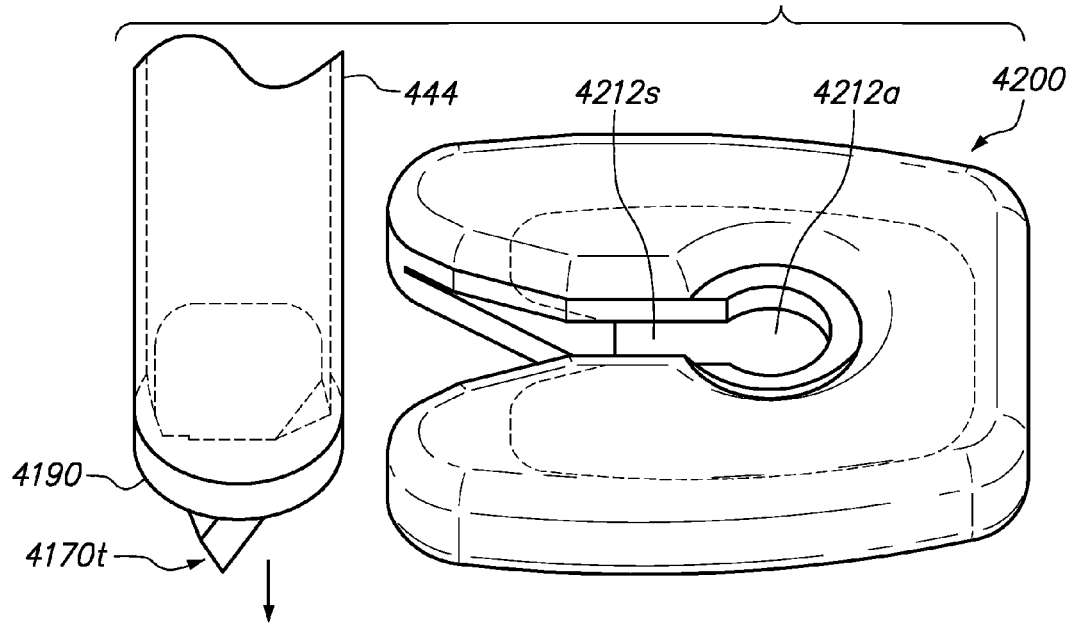
FIG. 24I shows the needle, suture and locking tip of FIG. 24H being advanced toward a suture trap or anchor.

FIG. 24G illustrates a distal end portion of a needle 4170 that can be used to lock a suture 444 and locking tip 4190 to a suture anchor such as shown in FIGS. 24A-24F. The needle tip is formed with a tri-facet sharp 4170*t* and a shoulder 4170*s* is formed against which the locking tip 4190 seats. A narrowed, neck portion 4170*n* is provided to facilitate entry of the needle 4170, suture 444 and locking tip 4190 into suture anchor 4200 as described below. FIG. 24H shows locking tip 4190 and suture 444 mounted over the tip 4170*t* of needle 4170. As the needle 4170 is advanced into and back out of the surgical target, as described above, the needle 4170 carries the suture braid 444 and co-molded locking tip 4190 through the tissue of the surgical target and to a location adjacent the suture anchor as illustrated in FIG. 24I.

Figure 24J:
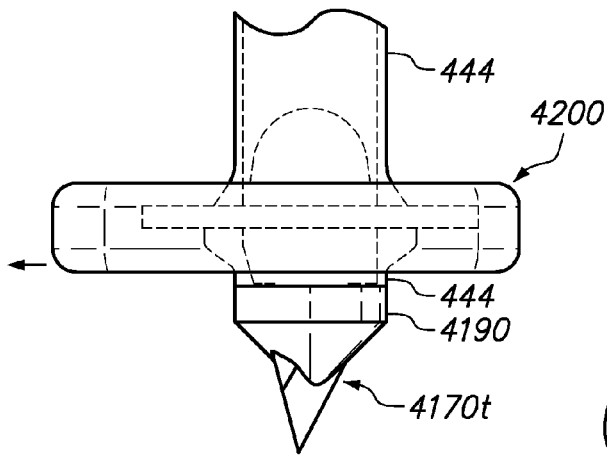
FIGS. 24J-24K are side and bottom views of the needle, suture and locking tip of FIG. 24H received in the suture trap or anchor.
Figure 24K:
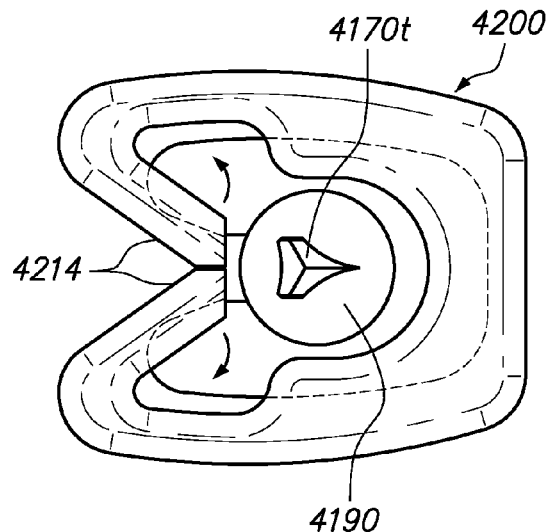
Figure 24L:
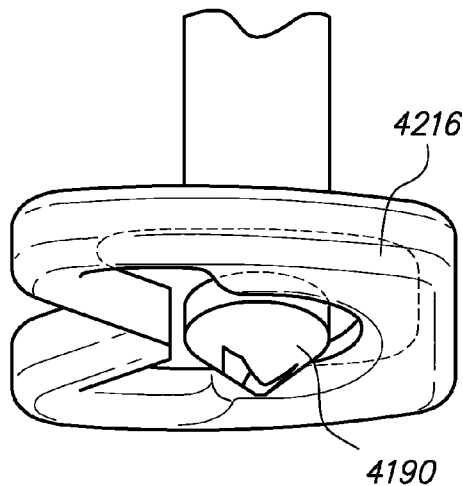
FIGS. 24L-24M are views of the suture and locking tip of FIGS. 24J-24K anchored to the suture anchor or trap after removal of the needle.
Figure 24M:
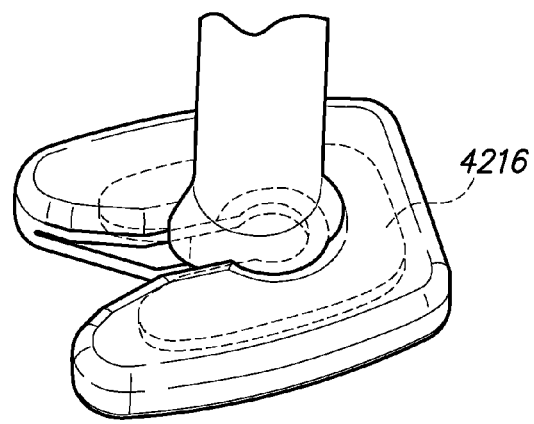

In this embodiment the stitching instrument 400 or 4000 pushes the suture anchor 4200 toward the needle 4170, whereby the needle 4170, suture 444 and locking tip 4190 become engaged in the suture anchor 4200 as illustrated in FIGS. 24J-24K. This action also releases the suture anchor from the stitching instrument 400 or 4000. The flexures 4214 of the main body 4218 flex (in the directions of the arrows shown in FIG. 24K) to allow the needle 4170 and suture 444 to slide into the slot 4212*s* and then into opening 4212*a*. When the needle 4170 is positioned in opening 4212*a*, the flexures 4214 spring back to their unflexed positions shown in FIGS. 24K-24M, thereby preventing needle 4170 and suture 444 from backtracking out of the slot 4212*s*. When the needle 4170 retracts from the suture lock, the locking tip 4190 seats on the keyhole component 4190 as illustrated in FIGS. 24L-24M. The opening 4212*a* has a smaller diameter than the outside diameter of locking tip 4190 and this prevents locking tip 4190 from retracting our of the keyhole component 4216.

Figure 25D:
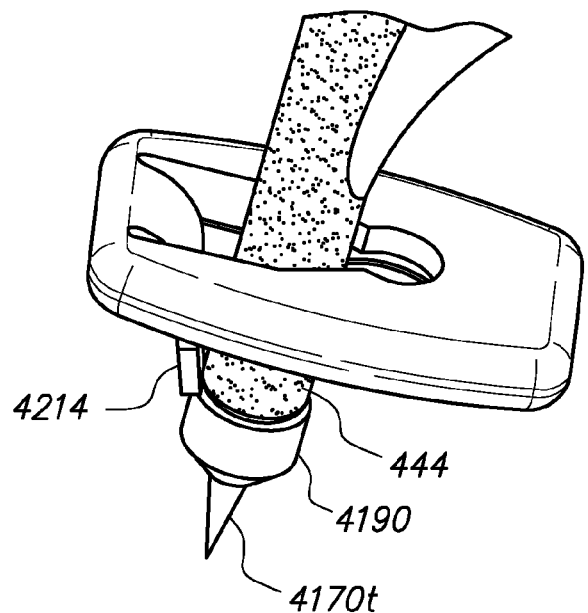
Figure 25E:
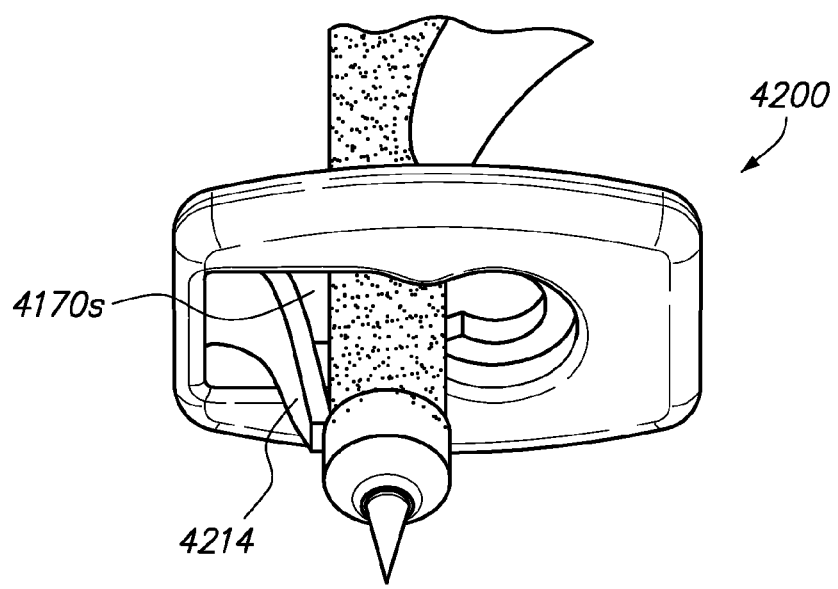

FIGS. 25A-25B show top and bottom perspective view of another embodiment of a suture anchor 4200 according to the present invention. This embodiment is similar to the embodiment described above with regard to FIG. 23A, but is a one-piece anchor, in which all features are integrated into the main body 4218. In this embodiment, flexure 4214 extends from a portion of the perimeter of main body 4218 into the slot portion 4212*s* of opening 4212 and the end 4214*e* of flexure 4214 forms a part of the circumference of opening 4212*a*.

Figure 25F:
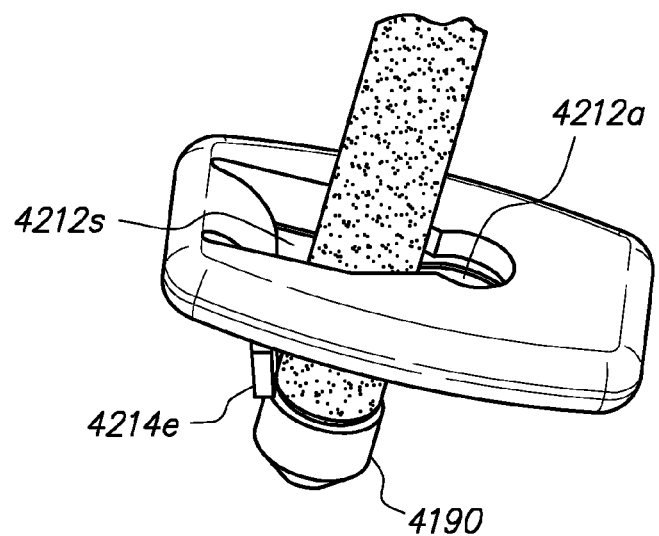
Figure 25G:
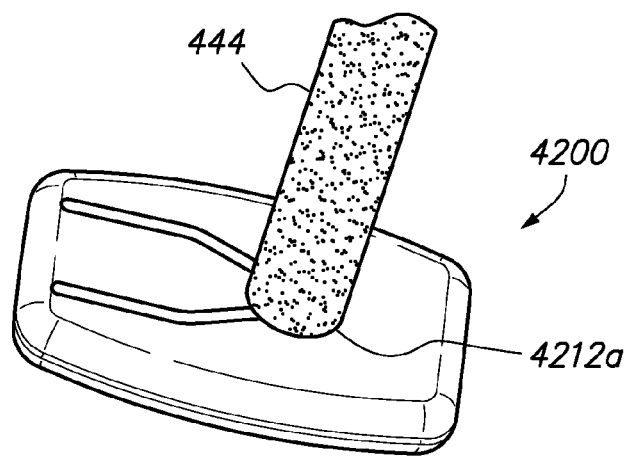
Figure 25H:
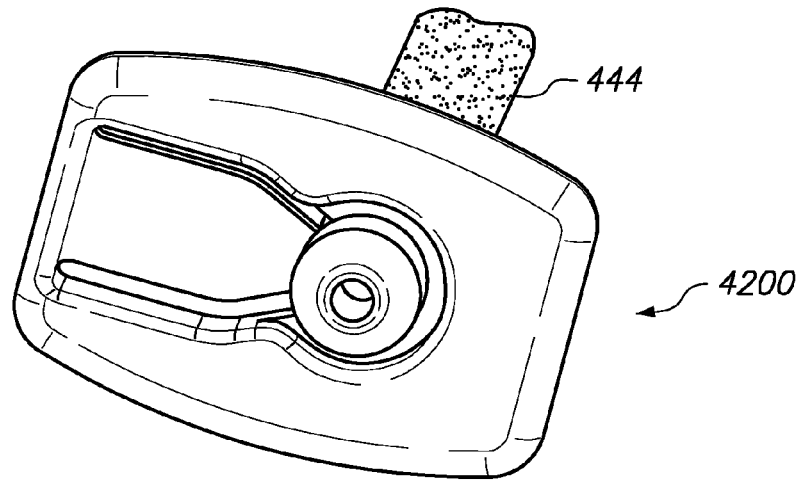

FIGS. 25C-25H show an embodiment of a suture 444 and locking tip 4190 being anchored in suture anchor 4200. As the needle tip 4170*t*, locking tip 4190 and suture 444 (locking tip 4190 is co-molded with suture braid 444 in this embodiment) approach suture anchor 4200 (FIG. 25C), the needle tip 4170*t* strikes the trap door (flexure) 4214. As the needle 4170 passes through the opening 4212, it deflects the trap door flexure 4214 as illustrated in the top and bottom views of FIGS. 25D-25E, respectively. The opening 4212*s* is large enough to allow the needle 4170 and locking tip 4190 to pass therethrough When the needle 4170 beings to retract, the edge 4214*e* of the trap door 4214 catches on the proximal end of the locking tip 4190 as shown in FIG. 25F. The trap door 4214 straightens, driven by the retraction force of the needle 4170 and elastic recoil of the flexed trap door 4214. This pushes the suture braid 444 into the smaller portion 4212*a* of the opening 4212, as shown in FIG. 25G. The diameter of the smaller portion 4212*a* is smaller than the outside diameter of locking tip 4190. Accordingly, the locking tip 4190 top cannot retract back through the suture anchor 4200, as it is locked in place by trap door flexure 4214 and the smaller opening portion 4212*a*, as shown in FIG. 25H.

Figure 26A:
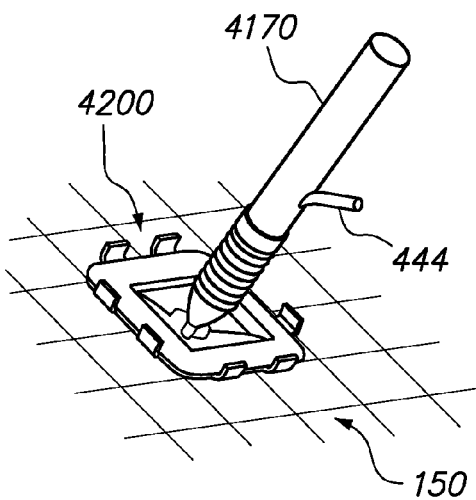
FIGS. 26A-26B illustrate another embodiment of a suture anchor or trap according to the present invention.
Figure 26B:
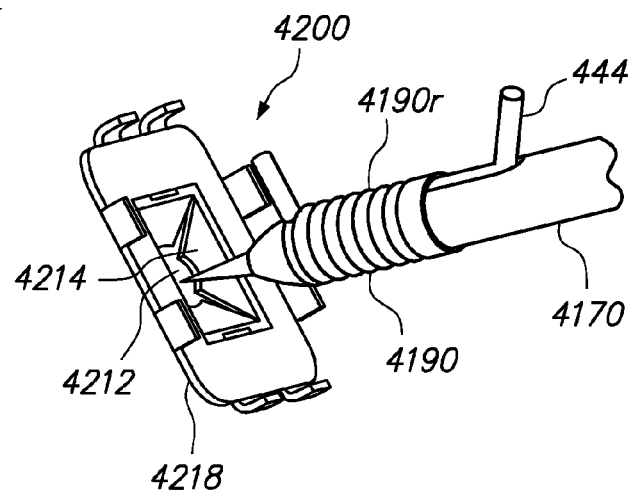

FIGS. 26A-26B illustrate another embodiment of a suture anchor 4200 according to the present invention. In this embodiment suture anchor 4200 could be used as described above with regard to FIG. 15A or FIGS. 19A-19I. Alternatively, suture anchor can be attached to the mesh of attachment tab 150, as indicated in FIG. 26A. In this embodiment, suture lock 4200 is made of metal, such as stainless steel, nickel-titanium alloy, or other biocompatible metal. Flexures 4214 are separated by slots and are oriented similarly to those shown and described above with regard to FIG. 20. Ribs 4190*r* on locking tip 4190 are abutted against by the ends of flexures 4214 after the tip 4190, needle 4170 and distal end of suture 444 have been passed through opening 4212 and upon retracting needle 4170. The abutment of the flexures against rib 4190*r* straightens the flexures to be more in line with the plane of the main body 4218. This reduces the diameter of the opening 4212 such that flexures 4214 clamp down on the locking tip 4190 and prevent it from being retracted out of the suture anchor 4200.

Figures 27A, 27B, 27C:
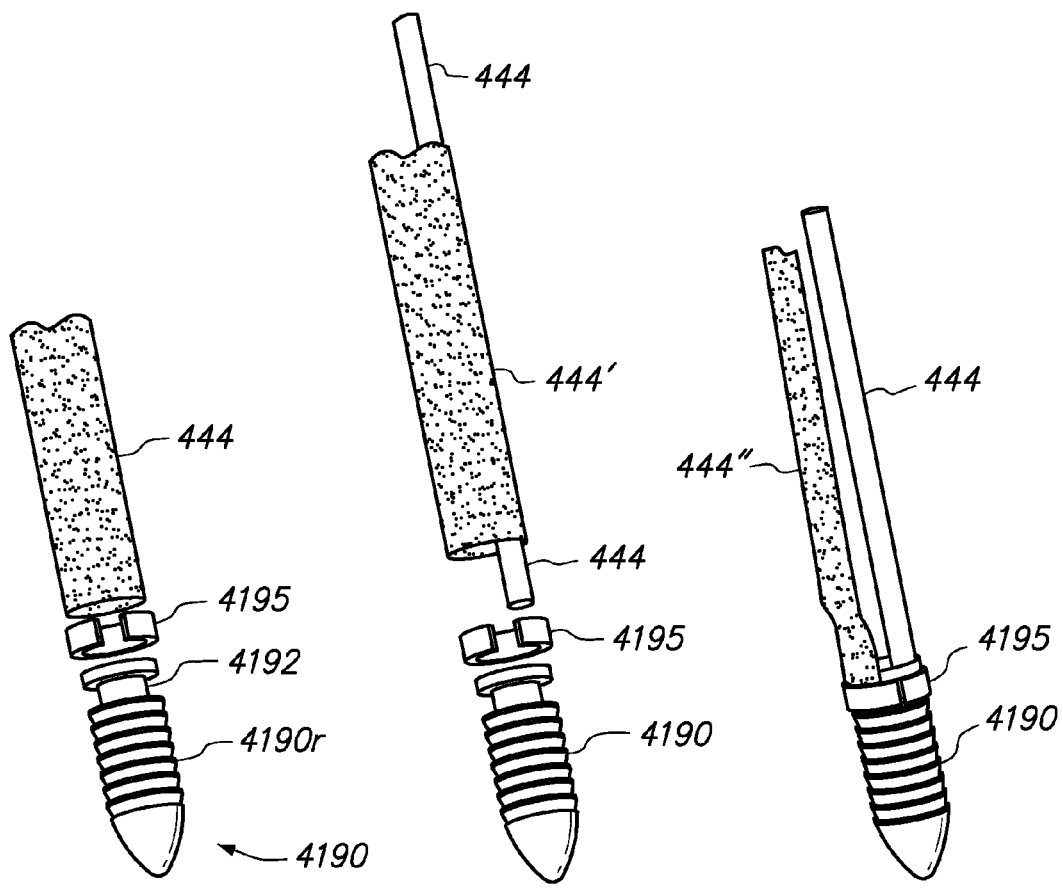
FIGS. 27A-27C show various embodiments of sutures that can be used with the locking tip shown in FIGS. 26A-26B.

FIGS. 27A-27C show various embodiments of sutures 444 that can be used with the locking tip 4190 shown in FIGS. 26A-26B. In FIG. 27A, suture 444 is a tubular suture braid and if clamped to locking tip 4190 using a collar 4195 that is compressed over suture 444 into recess 4192. Additional fixation may include, but is not limited to adhesives, heat welding, etc. FIG. 27B shows a monofilament suture 444, with at least a distal end portion of suture being surrounded by a suture braid 444'. Both suture 444 and suture braid 444' are attached to locking tip 4190 similarly to that described with regard to FIG. 27A. FIG. 27C shows a monofilament suture 444, with a flat suture braid 444" running alongside suture 444. Both suture 444 and flat suture braid 444" are attached to locking tip 4190 in a similar manner to that described with regard to FIG. 27A.

Figure 28A:
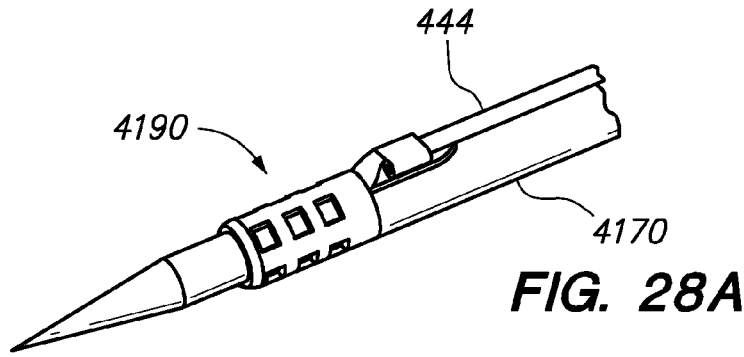
FIGS. 28A-28B show another embodiment of a locking tip that can be attached to a distal end of a suture for anchoring to a suture anchor or trap according to embodiments of the present invention.
Figure 28B:
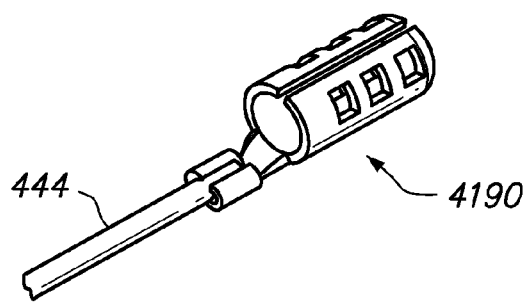
Figure 28C:
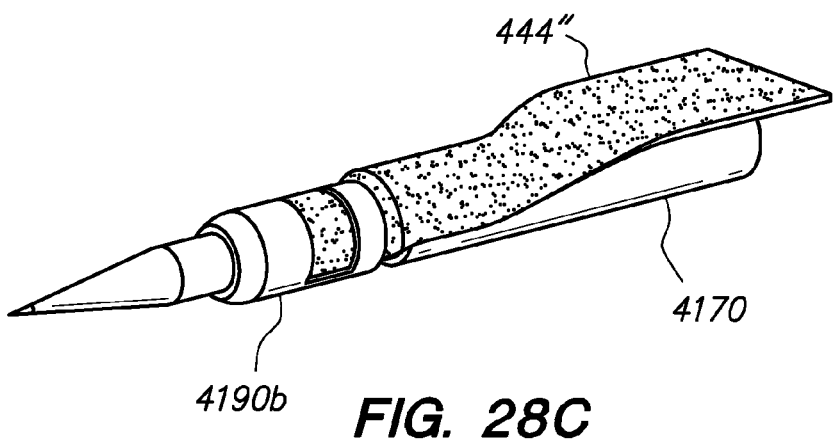
FIG. 28C shows a locking tip that additionally includes an outer body that sandwiches a suture braid between itself and the inner body shown in FIG. 28B.

FIGS. 28A-28B show another embodiment of a locking tip 4190 that can be attached to a distal end of a suture 444 for anchoring to a suture anchor 4200. In this embodiment, the main body of locking tip 4190 is a slotted metallic cylinder that is crimped or otherwise fixed to suture 444. Windows 4190*w* are provided in the main body which can be engaged by flexures 4214 to prevent the locking tip 4190 from retracting back out of a suture anchor 4200 once it has been passed through the suture anchor 4200. FIG. 28C shows a variation of the embodiment of FIGS. 28A-28C wherein locking tip additionally includes an outer body 4190*b* that sandwiches suture braid 444' between itself and the inner body 4190 shown in FIG. 28B. Thus, outer body form a compression fitting over the inner body 4190 and sandwiches ribbon (flat) braid 444" therebetween Suture 444 may also be fixed to inner body 4190 in the embodiment of FIG. 28C in the same manner as described above with regard to FIGS. 28A-28B, or, alternatively, may be omitted.

Figure 29A:
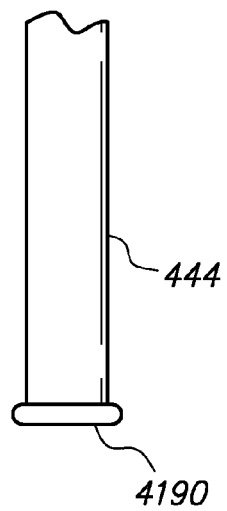
FIGS. 29A-29B illustrate another embodiment of a locking tip together with suture braid and capture thereof by a suture anchor or trap according to an embodiment of the present invention.
Figure 29B:
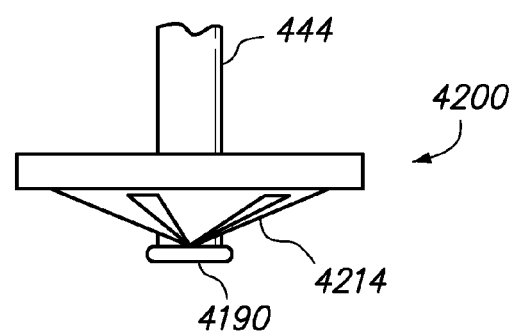

FIGS. 29A-29B illustrate another embodiment of a locking tip 4190 together with suture braid 444 and capture thereof by a suture anchor 4200. In this embodiment, locking tip 4190 is an O-ring (made of polyester or other implantable plastic or metal ring, such as stainless steel, titanium, nickel-titanium alloy or the like) that is braided into the distal end of suture braid 444 so as to capture the locking tip within the fibers of the suture braid 444. FIG. 29B shows the locking tip 4190 and suture braid 444 having been inserted and the needle 4170 having been retracted. The flexures 4214 spring back and abut against the O-ring to prevent the locking tip from being able to retract out of the suture anchor 4200.

Figure 30A:
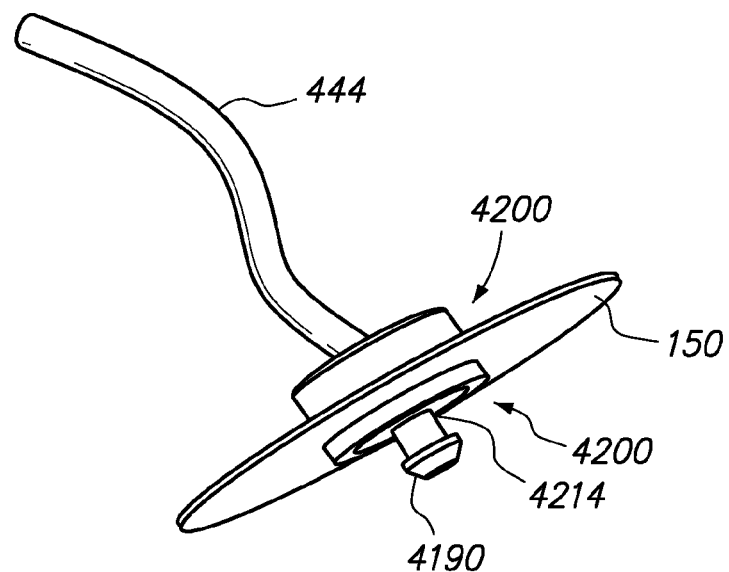
FIGS. 30A-30C illustrate another embodiment of a suture anchor or trap according to the present invention.
Figures 30B, 30C:
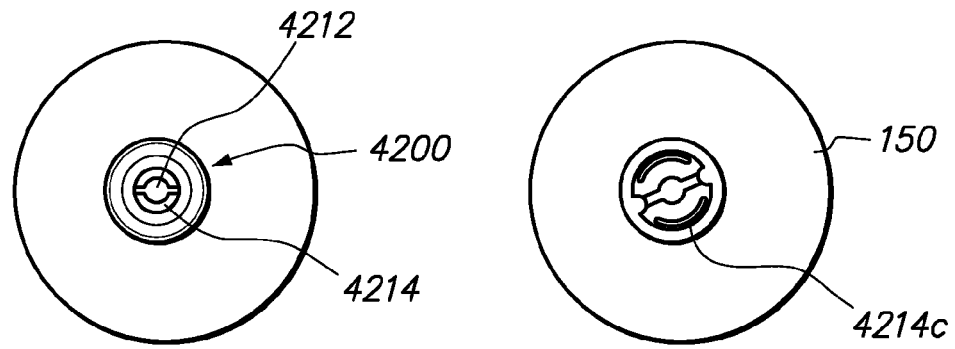

FIGS. 30A-30C illustrate another embodiment of a suture anchor 4200 according to the present invention. In this embodiment suture anchor 4200 could be used as described above with regard to FIG. 15A or FIGS. 19A-19I. Alternatively, as shown, suture anchor 4200 can be attached to the mesh of attachment tab 150. In this embodiment, suture lock 4200 includes a pair of flexures 4214, that are provided with cutouts 4214c (see FIG. 30C) to enhance flexibility. FIG. 30B shows the top (entry) side of suture anchor 4200 and FIG. 30C shows the bottom (exit) side of the suture anchor.

Figure 31A:
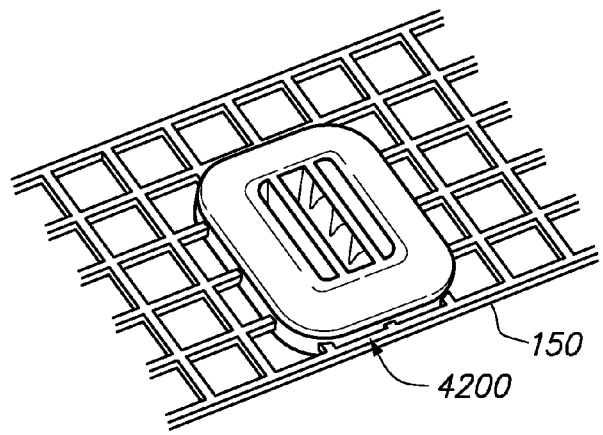
FIG. 31A illustrates another embodiment of a suture anchor or trap according to the present invention.
Figure 31B:
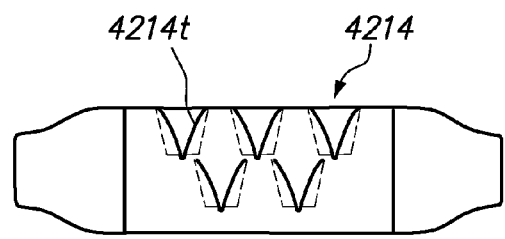
FIG. 31B shows an isolated, side view of teeth of one of the flexures of FIG. 31A.

FIG. 31A illustrates another embodiment of a suture anchor 4200 according to the present invention. In this embodiment suture anchor 4200 could be used as described above with regard to FIG. 15A or FIGS. 19A-19I. Alternatively, as shown, suture anchor 4200 can be attached to the mesh of attachment tab 150, in this case, by co-molding the suture anchor 4200 into the ingrowth mesh of the attachment tab 150. In this embodiment suture lock 4200 includes a pair of flexures 4214, that are provided with teeth 4214t that bite into the suture 444 and suture overbraid 444' that are used with this device. FIG. 31B shows an isolated, side view of teeth 4214t of one of the flexures 4214.

Figure 31C:
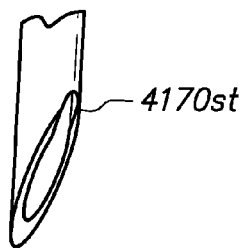
FIG. 31C illustrates that the needle shown includes a slot that captures an enlarged head of the suture therein, according to an embodiment of the present invention.
Figure 31D:
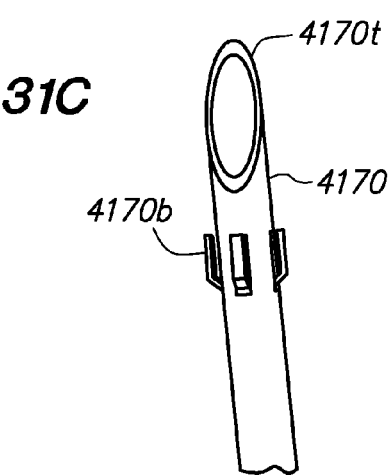
FIG. 31D shows overbraid retention features on a needle according to an embodiment of the present invention.
Figure 31E:
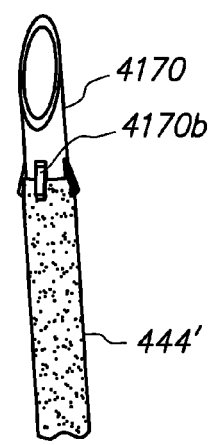
FIG. 31E shows a suture overbraid temporarily fixed by the overbraid retention features of FIG. 31D.
Figure 31F:
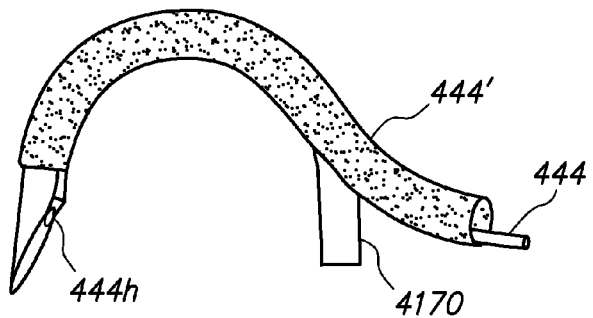
FIG. 31F shows the enlarged head of the suture of FIG. 31C.
Figure 31G:
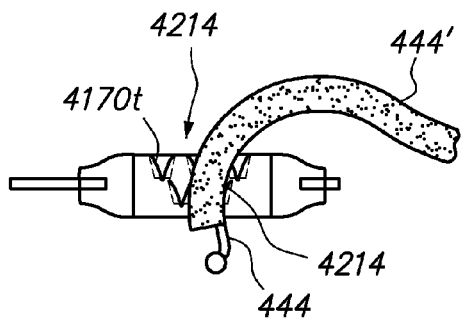
FIG. 31G is an isolated view showing the flexures of the embodiment of FIG. 31A.
Figure 31H:
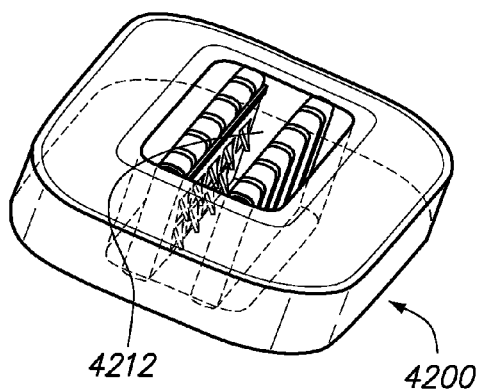
FIGS. 31H and 31I are views showing the flexures and flexure teeth of the embodiment of FIG. 31A.
Figure 31I:
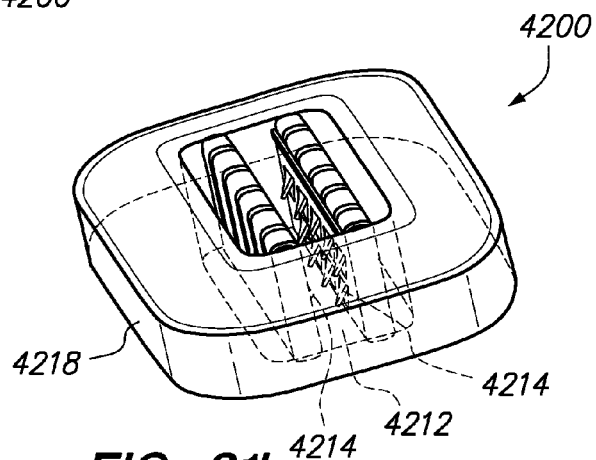

FIG. 31C illustrates that needle 7170 includes a slot 4170s that captures an enlarged head 444h of suture 444 therein, as shown in FIG. 31F. Enlarged head 444h may be a ball or a knot, for example, but has a cross-sectional dimension or diameter that is larger than a width of slot 4170s so that it is captured by slot 4170s and cannot pull through slot 4170s. FIG. 31D shows overbraid retention features 4170b such as tabs, tines, barbs or the formed in the distal end portion of needle 4170 proximal of the needle tip 4170t, and each feature 4170b has a free end directed distally. In this way, overbraid (tubular braided suture) 444' can be temporarily fixed to needle 4170, by piercing the free ends of features 4170b through the braid 444' near a distal end of the braid as shown in FIG. 31E. This arrangement prevents overbraid 444' from slicing proximally relative to needle 4170, but allows the needle 4170 to be retracted proximally out of the overbraid 444'. Thus, after insertion of the arrangement show in FIG. 31F through the suture anchor 444, when the needle 4170 retracts, the suture 444' and suture overbraid 444' are captured by teeth 4214t, head 444h slides out of slot 4140st overbraid 444' slides off of features 4170b and the suture 444 and suture overbraid 444' are anchored by the suture anchor 4200 as illustrated in the isolated view of FIG. 31G and the needle 4170 retracts out of the suture anchor 4200. FIGS. 31H and 31I are views showing the flexures 4214 and flexure teeth 4214t in more detail FIG. 32 illustrates another embodiment of suture anchor 4200. In FIG. 32, a plurality of suture locks 4200 are rotationally mounted to working portion 4010. Suture anchor 4200 is provided with tapered slots 4214ts that taper in width from a beginning end 4217 to a finishing end 4219, wherein the width of slot 4214ts at the beginning end portion 4217 is greater than at the finishing end portion 4219. As needle 4170, locking tip 4190 and suture 444 (locking tip 4190 and suture 444 not shown in FIG. 32, for clarity) are 4 inserted through slot 4214ts, suture anchor is rotated (counter-clockwise in FIG. 32 as shown). To change alignment of the slots 4214ts with the needle 4170 from the beginning end portion 4217 to the finishing end portion 4219. While the width of the slot at the beginning end portion 4217 is sufficient to allow the locking tip 4190 to pass through, the width of the slot at the finishing end portion 4219 is less than the outside diameter of the locking tip 4190 and prevents the locking tip from being able to be retracted back out of the suture anchor 4200.

FIG. 33 illustrates another embodiment of a locking tip that has the form of a grappling hook, having tines 4190t that extend radially outwardly from the main body of the locking tip and curve in a proximal direction, such that the free ends of the tines 4190 extend in a proximal direction.

FIG. 34 illustrates another embodiment of a locking tip 4190 that has a wire loop 4190w that extends radially outwardly from the main body of the locking tip and curves in a proximal direction, such that the free ends of the wire loop 4190w extend in a proximal direction. Either of the embodiments of FIGS. 33 and 34 can be used to lock directly to the mesh of an attachment tab 150, as illustrated by the embodiment of FIG. 34 in FIG. 34.

Figure 35:
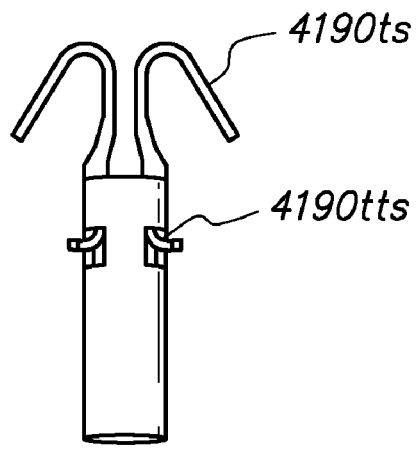
FIG. 35 illustrates another embodiment of a locking tip according to an embodiment of the present invention.
Figure 36:
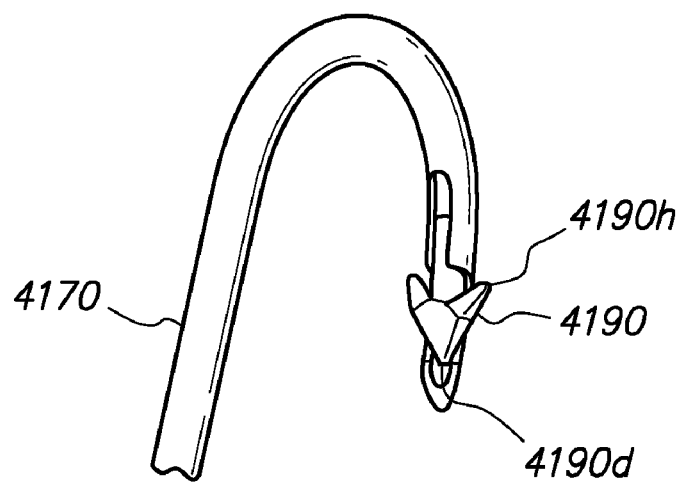
FIG. 36 illustrates another embodiment of a locking tip according to an embodiment of the present invention.

Like the embodiments of FIGS. 33-34, the embodiments of locking tips 4190 shown in FIGS. 35 and 36 can be used to directly lock to an attachment tab. FIG. 35 shows a locking tip 4190 that includes tabs 4190ts that extend distally from a distal end of the main body and then bend back such that the free ends of the tabs 4190ts extend is a radially outward, proximal direction. Additionally cutout portions of the main body may be bent radially outwardly to form additional tabs 4190tts.

Figure 37A:
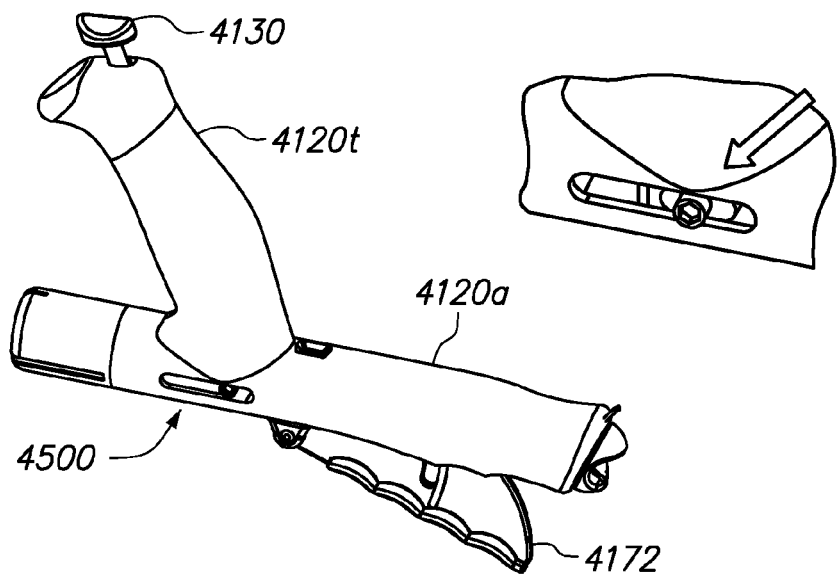
FIGS. 37A-37E illustrate a bailout feature and procedure for using in accordance with an embodiment of the present invention.
Figure 37B:
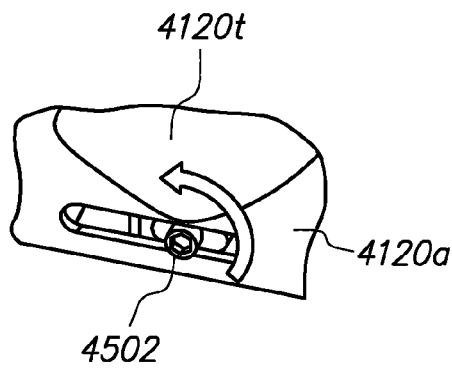
Figure 37C:
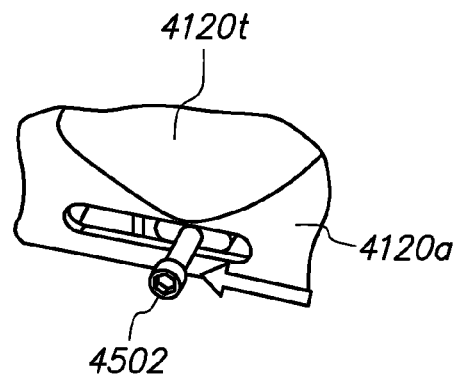
Figure 37D:
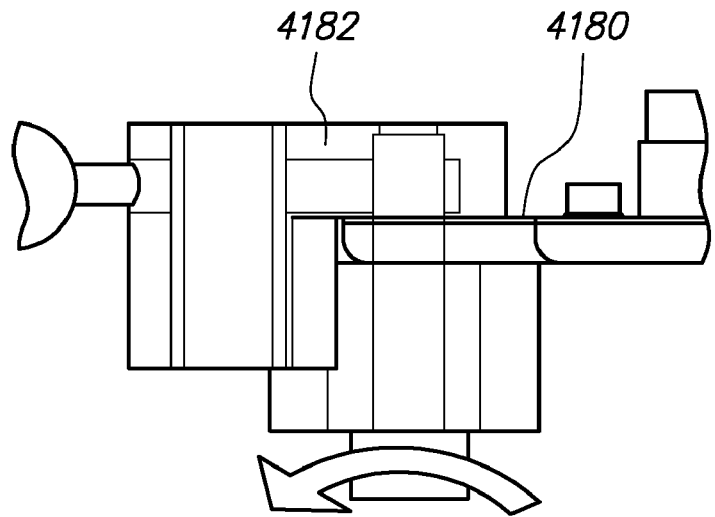

FIG. 36 shows a harpoon-shaped locking tip 4190, including proximally, radially outwardly directed tips 4190h and a distal tip 4190d FIGS. 37A-37E illustrate a bailout feature 4500 and procedure for using in cases where it is desirable to retract the stitching needles 4170 back into their concealed positions within the working portion 4010. This bailout procedure can be carried out any time prior to anchoring the locking tips 4190 within the suture anchors or traps 4200. The bailout procedure can be carried out after anchoring the tips 4190 into suture traps or anchors 4200, but the stitches would be left in place in this instance and the bailout would be useful only to retract the needles Bailout feature 4500 includes an attachment member 4502, such as a screw (as shown) or other equivalent attaching feature, that joins traveler block 4180 to wire or rod 4182, as schematically represented in FIG. 37D. Part 4182 is connected to 4180 by 4502. When the components are all coupled together, the handle mechanism (lever, actuator, pawl, wheel, etc.) drives the movement of 4180 which translates to 4182 and drives the needles. By breaking the connection, a user can manually push 4182 forward (distally) to retract the needles.

Figure 37E:
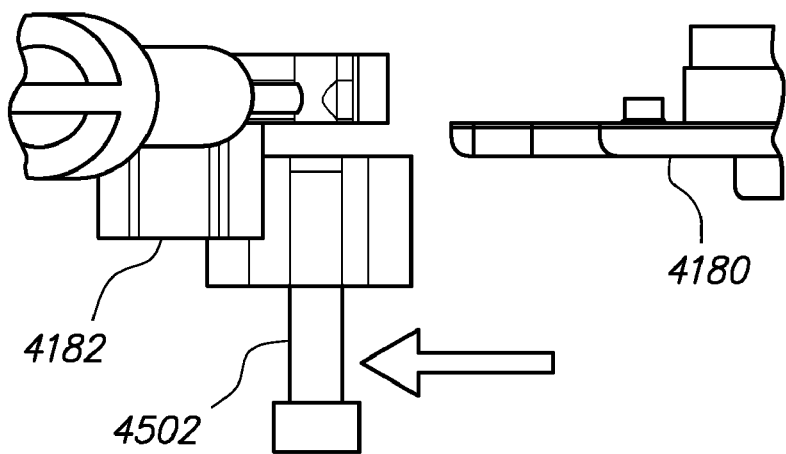

The attachment member 4502 can be operated so as to disconnect the traveler block 4180 from the rod or wire 4182 as illustrated in FIG. 37E. In the case of a screw, the screw 4502 the can be rotated out of engagement with the traveler block as illustrated in FIGS. 37B, 37C and 37E. As the screw is unthreaded (FIG. 37C), it rotates out of the mating threads and extends progressively further out of the handle 4120a.

This provides an actuator that can be slid proximally relative to handle 4120a to cause the stitching needles 4170 to retract back into the working portion 4010.

Figure 38A:
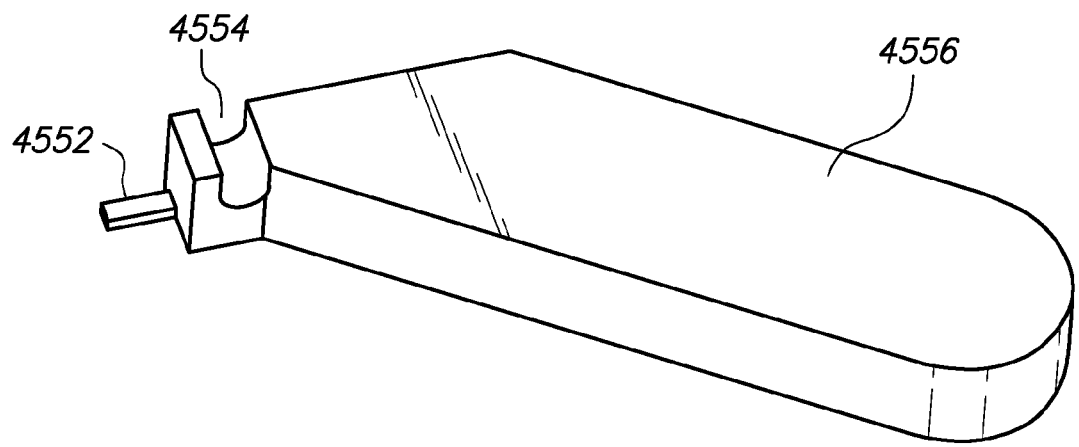
FIGS. 38A-38B illustrate an optional tool that may be provided to facilitate use of the bailout mechanism of FIG. 37A.
Figure 38B:
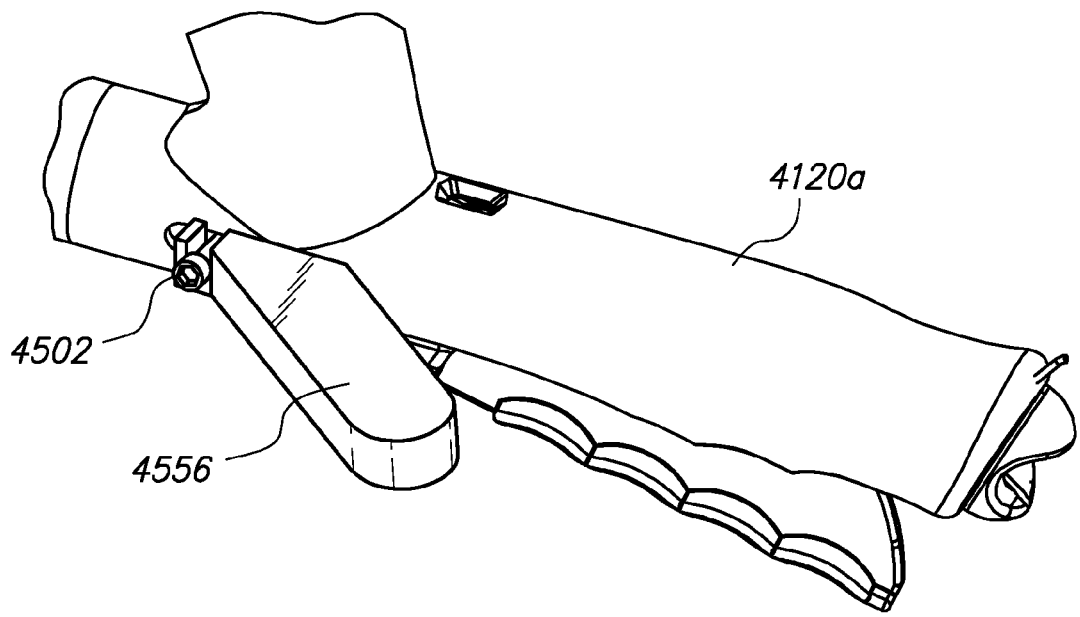

FIGS. 38A-38B illustrate an optional tool 4550 that may be provided to facilitate use of the bailout mechanism. In the case where attachment member 4502 is a screw, tool 4550 can be provided with a hex key, Phillips key, or standard key 4552 to match the pattern of the screw head so that tool 4550 can be used as a screwdriver to detach the traveler block 4180 from the wire or rod 4182. Additionally, tool 45 is provided with a slot 4552 configured to engage with the screw shaft when it extends out from the handle 4202a as shown in FIGS. 37C and 38B. The handle 4556 of the tool 4550 extends radially out from the longitudinal axis of the key 4552 to provide mechanical advantage for use as a screwdriver. Additionally, when the slot 4554 is engaged over the shaft of the screw 4502, the handle 4556 extends out from the handle 4120a to provide mechanical advantage for pushing the screw 4502 axially and proximally relative to the handle 4120a.

Figures 39A, 39B:
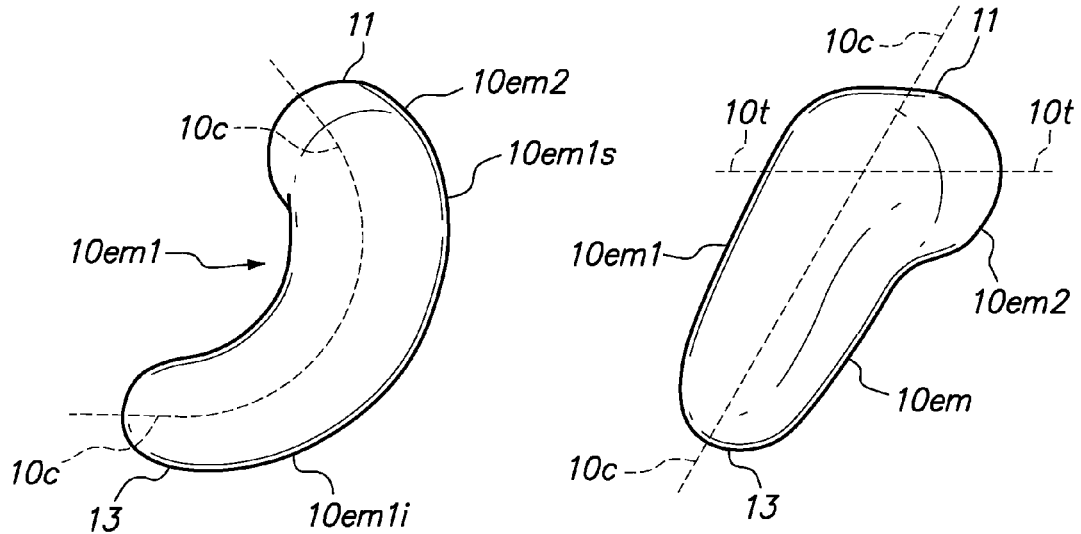
FIGS. 39A and 39B show a front view and a right side view of an expandable member of an implantable device according to the embodiment shown in FIGS. 4A-4D.

FIGS. 39A and 39B show a front view and a right side view of the expandable member 10em of device 10 according to the embodiment shown in FIGS. 4A-4D. The main expandable body portion 10em1, when m an expanded configuration as shown, extends along a central axis of curvature 10C that extends generally in a single plane. The right side view of FIG. 39B shows that the curved axis 10c lies generally in a plane in the dimension shown in FIG. 39B. The main body 10em1 has a superior portion 10em1s and an inferior portion 10em1i, wherein said superior portion 10em1s has a substantially larger cross-sectional area transverse to the axis 10c than a cross-sectional area transverse to the axis 10c of the inferior portion 10em1i when the expandable member 10em1 is in an expanded configuration. The expandable portion of device 10 further includes a superior lobe portion 10em2 in fluid communication with main body 10em1 and extending along a transverse axis 10T that is generally transverse to the central axis of curvature 10C at a location from which the superior lobe 10em2 extends. Thus, the majority of superior lobe portion 10em2 extends out of the plane of central axis 10C and therefore extends out of the general plane along which the main body portion 10em1 generally extends, as can be seen best in FIG. 39B.

With this embodiment device 10 is configured to be implanted so that the main body 10em1 extends substantially in a superior-inferior direction in a patient while the superior lobe 10em2 extends substantially posteriorly from the superior portion 10em1s of main body 10em1. With this configuration, the superior lobe 10em2 extends deeper into the abdominal cavity and displaces more volume in the abdominal cavity where the stomach (particularly the fundus, but also the main body) would normally be able to expand into.

The superior portion 10em1s has a substantially larger cross section than the inferior portion 10em1i when expandable member is expanded. The cross-sectional area of the main body 10em1 continuously increases in a direction from said inferior portion 10em1i to said superior portion 10em1s over at least eighty percent of the length of said main body 10em1 measured from an inferior end of said main body. Additionally, in the embodiment of FIGS. 39A-39B, the cross-sectional area of the expandable member 10em (including main body 10em1 and superior lobe 10em2) continuously increases in a direction from said inferior portion 10em1i to said superior portion 10em1s over at least eighty percent of the length of said expandable member 10em measured from an inferior end of said expandable member 10em.

Figure 40:
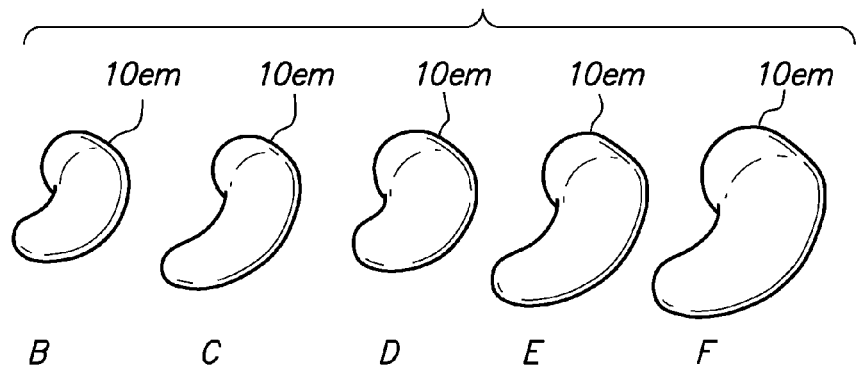
FIG. 40 shows a series of different sized expandable members according to the present invention.
Figure 41:
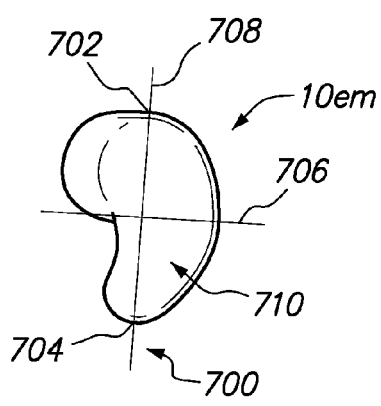
FIG. 41 illustrates division of an expandable member between superior and inferior portions according to an embodiment of the present invention.

In order to optimally take up the volume that the stomach is normally allowed to expand into, it is preferred to provide implants 10 having expandable members 10em that are substantially larger at the superior portions that at the inferior portions. More particularly, a superior portion should have a size relative to the inferior portion (where portions are defined in the manner described in detail below) that provides a volume ratio of about 2.0 to about 2.5, more preferably about 2.2 to about 2.3 or a surface area ratio of about 1.5 to about 2.0, and more preferably about 1.6 to about 1.8. FIG. 40 shows, for comparison purposes, a series of different sized expandable member 10em that may be employed in different sizes of implants designed to treat different sized patients and or different circumstances, such as to the particular arrangement proportion, etc. of the anatomy in the abdominal cavity. Size shown includes sizes B, C, D, E and F. An analysis of the sizes and shapes of expandable members 10em was performed for each of sizes B-F. In FIG. 41, a straight line 700 defining the maximum length of the expandable member 10em was found between point 702 and 704. The expandable member 10em was then bisected along a slice 706 that was normal to the line 700, to define head end or superior portion 708 and tail end or inferior portion 710. The volume and surface area were each then separately calculated for portion 708 as well as portion 710, to calculate a surface area ratio (head end/tail end) as well as a volume ratio (head end/tail end). These calculations were performed in the same manner for each of sizes B-F, The results of the calculations are summarized in Table 1 below.

TABLE 1

| Size | Surface Area Ratio (Head End/Tail End | Volume Ratio (Head End/Tail End |
|---|---|---|
| B | 1.7 | 2.3 |
| C | 1.7 | 2.2 |
| D | 1.6 | 2.2 |
| E | 1.7 | 2.2 |
| F | 1.8 | 2.3 |

The actual volumes and surface areas calculated for each size are presented in Table 2 below.

TABLE 2

| Size | Head End Surface Area (in²) | Tail End Surface Area (in²) | Head End Volume (in³) | Tail End Volume (in³) |
|---|---|---|---|---|
| B | 45.02 | 26.97 | 33.40 | 14.81 |
| C | 54.17 | 31.76 | 39.86 | 18.37 |
| D | 54.65 | 35.23 | 47.67 | 22.10 |
| E | 70.82 | 40.72 | 60.61 | 27.30 |
| F | 92.35 | 52.54 | 92.89 | 41.11 |

Figure 42A:
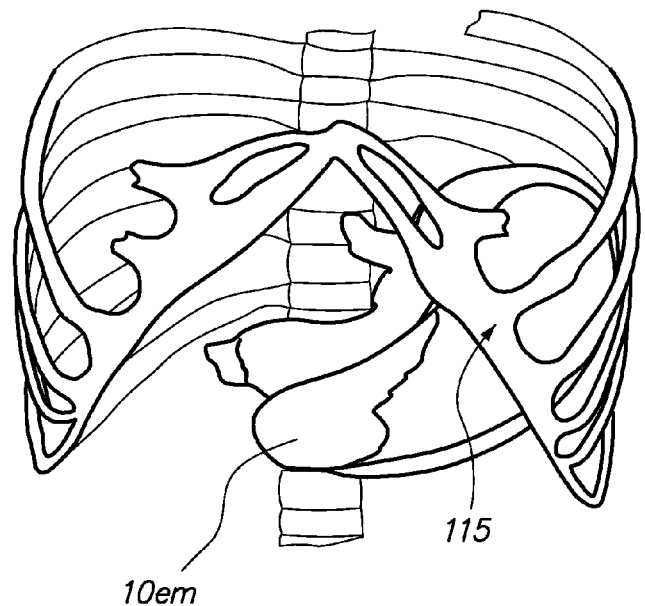
FIGS. 42A-42B show frontal and left side (patient's left side) views of an implantable device according to an embodiment of the present invention.
Figure 42B:
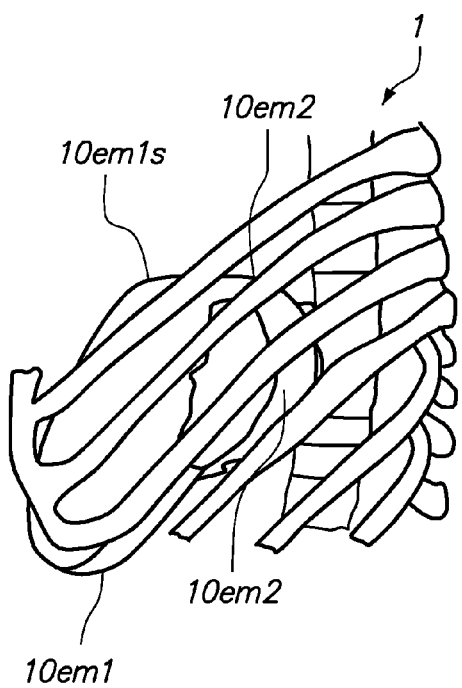

FIGS. 42A-42B are frontal and left side (patient's 1 left side) views of an implantable device 10 having an expandable member 10em like that described with regard to FIGS. 39A-39B after expansion and implantation of the device 10. It can be seen in the frontal view that the main body portion 10em1 extends from the inferior portion at a more medial location laterally and superiorly up into a location under the ribs 115 of the patient 1. Thus, the main body 10em1 extends substantially in a superior-inferior direction in the patient 1, while the superior lobe 10em2, as shown in FIG. 42B extends substantially posteriorly from the superior portion 10em1s of main body 10em1. With this configuration, the superior lobe 10em2 extends deeper into the abdominal cavity to apply compression to the fundus of the stomach and to the angle of His.

Figure 43A:
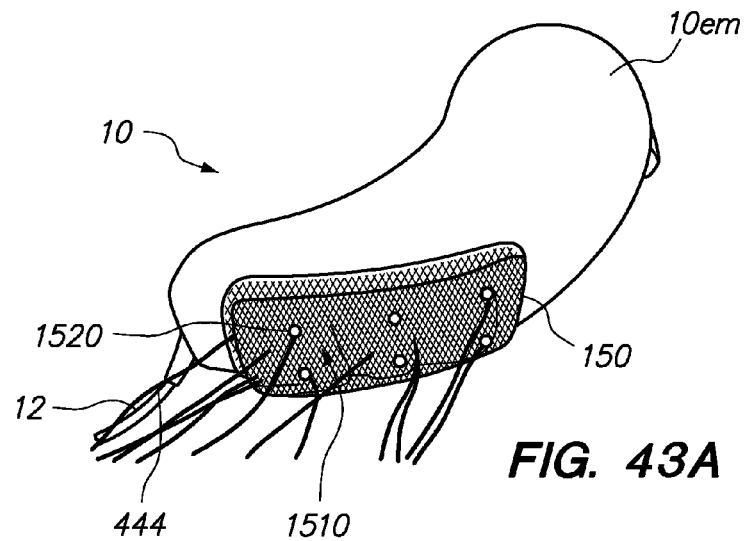
FIGS. 43A-43C illustrate an embodiment of an implantable device according to the present invention having border "wings".

FIG. 43 illustrates an embodiment of an implantable device 10 according to the present invention, configured for percutaneous delivery and paragastric, extragastric implantation.

Device 10 includes expandable member 10em, a filling tube 12 in fluid communication with expandable member 10em and having sufficient length to extend out of a percutaneous opening formed in a patient through which the device 10 is delivered, when device 10 has been anchored to a surgical target such as the internal wall of the abdominal wall 127, peritoneum and or fascia 127f Device 10 further includes an attachment tab 150 bonded to expandable member 10em, and having suture retainers 1520 embedded in a top mesh layer 1510 of attachment tab 150. Sutures 444 extend through the suture retainers 1520.

Figure 43B:
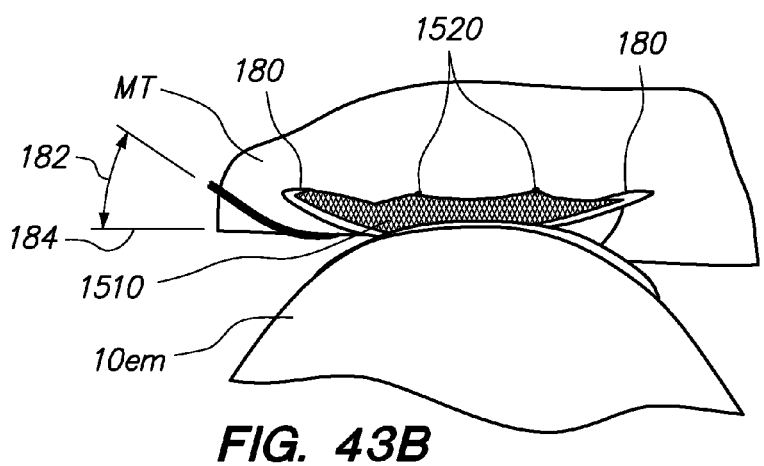
Figure 43C:
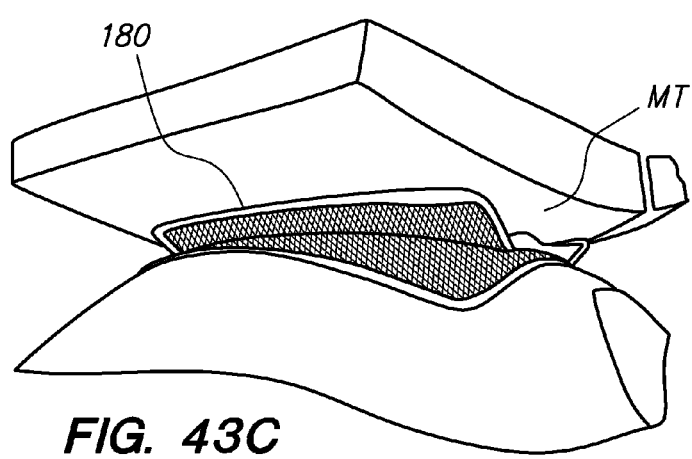

FIGS. 43B and 43C illustrated end and side views of border "wings" 180 that attachment tab 150 is configured with in order to prevent omentum, bowel and other unwanted tissues from extending into the tissue ingrowth area of the mesh 1510 that the suture retainers 1520 are embedded in. In FIGS. 43B and 43C, device 10 has been sutured to a mock surgical target MT to illustrate the performance of the border wings 180. Border "wings" 180 are deflectable, but are substantially more rigid than the mesh material 1510. In one embodiment, border "wings" 180 are molded from silicone. In another embodiment, as shown, border "wings" 180 are mesh reinforced silicone, as shown in FIGS. 43B-43C. Border "wings" 180 are substantially planar and angle away from the expandable member 10em at an angle 182 of about thirty to about 60 degrees, typically about forty to about fifty degrees to an tangent to expandable member that passes transversely across the attachment tab and intersects where the center of the attachment tab 150 contacts the expandable member 10em as shown in FIG. 43B. The free end of the angled border "wings" contact the surface of the surgical target MT when device 10 is sutured to the surgical target, as illustrated in FIGS. 43B-43C. This prevents omentum, bowel and other tissues from working in from the sides of the attachment tab 150, between the surface of the surgical target MT and the mesh 1510 sutured thereto at the locations of suture retainers 1520.

Figure 44A:
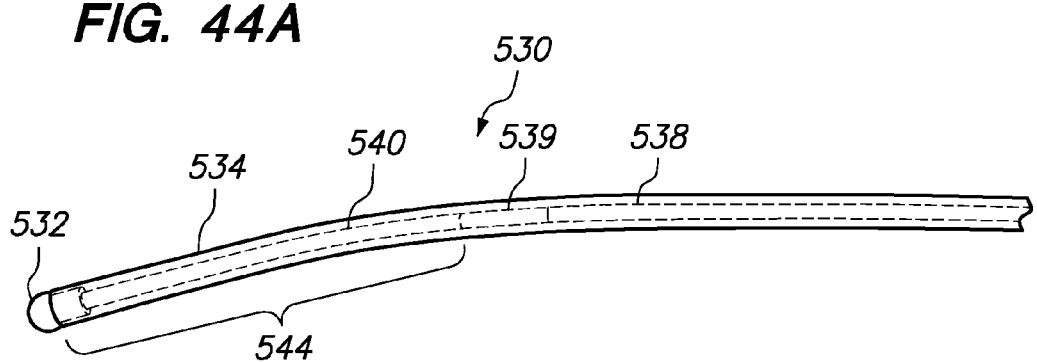
FIGS. 44A-44B illustrate an embodiment of a guide according to an embodiment of the present invention.
Figure 44B:
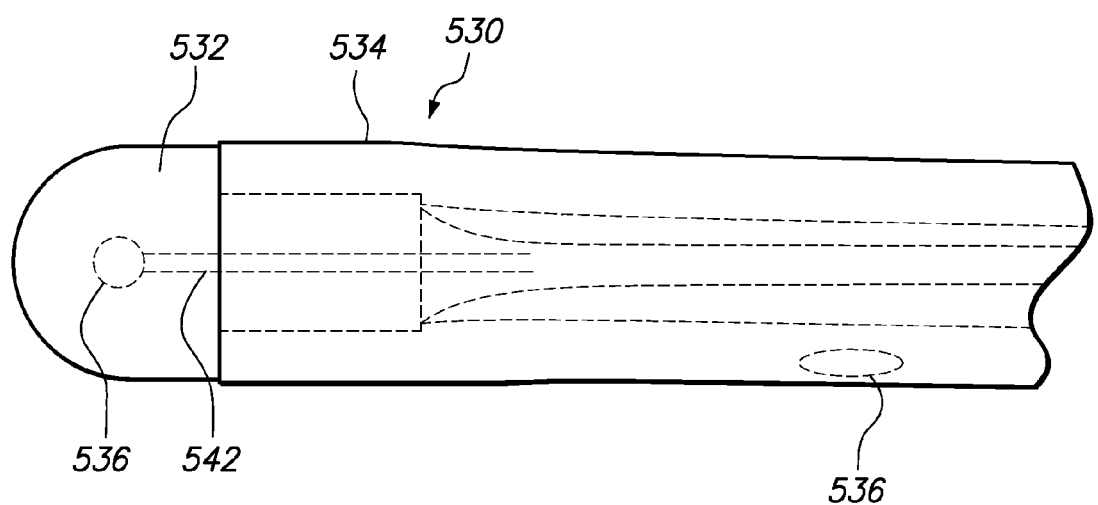

FIGS. 44A-44B illustrate an embodiment of a guide that may be used in procedures that also use the instruments and devices described above, according to the present invention. Guide 530 is provided with a blunt atraumatic distal tip 532 with bluntness provided by the curvature of the distal end of the tip 532. Guide 530 includes an elongated, flexible tube 534 that has a floppy action at least its distal end portion (excluding distal tip 532) when in an unreinforced configuration, as illustrated in FIG. 1A. Tube 534 may be formed of polyvinyl chloride (PVC) to ensure that the tube is transparent for maximizing visualization via an endoscope 330 inserted therein. Alternatively, polyethylene, polyurethane, PEBAX or MILIFLEX® (thermoplastic elastomer, thermoplastic olefin, Melitek, Dusseldorf, Germany) may be used. Tube 534 typically has a length of about eighteen inches to about twenty-six inches, typically about twenty inches to about twenty-four inches, although this length may vary depending upon the tract length along which guide 530 is to occupy, which will, of course vary with such factors including, but not limited to: surgical target location, location of the external opening through which guide 530 is inserted, age of the patient (e.g., child vs. adult), etc. In one particular example, tube 534 has a length of about 22.5" and is a single flexible tube, wherein a stylet or rigid endoscope can be slid within the tube to rigidify it during use, when needed. In another embodiment a distal end portion (e.g., distal most length of about three inches to about eight inches, typically about four inches to about seven inches, in one particular embodiment about five and a half inches) may be flexible while the remaining proximal portion is stiff or relatively rigid so that it does not bend under use and therefore does not require the use of a stylet or rigid endoscope 330 to rigidify it. One advantage of this embodiment, is that a flexible endoscope 330 can be inserted into guide 530 without the need for a stylet. This arrangement can be advanced without a stylet due to the stiffness of the stiff proximal tube portion of guide 530. Flexible endoscope 330 can be advanced up into the flexible distal portion of guide 530 to provide views along a curved pathway of a tract leading to a surgical target location, for example. FIGS. 1A-1B illustrate an embodiment of guide 530 in which the entire length of tube 534 is flexible and of the same material and construction.

FIGS. 45A-45 illustrate an embodiment of guide 530 in which a distal end portion 534a of tube 534 is flexible, while the proximal end portion 534b of tube 534 is rigid. The tube portions 534a and 534b may be made of the same material composition, but where the hardness of the material composition used to make portion 534b is greater than the hardness of the material composition used to make portion 534a. In one particular embodiment portion 534b was made from PVC (polyvinylchloride) having a Shore hardness of 100 A, while portion 534a was made from PVC having a Shore hardness of 80 A. The clear tip 532 was also formed of PVC. In the embodiment of FIGS. 2A-2C, tip 532 does not have a lumen or opening to allow a guide wire 502 to pass through it, but is closed off, thereby preventing inflow of fluids or tissues into the tube 534. Thus, the distal end of tube 534 is closed by tip 532. Alternatively, this configuration may be provided with a lumen 536 that passes through the distal tip 532 to allow guide 530 to be passed over a guidewire 502. Likewise, embodiments of guide 530 comprising a tube 534 that is flexible over its entire length need not be provided with an opening through tip 532 or at any location of the distal end portion, but may be closed off to prevent fluid inflow, alternative to the embodiment shown in FIGS. 44A-44B. Although not shown, embodiments of guide 530 of the type shown in FIGS. 45A-45C may include one or more radiopaque markers along any locations thereof to facilitate tracking of the guide under fluoroscopy.

The longitudinal sectional view of FIG. 45B illustrates the interconnection of the tube portions 534a and 534b at joint 537. Joint 537 may be a lap joint, a sleeve joint or other known mechanical configuration and/or joined with adhesive, ultrasonic welding, heat welding, etc. Tip 532 is joined to the distal end of tube 534 at joint 539 which may be any of the same types and or methods of joining described with regard to joint 537. Rigid portion 534b, in one embodiment, had an outside diameter of about 0.5 inches and an inside diameter (formed by the lumen passing therethrough) of about 0.225 to about 0.25 inches.

Optionally, any embodiment of guide 530 described herein may be provided with an extension tube 543 like that illustrated in FIGS. 45A-45C. Extension tube 543 may be rigid or flexible. Extension tube 543 is configured to be maintained outside of the patient's body at all times, but provide an additional length for grasping by the user in instances where nearly all of the guide 530 (i.e., tube 534) is inserted into the body. Extension 543 further facilitates introducing a tool or implant/device over the guide 530, particularly when there is not much length of the tube 534 extending out of the patient's body. Optionally, extension tube 543 may be provided to be easily removable, such as by a screw threaded joint with the proximal end of tube 534, for example, to allow installation or removal during use of the guide 530. In instances where extension tube 543 is flexible, it may be bent transversely to the longitudinal axis of the guide 530, as illustrated in phantom lines in FIGS. 45A and 45C. This may be desirable for example for use as an endoscope port, particularly when a flexible endoscope is used. In the particular example shown, extension tube 543 has a length of about six inches, is flexible, and is made of PVC having a Shore hardness of about 80 A.

Figure 46A:
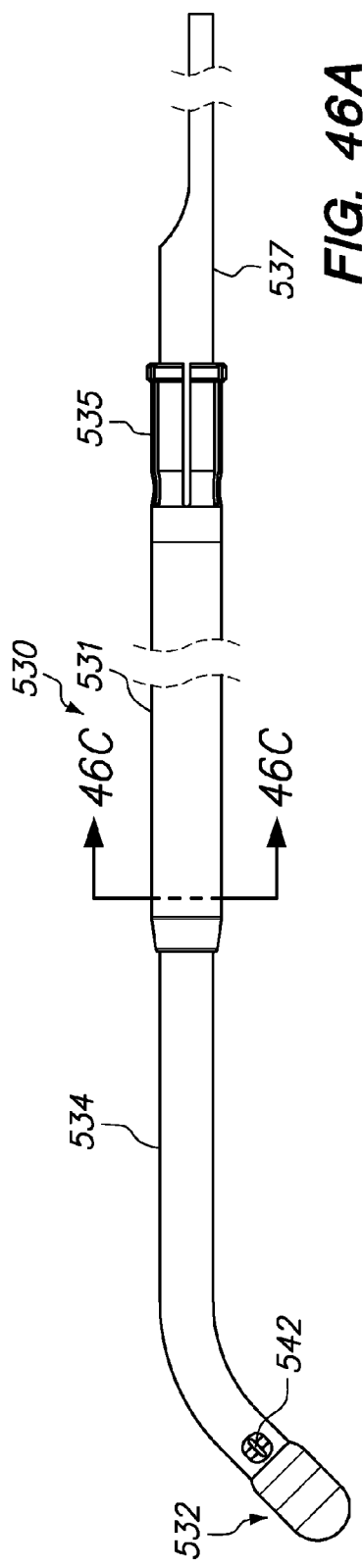
FIGS. 46A-46B illustrate an embodiment of a guide having a single, flexible, transparent tube and an outer sleeve that is rigid.
Figure 46B:
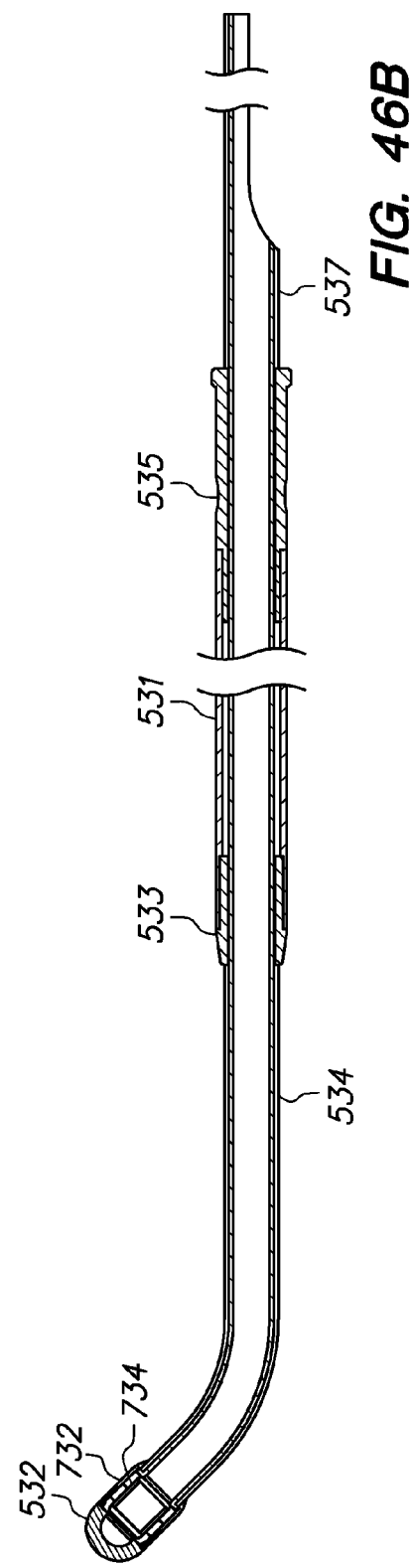
Figure 46C:
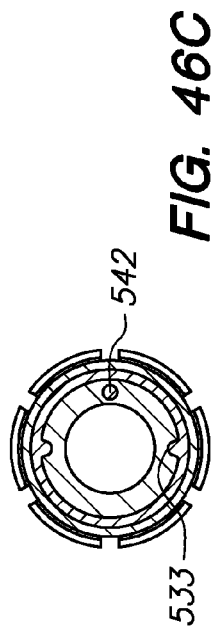
FIG. 46C is an end view of a tube according to an embodiment of the present invention.

In another embodiment where tube 534 is a single, flexible, transparent tube (e.g., see embodiment of FIGS. 46A-46B), an outer sleeve 531 (FIG. 46B) is provided that is rigid, thin-walled and fits closely over tube 534 while still allowing tube 534 to freely slide relative to sleeve 531. In this way, sleeve 531 can be slid over tube 534 (whether or not a flexible endoscope 330 has been inserted into the guide 530, see FIG. 46B) to function like the stylet or rigid endoscope described in the embodiment above. Sleeve 531 can be translucent or opaque, but is preferably transparent, and, for example, can be made of PVC. Sleeve 531 may be keyed to tube 534 via one or more keys 533 as illustrated in the end view of tube 534 inserted into sleeve 531 shown in FIG. 46C. This keying 533 allows torque to be transferred to guide 530 by the user torquing on sleeve 531, which is useful for steering guide 530 as well as applying other rotational forces for repositioning and/or controlling movements of guide 530.

Tip 532 is blunt, and formed of a polymer, such as PVC or acrylic polymer, to ensure that guide 530/tip 532 will not penetrate tissues such as bowel or other internal body structures not intended to be penetrated, and will not cause trauma to any of these tissues or structures. Tip 532 and or tube 534 may optionally be provided with one or more radiopaque markers 536 at any location(s) therealong, to aid fluoroscopic visualization. Rod 538 will typically be made of a material that is visualizable under fluoroscopy and thus will not require a radiopaque marker since it can be visualized without the need for one.

A stiffening rod stylet 538 is provided that is sidable through lumen 540 of tube 534 for the embodiment of FIG. 44A. Accordingly, when the distal end portion of tube 534 does not contain rod 538, it is flexible and functions like a guidewire, albeit with a less traumatic tip 532. However, in situations such as when there is too much resistance from fatty tissues or other tissues or obstruction to allow tube 534 to be pushed along the intended tract, rod 538 (or a rigid endoscope 330 or sleeve 531) can be slidably advanced into (or over, e.g., when sleeve 531 is used in the embodiment of FIG. 46B) the distal end portion to increase the stiffness of the distal end portion. Rod 538 is continuously positionable so that the distal tip 539 thereof can be located anywhere along tube 534 with lumen 540. Likewise, sleeve 531 is continuously positionable. Accordingly, the amount of stiffness of the distal end portion of tube 534 is also continuously variably adjustable. In one embodiment rod 538 is formed of aluminum. Alternatively, rod 538 may be formed of any other rigid, biocompatible metal, alloy, polymer and/or ceramic/composite. Rod 538 can be advanced within tube 534 as described, and this runs no risk of damaging any tissues, since rod 538 is contained entirely within tube 534 and tip 532. Also, the blunt configuration of tip 532 ensures that no tissues such as bowels, diaphragm, or other soft tissues will be penetrated or traumatized even when rod 538 has been inserted all the way distally, into distal tip 532, where guide 530 is in its stiffest configuration. Further since blunt tip 532 is transparent viewing through it via endoscope 330 is also possible. Accordingly, guide 530 also functions as a blunt introducer, and further provides visualization capabilities.

Tube 534 may optionally be provided with a lumen 542 that runs alongside the main lumen of tube 534 to facilitate delivering guide 530 over a guide wire 502 in an optional alternative procedure, or to deliver anesthetic or other fluids, as described above as well as in examples below. Alternatively, the lumen 542 can allow for an exchange with a guidewire 502. In this embodiment the guide 530 would enable placement of a guidewire in the desired location by first enabling the user to place the guide 530 in a desired location. The guidewire 502 would be pre-assembled in the lumen 542, or it could be inserted into the lumen by the user. The guidewire 502 would be pushed out the distal end of the lumen 542 as the guide 530 would be retracted from the patient. This exchange would leave the guidewire in place at the desired location, where it otherwise could not have been placed, without the assistance of the guide 530. The guidewire 502 could then be used to guide an implant's delivery and placement.

FIGS. 47A-47K show another embodiment (and portions thereof) of a guide 530 according to the present invention. FIG. 47A shows a side view of guide assembly 530 and FIG. 47B shows a view of the assembly 530 of FIG. 47A after rotating the assembly 530 ninety degrees counterclockwise about its longitudinal axis, as viewed from the proximal end of the assembly. In this embodiment, the distal end portion 534a of tube 534 is flexible, while the proximal end portion 534b of tube 534 is rigid. The tube portions 534a and 534b may be made of the same material composition, like the embodiment of FIG. 45A, and may have about the same length ranges. In one particular embodiment distal portion 534a had a length of about seven inches and proximal portion 534b had a length of about thirty-two inches, with the entire assembly 530 having an overall length of about forty-one inches. Alternatively, flexible portion 534a may be formed of a first material and rigid portion 534b may be formed of a second material. For example, flexible portion 534a may be formed from PVC having a hardness of about 78 A to about 85 A, and rigid portion 534b may be made of polycarbonate. The clear tip 532 may also be formed of PVC. Radiopaque marker bands 734 also function as lock collars to maintain connections between the tip 532, tube 534a and coupling 537c used in forming joint 537.

In the embodiment of FIGS. 47A-47K, tip 532 does not have a lumen or opening to allow a guide wire 502 to pass through it, nor does it have any other opening on its distal surface, but is closed off, thereby preventing inflow of fluids or tissues into the tube 534. Thus, the distal end of tube 534 is closed by tip 532. However, an additional tube 541 is provided externally of tube 534 and connect thereto to extend parallel thereto (or to follow the contour thereof when tube 534 is bent) A lumen 542 extends through tube 541, with the distal end of the tube 541 and lumen 542 being open to allow delivery of medications, irrigation, suction, etc. therethrough. Note that the lumen 542 does not extend through or into tip 532. Assembly 530 may also be provided with an injection port 542p on the surface of tube 534 or 541 that is in fluid communication with lumen 540 and that is configured to allow a user to insert a blunt tip medical hypodermic needle into, to inject medication, saline, or other fluid for delivery out of the distal opening of lumen 542.

Alternatively, the embodiment of FIG. 47A can be provided with a lumen 536 that passes through the distal tip 532 to allow guide 530 to be passed over a guidewire 502, although the preferred embodiment employs a closed tip 532.

Joint 537 may is formed by coupling 437c inserted into the proximal end of tube 534a and the distal end of tube 534b, see also the explode views of FIGS. 47F and 47G which correspond to the orientations of FIGS. 47B and 47A respectively. As already noted, one or more lock collars 734 may be employed to provide compression of the tube portion 534a or 534b against collar 537 to help maintain the joint. As also already noted, collars 537 may be radiopaque, made from stainless steel or some other rigid, biocompatible, radiopaque material. FIG. 47G illustrates a coupling 545 used to connect the proximal portion 541b of tube 541 to the distal portion 541a. Coupling 545 may be a stainless steel tube or rigid plastic tubing, for example.

Tip 532 is joined to the distal end of tube 534 at joint 539, using a lock collar 734 like that described above. Rigid portion 534b, in one embodiment had an outside diameter of about 0.5 inches and an inside diameter (formed by the lumen passing therethrough) of about 0.3 inches, flexible portion 534a had an outside diameter of about 0.438 inches and an inside diameter of about 0.318 inches, and tube 541 had an outside diameter of about 0.04 inches to about 0.05 inches.

A stiffening rod stylet assembly 538' is provided that is slidable through lumen 540 of tube 534, see FIG. 47C. Assembly 538' may have the same length dimension as earlier described embodiments, or may be varied according to the overall length of tube 534. In the example shown in FIG. 47C, assembly 538' has a length of about 30.5 inches. Stylet/rod assembly 538' includes a slide actuator 559 that includes a slider 559s connected to the proximal end of the rod/stylet 538 (see FIG. 47E) and that is dimensioned to slide within the lumen 540 of tube 534. The actuatable portion 559a of slide actuator 559 rides externally of tube 534 as stylet/rod assembly 538' is slid relative to the tube 534 and necked portion 559n has a reduced sectional dimension and rides in a slot 534s formed in tube 534 as stylet/rod assembly 538' is slid relative to tube 534. Accordingly, a user can slide the actuator 559 by applying a thumb to the actuatable portion 5591, for example and slide the actuator 559a while holding the tube 534 to prevent axial advancement of the tube 534. When the distal end portion of tube 534 does not contain rod 538, it is flexible and functions similar to a guidewire, albeit with a less traumatic tip 532. However, in situations such as when there is too much resistance from fatty tissues or other tissues or obstruction to allow tube 534 to be pushed along the intended tract or to change the curvature of the distal end portion 534a (note that tube 534 may be formed with a preset curve to form an angle α of about 100 to about 130 degrees, typically about 110 to 120 degrees, about 115 degrees in the embodiment shown in FIG. 47A) rod 538 (or a rigid endoscope 330 or sleeve 531) can be slidably advanced into the distal end portion to increase the stiffness of the distal end portion. Accordingly, the amount of stiffness of the distal end portion of tube 534 is also continuously variably adjustable. In one embodiment rod 538 is formed of stainless steel tubing. In one particular example, rod 538 is a stainless steel hypotube having a outside diameter of about 0.219" and an inside diameter of about 0.205 inches. Alternatively, rod 538 may be formed of any other rigid, biocompatible metal, alloy, polymer and or ceramic/composite, or the rod 538 can be a rigid endoscope, for example, a glass scope with a steel sleeve for rigidity.

Rod 538 is preferably provided with an external jacket or coating 557 to reduce the force required to slide the assembly 538' through the tube 534 and also allows the stylet lock (described below) to have a deformable portion to grip and lock onto. In the example of FIG. 47D, jacket 557 is made from FEP (fluorinated ethylene propylene) tubing having an outside diameter of about 0.24 inches. Rod 538 can be advanced within tube 534 as described, and this runs no risk of damaging any tissues, since rod 538 is contained entirely within tube 534 and tip 532. Also, the blunt configuration of tip 532 ensures that no tissues such as bowels, diaphragm, or other soft tissues will be penetrated or traumatized even when rod 538 has been inserted all the way distally, into distal tip 532, where guide 530 is in its stiffest configuration. Blunt tip also prevents fluids and debris from entering the lumen of tube 534, which is desirable, as fluids and/or debris could impair the functioning of the stylet making it difficult to slide.

Further since blunt tip 532 is transparent, viewing through it via endoscope 330 is also possible. Accordingly, guide 530 also functions as a blunt introducer, and further provides visualization capabilities.

In some circumstances it is desirable to extend the overall length of the assembly. If the user wants to maintain the position of the tip of the guide 530 within the body and be able to pass something of significant length (e.g., conduit 600, obturator 630, or other lengthy tool or object) over the guide 530, it is desirable to be able to lengthen the assembly, increasing the effective length of guide 530 while maintaining the position of the guide 530 within the patient 1. For this reasons, a stylet lock 620 is provided to releasably lock the position of the stylet assembly 538' relative to the tube 534 at any desired location that the stylet assembly 538' is capable of sliding to. In use the stylet 538 and jacket or coating 557 are slidable through the open channel 620c provided in stylet lock 620. The isolated view of stylet lock 620 in FIG. 47H shows channel 620c clearly. The main body 620m of the stylet lock 620 is connected to head 620h via flexures 620f. Flexures 620f allow head 620h to be slightly bent away from the stylet 538/coating 577 when in an unlocked configuration as shown in FIG. 47I, which allows the stylet to be slid relative to tube 534. When it is desired to lock the stylet 538 to prevent its axial movement relative to tube 534, the head 620h is pressed to rotate it back into alignment with the main body 620m causing rib, tooth, or other engagement member 620r to engage against coating 557 and/or stylet 538, thereby forming a friction lock. When a coating such as jacket 577 is present, engagement member presses or "bites" into the jacket 577, temporarily deforming it and enhancing the braking action. FIG. 47P illustrates this locking action. The endoscope 330 is removed from the guide 530 prior to performing the locking action. FIGS. 47Q and 47R show the stylet lock installed on the guide assembly, in the locked and unlocked configurations, respectively. When it is desired to lock the stylet 538 to prevent its axial movement relative to tube 534, the head 620h is pressed to rotate it back into alignment with the main body 620m causing rib, tooth, or other engagement member 620r to engage against coating 557 and/or stylet 538, thereby forming a friction lock. When a coating such as jacket 577 is present engagement member presses or "bites" into the jacket 577, temporarily deforming it and enhancing the braking action. The endoscope is removed when this locking engagement is carried out.

FIG. 47H is an enlarged, isolated view of an endoscope lock 625 that may be provided with guide assembly 530. Endoscope lock 625 includes an enlarged proximal end portion 625p and an elongated shaft portion 625s extending distally from the proximal end portion 625p. The shaft portion 625s may be keyed 625k to provide an interlocking fit with a notch 534n formed in a proximal end portion of proximal tube portion 524p, see FIG. 47K. The opening 625i of the proximal portion 625p is dimensioned to form a friction fit with a proximal end portion of endoscope 330. This frictional lock combined with the lock provided between key 625k and notch 534n prevents endoscope 330 from rotating relative to tube 534 once it has been inserted therein and locked by the scope lock 625. Accordingly, the field of view provided by the scope 330 maintains a constant orientation/attitude relative to the orientation of tube 534 over the entire course of use. Shaft 625 may optionally be provided with one or more sets of detents 625d or slots, or other features that can interface with stylet lock 620.

FIG. 47J is an enlarged, isolated view of an endoscope lock 625 that may be provided with guide assembly 530. Endoscope lock 625 includes an enlarged proximal end portion

625p and an elongated shaft portion 625s extending distally from the proximal end portion 625p. The shaft portion 625s may be keyed 625k to provide an interlocking fit with a notch 534n formed in a proximal end portion of proximal tube portion 524p, see FIG. 4K. The opening 625i of the proximal portion 625p is dimensioned to form a friction fit with a proximal end portion of endoscope 330. The endoscope is affixed with two radial protrusions (or bayonets) which interlock into the grooves shown in 625i. The width of the grooves narrow as the endoscope is rotated, thus locking it in place. This frictional lock combined with the lock provided between key 625k and notch 534n prevents endoscope 330 from rotating relative to tube 534 once it has been inserted therein and locked by the scope lock 625. Accordingly, the field of view provided by the scope 330 maintains a constant orientation attitude relative to the orientation of tube 534 over the entire course of use, even when the stylet is slid back and forth. The scope lock and endoscope are removed from the guide when it is extended for purposes of passing elongated device (e.g., the conduit 600 and obturator 630 over the guide 530).

Figure 47M:
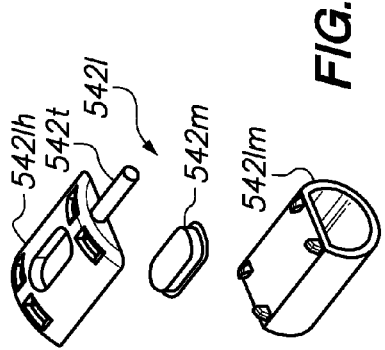
FIGS. 47L-47P illustrate a variation of the assembly shown and described above with regard to FIGS. 47A-47K.
Figure 47P:
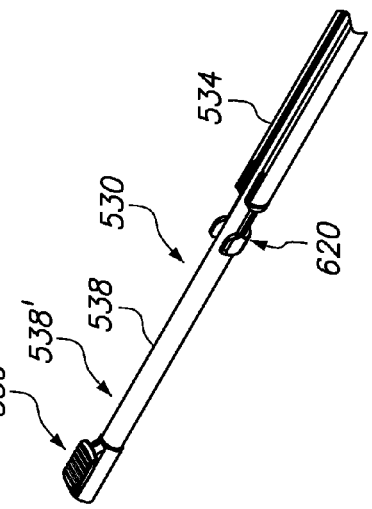
Figure 47O:
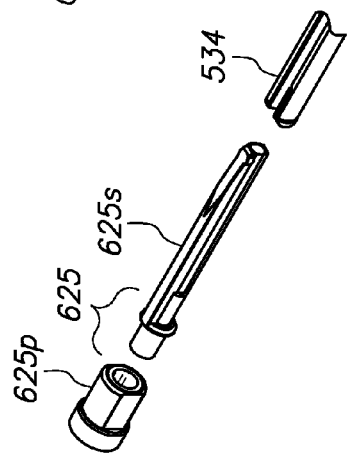
Figure 47L:
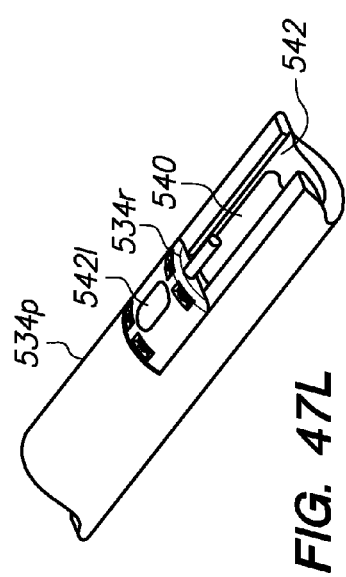

FIGS. 47L-47P illustrate a variation of the assembly shown and described above with regard to FIGS. 4A-4K. In FIG. 4L a septum 542L is provided in the wall of tube 534p, alternative to the port 542p shown in FIG. 4F. Note that lumen 542 is alternatively configured between the external and internal walls of tube 534, rather than as an external tube as described above with regard to FIGS. 4A-4K. However, this configuration can also be provided alternatively with a port 542p. FIG. 47M shows an exploded view of septum 542L showing a main housing 542LM, a membrane 542M (e.g., silicone, or the like) and a secondary housing portion 542LH that includes a tube 542T that connects with lumen 542 to configure septum 542L in fluid communication therewith. Septum 542L is received in a recess 534r in tube 534. It is adhesively bonded in place and is low profile, to fit within the wall thickness of the rigid main outer tube.

Figure 47N:
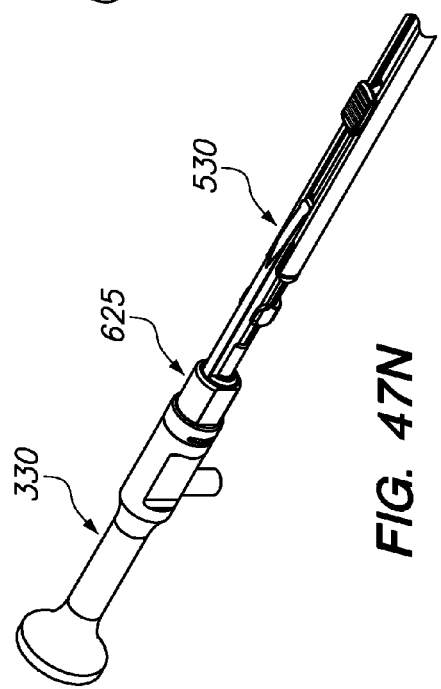
Figure 47Q:
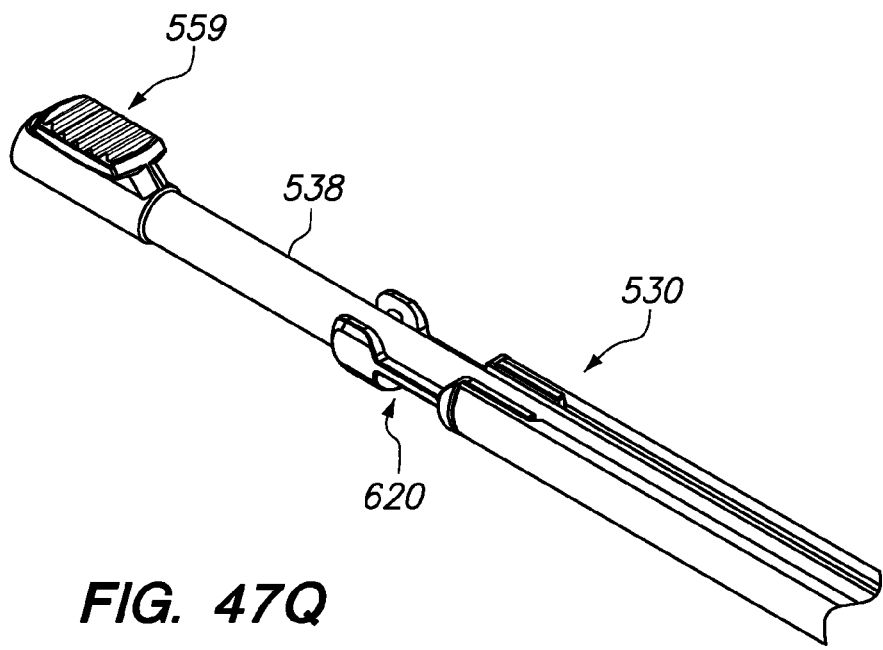
Figure 47R:
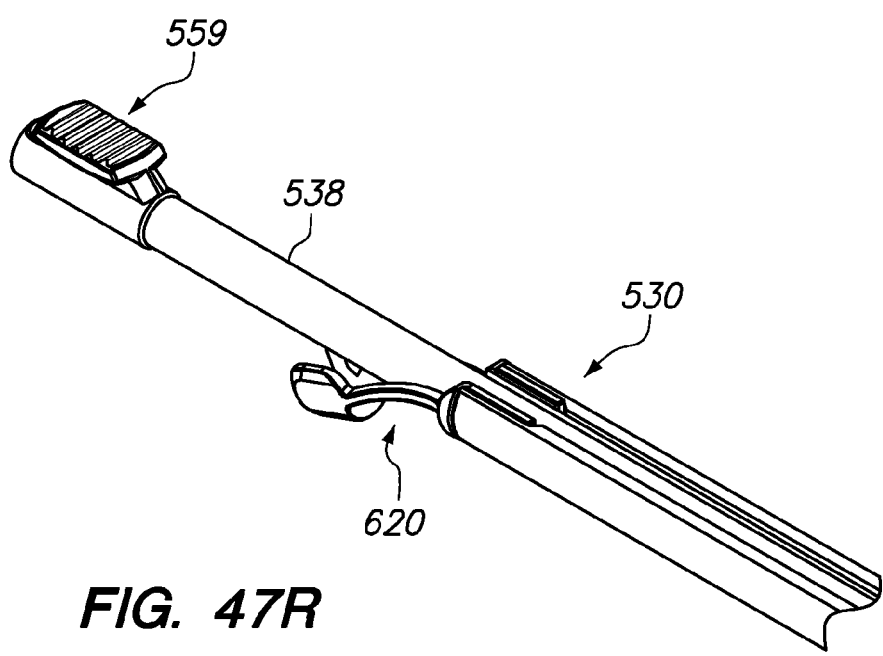

FIG. 47N illustrates a partial proximal end portion) view of the guide assembly 530 with an endoscope 330 having been inserted therein. Scope lock 625 includes two parts that snap together (see FIG. 40) in this embodiment and allow rotation of the endoscope 330 relative thereto, but prevent rotation of the lock 625 relative to tube 534 in the manner described above. Part 625p rotates freely with respect to 625k (see FIG. 4J), while portion 625k is friction fit into the proximal part of the slot in guide 530. The slot acts like a spring, clamping shut on the raised portion of 625k and providing stiff resistance to axial movement of 625k relative to 530.

The length of assembly 530 may be extended when needed, such as for guiding a conduit 600 and obturator 630 thereover, or in other situations where an extended length is desirable. FIG. 47P illustrates that lengthening may be accomplished by removing the endoscope 330 from assembly 530 and retracting the stylet assembly 538' so that a portion of the stylet 538 extends proximally of the proximal end of tube 534. When stylet assembly 538' has been retracted sufficiently to meet the needs of the user, the stylet lock 620 can then be locked down against the stylet 538 and or coating or jacket 557.

FIGS. 48A-48D show an embodiment of tip arrangement useable with any of the embodiments of guide 530 described herein. Tip 532" may be attached to guide 530 in any of the same manners described above with regard to tip 532'. Tip 532" may be made of any of the same transparent materials described above with regard to previously described tips 532 and 532'. Tip 532" however, does not have a conical exterior shape, unlike the shapes of tips 532 and 532'. Rather, the outer surface of the bottom portion of tip 532" has a tapering curvature that tapers from the circular cross-section of the proximal portion 532p" to a blunt curved transversely extending segment 532d" (see FIG. 6C) at the distal end of the tip, where the outer surface of the bottom portion 532t" joins the outer surface of the top exterior portion 532b". The outer surface of the top portion 532b" is substantially flat (substantially planar). The curved transversely extending segment 532d" is formed to one side of the central longitudinal axis L of the lumen 5321 formed in tip 532" and is therefore also extends transversely above the central axis of the lumen of the tube 530 to which it is attached, and also therefore extends transversely and above the central axis of an endoscope 330 inserted in a guide 530 to which tip 532" is attached.

The inner surfaces of the tip 532" do not have a different curvature than the outer surfaces, but generally follow the same contours. Thus, the thickness of the tip walls is substantially constant thereover, as the upper inner surface is substantially flat or planar and the inner lower surface has a curvature that substantially corresponds to the curvature of the outer lower surface. The sides of tip 532" in this embodiment are also convexly curved, with the inner surfaces having substantially the same curvature as the outer surfaces to maintain the wall thicknesses substantially constant. Because of the asymmetric configuration of the lower portion 532t" relative to the upper portion 532b", reflections and artifacts are greatly reduced. Also, because the curved transversely extending segment 532d" is below the central longitudinal axis (viewing axis) of an endoscope 330 inserted into guide 530 (and optionally into tip 532"), and distortion caused by 532d" is below the main field of view of the endoscope 330 and establishes a horizon reference line therefore. Viewing can also be accomplished below this horizon line, through upper portion 532b".

Optionally, tip 532" (or any of the other tips described herein) may be provided with a recess or groove 532g" (see FIG. 6D) that is aligned with the longitudinal axis of the tip and is recessed into the external surface thereof. Groove 532" may function for alignment with a secondary lumen 542, which may be formed within the main wall of the tube 534 for example, or by an additional small tube running externally of the tube 534, and to facilitate delivery of a fluid through the secondary lumen and out of the device 530,532". However, tip 532" does not have an opening joining the inside of the tip to the outside of the tip once the proximal end of the lumen 5321 is closed off by mounting tube 530 thereover (see FIG. 48E).

FIGS. 49A-50A show an embodiment of tip arrangement useable with any of the embodiments of guide 530 described herein. Tip 532'" may be attached to tube 530 in any of the same manners described above with regard to tip 532'. Tip 532'" may be made of any of the same transparent materials described above with regard to previously described tips 532, 532' and 532". Tip 532'", like tip 532" does not have a conical exterior shape. Rather, the outer surface of the bottom portion of tip 532" has a tapering curvature that tapers from the circular cross-section of the proximal portion 532p" to a blunt, curved transversely extending segment 532d" at the distal end of the tip, where the outer surface of the bottom portion 532f joins the outer surface of the top exterior portion 532b". The outer surface of the top portion 532b" is substantially flat (substantially planar). Additionally, in this embodiment side portions 532s'" are substantially flat. Accordingly, blunt straight axially extending segments 532sb'" formed at the junctions of the side portions 532s'" and the top portion 532b'" extend distally from the ends of the curved transversely extending segment 532d" from the locations where the segments meet. The curved transversely extending segment 532d" and segments 532sb'" are formed below the level of the central longitudinal axis of the lumen 5321 formed in tip 532'''. These segments are visible in the viewing field of an endoscope 330 inserted into a guide 530 fitted with tip 532''' in a manner as illustrated in FIG. 49B. Thus, segments 532d''' and 532s''' allow the user to easily identify the orientation of the tip 532''' even when tip is inserted within the body, by viewing through endoscope 330.

Like the embodiment of FIGS. 48-48B, the inner surfaces of the tip 532''' do not have a substantially different curvature than the outer surfaces, but generally follow the same contours. Thus, the thicknesses of the tip walls are substantially constant thereover, as the upper inner surface is substantially flat or planar and the inner lower surface has a curvature that substantially corresponds to the curvature of the outer lower surface. The sides of tip 532''' in this embodiment are also substantially flat, with the inner surfaces being substantially flat and thus having substantially the same conformation as the outer surfaces to maintain the wall thicknesses substantially constant. Because of the asymmetric configuration of the lower portion 532t''' relative to the upper portion 532b''' and sides 532s''', reflections and artifacts are greatly reduced. Also, because the curved transversely extending segment 532d'' and segments 532sb''' are above the central longitudinal axis (viewing axis) of an endoscope 330 inserted into guide 530 (and optionally into tip 532'', and distortion caused by 532d''' and segments 532sb''' is above the main field of view of the endoscope 330, this establishes a horizon reference line therefore. Viewing can also be accomplished above this horizon line, through top portion 532b'''.

Optionally, tip 532''' (or any of the other tips described herein) may be provided with a recess or groove 532g'' that is aligned with the longitudinal axis of the tip and is recessed into the external surface thereof. Groove 532'' may function for alignment with a secondary lumen 542, which may be formed within the main wall of the tube 534 for example, and to facilitate delivery of a fluid through the secondary lumen and out of the device 530,532''. However, tip 532''' does not have an opening joining the inside of the tip to the outside of the tip once the proximal end of the lumen 5321 is closed off by mounting tube 530 thereover.

FIG. 50B is a side view of tip 532''' in the upright orientation. Tip 532''' may be provided with a marker 5320 located on the inside surface of the tip lens that is located in font and along the curvature of the lens near the top 532b''' flat portion separated by a distance 5322 from the inner surface 532bi''' of the top of the lens 532''', as shown in the end view of FIG. 50B. In one embodiment distance 5322 is about 0.056" although this distance may vary. One example of an orientation marker 5320 is a chevron-shaped orientation marker 5320 as shown in FIG. 50C which represent how the chevron 5320 would appear to a user during use. In one embodiment the line segments of the chevron 5320 are about 0.002" to about 0.005" wide, about 0.015" in length and about form an angle between them of about eighty degrees and the chevron can be raised or lowered from the inner surface of the lens by a height or depth of about 0.005", although any and all of these specifications may vary. Preferably, the chevron 5320 points to the top of the lens 532'''. When viewed by a user, the chevron 5320 appears near the top edge of the field of view 5324 of the tip 532'''.

In another embodiment, the orientation marker 5320 is in the form of a vertical line as shown in the end view of FIG. 50D. Vertical line 5320 is located as described above with regard to chevron 5320. In on embodiment the end of the vertical line 5320 farthest away from the top inner surface 532bi''' was about 0.056" from the inner surface 532bi''' and line 5320 was about 0.015" in length, with the other end connecting to the inner surface 532bi''', the line width was about 0.005" and was raised about 0.005' above the inner surface of the tip lens. However, any and all of the foregoing dimensions may vary. FIG. 50E illustrates the appearance of the line 5320 when viewed by a user. Line 5320 appears near the top edge of the field of view 5324 of the tip 532'''.

FIGS. 51A-51F illustrate one embodiment of use of dilator 570 and large cannula 310L with guide 530 to enlarge an opening. In this embodiment, an opening through the fascia 127 leading into the abdominal cavity is enlarged. However, these techniques are not limited to enlarging an opening into the abdominal cavity, as they can also be used to enlarge an opening into the thoracic cavity, or to enlarge another opening leading into the patient.

Figure 51A:
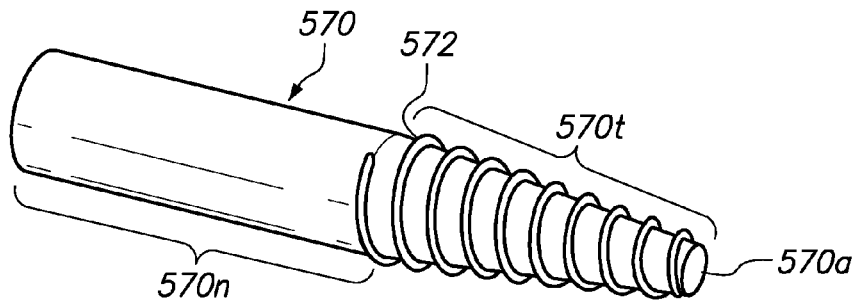
FIGS. 51A-51F illustrate an embodiment of use of a dilator and large cannula/introducer with guide to enlarge an opening.

FIG. 51A illustrates a dilator 570 that may be used to perform the dilation of the opening (e.g., through the fascia 127f and or abdominal muscle, or some other opening). Dilator 570 is tapered, with a large threadform 572 along the tapered portion 570t and transitioning to the non-tapered portion 570n. In at least one embodiment the threadform 572 is about 2.67 threads per inch, has a pitch of about 0.375 and wherein the tapered portion has a taper of about eight degrees. Each of these specifications may vary, but the threadform should remain large (e.g., about 1.1 to about 3.3 threads per inch) and the threads should extend sufficiently from the surface of the taper, e.g., about 0.065" to about 0.125", typically about 0.080", but be blunt (rounded) so as to grab the tissues to drive the dilator into the abdominal cavity as the dilator 570 is rotated, without cutting the tissues that the threadform 572 contacts. Dilator 70 has a central annulus or lumen 570a extending therethrough which has a diameter slightly larger than the outside diameter of guide 530. Accordingly, annulus 570a may have a diameter of about 0.5" or slightly larger. In one particular embodiment dilator 570 has an inside diameter of about 0.505" formed by annulus or lumen 570a, and an outside diameter of the non-tapered portion is about 1.5" to about 1.75". The distal end of dilator 570, where the tapered portion begins has an outside diameter of slightly greater than the annulus diameter, e.g., about 0.6" to about 0.7" and tapers to the cross-sectional dimension of the non-tapered section 570n, which may, for example, have an outside diameter of about 1.0 inches to about 1.5 inches. In another example, the outside diameter of the non-tapered portion 570n was about 1.2 inches. The profile of the threadform 572 can be radiused so that there are no sharp edges on the threadform 572, thereby greatly reducing the risk of trauma. Dilator 570 (including threadform 572) may be made of a relatively rigid, but lubricious polymer, such as DELRIN® (acetal copolymer) or other acetal copolymer, or other suitable biocompatible polymer, such as an injection moldable polycarbonate with out without a radiopaque filler or radiopaque marker band.

Figure 51B:
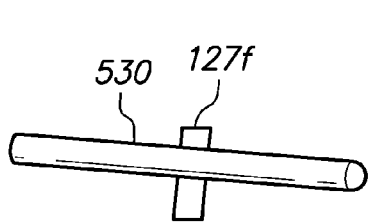

FIGS. 51B-51E schematically illustrate use of dilator 570 to increase the size of the opening in the fascia 127f and or abdominal muscle or other tissue so as to make it easier to insert an implantable device and/or tool therethrough. FIG. 51B illustrates guide 530 positioned through the fascia abdominal muscle 127f after establishing a tract therethrough. Although not shown in the schematic illustration of FIG. 51B for reasons of simplicity of illustration and clarity, at least to the extend where guide 530 passes through the opening 127f and proximally thereof at least until exiting the patient are rigid, or made at least temporarily rigid by any of the techniques described herein, so as to maintain the orientation of the guide 530 while also providing a low profile arrangement that allows the dilator to be easily passed over the proximal end of guide 530.

Figure 51C:
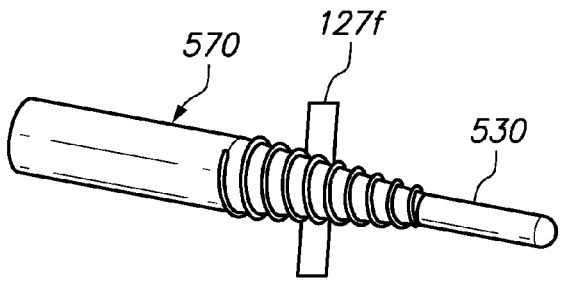

Dilator 570 is then slid over the proximal end of guide 530, distal end first and advanced into the opening in the patient. Dilator 570, upon reaching the fascia 127*f* or even prior thereto, can be rotated (clockwise if threadform 572 is arranged in a right-handed thread or counter clockwise if the threadform 572 is arranged in a left-handed thread) to draw the tapered portion through the fat layer (when rotated prior to reaching the fascia 127*f*) and through the fascia abdominal muscle 127*f*. The distal tip of the dilator 570, having the smallest outside dimension, can enter the opening through the fascia 127*f* by slight pushing (and manipulation such as "wigging") on the dilator 570, for example. By further rotating the dilator, the blunt edged threadform 572, threads its way into and through the fascia/abdominal muscle 127 without cutting it, but drawing the tapered portion of the dilator 570 along with it, thus gradually dilating the opening in the fascia 127*f*. Thus, the threadform 572 provides mechanical advantage for enlarging the opening through the fascia/abdominal muscle 127*f* without cutting, but rather by dilating. Alternatively, the tapered surface of the dilator 570*t* between the threads could have a texture like a file, which would serve to help break the fascial tissues during dilation. FIG. 51C illustrates dilator 570 being turned to draw the tapered portion 570*t* through the fascia 127*f* via the action of the threadform 572 on the fascia 127*f*.

Figure 51D:
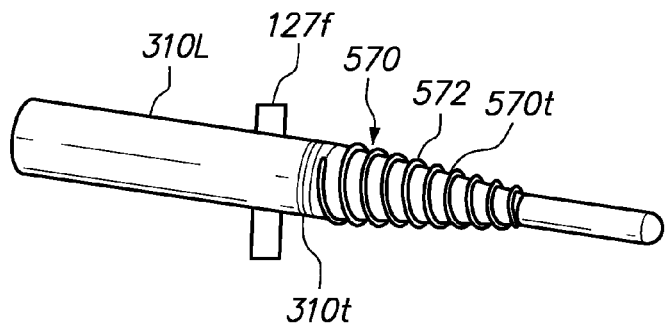
Figure 51E:
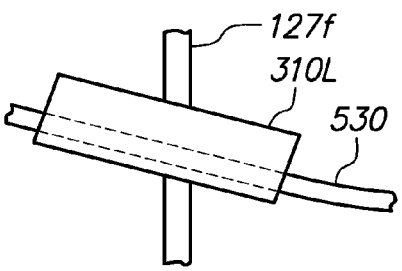
Figure 51F:
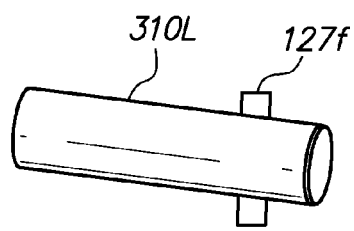

Continued turning of the dilator 570 continues the drawing of the dilator 570 through the hole in the fascia 127*f* and or abdominal muscle. A large cannula 310L can be slid over the non-tapered portion of dilator 570 (or can be pre-mounted thereon) to follow the dilator 570 as it is drawn in through the opening in the fascia, as illustrated in FIG. 51D. Large cannula 310L may have a tapered distal tip 310*t* that facilitates it following the dilator 570 through the opening in the fascia 127*f*. In addition, the large cannula 310L may also have threadforms similar to the threadforms 572 on the dilator 570. Once large cannula 310L has been successfully placed through the opening and across the walls of the fascia and/or abdominal muscle, dilator 570 can be slid out of large cannula 310L and therefore out of the patient leaving the cannula 310L and guide 530 in place, as illustrated in FIG. 51E. If endoscope 330 was removed during the dilation process illustrated in FIGS. 51B-51D, it may then be reinserted into guide 530, if desired by the surgeon during the part of the process illustrated in FIG. 51E. Alternatively, guide 530 can also be removed along with dilator 570 at this stage, leaving only the cannula 310L extending through the opening in the fascia, as illustrated in FIG. 51F. This will depend upon whether it is desired to view with an endoscope 330 inserted into guide 530 as it extends alongside another tool or implantable device advanced along the tract, or if an endoscope is to be used in another tool extended along the tract. Further alternatively, other visualization schemes may be used, during which the guide 530 may be removed from the patient. While the example of FIGS. 51A-51F has been directed to dilating an opening in the fascia and/or abdominal muscle, it is again emphasized here that neither the dilator nor any of the other tools and devices described herein are limited to placement through the fascia of the abdominal cavity, but may be used through other openings in the body.

FIGS. 52A-52E show another embodiment of a dilator 570 and large cannula or introducer 310L that can be used in any of the same manners described above with regard to the dilator 570 and large cannula 310L described previously with regard to FIGS. 51A-51F, including use for delivery and placement of a conduit through which an implantable device and/or tool can be delivered to a target surgical location. The tools of FIGS. 52A-52E, like those of FIGS. 51A-51F, can be made from one or more of the following materials: polycarbonate, glass-filled polycarbonate, glass-filled nylon, Grilamid® (semi-lubricious nylon product) Grivory® (semi-lubricious nylon product), polyetheretherketone (PEEK), Teflon® (polytetrafluoroethylene) and or Delrin® (acetal resin) or other injection molded, biocompatible plastic.

Figure 52A:
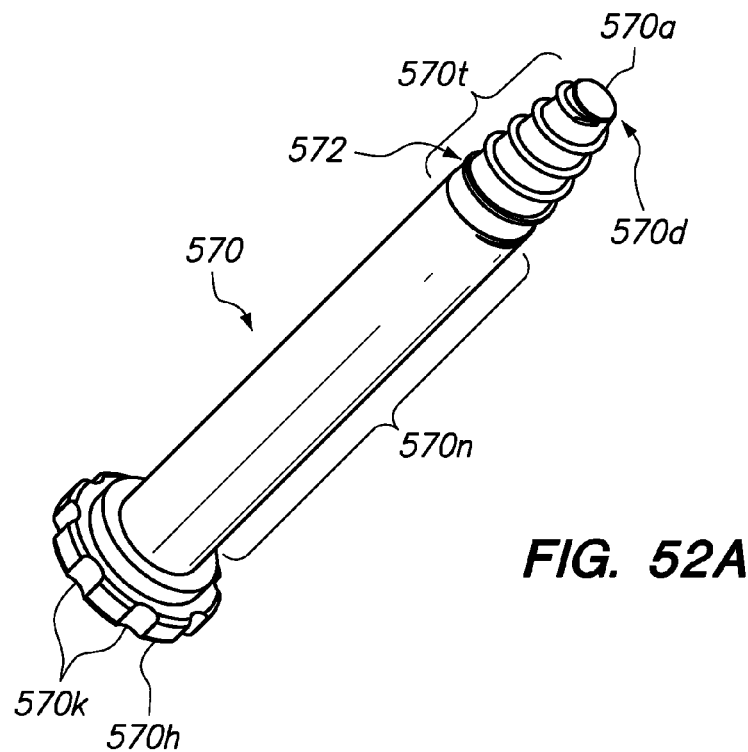

Like the embodiment of FIG. 51A, the dilator 570 of FIG. 52A is tapered, with a large threadform 572 along the tapered portion 570*t* and transitioning to the non-tapered portion 570*n*. FIG. 10C illustrates one specific embodiment of a threadform 572 that extends from the surface of the taper 570*t* by a distance 580 of about 0.080 inches and wherein the free or exposed edge of the threadform 572 has a radius of curvature 582 of about 0.030".

Dilator 570 has a central annulus or lumen 570*a* extending therethrough which has a diameter slightly larger than the outside diameter of guide 530. Accordingly, annulus 570*a* may have a diameter of about 0.5" or slightly larger. In one particular embodiment, dilator 570 has an inside diameter of about 0.505" formed by annulus or lumen 570*a*, and an outside diameter of the non-tapered portion is about 0.995", with a length of the overall dilator 570 being about 8.7". In another particular embodiment, the inside diameter and length were the same, but the outside diameter of the non-tapered portion 570*n* was about 1.060". In still another embodiment, the inside diameter is the same, but the length of the dilator 570 is about 16.16" and the outside diameter of the non-tapered portion 570*n* is about 1.588". Thus, the inside diameter of dilator 570 at the distal end 570*d* closely matches the outside diameter of tube 534 being only slightly larger (e.g., about 0.005"±about 0.002") to allow free sliding of the dilator 570 over the guide 530, but fitting closely to prevent this interface from grabbing tissues as the dilator 570 is advanced over guide 530. The distal end of dilator 570, where the tapered portion begins has an outside diameter of slightly greater than the annulus diameter, e.g., about 0.6" to about 0.7" and tapers to the cross-sectional dimension of the non-tapered section 570*n*, which may, for example, have an outside diameter of about 0.8 inches to about 1.7 inches.

In FIG. 52A, dilator 570 additionally includes an enlarged handle 570*h* at a proximal end thereof that is configured to be grasped by a user to facilitate an increase in the amount of torque the user can apply to the dilator 570 by rotating handle 570*h*. Thus, handle 570*h* has a larger outside diameter than the non-tapered cylindrical portion 570*n* of dilator 570. Further, handle 570*h* can be provided with knurls 570*k* or other features that render handle 570*h* less smooth or otherwise increase friction, to prevent the user's hand from slipping during torquing.

Figure 52B:
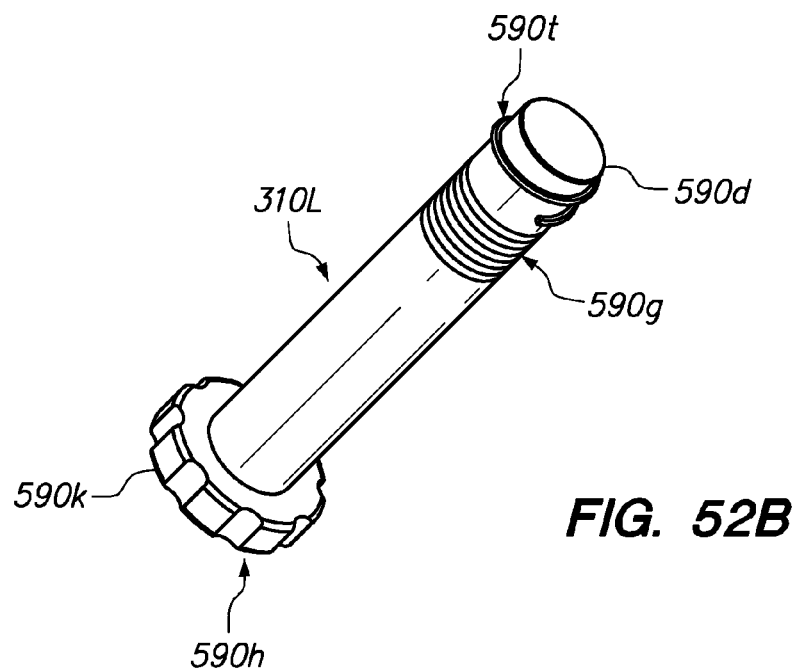

The large cannula 310L of FIG. 52B is configured to slide over dilator 570 with a close, but freely sliding fit (e.g., inside diameter of large cannula 310L is about 0.005"±about 0.002" greater than outside diameter of portion 570*n*) and large cannula 310L has a length such that when handle 590*h* contacts handle 570*h*, the threaded, tapered portion 570*t* of dilator 570 extends distally of the distal end of large cannula 310L as shown in the assembled view of FIG. 52D. In another embodiment, the close, but freely sliding fit is provided wherein the inside diameter of large cannula 310L is about 0.012"±about 0.005" greater than outside diameter of portion 570*n* In one embodiment where the dilator had a length of about 8.67", and inside diameter of about 0.505" and the portion 570*n* had an outside diameter of about 0.995", the large cannula 310L had a length of about 6.375", an inside diameter of about 1.055" and an outside diameter of about 1.105". In another embodiment where the dilator had a length of about 16.16", and inside diameter of about 0.505" and the portion 570*n* had an outside diameter of about 1.588", the large cannula 310L had a length of about 11.855", an inside diameter of about 1.610" and an outside diameter of about 1.690". In another particular embodiment the dilator had the a length of about 8.67" and the same inside diameter as the previous embodiments, but an outside diameter of about 1.060" and the large cannula had a length of about 6.375", an inside diameter of about 1.065" and an outside diameter of about 1.115". In all embodiments, the inside diameter of large cannula 310L forms a close fit with the outside diameter of the cylindrical portion 570 to allow free sliding between the components, but to prevent snagging of tissue between the distal end of large cannula 310L and dilator 570 as these components are inserted into the body. The distal end portion of large cannula 310L may comprise a radiopaque material or may be provided with a radiopaque feature for enhanced visibility under fluoroscopy. Likewise, the distal end portion of dilator 570 may comprise a radiopaque material or may be provided with a radiopaque feature for enhanced visibility under fluoroscopy.

Large cannula 310L may be provided with a first threadform 590t that matches the pitch of the threadform 570t and extends from the surface of the cylindrical main body of large cannula 310L by a distance equal or similar to the distance that threads 570t extend from the conical portion of the dilator 570. In this way, threads 590t can be aligned with threads 570t so that the threadform 590t acts as a continuation of threadform 570t by extending smoothly and substantially continuously therefrom as illustrated in FIG. 52D. However, it is not critical that the threads 570t and 590t are aligned in this manner, as threads 590t can start independently of the thread 570t after the thread 570t has passed through the fascia or other opening being enlarged. Further alternatively, the threads 590t may, but need not match the thread height of the thread 570t of the dilator 570. The threads 590t of the large cannula 310L can alternatively have a different threadform and pitch than threads 570t of the dilator 570. In one embodiment where the height of threads 570t (measured from the peak of the thread to tapered outer surface of tapered portion) was about 0.085", the height of threads 590t (measured from the peak of the thread 590t to the non-threaded surface of the large cannula 310L) was about 0.065". The threads 590t can be alternatively replaced by a series of spaced, parallel ribs that extend around the circumference of the introducer in a direction substantially normal to the longitudinal axis thereof, or such ribs can be provided in addition to the threads 590t. To assist in alignment of the threads 570t, 590t and maintenance of the alignment handle pattern 590k is provided that both assists grip by the user, and matches up with the pattern 570k on the handle 570h of the dilator. Accordingly, as shown in FIG. 52D, when threads 570t are aligned with threads 590t the knurling pattern 590k aligns with knurling pattern 570k. By maintaining alignment of the patterns 570k, 590k (the user can maintain alignment by grasping both 570k and 590k in his or her hand) during torquing, threads 570t, 590t can be seamlessly threaded in through an opening, e.g., in the fascia, muscle, diaphragm or other tissue.

Alternatively or additionally, handle 570h may be provided with at least one fastening component 570f and handle 590h may be provided with at least one mating fastening component 590f, one for each respective fastening component 570h. As shown in FIG. 10E, handle 570h includes two male fastening components 570h and handle 590h includes two corresponding mating female components 590f. However, one or more than two such components may be provided on handle 570h and, correspondingly, in handle 590h. Further, the male component(s) can be provided on handle 590h and the female components can be provided in handle 570h. Still further, although bayonet couplings 570f and mating female receptacles 590f are shown, alternative mating components may be used, such as shafts with ball and detent arrangements, or any of a number of mating, releasable mechanical fixtures. The mating mechanical members 570h and 590h, when connected, maintain the large cannula 310L fixed relative to the dilator 570, both in the axial direction, as well as rotationally. Accordingly, these fixtures can be arranged so that when they are connected together, the threads 570t and 590t are aligned, and the distal end of the large cannula 310L is properly axially aligned with the distal end portion of the dilator 570 as intended. A release mechanism 591 may be provided that the user can actuate, once the cannula 310L has been properly positioned so that the distal portion including threads 590t has been threaded through the opening in the fascia, to release the mechanical fixation member 570h, 590h and then the operator can remove the dilator 570 from the large cannula 310L and the patient by withdrawing on handle 570h while holding handle 590h stationary relative to the patient. In the example shown in FIG. 52E, the release mechanism 591 comprises a pair of release buttons 591 that the operator can press on to release the bayonet male members 570f from the receptacles 590f. Handles 570h, 590h can have substantially the same size/outside diameter, as shown in FIG. 52D, but this is not necessary.

The distal end 590d of large cannula 310L may be chamfered so that it tapers towards the dilator 570 when assembled thereover, thereby further reducing the risk of snagging tissue (e.g., fascia) as the tools are threaded into the body. Alternatively, the tip 590d may be flexible and tapered to a smaller diameter to create intimate contact and smooth transition with the dilator 570. In this embodiment, the tip 590d could be composed of an elastomeric material or a more rigid material where the tip 590d is radially interrupted to allow the stiffer material to flex radially outwards to allow an interference fit that slides under low force. This same type of transition could be applied to the dilator tip 570d, to provide a smooth transition to the guide tube 530. In addition to aiding in the dilation procedure, threads 590d provide tactile feedback to the user to let the user know when the distal end of large cannula 310L has been threaded into the abdominal cavity through the hole in the fascia, as the user can feel the cannula 310L being drawn in through the hole in the fascia by the threads 590t as the cannula 310L is rotated. Further, the threadforms allow the user to feel when they have passed through the fascial hole such that the large cannula 310 can then translate forward more easily. This tactile feedback allows the user to feel when the end of the large cannula 310 has appropriately passed beyond the fascia. Further, the distal threads 590t on the introducer 310L are configured to help prevent the large cannula 310L from accidentally pulling out of the abdominal cavity. Coarse ridges 590g may be provided on the distal end portion of large cannula 310L proximal of threads 590t. The coarse ridges 590g function to increase friction between them and the surrounding tissues to help prevent movement of the large cannula 310L relative to the patient's body, once it has been inserted in the desired position. As shown, the coarse ridges are parallel to one another and closely spaced. Once the distal end portion of large cannula 310L has been installed through the opening in the fascia, dilator 570 can be withdrawn from the cannula 310L and the patient 1 leaving the large cannula 310L in place to provide access to the abdominal cavity by tools and/or implants. Guide 530 may also be left in place to guide tools and/or implants. Alternatively, guide 530 may be removed to provide greater cross-sectional area of the large cannula 310L, such as for insertion and use of one or more tools and or implantable devices.

Figure 53A:
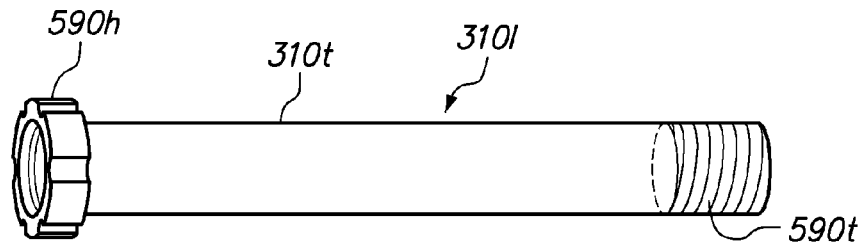
FIGS. 53A-53C show another embodiment of a dilator and large cannula introducer according to the present invention.
Figure 53B:
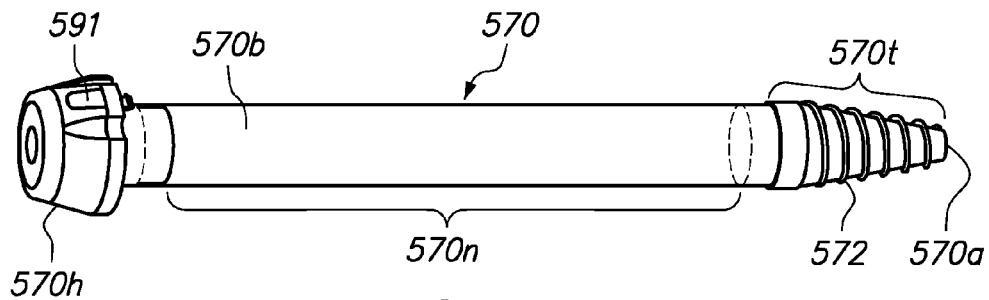
Figure 53C:
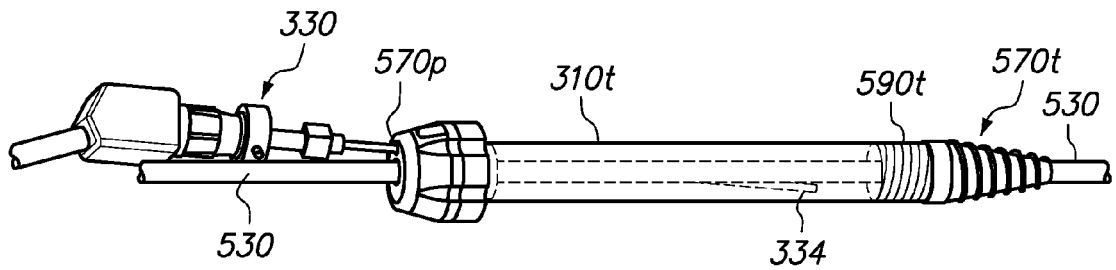
Figure 53D:
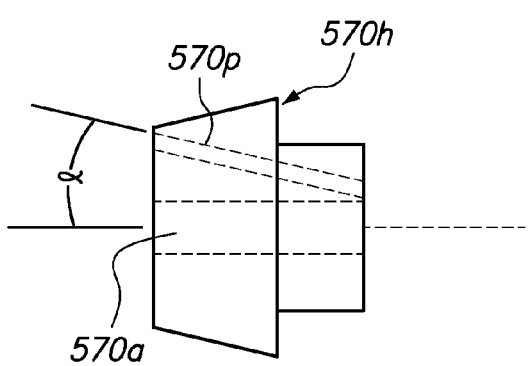
FIG. 53D is a side view of the handle of the dilator shown in FIG. 53B.

FIGS. 53A-53C show another embodiment of a dilator 570 and large cannula or introducer 310L that can be used in any of the same manners described above with regard to the dilator 570 and large cannula 310L described previously with regard to FIGS. 51A-51F as well as the embodiment described with regard to FIGS. 52A-52E, including use for delivery and placement of a conduit through which an implantable device and/or tool can be delivered to a target surgical location. In the embodiment shown in FIG. 53A, large cannula/introducer 310L includes a transparent main body tube with a handle portion 590h and may include threads 590t and/or ribs on the distal end portion thereof. Like the previous embodiments, the handle 590h and distal end portion of introducer 310L in FIG. 53A are opaque, but alternatively, can be transparent.

Like the previous embodiments, the dilator 570 of FIG. 53B is tapered, with a large threadform 572 along the tapered portion 570t and transitioning to the non-tapered portion 570n. Like the previous embodiments, the angle of taper of the outer surface of the tapered portion 570t relative to a central longitudinal axis of the dilator 570 is in the range of about seven degrees to about 13 degrees, typically about eight degrees to about 12 degrees. In one embodiment the angle was about 10.5 degrees (or 21 degrees measured from outer surface to opposite outer surface of the cone).

In this embodiment non-tapered portion 570n is transparent. Tapered portion 572 is opaque, like in previous embodiments. Dilator 570 has a central annulus or lumen 570a having at its distal end a diameter slightly larger than the outside diameter of guide 530. Accordingly, annulus 570a may have a diameter of about 0.5" or slightly larger. Annulus 570a expands to an enlarged annulus 570b within the non-tapered portion that is only slightly smaller than the inside diameter of tube 310t.

Figure 53E:
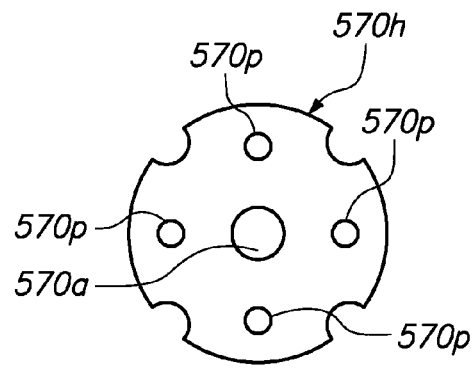
FIG. 53E is a proximal end view of a handle usable with the dilator of FIG. 53B, showing a variation that includes multiple endoscope ports.

Handle 570h fits in the annulus 570b to close the proximal end thereof. Handle 570h extends the annulus 570b via annulus 570a, which is the same dimension of the annulus 570a at the distal end of dilator 570 and therefore closely follows over guide 530. Additionally, handle 570h may be provided with one or more endoscope ports 570p dimensioned and configured to allow an endoscope 330 (typically a rigid endoscope) to be inserted therethrough, such that the endoscope shaft 332 and tip 334 are inserted at an angle α relative to the longitudinal axis of the handle 570h and dilator 570. In one embodiment, port 570p has a diameter of about 0.295" to about 0.305" (about 7.62 mm) to allow for insertion of a five mm endoscope shaft therethrough. These dimensions may vary, as the dimension of the endoscope shaft to be received may vary. Angle α may range from about twenty degrees to about seventy degrees, or from about twenty-five degrees to about forty-five degrees. In the embodiment shown in FIG. 11D, α is about thirty degrees. When providing multiple endoscope ports 570p, the multiple ports may each be provided at the same angle α and simply located at different angles (i.e., "clock" positions) about the circumference of the handle 570h. Alternatively, one or more ports 570p may be formed at different angles α relative to the longitudinal axis of the handle. This may also cause ports 570p to have varying radial distances from the central axis of lumen 570a, as shown in FIG. 53E. With the angles that are used, the endoscope shaft 332 bypasses the inside surface of handle 590h without contacting it, so that handle 590h does not have to be modified from previously described embodiments.

By inserting endoscope 330 through port 570p in the manner exemplified in FIG. 53C, the surgeon can view the anatomy by viewing through the tubes 570n and 370t. Thus, for example, in a situation like shown in FIG. 9D, the surgeon would be able to view the fascia 127f through endoscope 330 and ascertain whether or not the dilator 570 has successfully passed through the fascia.

The transparent tube 310t and 570n can be extruded from parts (e.g., polycarbonate) and the opaque components 590h, 590t, 570t and 570h can be molded from polycarbonate.

In one particular embodiment dilator 570 has an inside diameter of about 0.505" formed by annulus or lumen 570a, and an outside diameter of the non-tapered portion is about 0.995", with a length of the overall dilator 570 being about 8.7". In another particular embodiment, the inside diameter and length were the same, but the outside diameter of the non-tapered portion 570n was about 1.060". In still another embodiment, the inside diameter is the same, but the length of the dilator 570 is about 16.16" and the outside diameter of the non-tapered portion 570n is about 1.588". Thus, the inside diameter of dilator 570 at the distal end 570d closely matches the outside diameter of tube 534 being only slightly larger (e.g., about 0.005"±about 0.002") to allow free sliding of the dilator 570 over the guide 530, but fitting closely to prevent this interface from grabbing tissues as the dilator 570 is advanced over guide 530. The distal end of dilator 570, where the tapered portion begins has an outside diameter of slightly greater than the annulus diameter, e.g., about 0.6" to about 0.7" and tapers to the cross-sectional dimension of the non-tapered section 570n, which may, for example, have an outside diameter of about 0.8 inches to about 1.7 inches.

FIG. 54 illustrates an embodiment of a conduit 600 that can be inserted through large cannula 310L to extend distally far past the distal end of large cannula 310L, for delivery of one or more tools and or implants therethrough, to a surgical target location, such as in the abdominal cavity, in the thoracic cavity, in an internal organ or other internal location in the body where implantation of one or more devices or performance of one or more surgical procedures not requiring an implant is to be accomplished. The location can actually be quite shallow, relative to skin lying directly over it such as a location along the fascia or ribs. However, the location is "far" in the sense that it located away from the opening through the skin by a relatively large distance, a distance that is significantly greater than the length of the large cannula 310L, as noted above. Of course, the location can, alternatively, be located deep within the body of the subject. The length of conduit 600 is typically at least about 1.5 times the length of large cannula 310L, and may be at least 2 times, at least 2.25 times, at least 2.5 times or at least 3 times the length of large cannula 310L The embodiment of FIG. 54 is formed of relatively rigid plastic. In one embodiment this relatively rigid conduit 600 had a length of about 28.25 inches, an inside diameter of about 1.00 inches and an outside diameter of about 1.05 inches. In another embodiment this relatively rigid conduit 600 had a length of about 24.325 inches, an inside diameter of about 1.425 inches and an outside diameter of about 1.05 inches. Conduit 600 may include a chamfered or otherwise tapered distal end 600d so that it tapers towards the obturator 630 when assembled thereover, thereby reducing the risk of snagging tissue as the tools are inserted into the abdominal cavity, and generally helping to keep fluids and other tissues out of the conduit 600 as it is being advanced. Further optionally, the tapered distal end 600d may compress against the distal tip of the obturator 630 and/or form an interference fit therewith, preventing the distal tip of the obturator 630 from passing therethrough so that the obturator 630 be used to push against the conduit 600 via this contact to drive the conduit into the abdominal cavity and prevent the distal end of the conduit 600 from compressing or buckling toward the proximal end of the conduit 600. This fit between the distal end 600d and distal tip of the obturator 630 can also effectively seal the contact between the tapered distal end 600d and the distal end part/distal tip of the obturator 630, thereby preventing fluid inflow and tissue ingress into conduit 600 as it is advanced.

A flared or funnel portion 602 may be provided, either integrally with or attached to the proximal end portion of conduit 600. A seal 604 such as an o-ring may be provided to seat with the proximal end portion of the obturator 630 or proximal end of a tool. Further, a grasping tab 606 may be provided that can be pulled by the user to remove a perforated strip from the funnel portion 602 to expose slot 608. In instances where funnel portion 602 and the proximal end portion of conduit 600 are flexible, this allows deformation of the funnel portion 602 and proximal end portion of the conduit along slot 608 to allow a shaft handle or tube that extends transversely from a tool (e.g., light post of an endoscope, handle 412t of tool 400, etc.) to slide therealong, thereby reducing the effective length of the tool 400, endoscope 330 or other tool that needs to be provided to enable a distal end thereof to extend distally of the conduit 600. In embodiments where funnel portion 602 (and optionally, the proximal end portion of conduit 600) are rigid, the funnel portion 602 and adjoining proximal end portion of conduit 600 can be provided as half pieces that are hinged together, wherein a pair of opposing separations are formed between the halves (one in the location of and replacing slot 608 and one at a location about 180 degrees from there) to allow separation of the funnel portion 602 and proximal end portion.

FIGS. 55A-55C illustrate another embodiment of a conduit 600 in which at least a distal end portion thereof is flexible. In this embodiment the main tube of the conduit is formed of an elastomer, such as silicone, and a coil 610, such as a stainless steel coil, Nitinol coil, or the like, is encapsulated in the elastomer along at least the distal end portion of the conduit 600. Note that the chamfered or tapered distal end 600d is not reinforced with the coil 610. At least a 4" length of the conduit 600 extending proximally from the unreinforced distal end 600d is reinforced with coil 610. In other embodiments, a least a quarter or at least a third or at least half of the length of the conduit 600 extending proximally from the unreinforced distal end 600d is reinforced with coil 610. In the example shown in FIG. 55A and the sectional view of FIG. 55C, coil 610 reinforces more than half of the entire length of the main body tube of conduit 600, extending proximally from the unreinforced distal end 600d. In still other embodiments, coil 610 may extend proximally from unreinforced distal end 600d and support the entire length of the tube up to the distal end of slot 608. In embodiments where slot 608 is not present, coil 608 may reinforce the entire length of the tube of conduit 600, but typically not the tapered distal end 600d or funnel portion 602. Portions of the main tube of conduit 600 that are proximal of the proximal end of coil 610 may be made of an alternative material, such as a rigid polymer, so that this portion of the conduit is not flexible. Alternatively, portions of the main body of conduit 600 that are proximal of the proximal end of coil 610 may be flexible. Further alternatively, the main body of the conduit 600 can have no coil reinforcement but instead have reinforcements running longitudinally to allow bending but prevent stretching and/or buckling.

The reinforcement provided by coil 610 helps preserve the substantially circular cross section of the conduit 600 as it bends along a portion supported by coil 610, and coil 610 serves to prevent kinking along a supported portion as it is bent. In one particular embodiment a conduit of the type described with regard to FIGS. 55A-55C had a length of about 28.25 inches, an inside diameter of about 1.00 inch and an outside diameter of about 1.060 inches. In another particular embodiment, a conduit of the type described with regard to FIGS. 55A-55C had a length of about 24.325 inches, an inside diameter of about 1.425 inches and an outside diameter of about 1.505 inches.

In at least one embodiment where the funnel portion 602 is flexible, a notch 608n may be molded into the funnel portion 602 and proximal portion of tube 600 to produce a thinner portion along the line formed by notch 608n to facilitate a controlled tear of the material over a predefined length that is defined by the length of notch 608n. In the enlarged partial views of FIGS. 55D and 55E, notch 608n is formed as a triangular-shaped (in cross-section) notch and the thinner material portion can be seen at 608t in FIG. 55E.

At least the inside surfaces of conduit 600 may be coated with a lubricious coating such as a hydrophilic coating or other lubricious coating to reduce friction between an implant, device or tool inserted therethrough as it is delivered toward the surgical target location. In at least one embodiment, the lubricious coating comprises LUBRILAST™ (AST Products, Inc., Billerica, Mass.), e.g., see U.S. Pat. No. 6,238,799, which is hereby incorporated herein, in its entirety, by reference thereto. Additionally, at least a portion of the outside of conduit 600 may also be coated with a lubricious coating, which may be the same as the inside coating, for example.

FIGS. 56-56B illustrate a plan view and a proximal end view of an obturator 630 that is configured to be placed in conduit 600 and used to deliver conduit 600 through large cannula 310L and over guide 530 to deliver a distal end portion of conduit 600 far distally of the large cannula 310L. Obturator 630 has a length slightly greater than the length of conduit 600 so that when the tapered portion of distal tip 632 contacts chamfered end 600d, the handle 634 at the proximal end of obturator 630 extends slightly proximally of the proximal end of conduit 600 or the proximal end of funnel portion 602 when provided at the proximal end of conduit 600. Handle 634 and distal tip 632 are typically rigid and may be injection molded from hard plastic. Shaft 636 is relatively flexible and may be formed of extruded PEBAX® (polyether bock amides) or similar lubricious polymer extrusion that facilitates it sliding over guide 530 or may have a corrugated geometry or an interrupted linked geometry to allow flexibility.

A textured surface 634t such as grooves or the like may be provided on handle 634 to enhance grip by a user, as well as interfacing with seal 604. In one particular embodiment obturator 630 had an overall length of about 29.64", an inside diameter 638 (see proximal end view of FIG. 14B) of about 0.505", an outside diameter of shaft 636 of about 0.565", an outside diameter of distal tip 632 of about 0.995" and an outside diameter of handle of about 1.880". In another particular embodiment, obturator 630 had an overall length of about 26.307", an inside diameter 638 (see proximal end view of FIG. 14B) of about 0.505", an outside diameter of shaft 636 of about 0.565", an outside diameter of distal tip 632 of about 1.375" and an outside diameter of handle of about 1.950".

A textured surface 634t such as grooves or the like may be provided on handle 634 to enhance grip by a user. Additionally, a groove 635 may be provided that is configured and dimensioned to receive the molded O-ring 604 so that o-ring 604 seats in groove 635. In one particular embodiment obturator 630 had an overall length of about 29.64", an inside diameter 638 (see proximal end view of FIG. 56B) of about 0.506" (for use with a guide 530 having an outside diameter of about 0.505"), an outside diameter of shaft 636 of about 0.565", and an outside diameter of distal tip 632 (non-tapered portion) of about 0.995" and an outside diameter of handle of about 1.880".

FIG. 56C illustrates an alternative embodiment of obturator 630 in which shaft 636 is made of corrugated tubing. In one example, the corrugated tubing is fluorinated ethylene polypropylene (FEP) tubing. Alternative polymer materials may be used, e.g., polyethylene nylon, polypropylene, perfluoroalkoxy (PFA) copolymer, etc. Corrugated tubing shaft 636' allows the conduit 600, when installed over the obturator 630, to take tight bends without kinking. The relatively large diameter of the obturator shaft 636,636' also prohibits the conduit 600 from collapsing while the obturator 630 is installed in the conduit 600.

The obturator tip 632 may be an injection molded part and is provided with a central lumen/annulus 638 configured and dimensioned to slide over the guide 530, while providing a close fit with the guide 530 to prevent tissues or other obstructions from entering between the obturator tip 632 and guide 530, as the obturator 630 having the conduit 600 assembled therewith is passed over the guide to deliver the distal end of the conduit 600 to the surgical target location. Further alternatively, the obturator handle 634' may be funnel-shaped or otherwise tapered to follow the tapered contour of the tapered portion 602 of conduit 600. The obturator handle 634,634' may also be made of injection molded plastic. By providing the handle 634' with a tapered section, this further enhances the ability of handle 634' to prohibit the tapered portion 602 (when provided as a flexible component) from collapsing and inadvertently decoupling from the obturator 630. In one embodiment, obturator 630 had an outside diameter of shaft 636' of about 1.380" and obturator 630 had a length of about 24.438", measured from the distal surface of boss 634p to the proximal end of the tapered surface of tip 632. The angle of an outer surface of the tapered distal tip 632 to the central longitudinal axis of the obturator 630 is in the range from about thirteen degrees to about nineteen degrees, making the angle of the cone formed by tip 632 twice that or about twenty-six degrees to about thirty eight degrees. The obturator tip 638 may comprise radiopaque material to facilitate viewing it under fluoroscopy.

FIG. 56D illustrates an alternative embodiment of obturator 630 in which shaft 636" is made of rigid links 637. Rigid links 637 may be formed of glass-filled (10%, by weight) polycarbonate for example. Alternatively, links 637 can be made from polycarbonate, acrylonitrile butadiene styrene (ABS)-polycarbonate blend, glass-filled Nylon, Nylon (polyamides), polyethylene, ABS, polyether block amides (PEBAX), polyetheretherketones (PEEK), liquid crystal polymers (LCP), stainless steel or other biocompatible metals, etc.

Each rigid link 637 has a concave inner surface 637c formed in one end portion thereof and a convex outer surface 637x formed on an opposite end portion thereof. In the preferred embodiment shown, the link 637 has the convex outer surface 637x formed on the distal end portion of the link 637 and concave inner surface 637c is formed in the proximal end portion of the link 637. However, this arrangement could be reversed, so that link 637 has the convex outer surface 637x formed on the proximal end portion of the link 637 and concave inner surface 637c is formed in the distal end portion of the link 637, as long as all links 637 are arranged in the same way (i.e., so that surfaces 637x are all either proximal or distal, and surfaces 637c are all in the opposite end portion).

Optionally, only the distal portion of obturator need be flexible and formed by links 637. Accordingly, a proximal portion can be alternatively be formed as a rigid extension 637r of handle portion 634 and may comprise at least a quarter, at least a third or about half of the length of the obturator, with the remaining distal portion be flexibly formed by links 637. Further alternatively, the proximal portion may be formed with a fewer number of links that are substantially longer than the links 637 in the distal portion, since the proximal portion does not need to be as flexible (or may not need to be flexible at all) and this could reduce costs of manufacturing, as well as reduce the potential amount of elongation under tension. Further alternatively links as shown in FIG. 14D can be fused together in the proximal portion so that they do not articulate with one another.

Links 637 snap together to form a series of connected links 637 as shown in FIG. 14D. The snap fittings are loose enough to allow the links 637 to freely rotate relative to one another, about the longitudinal axis of the obturator 630, as well as to pivot (bend) relative to one another in any direction, 360 degrees about the longitudinal axis. However, the snap fittings maintain the connections between the links even under tensile forces at least up to twenty-two pounds, and in some embodiments up to about ninety-seven pounds. Likewise, the snap fitting connections maintain the connections between the links even under bending forces typically experienced during the uses described herein. Advantageously, since the links are relatively rigid, they do not stretch under tension or shorten under compression during use. Thus, the only change in length of obturator 630 of FIG. 56D during use (insertion into the body, as well as pulling the obturator out of the body) is due to the tolerances in the snap fittings between links 637, and this change is negligible for the purposes that the obturator is used, as described herein.

Surface 637x articulates with surface 637c to function like a ball joint, allowing the three-dimensional articulation ability described above. In the embodiment shown, the proximal end portion of link 637 includes a ribbed inner surface 637i having ribs 637b (see FIGS. 56E and 56F) that function to help direct the guide and keep it centered toward the central lumen/annulus 638. Handle 634 is provided with ramped surfaces 634a that angle toward the central longitudinal axis of the handle and help guide the guide 530 therethrough, see FIG. 56J. Surface 637i (not considering ribs 637b, see FIG. 56F) can be concave, as shown, but need not be. FIG. 56G is an end view of link 637 (proximal end view for the embodiment shown) that shows the smooth surface provided by concave surface 637c that allows the convex surface 637x to articulate freely against. Note also, that in the embodiment of FIG. 56D, obturator tip 632 may be provided with an inner concave surface 637c (or outer convex surface 637x, depending upon the particular embodiment) to articulate with the distal-most link 637. Alternatively, tip 32 may be fixed to, or integral with the distal most link 637. Similarly, handle 634 may be provided with an outer convex surface 637x (or an inner concave surface 637c, depending upon the particular embodiment) to articulate with the proximal-most link 637. Alternatively, handle 634 may be fixed to, or integral with the proximal-most link 637. Handle 634 may further be provided with one or more pins (or bosses) 634p for temporarily securing a portion of the funnel 602, when portions of the funnel 602 are provided with through holes 602h that allow pins 634p to extend therethrough when the funnel portions are held on handle 634, as shown in FIG. 56H. The funnel portions can be peeled or pried away from pins 634p to allow obturator 630 to be withdrawn from conduit 600.

FIG. 56I shows the conduit 600 from FIG. 56H, without the obturator 630. The distal portion 600d of conduit 600 is flexible (e.g., silicone, or the like) and reinforced with coil

610. Coil 610 is closed-wound or nearly closed-wound at the ends (e.g., the last two to five wraps, typically the last four wraps of each end) to allow the closed-wound wraps to be laser welded to each other to terminate the coil. To be closed-wound or nearly closed-wound, the coils must touch or be very close to each other to allow for the welding process. In between these closed-wound or nearly closed-wound coils, the coils are separated by gaps of about 0.012" in one embodiment (although this may vary), as they are wound at about thirty-three wraps/inch with a 0/018" diameter wire. This construction facilitates the prevention of kinking and which also helps prevent buckling of the distal portion when under axial compression. Coil 610 may be made of stainless steel or other biocompatible spring wire or elastic material that is visible under fluoroscopy and will perform as described.

The proximal portion 600d of conduit 600 is rigid and includes funnel portion 602. In at least one embodiment rigid portion 602 is made from PEBAX. In at least one embodiment, rigid portion 602 is made from PEBAX having a hardness of 63 A durometer. Slot 608 may be radiused 608R at its distal end for stress reduction to prevent cracking. Although the embodiment of FIG. 56I has only one slot 608, it may alternatively be provided with two or more slots 608 (e.g., a pair of oppositely located slots 608, or three or four circumferentially spaced slots or more). Conduit 600 may be provided with a lubricious coating (such as LUBRILAST™ of the like) to facilitate its passage through the large conduit 310L. Likewise, a lubricious coating is provided over the interior of conduit 600 to facilitate insertion of obturator therein and withdrawal of obturator 630 therefrom. In one particular embodiment the main tube of obturator 600 had an outside diameter of about 1.595", an inside diameter of about 1.425" and a working length of about 22.65" measured from the minimum diameter of the funnel portion 602 to the distal tip of the conduit 600, and a slit 608 length of about 13.3".

Links 637 of obturator 630 allow the conduit 600, when installed over the obturator 630, to take tight bends without kinking. For example, for a conduit 600 having a working length of about 22.65" and an inside diameter of about 1.425", obturator 630, when installed in conduit 600 allows conduit 600 to be bent at a radius of curvature of at least about 2.5" without kinking. The relatively large diameter of the links 637 and rigidity thereof, also prohibits the conduit 600 from collapsing while the obturator 630 is installed in the conduit 600. Although the conduit 600 is generally robust enough to prevent itself from kinking and collapsing, the links 637 may help the conduit 600 achieve a slightly tighter bend radius (about 10% smaller, for example). Links 637 only contact the inner wall of the conduit 600 at two point contacts per link or less. Many links 637 may not contact the conduit 600 at all. For example, in one embodiment, the inner wall of the conduit 600 has a diameter of about 1.425" and the large outside diameter of a link in this embodiment is about 1.259". The small space between the obturator and the conduit is desirable because it minimizes tip shift between the obturator 630 and the conduit 600 during bending, but also provides enough room for the obturator to bend freely around the guide 530. The relatively large diameter of the links 637 and rigidity thereof, also prohibits the conduit 600 from collapsing while the obturator 630 is installed in the conduit 600.

The obturator tip 632, handle 634 and links 637 may all be injection molded parts, e.g., injection-molded from polycarbonate or 10% glass-filled polycarbonate, or alternative materials to 10% glass-filled polycarbonate that were listed above. Additionally, tip 632 may have 10% barium additive to make it radiopaque. The central lumen/annulus 638 of obturator configured and dimensioned to slide over the guide 530, while providing a close fit with the guide 530 to prevent tissues or other obstructions from entering between the obturator tip 632 and guide 530, as the obturator 630 having the conduit 600 assembled therewith is passed over the guide to deliver the distal end of the conduit 600 to the surgical target location. Further alternatively, the obturator handle 634 may be funnel-shaped or otherwise tapered to follow the tapered contour of the tapered portion 602 of conduit 600. By providing the handle 634' with a tapered section, this further enhances the ability of handle 634' to prohibit the tapered portion 602 (when provided as a flexible component) from collapsing and inadvertently decoupling from the obturator 630.

Obturator 630 has a length slightly greater than the length of conduit 600 so that when the tapered portion of distal tip 632 contacts chamfered end 600d, the handle 634 at the proximal end of obturator 630 extends slightly proximally of the proximal end of conduit 600 or the proximal end of funnel portion 602 when provided at the proximal end of conduit 600. Like previous embodiments, a textured surface, such as grooves or the like may optionally be provided on handle 634 to enhance grip by a user. Further optionally, a groove may be provided that is configured and dimensioned to receive the molded o-ring 604 so that o-ring 604 seats in the groove.

FIG. 57 illustrates an embodiment of obturator 630 having been inserted into conduit 600. When the obturator embodiment of FIG. 14A is used, preferably, the contact between obturator 630 and conduit 600 occurs only between the distal tip 632 (tapered portion) and the chamfered end 600d, and between the funnel portion 602/seal 604 and the handle 634. This maximizes the ability of conduit 600 to make bends of the smallest possible bend radii, without kinking or distortion. However, the other embodiments of obturator typically do contact the conduit 600 at locations intermediate of the distal tip 632 and handle 634.

Figure 58A:
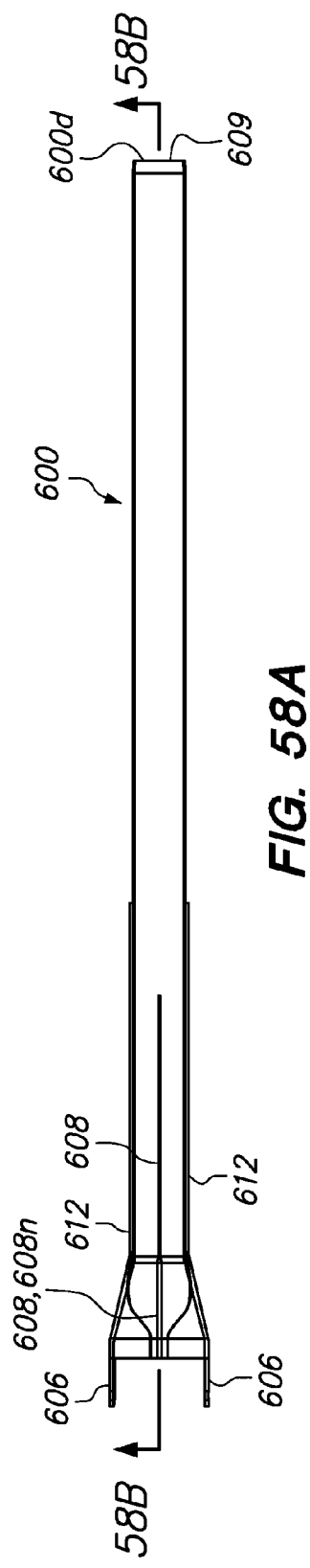
FIGS. 58A-58C illustrate an alternative embodiment of conduit according to the present invention.
Figure 58B:
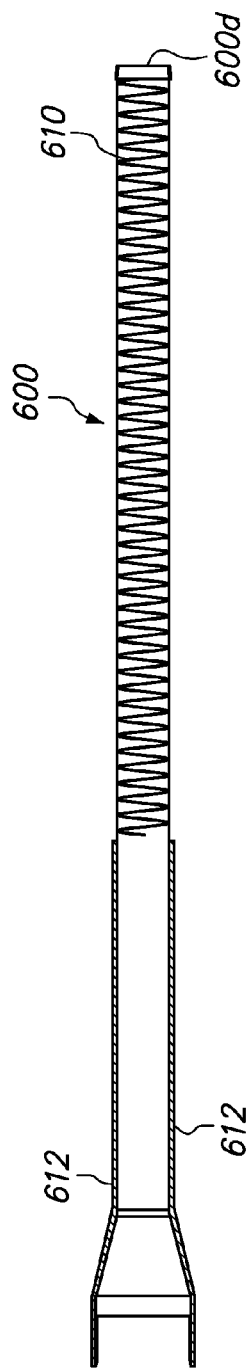
Figure 58C:
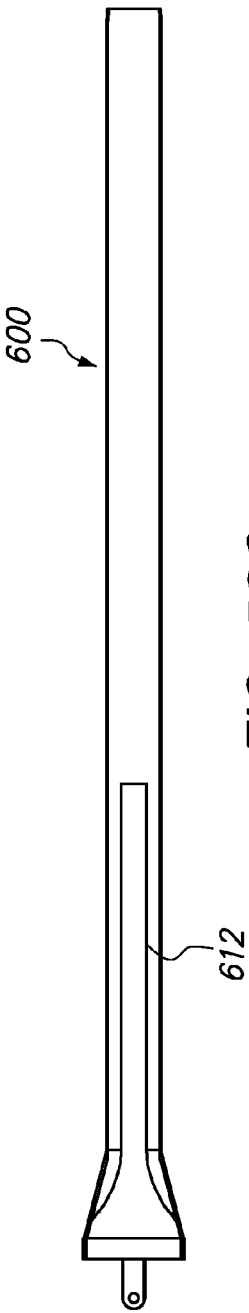

FIGS. 58A-58C illustrate an alternative embodiment of conduit 600 according to the present invention. Like the embodiment of FIGS. 55A-55E, the main tube of the conduit 600 is flexible and is formed of an elastomer, such as silicone, and a coil 610, such as a stainless steel coil, Nitinol coil, or the like, is encapsulated in the elastomer along at least the distal end portion of the conduit 600. Also like the embodiment of FIGS. 55A-55E, the chamfered or tapered distal end 600d is not reinforced with the coil 610. At least a 4" length of the conduit 600 extending proximally from the unreinforced distal end 600d is reinforced with coil 610. In other embodiments, a least a quarter or at least a third or at least half of the length of the conduit 600 extending proximally from the unreinforced distal end 600d is reinforced with coil 610. In the example shown in FIGS. 58A-58C, coil 610 reinforces more than half of the entire length of the main body tube of conduit 600, and extends proximally from the unreinforced distal end 600d to a location distally adjacent the distal ends of stiffening members 612. The proximal end portion of the main tube of conduit 600 that is proximal of the proximal end of coil 610 is reinforced by one or more stiffening member 612 (two stiffening members 612, as shown, although one, or more that two stiffening members 612 may be employed). Stiffening members 612 are attached to the outer surfaces of proximal end portion (such as by adhesive bonding thereto and/or mechanical fixation) or embedded in proximal end portion of conduit 600 to maintain a smooth, continuous surface interiorly where the lumen 609 is formed, so as to provide a smooth, continuous surface along which an implant and/or tools can be delivered while reducing friction to the extent possible. Likewise, as noted above, coil 610 is embedded so that it does not form a part of the inner surface that defines the lumen 609.

Stiffening members 612 may be thin strips of polymer, such as polycarbonate, Nylon, ABS, PEBAX, polyethylene, or the like that, when installed as shown, increase the column strength of the proximal end portion of conduit 600 to resist buckling, as well as longitudinal stretching of the proximal end portion under longitudinal forces that would cause buckling or stretching in the same proximal end portion when unreinforced by members 612. Stiffening members 612 may flare out at the proximal end portions thereof overlying the funnel portion 602 of conduit 600 to provide even more rigidification of the funnel portion, not only longitudinally, but also circumferentially. Slots and/or notches 608,608*n* may be provided to run longitudinally along conduit 600 between the stiffening members 612 to facilitate splitting the proximal end portion open in a manner described previously. Note that in this example, tabs 606 extend longitudinally and proximally from the proximal ends of stiffening members 612.

FIGS. 59A-59D illustrate alternative embodiments of conduit 600 according to the present invention. Like the embodiment of FIGS. 55A-55E, the main tube of the conduit 600 is flexible and is formed of an elastomer, such as silicone, and a coil 610, such as a stainless steel coil, Nitinol coil, or the like, is encapsulated in the elastomer along at least the distal end portion of the conduit 600. Also like the embodiment of FIGS. 55A-55E, the chamfered or tapered distal end 600*d* is not reinforced with the coil 610. At least a 4" length of the conduit 600 extending proximally from the unreinforced distal end 600*d* is reinforced with coil 610. In other embodiments, a least a quarter or at least a third or at least half of the length of the conduit 600 extending proximally from the unreinforced distal end 600*d* is reinforced with coil 610. In the examples shown in FIGS. 59A-59D, coil 610 reinforces more than half of the entire length of the main body tube of conduit 600, and extends proximally from the unreinforced distal end 600*d* to a location distally adjacent the distal ends of "petals" 614 that open away from the opening into the distal portion of the conduit 600. The proximal end portion of the main tube of conduit 600 that is proximal of the proximal end of coil 610 is formed by petals 614 (two petals 614 in the embodiment shown in FIGS. 59A-59C, although more than two petals 614 may be employed to form the proximal end portion of conduit 600, e.g., see FIG. 59D). Petals 614 are thin, broad and elongated leaf-like structures that are flexible and are typically formed of the same material as the main tubular portion of conduit 600. These thin, flexible elongate members (petals) 614 are separated from one another along the lengths thereof by longitudinally extending spaces 616, and are connected/integral at their distal ends with the tubular portion of conduit 600. Petals 614 may flare or taper from their distal ends to form wider portions 614W. It is preferred to have the petals narrower at the distal ends to create more overall strength and rigidity on the proximal end, yet influence reliable bending on the distal end. With narrow distal ends, the petals bend at substantially the same locations every time and do so easier than would be the case if they were not narrowed.

Although petals 614 are not typically physically connected to one another along the lengths thereof, they can be held together by the hand of a user as a tool or implant is passed therethrough. Petals 614 can be subsequently bent/flexed apart as illustrated in FIG. 59C to reduce the overall length of conduit 600 when needed, or to increase the effective diameter of the annulus/lumen of the conduit at the proximal portion. The proximal-most portions of petals 614T may optionally be tapered to narrow back down to a narrow width proximal end to facilitate grasping by a user, whereby the proximal ends of the petals 614 function as tabs 606. Further optionally, the proximal ends 614*p* of petals 614 may be additionally or alternatively preshaped to flare radially outwardly as shown in FIG. 59D, to facilitate both grasping by the user and introduction of implants/tools into conduit 600.

FIGS. 60A-60D illustrate alternative embodiments of conduit 600 and obturator 630 according to the present invention. Like the embodiment of FIGS. 55A-55E, the main tube of the conduit 600 is flexible and is formed of an elastomer, such as silicone, and a coil 610, such as a stainless steel coil, Nitinol coil, or the like, is encapsulated in the elastomer along at least the part of the distal end portion 600*dt* of the conduit 600. Also like the embodiment of FIGS. 55A-55E, the chamfered or tapered distal end 600*d* is not reinforced with the coil 610. At least a four inch length of the conduit 600 extending proximally from the unreinforced distal end 600*d* is reinforced with coil 610. In the example shown in FIGS. 60A, 60C and 60D, coil 610 reinforces substantially all of the tubular, distal end portion 600*dt* of conduit 600 except for the distal tip 600*d*, as noted, and a proximal end portion 600*dp* of the distal end portion 600*dt*.

The proximal end portion of 600*p* of conduit 600 in this embodiment is not tubular, but is rather an elongated member or "control stick" that extends proximally from proximal end portion 600*dp* of tubular distal end portion 600*dt*. Both proximal end portion 600*dp* and proximal end portion/control stick 600*p* may be formed of a more rigid material that that the elastomer used to make the tubular distal portion 600*dt*, to improve resistance to bucking during delivery of the conduit 600 over guide 530, as well as to improve control characteristics of the control stick 600*p* by reducing whip and other undesirable effects that would occur with a more flexible control stick. For example, portions 600*dp* and 600*p* may be made of By making the proximal end portion 600*p* of the conduit 600 to be non-tubular and only a slender, rigid shaft or stick, this greatly reduces the amount of friction between the conduit 600 and large cannula 310L, so that if the operator needs to rotate or otherwise position the conduit 600 relative to the large cannula 310L, this action is easier to accomplish and is more accurately controlled by simply manipulating (rotating and/or pushing or pulling on) the proximal end of control stick 600*p* that extends proximally of the outer conduit 310L as illustrated in FIG. 18D.

Control stick 600*p* may include a handle 600*h* such as a ring or other structure located at a proximal end thereof and configured to facilitate grasping and manipulation by a user. There is also less of a pathway that an implant or tool needs to be inserted through conduit 600. For example, large cannula 310L can be formed of a more rigid material and can be made to reduce friction, such as by making it of polytetrafluoroethylene, expanded polytetrafluoroethylene or some other lubricious material, or at least coating the inner walls of the cannula 310L with the same. By providing the proximal opening of tubular distal portion with an angle in a direction from where proximal end 600*dp* meets control stick 600*p* to an opposite site of the proximal end 600*dp*, this also facilitates insertion of an implant into the tubular portion 600*dt*, when proximal end 600*dp* is contained within large cannula 310L as illustrated in FIG. 60D.

Figure 60A:
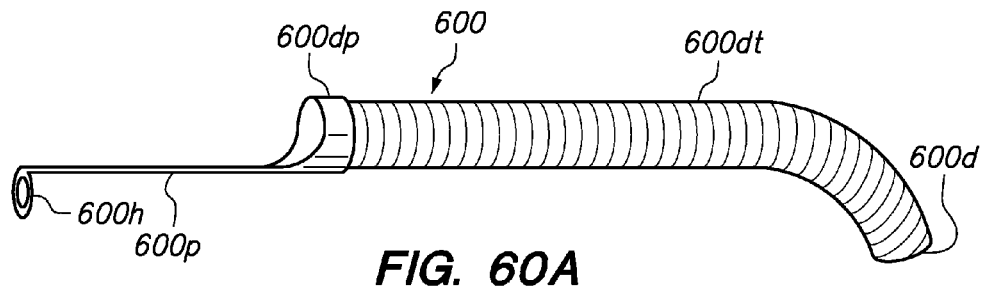
FIGS. 60A-60D illustrate alternative embodiments of conduit and obturator according to the present invention.
Figure 60B:
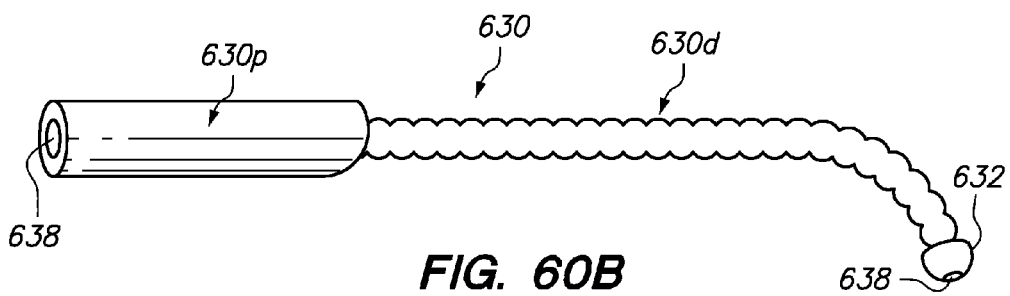

An embodiment of an obturator 630 configured for use with the embodiment of the conduit 600 shown in FIG. 60A is shown in FIG. 60B. The distal end portion 630*d* may be configured essentially the same as that described above with regard to FIG. 56C (or alternatively, FIG. 56A) for example.

Figure 60C:
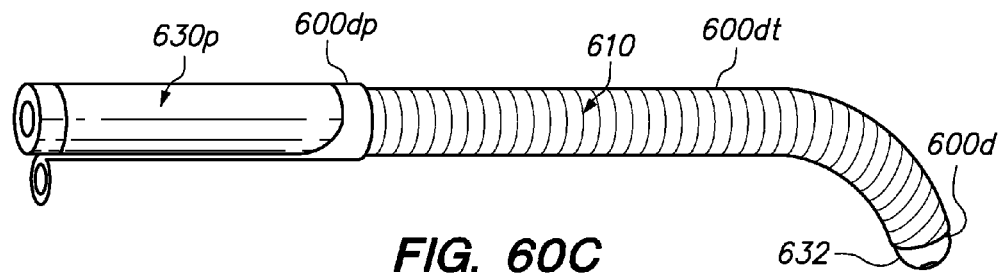

The proximal end portion is rigid and is configured to mate against the proximal end 600*dp* of distal end portion 600*dt* of conduit 600 when distal tip 600*d* is engaged with the distal tip 632 of obturator 630, as shown in FIG. 60C. Thus, when conduit 600 is assembled over obturator 630 as shown in FIG. 60C, obturator 630 helps prevent conduit from buckling, as well as from its walls collapsing inwardly, while still allowing distal portion 600*dt* to flex and bend as it is advanced over the guide 530 toward a surgical target location. The rigid proximal portion 630*p* of obturator 630 can be made of or coated with the same material that cannula 310L is made of or coated with, or made from or coated with a different material which is designed to have very low friction relative to the inner walls defining the annulus of cannula 310L. This facilitates advancement of conduit 600 by reducing friction at the proximal end.

Figure 60D:
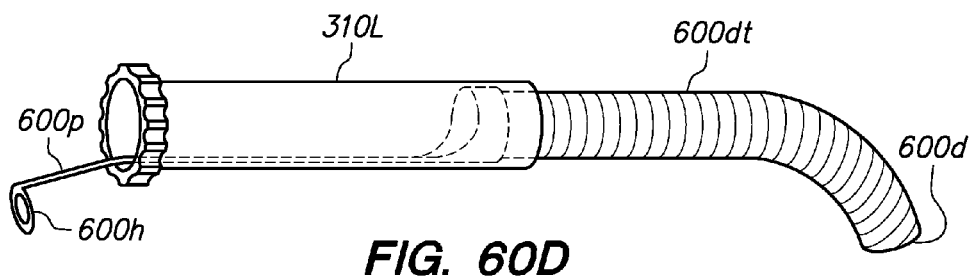

Once conduit 600 has been delivered to or near the desired surgical target location, obturator 630 can be removed, as illustrated in FIG. 60D, while maintaining conduit 600 and cannula 310L in place. At this stage, cannula 600 can be further repositioned, tweaked, etc., if necessary, by manipulation of control stick 600*p*/handle 600*h* from a location outside of the patient. Implants and or tools can be inserted through cannula 310L and conduit 600 to deliver at least distal end portions thereof to the surgical target location distal of distal end 600*d*.

Figure 61:
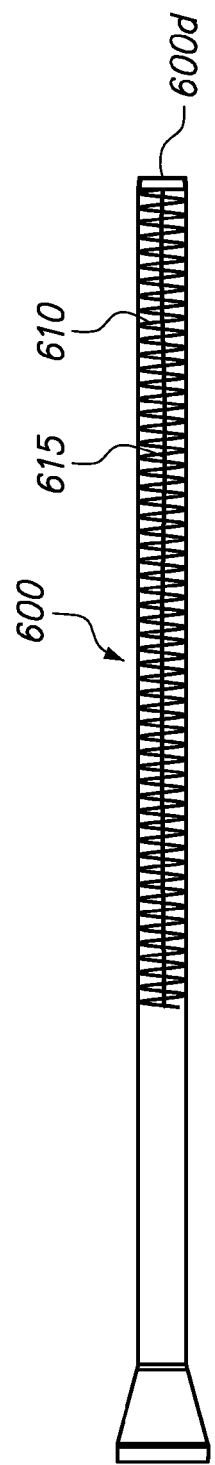
FIG. 61 illustrates an optional feature that may be provided with a conduit according to the present invention to resist stretching of the conduit and/or to resist axial compression of the conduit.

FIG. 61 illustrates an optional feature that may be provided with conduit 600 to resist stretching of the conduit 600 and/or to resist axial compression of the conduit 600. One or more resistive members 615 may be provided longitudinally along the main body of conduit 600. In the example shown in FIG. 61, one metallic wire extends along the entire length of coil 610 and is fixed (such as by soldering, welding, etc.) to at least two different coils of the coil 610 to prevent elongation thereof and also to fortify the resistance to buckling. Alternatively the one or more resistive members 615 may be provided along only a portion of the length of tube 600 and/or coil 610. Multiple resistive members 615 may be provided along various different longitudinal locations an/or various radial positions along the tube 600. Resistive member(s) need not connect to a coil 610, but can be embedded in or molded into a tube 600 that is not reinforced by coil 610. Further alternatively, resistive member(s) 615 may be made of flexible material, such as suture material or other polymer, in which case, it/they will prevent elongation of the tube, but will not necessarily fortify against buckling.

FIG. 62A is a partial view of an endoscope 330 that may be inserted into tube 534 of guide 530 and also may be inserted into conduit 600 or conduit 310L, in each instance, to provide visualization during performance of one or more steps of a procedure as described herein. FIG. 62B shows a longitudinal sectional view of FIG. 62A. The elongated shaft 332 is only partially shown in FIGS. 62A and 62B, so as to be able to show the views in a larger scale while still allowing them to fit on the page. The proximal portion 332*p* of shaft 332 is rigid, while the proximal portion 332*d* is flexible. The lengths of each portion 332*p* and 332*d* may vary. In one embodiment the length of rigid portion was about sixteen inches and the length of the distal portion 332*d* plus tip 334 was about twenty-s even inches.

Light post 336 is configured in the proximal handle portion 330*h* of the endoscope and, as noted previously, endoscope 330 can be inserted into conduit in a manner that light post 336 extends out of and slides along slot 608. An eye cup 330*e* is provided at the proximal end of the endoscope. Bevels 330*b* may be provided at the junctures of proximal with distal portions 332*p*, 332*d* and distal portion with distal tip 330*d*, 334. The maximum diameter of the elongated shaft 332 (including tip 334) in one embodiment is less than or equal to about five millimeters. In the same embodiment, the working length of the elongated shaft 332 (including tip 334) is about 42 inches to about 44 inches. The flexibility of distal flexible portion allows the guide 530 to bend, and therefore allows the endoscope 330 to be located in the guide 530 even when the guide is being inserted into the patient as it does not restrict the ability of the guide 530 to be steered or to bend, and it provides imaging to the surgeon so that the surgeon can see where the guide is being driven too. Additionally, the rigid portion 332*p* provides some stiffening support to the guide 530 to facilitate pushing the tube 530 into the patient.

Illumination fibers 330*m* extend through the main lumen of endoscope 330 and are connectable at a proximal end thereof to a light source (not shown) via light post 36 to deliver light out the distal tip 334 of endoscope 330. Lenses 330L are provided in the main lumen at the location of the distal tip 334 and proximal portion of the handle 330*h* to provide an image of the light reflected off of the environment as the illumination light exits the tip 334, reflects off objects and is reflected back into tip 334. Imaging fiber(s) connect the distal lens 330L with the proximal lens 330L arrangement in the handle 330*h*. A camera (not shown) may be connected to the endoscope for providing the ability to display images on a computer screen, provide image prints, etc.

Figure 63A:
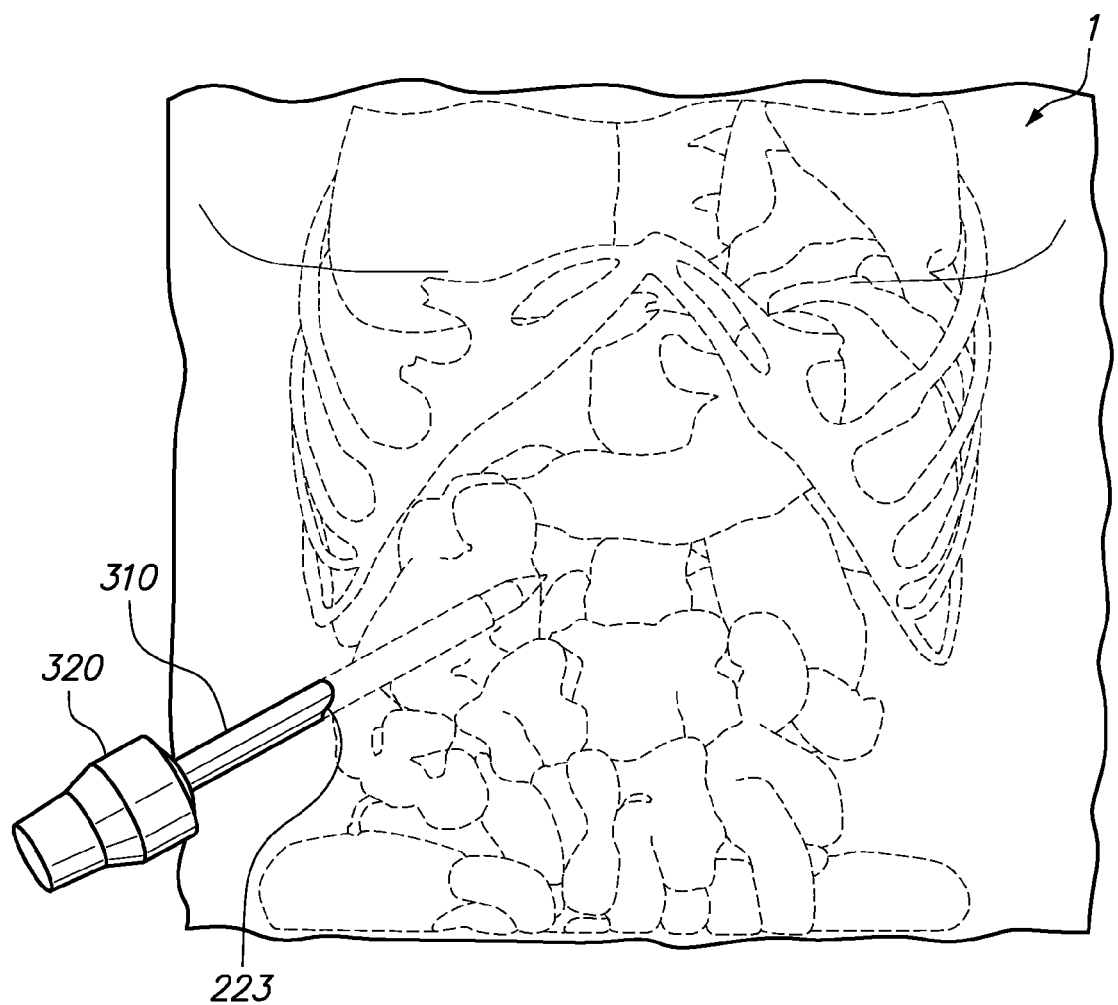
Figure 63D:
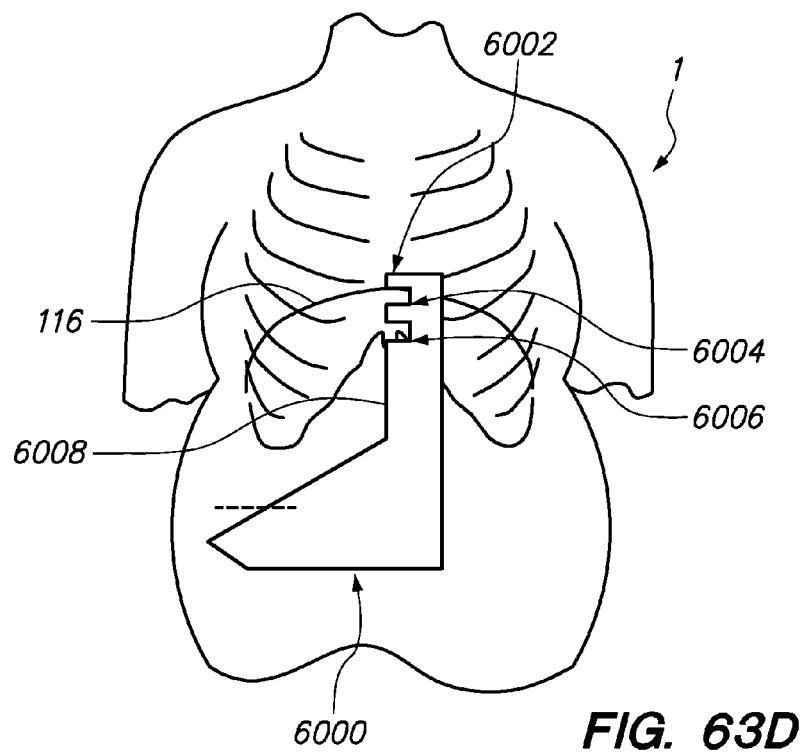
Figure 63E:
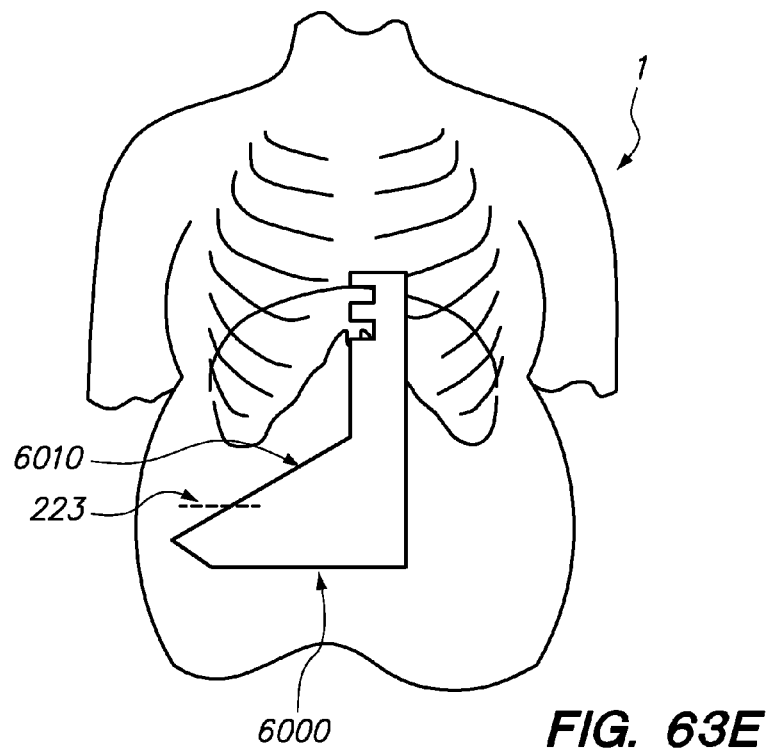
Figure 63H:
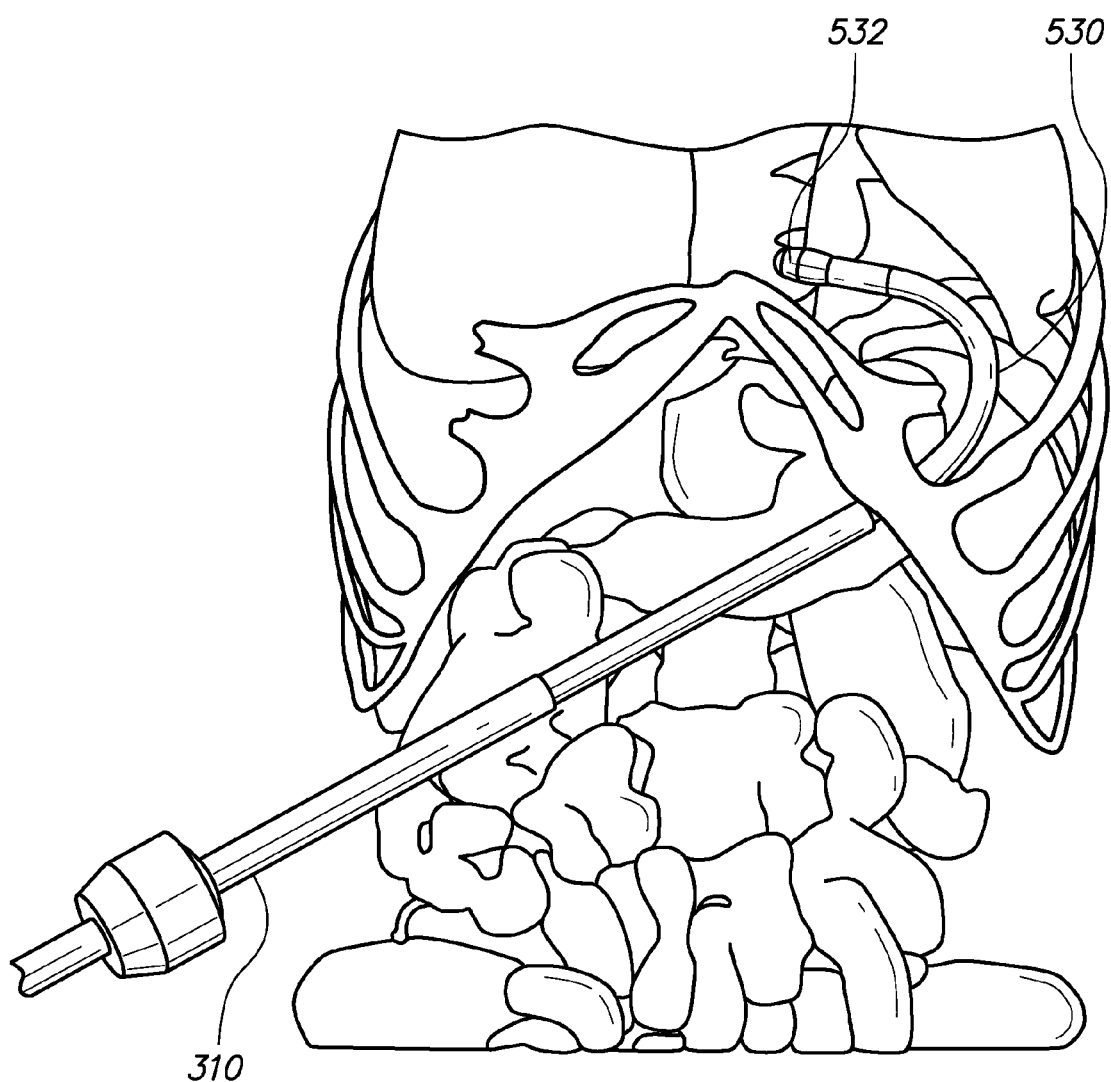
Figure 63I:
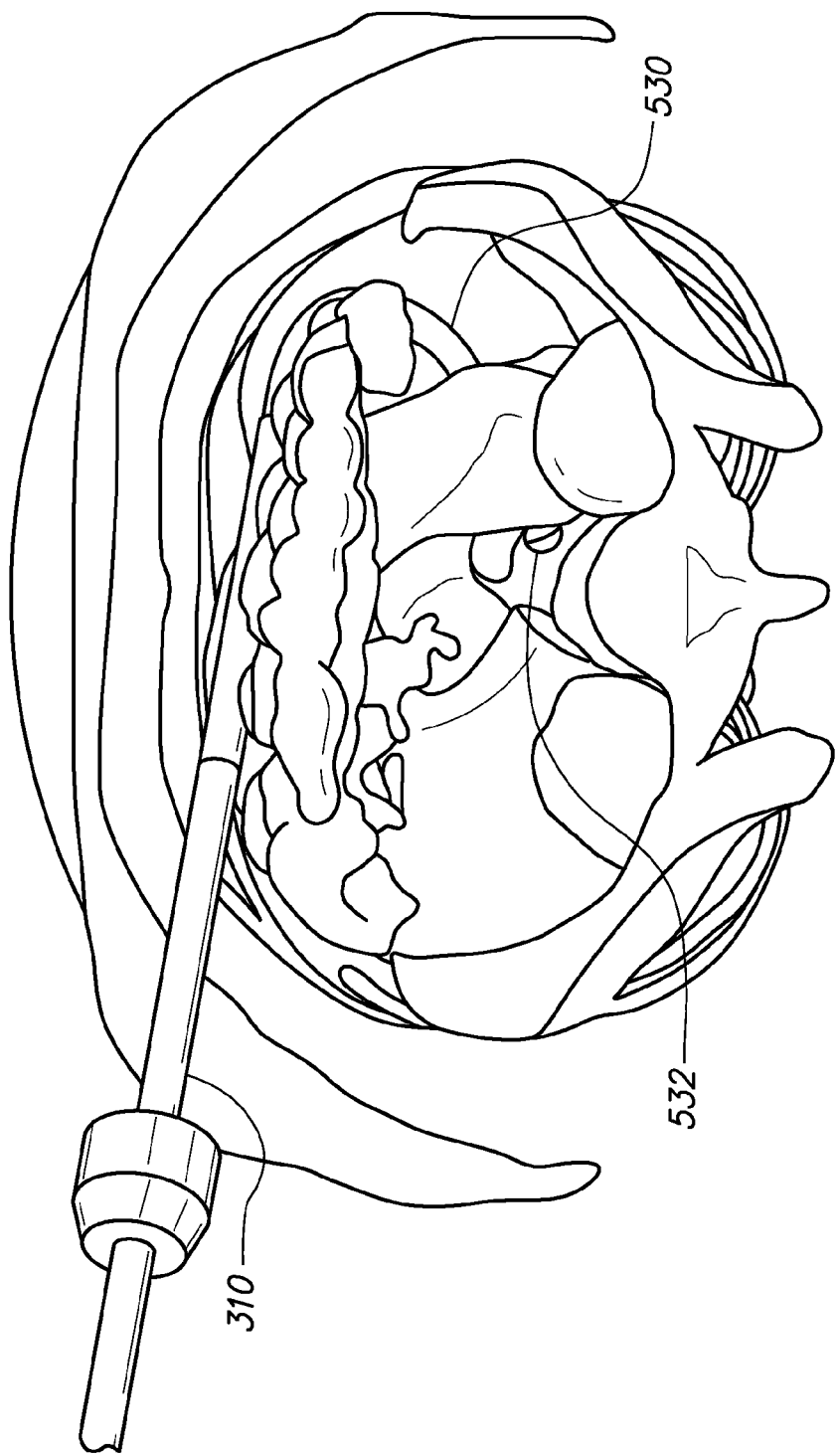
Figure 63J:
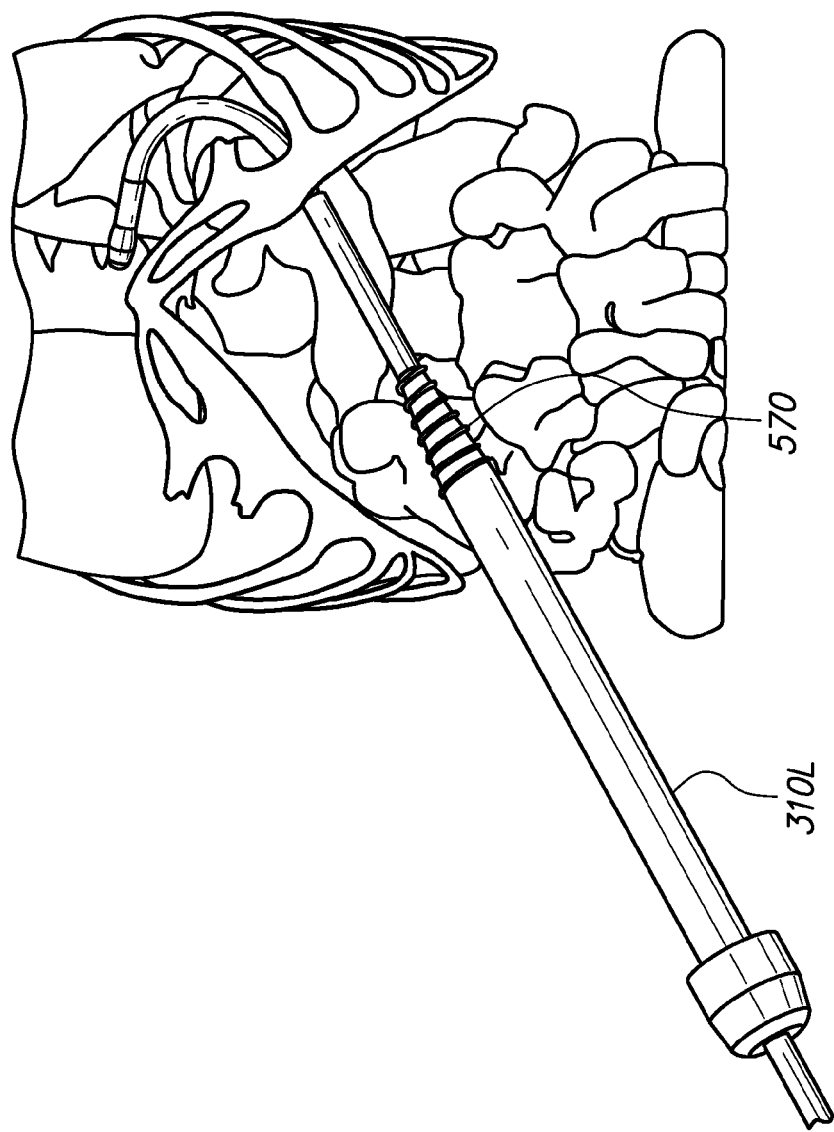
Figure 63K:
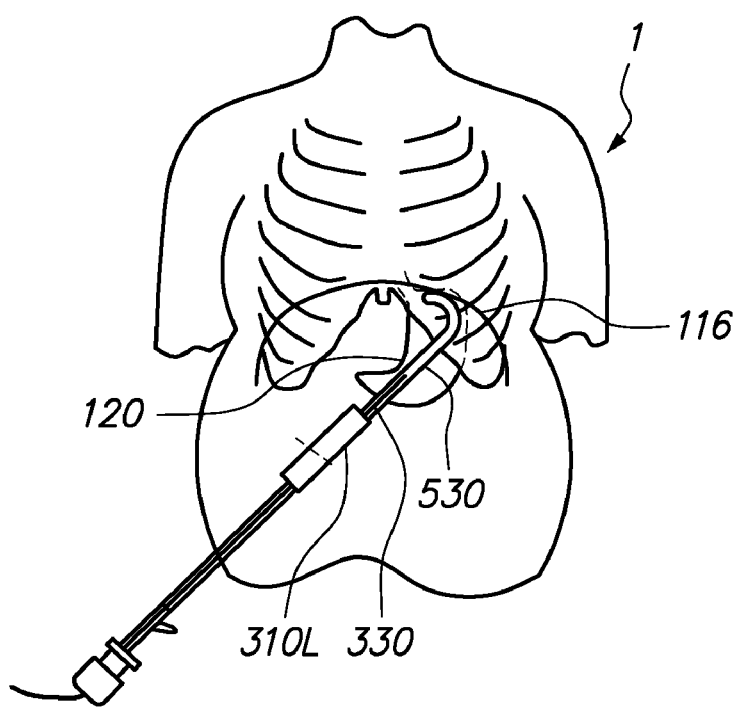
Figure 63L:
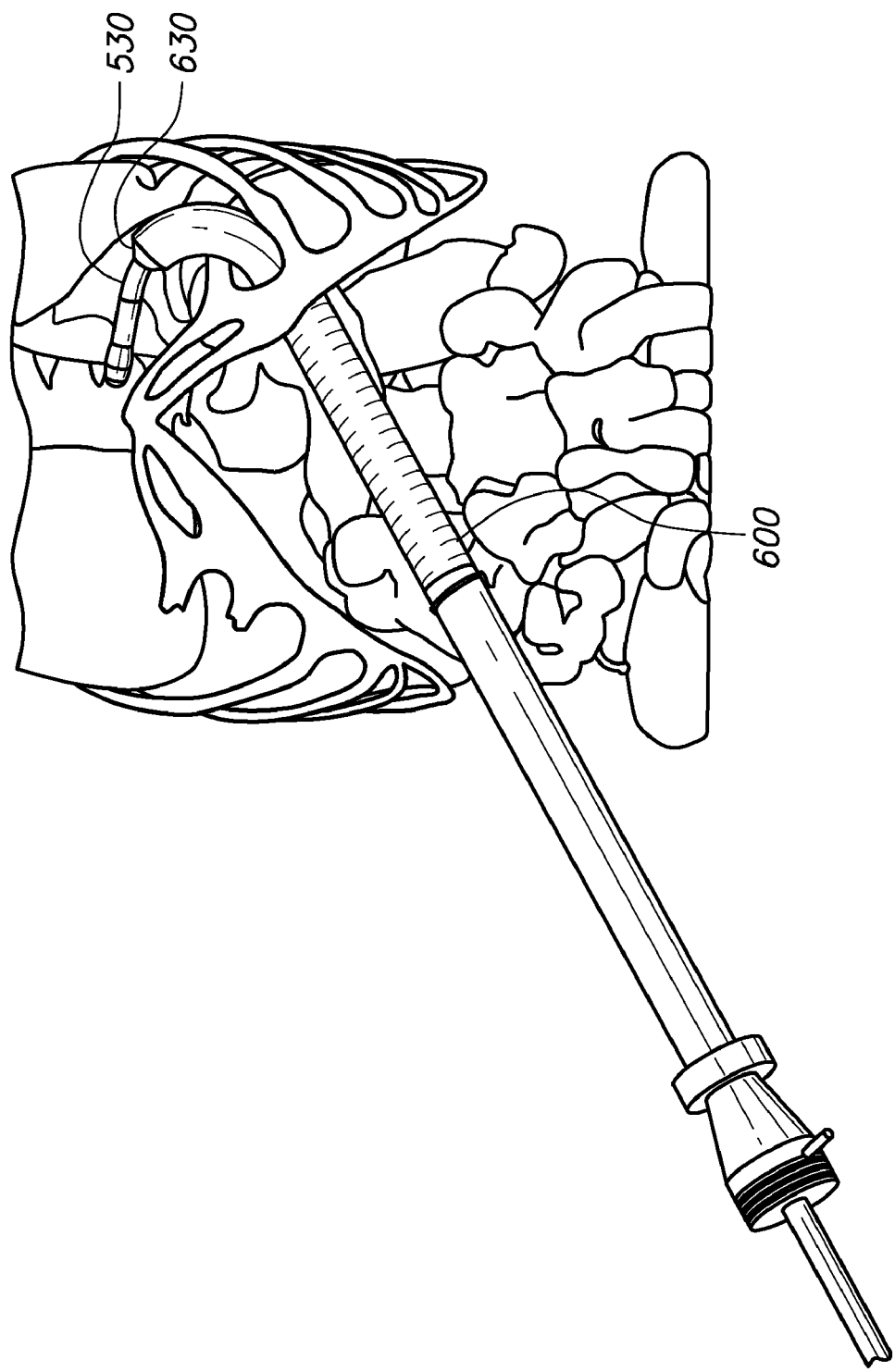
Figure 63M:
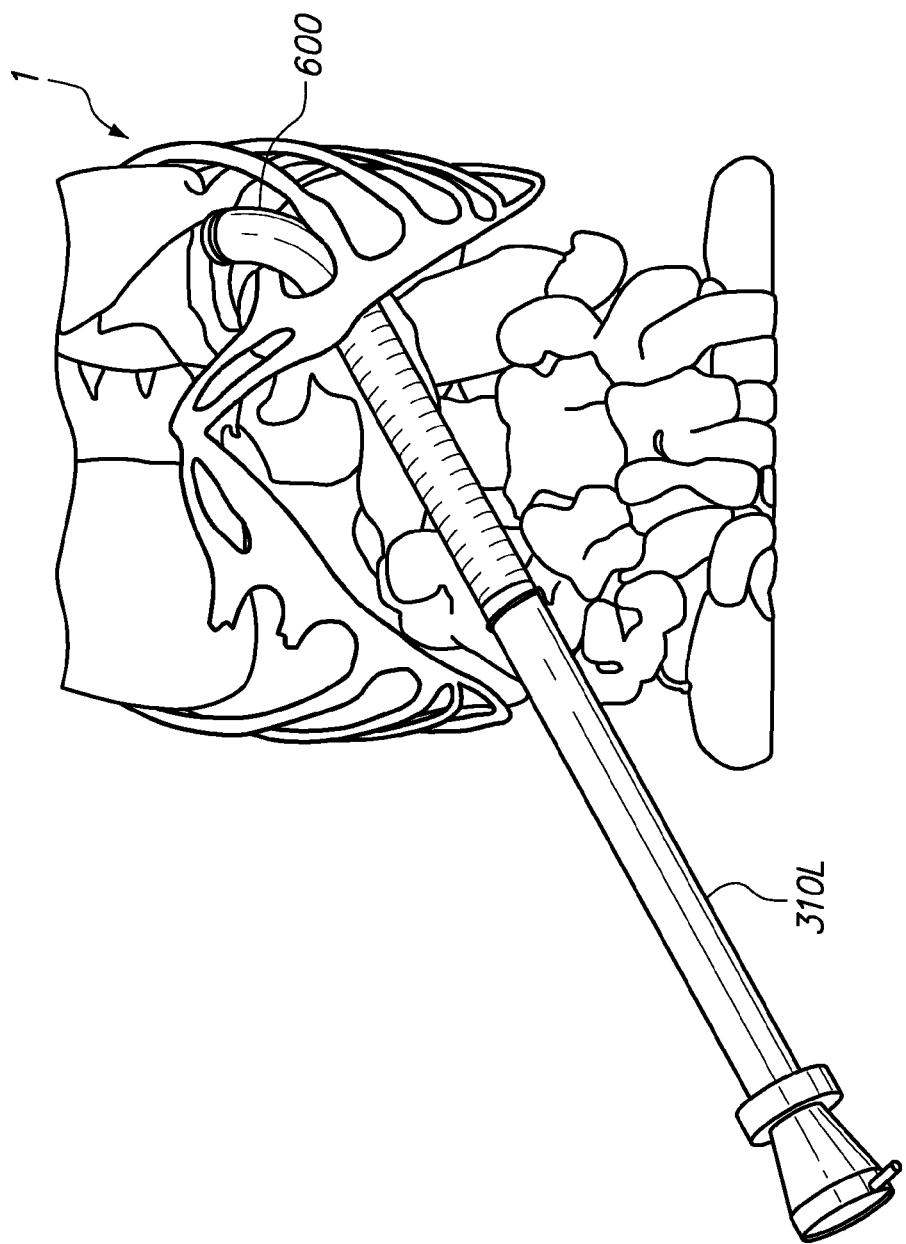
Figure 63T:
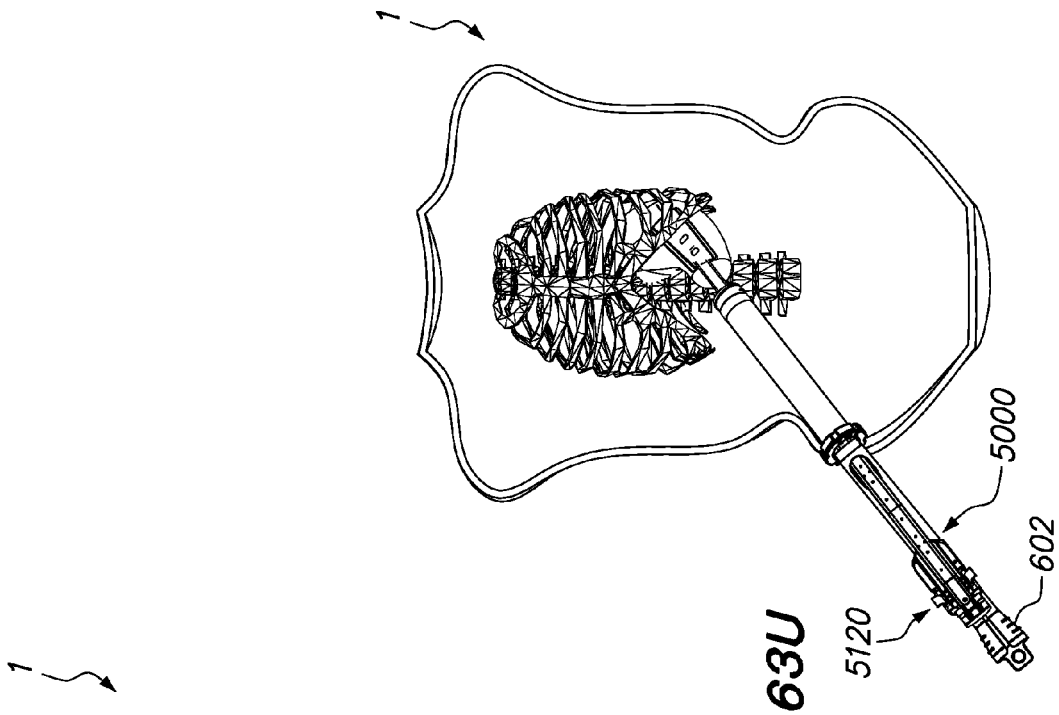
Figure 63U:
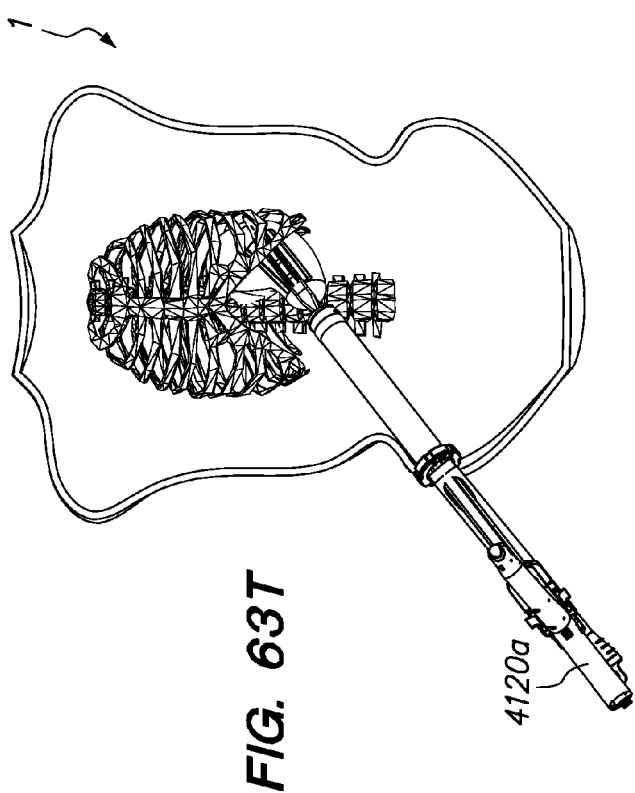
Figure 63W:
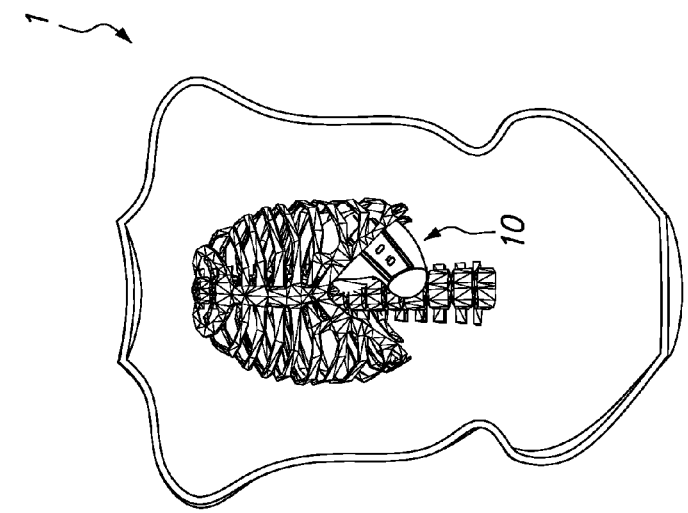
Figure 63V:
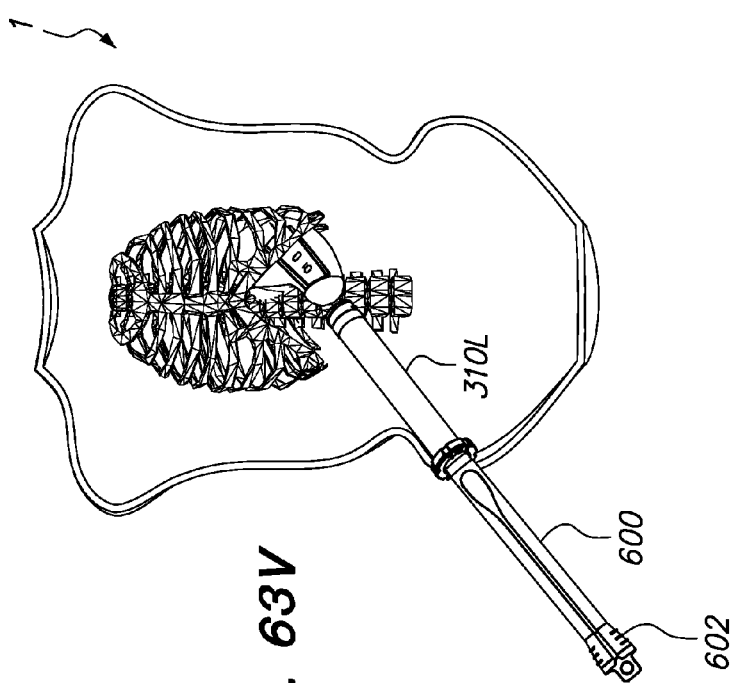
Figure 63X:
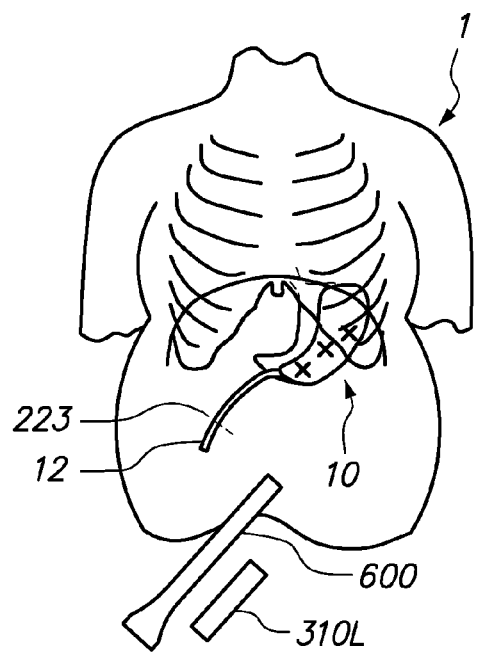
Figure 63Y:
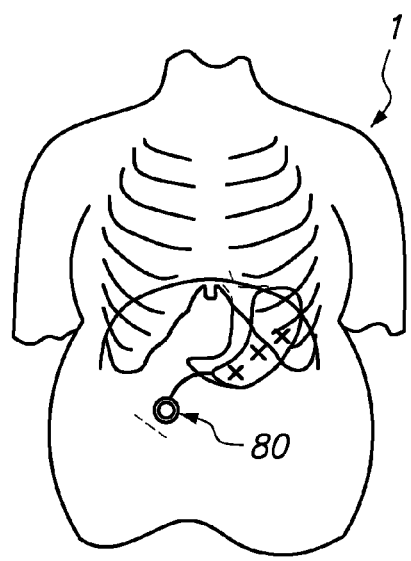

FIGS. 63A-63Y illustrate an example and variations thereof of a procedure for percutaneously implanting an extra-gastric, paragastric device 10 according to the present invention. As already previously noted, the stitching instruments 4000, 400, suturing instrument 5000, guide 530, obturator 630, conduit 600, introducer 310L, dilator 570 and endoscope 330 are not limited to the type of procedure described with regard to FIGS. 63A-63Y, but this procedure is described in detail to facilitate a detailed understanding of the use of these instruments and devices, whether for the particular procedure described, or for other procedures in the body of a patient. After preparing the patient 1 for surgery, an incision 223 is made and a trocar/cannula 320/310 (e.g., a standard 15 cm length trocar/cannula) and 10 mm endoscope (shaft has 10 mm outside diameter) 330 are inserted into the incision and advanced under visualization by endoscope 330 (see FIGS. 63A-63C).

After preparing the patient 1 for surgery, an incision 223 is made and a trocar/cannula 320/310 (e.g., a standard 15 cm length trocar/cannula) and 10 mm endoscope (shaft has 10 mm outside diameter) 330 are inserted into the incision and advanced under visualization by endoscope 330 (see FIGS. 63A-63C). A radiopaque ruler located at the costal margin on the patient's skin can be useful for the later reference. Optionally, a small amount of insufflation gas may be inputted to help place the trocar/cannula in the desired layer(s) of tissues. In this embodiment, incision 223 is made at a predetermined distance inferior of the xyphoid process and a predetermined distance to the fight of midline of the patient 1, see FIG. 63A. For example, the distance below the xyphoid process may be about 15 cm and the distance to the fight of midline may be about 6 cm, although these distances may vary. Initially, the trocar 320, cannula 310 and endoscope 330 are inserted into incision 223 at a substantially perpendicular orientation to the surface of the skin 125, as schematically illustrated in FIG. 63B. Once the sharpened tip of the trocar 320 has passed through the fascia 127*f*/abdominal muscle 127 and it and the distal tip of the cannula 310 have entered the abdominal cavity, the trajectory of the cannula 310, trocar 320 and endoscope 330 is flattened relative to the skin of the patient surrounding the incision 223, as schematically illustrated in FIG.

63C (and which orientation is also illustrated at FIG. 63A) to form an angle 331 relative to the original, perpendicular orientation of greater than about 60 degrees, typically greater than about 80 degrees, and, in some embodiments, 90 degrees or more.

Optionally, as illustrated in FIGS. 63D-63E, a positioning template 6000 may be used to locate where, on the patient's 1 abdomen, to make the incision 223 At FIG. 63D, after using fluoroscopy and a radiopaque marker to mark the approximate level of the diaphragm 116 on the skin, as identified using the fluoroscopy, the positioning template 6000 is placed on the patient 1 with the top portion aligned with the diaphragm 116 according to which implant 10 size is to be used. For example, in FIG. 63D, the top edge 6002 of the template 6000 is aligned with the diaphragm 116 when the largest available device 10/expandable member 10em is to be used (e.g., "implant size F"). In the example shown in FIG. 63D, the user is planning to implant the next smaller size device 10/expandable member 10em (e.g., "implant size E") and therefore the notch at 6004 has been aligned with the marking that indicates the level of the diaphragm 116. An additional notch 6006 is provided below notch 6004 for use when a yet smaller sized implant is to be implanted (e.g., implant size B, C or D). Additionally, the template is adjusted so that the left vertical edge 6008 of template 6000 is substantially aligned with the patient's spine.

Next, using the marking pen a line is drawn on the patient's abdomen along the trajectory edge 6010 of the template as indicated in FIG. 63E to indicate the intended trajectory for placement of the stitching instrument 4000 and suturing instrument 5000. The center of the abdominal incision 223 should be made where the line formed along 6010 crosses the right linea semiluminaris. A short-action local anesthetic (e.g., Lidocaine or the like) can be applied prior to making the incision 223. Incision 223 is made to have a length of approximately 5 cm in the location shown in FIG. 63E. Once the incision 223 is made, the procedure continues with FIGS. 63A-63C in the manner described above.

A delivery tract is formed as described above, and endoscope 330 is inserted distally to view along the tract up to the location of the intra-abdominal fat or possibly as the location of the stomach 120, as shown in FIG. 63F. The trocar 320 and endoscope 330 are then removed. Guide 530 is next inserted into the tract, and a smaller endoscope 330 (e.g., endoscope shaft having about 2 mm to about 5 mm outside diameter, which may be the endoscope 330 described above with regard to FIGS. 62A-62B, for example) is introduced into guide 530. Guide 530 and endoscope 330 are manipulated in a manner as described above to establish a pathway into a space between the fascia and the bowel, see FIG. 63O. This procedure optionally allows users to use a small amount of $CO_2$ if desired, to help get the guide 530 past the falciform and through the correct layers of tissues. The user can use the standard cannula 310 to put in about 0.5 liters of $CO_2$. Alternatively, the user can "puff" I about 60 cc to about 120 cc of air, saline or Marcaine from a syringe, or put in a standard trocar or retractor and physically lift to let ambient air into the patient or put in a trocar with a balloon around the tip that performs lifting when the balloon is inflated. If a flexible endoscope is used, or an endoscope that is flexible at least along a distal portion of the endoscope shaft 332d, alternatively to the rigid endoscope 330 shown in FIG. 63F, then viewing can be extended up to and along the diaphragm 116, for example, as illustrated in FIG. 63H. FIG. 63I illustrates a sectional view, where it can be readily observed that the tip 532 of the guide 530 also traverses around the stomach and dives down into the abdominal cavity as it is guided by the curvature of the diaphragm.

The cannula 310 and smaller endoscope 330 are then removed while leaving the guide 530 in place. Dilator 570 is next screwed and/or pushed through opening 223 and the opening through the fascia to enlarge the opening through the fascia/abdominal muscle 127f/127, to install a large cannula 310L, see FIG. 63J. During this procedure, a dilator 570 that includes at least one endoscope port 570p and which has a transparent tube 570n may be alternatively used with an introducer 310L that has a transparent tube 310t and an endoscope 330 can be inserted like shown in FIG. 53C to provide a view for the surgeon to observe the dilation procedure as it is performed. Once large cannula 310L is installed through the enlarged opening in the fascia, dilator 570 is removed, the smaller endoscope 330 can be reinserted into guide 530, which now extends through the large cannula 310L, see FIG. 63K. Guide 530 is stiffened by endoscope 330 (when a rigid endoscope 330 is used, or an endoscope like in FIGS. 62A-62B, where at least a proximal portion 332p of the endoscope shaft is rigid) which acts as a stylet as the guide 530 and endoscope 330 are advanced to establish the delivery tract to the diaphragm, between the fascia and bowel, and to view the diaphragm 116. Guide 530 is then advanced further, such that the distal portion does not contain endoscope 330 (when a rigid endoscope is used) so that it is floppy and follows around the curvature of the diaphragm 116 as illustrated in FIG. 63K. When endoscope 330 is flexible, or has at least a flexible distal portion 332p of the shaft, it can be inserted into the distal portion of guide 530 and follow with it along the bending trajectory that follows along the curvature of the diaphragm. Endoscope 330 can be used to view the advancement of guide 530 as well as to check the areas surrounding the delivery tract leading to the diaphragm 116. As noted, a flexible endoscope 330 may alternatively be inserted so that it remains within the flexible distal end portion of guide 530 as it is advanced along the diaphragm, so that this travel can be visualized via endoscope 330. This alternative is described in further detail below. Otherwise, when a rigid endoscope 330 is used, the flexible distal end portion of guide 530 can be tracked under fluoroscopy when one or more radiopaque markers are included on the flexible distal end portion of guide 530.

Endoscope 330 is next removed, and a conduit 600 and obturator 630 are inserted into the abdominal cavity, being guided over guide 530 as illustrated in FIG. 63L. Once the distal end of the conduit 600 has been advanced to a position adjacent the diaphragm 116 (when a rigid conduit 600 is used), or adjacent to the target implantation site after following around the curvature of the diaphragm 116 when a flexible conduit 600 as used as illustrated in FIG. 63L, guide 530 and obturator 630 are removed, leaving conduit 600 in position for guiding delivery of device 10, as illustrated in FIG. 63M. Alternative to use of a rigid conduit 600, a flexible conduit 600 and flexible obturator are preferably used, as shown in FIGS. 63L-63M. At least the distal end portion of each of conduit 600 and obturator 630 is flexible. The flexible distal end portions are configured to follow the flexible distal end portion of the guide 530 so that the distal end portion of the conduit can be delivered along the diaphragm 116 close to or flush with (or even extending slightly distally of) the distal end of guide 530, as described in further detail below.

An assembly 500 that includes the stitching instrument 4000 connected to the suturing instrument 5000 and having a perigastric, extragastic, expandable implant device 10 (in a contracted configuration) mounted thereon at a distal working portion 4010, 5010 thereof is inserted into the conduit 600 as illustrated in FIGS. 63N and 63O.

At FIG. 63O, the assembly 500 is advanced to place the implant 10 in the approximate target location where the implant device 10 is to be implanted. The device 10 is advanced into the abdominal cavity by advancing assembly 500 relative to conduit 600 until the distal end portion 10em of the device 10 is located at or extends distally of the distal end of conduit 600. This location of the device 10 can be determined by one or more of monitoring the amount of the tool 400 that remains proximal of the proximal end of conduit 600, as the length of the assembly 500 with device 10 mounted thereon relative to the length of conduit 600 may be known or predetermined; visual monitoring via endoscope 330; and/or visual monitoring by fluoroscopy. At this time, the position of the portion 10em of device 10 relative to the anatomy can also be adjusted, if needed, using assembly 500 and/or conduit 600 to adjust the position of the device 10

While holding the assembly 500 and device 10 in this desired location, conduit 600 is then retracted as illustrated in FIG. 63P, thereby exposing device 10. Slot 608 allows conduit 600 to be retracted, as the shafts 4140 and 5140 of the instruments 4000 and 5000 slide in the slot 608 as the conduit is retracted proximally relative to the instruments 4000 and 5000. This action can also be visually monitored under fluoroscopy. If an endoscope 330 is not used in instrument 4000 at this stage, then after expandable member 10em has been exposed out of the distal end of conduit 600, guide 530 having received endoscope 330 can be inserted alongside assembly 500 through conduit 600 to provide visualization of the device 10em at the target site.

Device 10 is next expanded, by inflating expandable member 10em via fill tube 12 as illustrated in FIG. 63Q (fill tube 12 not shown in FIG. 63O, for clarity). Fill tube 12 extends out of the incision 223 and is connectable to a source of pressurized fluid in order to perform the inflation.

At FIG. 63R, an endoscope 330 (e.g., 2.7 mm rigid endoscope or 5 mm rigid endoscope is inserted into a left side lumen 4330L that extends from a proximal end portion of instrument 4000 to a location just proximal of working end portion 4010 and to a location alongside of the working end portion 4010, and endoscope 330 is used to view between the abdominal wall 127 (e.g., fascia/peritoneum 1271) and the working end portion 4010 to ensure that no omentum, bowel or other organs or tissues are in the pathway along which the stitching needles 4170 are to be driven into and out of the fascia/peritoneum 127f, abdominal wall 127.

When it has been determined that the pathways for the stitching needles 4170 on the left side of the working end portion 4010 are clear to be advanced, then the endoscope 330 is removed from lumen 4330L and inserted into lumen 4330R on the right side of the instrument 4000, see FIG. 63S. Lumen 4330R extends from a proximal end portion of instrument 4000 to a location just proximal of working end portion 4010 and alongside of working end portion 4010 and endoscope 330 is used to view between the abdominal wall 127 (e.g., fascia/peritoneum 1271) and the working end portion 4010 to ensure that no omentum, bowel or other organs or tissues are in the pathway along which the stitching needles 4170 on the right side of the working end portion 4010 are to be driven into and out of the fascia/peritoneum 127f, abdominal wall 127. Endoscopic visualization via endoscope 330 through lumens 4330L and 4330R is used to confirm that the attachment location is clear of omentum, bowel, etc., e.g., that the tool 4000 and portion of the device 10 to be attached are positioned so that a clear pathway to the attachment site exists, such that no bowel, excessive fat or other obstruction exists between the attachment tab 150 and the attachment location, such as the abdominal wall, costal cartilage, or other internal body structure to which device 10 is to be attached.

When both sides have been visually confirmed as being clear, a local anesthetic, such as Lidocaine, Marcaine, or the like can be delivered to the target implantation site (e.g., the fascia/peritoneum 127f and abdominal wall 127) through a lumen in tool 4000, such as through lumen 4330L and/or 4330R, for example. Stitching instrument 4000 is next actuated at FIG. 63T to perform the stitching function and to thereby anchor the sutures 444 to the suture anchors or traps 4200 in a manner described in detail above. After completion of the stitching process, instrument 4000 is disconnected from tool 5000 in a manner as described in detail above and instrument 4000 is removed from conduit 600 and from the patient 1.

Next, the sutures 444 are cinched, secured by suture retainers 1520 and the excess proximal portions of the sutures 444 are cut off, as represented at FIG. 63U and as was described in detail above. The suturing instrument 5000 is then removed from the patient, leaving the conduits as shown in FIG. 63V. Next, the conduits 600 and 310L are removed, FIG. 63W showing the conduits having been removed.

Filling tube 12 extends proximally out of opening 223, as illustrated in FIG. 63X. At FIG. 63Y, filling tube 12 is cut to the appropriate length to join adjustment member 80 thereto and to reduce any excessive length of filling tube 12 that might otherwise exist. After securing adjustment member 80 to the fascia 127f/abdominal wall 127 to both anchor it as well as to close the opening through the fascia 127f, any adjustment of the volume of expandable member 10em can be performed as needed, and then the patient can be closed, including closing of opening 223 to complete the procedure. Adjustment member 80 can be installed/attached to the abdominal wall 127/fascia 127f at a location other than the opening 223. In such cases, opening 223 is closed around the fill tube 12 extending therefrom, and the adjustment member 80 is attached to the fascia 127f and/or abdominal muscle 127 at another location, so that attachment member 80 does not need to perform the closure function for closing the opening 223. Further details of this and other procedures that can be performed with the devices of the present invention are described in application Ser. No. 61/130,244, co-pending application Ser. No. 12/473,818, and co-pending application Ser. No. 12/474,118, each of which were incorporated herein above, in their entireties, by reference thereto.

Figure 64A:
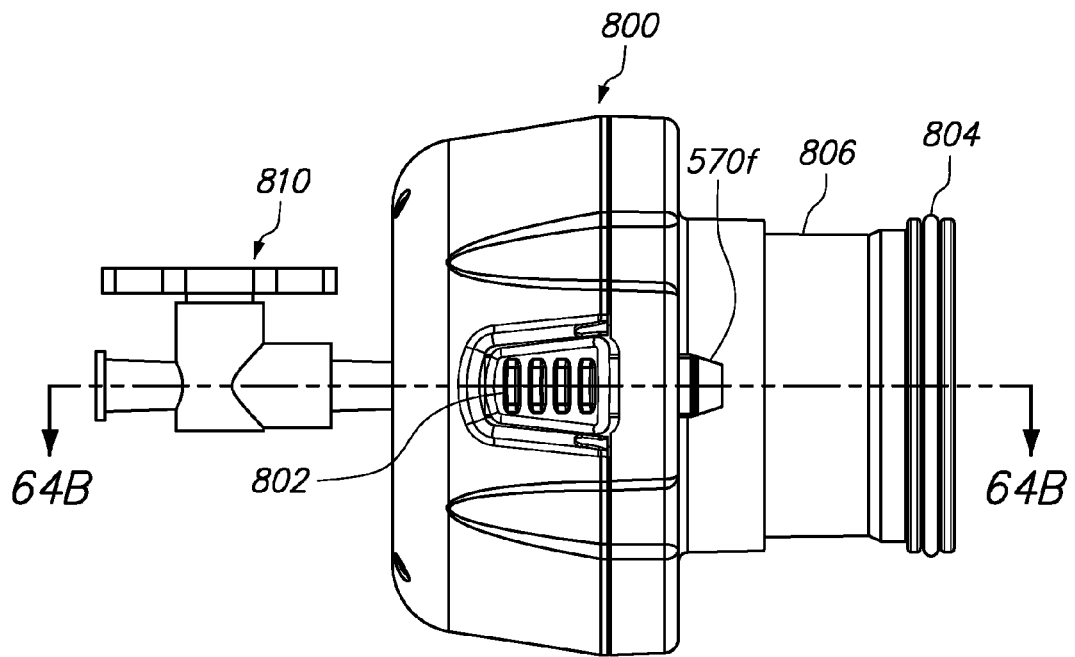

FIG. 64A is a side view of a cap 800 that may be used with large cannula 310L to seal off the large cannula 310L and form a pneumoperitoneum in the abdominal cavity. For example, if a misalignment of the implant may occur during a procedure, or some other portion of the procedure does not go according to plan, it may be desirable to form a pneumoperitoneum in the abdominal cavity to make it much easier to reposition the implant 10, remove the implant 10, or correct some other portion of the procedure. In the embodiment of FIG. 64A, cap 800 includes fastening components 570f, such as bayonets, retractable hooks or the like, that are the same as those described above with regard to FIGS. 52E and 53B, and contains actuators 802 that are the same as the actuator buttons of the dilator shown in FIG. 53B. Alternatively, or additionally, the tubular proximal portion 806 of cap 800 may be provided with threads (not shown) configured to mate with threads inside the proximal end portion of large cannula 310L. One or more seals 804 are provided on the proximal tubular portion 806 and are configured and dimensioned to form an airtight seal against the inner wall of the large conduit 310L.

Figure 64B:
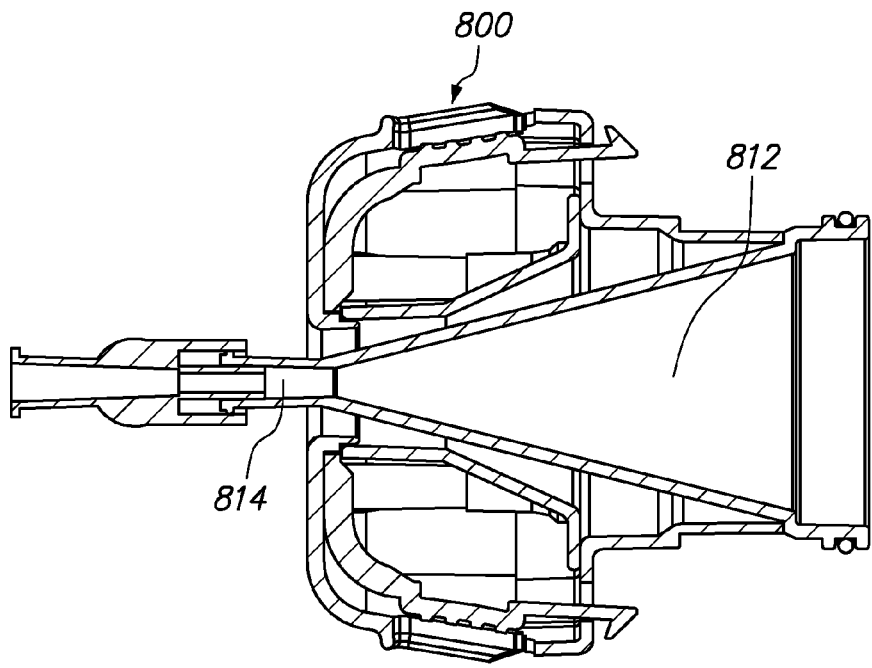

A stopcock 810 or other type of valve is in fluid communication with an internal channel 812 of the cap 800 (see longitudinal sectional view of FIG. 64B). Thus, stopcock can be operated to seal off the stopcock channel 814 to thereby seal off the cap channel 812. Alternatively, the stopcock 810 can be opened to open the channel 814 to allow insufflation to be performed therethrough when the cap 800 is sealed to the large cannula 310L. Additional ports can optionally be placed to perform a laparoscopic procedure with the aid of the pneumoperitoneum.

After forming the pneumoperitoneum and performing a repositioning of a component (implant, attachment tab, etc), removal of a component, or reaccomplishment of one or more procedural steps, the cap 800 can be removed, after which tools and instruments may optionally be again inserted through the large cannula 310L. Alternatively, if the procedure has been completed, then the large cannula can be removed and the procedure can carry on from there, as in FIG. 63Y, for example.

Figure 65A:
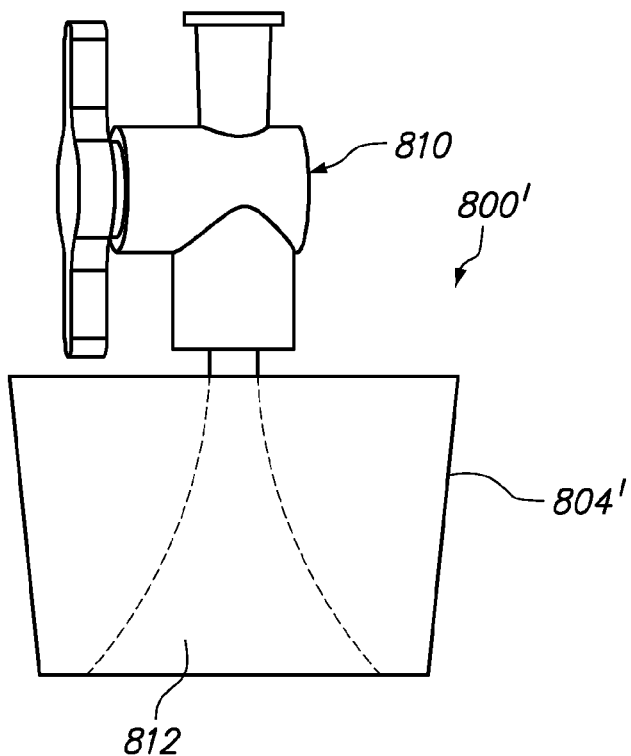
Figure 65B:
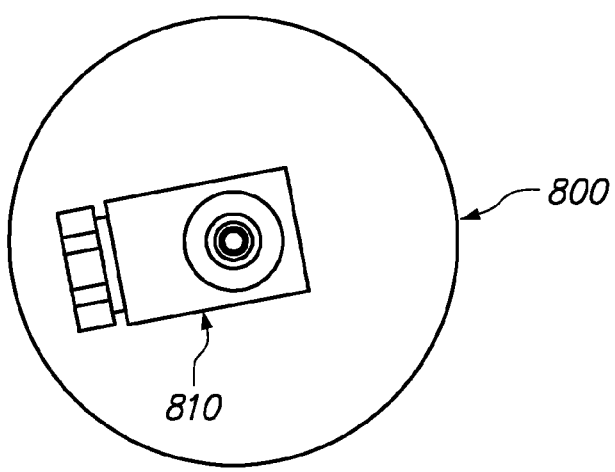

FIGS. 65A-65B are side and top views of another embodiment of a cap 800' that may be used with large cannula 310L to seal off the large cannula 310L and form a pneumoperitoneum in the abdominal cavity. Cap 800' also includes a stopcock or other valve positioned similarly to and functioning the same as the stopcock 810 of FIG. 64A. Stopcock 810 can be opened or closed in the same manner described above to join the proximal end of the stopcock in fluid communication with channel 812 or to seal it off. In this embodiment, the main body of the cap 800' functions like a stopper, as the walls 804' are configured and dimension to form a friction fit with the inner wall at the proximal end of the large cannula 310L.

In one method of using either of the caps 800, 800', an incision or puncture is made though the patient's skin, and an initial tract is established through an opening formed by the incision or puncture and through the abdominal wall of the patient. A guide member having a flexible distal portion and a distal tip is inserted into the initial tract and used to extend the initial tract to form a delivery tract leading to and following along a portion of the curvature of the diaphragm of the patient. The opening is dilated by torquing a distal end of a dilator therethrough, wherein an introducer cannula is mounted over the dilator and a distal end portion of the introducer cannula is passed through the abdominal wall along the tract. The dilator is removed from the introducer cannula and from the patient, while leaving the introducer cannula in position. Next the cap is affixed to a proximal end of the introducer cannula, thereby sealing off the proximal end of the introducer cannula, and next, a pneumoperitoneum is formed in the abdominal cavity.

In one embodiment, the pneumoperitoneum is formed by opening the stopcock and delivering insufflation gas through the stopcock, cap and introducer cannula.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A surgical instrument comprising:
    an elongate shaft;
    a working end platform formed on a distal end portion of the elongate shaft;
    a stabilizing pin movably mounted to said platform, said stabilizing pin actuatable from a recessed position in which a tip of said stabilizing pin is concealed within said platform to a stabilizing position where said tip extends out of said platform, and vice versa;
    a stitching needle rotatably mounted relative to said elongate shaft and rotatable from a concealed position in which a tip of said stitching needle is concealed within said platform to an exit position where said tip is inserted into a suture anchor releasably attached to said platform, and counter-rotatable from said position where said tip is inserted into said suture anchor to said position in which said tip is concealed within said platform; and
    a suture releasably mounted on said stitching needle, said suture including a catch member fixed to a distal end portion of said suture, wherein said stitching needle delivers said suture to said suture anchor when driven from said concealed position to said exit position, and wherein said catch member is retained by said suture anchor, preventing said suture from returning to said concealed position when said stitching needle counter-rotates to said concealed position.

2. The surgical instrument of claim 1, further comprising:
    a sleeve extending distally from said catch member over a portion of said suture.

3. The surgical instrument of claim 2, wherein said sleeve is fixed at a distal end to said catch member and a proximal end of said sleeve is free.

4. The instrument of claim 1, wherein said stabilizing pin, in said stabilizing position angles away from a direction of movement of said stitching needle as said stitching needle moves from said concealed position to said exit position.

5. The instrument of claim 1, further comprising a stabilizing pin actuator, operable by a user from a location proximal of said elongate shaft, said stabilizing pin actuator configured to actuate said stabilizing pin to move from said recessed position to said stabilizing position and vice versa; and
    a stabilizing pin mechanism extending from said actuator to said stabilizing pin, along said elongate shaft, said stabilizing pin mechanism configured to drive as well as retract said stabilizing pin.

6. The instrument of claim 5, further comprising a safety mechanism configured for actuation from a safe position and a release position, wherein in said safe position, said stabilizing pin actuator is prevented from actuating said stabilizing pin to move from said recessed position to said stabilizing position, and, when in said release position, said safety mechanism allows said stabilizing pin actuator to actuate said stabilizing pin to move from said recessed position to said stabilizing position.

7. The instrument of claim 1, further comprising a stitching needle actuator, operable by a user from a location proximal of said elongate shaft, said stitching needle actuator configured to actuate said stitching needle to move from said concealed position to said exit position; and
    a stitching needle mechanism extending from said actuator to said stabilizing pin, along said elongate shaft, said stitching needle mechanism configured to drive said stitching needle from said concealed position to said exit position.

8. The instrument of claim 7, further comprising a stitching needle retraction mechanism configured to automatically counter-rotate said stitching needle from said exit position to said concealed position, after said stitching needle has reached said exit position.

9. The instrument of claim 7, further comprising a safety mechanism configured for actuation from a safe position and a release position, wherein in said safe position, said stitching needle actuator is prevented from actuating said stitching needle to move from said concealed position to said exit position, and, when in said release position, said safety mechanism allows said stitching needle actuator to actuate said stitching needle to move from said concealed position to said exit position.

10. The instrument of claim 7, wherein said stitching needle mechanism comprises a ratchet mechanism, and said stitching needle actuator ratchets to incrementally rotate said stitching needle from said concealed position to said exit position.

11. The instrument of claim 7, further comprising a bailout mechanism, configured for operation by a user from a location proximal of said elongate shaft, wherein said bailout mechanism is operable to disconnect said stitching needle actuator from said stitching needle mechanism, and to counter-rotate said stitching needle.

12. An assembly for surgical treatment of a patient, said assembly comprising:
a stitching instrument comprising:
a first elongate shaft;
a working end platform formed on a distal end portion of the elongate shaft;
a stabilizing pin movably mounted to said platform, said stabilizing pin actuatable from a recessed position in which a tip of said stabilizing pin is concealed within said platform to a stabilizing position where said tip extends out of said platform, and vice versa;
a stitching needle rotatably mounted relative to said elongate shaft and rotatable from a concealed position in which a tip of said stitching needle is concealed within said platform to an exit position where said tip is inserted into a suture anchor releasably attached to said platform, and counter-rotatable from said position where said tip is inserted into said suture anchor to said position in which said tip is concealed within said platform;
a suture releasably mounted on said stitching needle, said suture including a catch member fixed to a distal end portion of said suture, wherein said stitching needle delivers said suture to said suture anchor when driven from said concealed position to said exit position, and wherein said catch member is retained by said suture anchor, preventing said suture from returning to said concealed position when said stitching needle counter-rotates to said concealed position; and
a suturing instrument connected to said stitching instrument, said suturing instrument comprising:
a second elongate shaft;
said suture extending proximally from said stitching needle, respectively, thorough said second elongated shaft and proximally of said second elongated shaft; and
a cutting mechanism configured to cut said suture at a location of a distal end portion of said second elongate shaft, proximal of said stitching needle, respectively.

13. The assembly of claim 12, wherein said stitching instrument is releasably connected to said suturing instrument.

14. The assembly of claim 12, further comprising a suture retainer on said suture located proximal of said stitching needle respectively, said suture retainer being configured to slide along said suture in a distal direction, while preventing sliding of said suture retainer along said suture in a proximal direction.

15. The assembly of claim 14, further comprising an implantable device releasably mounted to at least one of said stitching instrument and said suturing instrument.

16. The assembly of claim 15, wherein at least one of said at least one suture retainer is fixed to said implantable device.

17. The assembly of claim 16, wherein said implantable device comprises a hernia repair patch.

18. The assembly of claim 16, wherein the implantable device is an expandable implant configured for paragastric, extragastric implantation.

19. The assembly of claim 18, wherein said implant comprises:
an expandable member having a main body portion which, when in an expanded configuration, extends along a central axis of curvature that extends substantially in a single plane, said main body having a superior portion and an inferior portion, wherein said superior portion has a substantially larger cross-sectional area than a cross-sectional area of said inferior portion when said expandable member is in an expanded configuration;
said expandable member further comprising a superior lobe portion extending along a transverse axis that is transverse to said central axis of curvature at a location from which said superior lobe extends.

20. The assembly of claim 15, wherein said stitching instrument further comprises a decoupling mechanism operable from a proximal end of said stitching instrument to decouple said implantable device from a distal end portion of said stitching instrument.

21. The assembly of claim 12, wherein said stitching instrument comprises a first handle mounted at a proximal end of said first elongated shaft and said suturing instrument comprises a second first handle mounted at a proximal end of said second elongated shaft, wherein said first and second handles are releasably connected to one another, and, upon releasing said first handle from said second handle, said stitching instrument and said suturing instrument are separable from one another.

* * * * *

UNITED STATES PATENT AND TRADEMARK OFFICE
CERTIFICATE OF CORRECTION

PATENT NO. : 7,976,554 B2  
APPLICATION NO. : 12/474251  
DATED : July 12, 2011  
INVENTOR(S) : Newell et al.

It is certified that error appears in the above-identified patent and that said Letters Patent is hereby corrected as shown below:

Column 5, line 20, please delete "assembled on assembled on", and insert therefore --assembled on--;
Column 20, line 34, please delete "pints" and insert --points--;
Column 22, line 58, please delete "beings" and insert --begins--;
Column 23, line 51, please delete "our" and insert --out--;
Column 24, line 6, please delete "beings" and insert --begins--;
Column 27, line 23, please delete "m" and insert --in--;
Column 31, line 32, please delete "sidable" and insert --slidable--;
Column 38, line 51, please delete "with out without" and insert --without--;
Column 48, line 1, please delete "be alternatively be" and insert --alternatively be--; and
Column 54, line 11, please delete "too." and insert --to.--.

Signed and Sealed this
Twenty-sixth Day of June, 2012

David J. Kappos
*Director of the United States Patent and Trademark Office*